(12) United States Patent
Lee et al.

(10) Patent No.: US 10,873,033 B2
(45) Date of Patent: *Dec. 22, 2020

(54) ORGANIC COMPOUND, COMPOSITION, ORGANIC OPTOELECTRONIC DIODE, AND DISPLAY DEVICE

(71) Applicant: SAMSUNG SDI CO., LTD., Yongin-si (KR)

(72) Inventors: Han-Ill Lee, Suwon-si (KR); Su-Jin Han, Suwon-si (KR); Young-Kwon Kim, Suwon-si (KR); Eun-Sun Yu, Suwon-si (KR); Ho-Kuk Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/116,630

(22) PCT Filed: Jul. 21, 2014

(86) PCT No.: PCT/KR2014/006610
§ 371 (c)(1),
(2) Date: Aug. 4, 2016

(87) PCT Pub. No.: WO2015/156449
PCT Pub. Date: Oct. 15, 2015

(65) Prior Publication Data
US 2016/0351822 A1    Dec. 1, 2016

(30) Foreign Application Priority Data

Apr. 9, 2014    (KR) .................. 10-2014-0042630

(51) Int. Cl.
*H01L 51/00*     (2006.01)
*C07D 401/04*   (2006.01)
(Continued)

(52) U.S. Cl.
CPC ........ *H01L 51/0067* (2013.01); *C07C 13/567* (2013.01); *C07D 209/86* (2013.01);
(Continued)

(58) Field of Classification Search
USPC ....... 428/690, 691, 917, 411.4, 336; 427/58, 427/66; 313/500–512; 257/40, 88–104,
(Continued)

(56) References Cited

U.S. PATENT DOCUMENTS

| 6,057,048 A | 5/2000 | Hu et al. |
| 6,225,467 B1 | 5/2001 | Esteghamatian et al. |

(Continued)

FOREIGN PATENT DOCUMENTS

| CN | 1934213 A | 3/2007 |
| CN | 102439004 A | 5/2012 |

(Continued)

OTHER PUBLICATIONS

Daintith, John; Dictionary of Chemistry, 2008;Oxford University Press, 6th Edition. (Year: 2008).*

(Continued)

*Primary Examiner* — Jennifer A Chriss
*Assistant Examiner* — Sean M DeGuire
(74) *Attorney, Agent, or Firm* — Lee IP Law, P.C.

(57) ABSTRACT

The present invention relates to: an organic compound which is represented by formula 1 and has a molecular weight of less than 750; a composition for an organic optoelectronic diode which includes the organic compound; an organic optoelectronic diode which applies the organic compound and the composition; and a display device which includes the organic optoelectronic diode.

16 Claims, 1 Drawing Sheet

(51) Int. Cl.

| | |
|---|---|
| *C07D 209/88* | (2006.01) |
| *C07D 409/14* | (2006.01) |
| *C07D 213/53* | (2006.01) |
| *C07D 405/04* | (2006.01) |
| *C07D 409/04* | (2006.01) |
| *C07D 213/22* | (2006.01) |
| *H05B 33/20* | (2006.01) |
| *C07C 13/567* | (2006.01) |
| *C07D 405/14* | (2006.01) |
| *C07D 403/14* | (2006.01) |
| *C09K 11/06* | (2006.01) |
| *C07D 209/86* | (2006.01) |
| *C07D 213/16* | (2006.01) |
| *C07D 239/26* | (2006.01) |
| *C07D 251/24* | (2006.01) |
| *C07D 401/14* | (2006.01) |
| *C07D 487/04* | (2006.01) |
| *C09K 11/02* | (2006.01) |
| *H01L 51/50* | (2006.01) |

(52) U.S. Cl.
CPC ......... *C07D 209/88* (2013.01); *C07D 213/16* (2013.01); *C07D 213/22* (2013.01); *C07D 213/53* (2013.01); *C07D 239/26* (2013.01); *C07D 251/24* (2013.01); *C07D 401/04* (2013.01); *C07D 401/14* (2013.01); *C07D 403/14* (2013.01); *C07D 405/04* (2013.01); *C07D 405/14* (2013.01); *C07D 409/04* (2013.01); *C07D 409/14* (2013.01); *C07D 487/04* (2013.01); *C09K 11/025* (2013.01); *C09K 11/06* (2013.01); *H01L 51/0054* (2013.01); *H01L 51/0058* (2013.01); *H01L 51/0072* (2013.01); *H05B 33/20* (2013.01); *C07C 2603/18* (2017.05); *C07C 2603/42* (2017.05); *C09K 2211/1007* (2013.01); *C09K 2211/1029* (2013.01); *C09K 2211/185* (2013.01); *H01L 51/0085* (2013.01); *H01L 51/5016* (2013.01); *H01L 2251/5384* (2013.01)

(58) Field of Classification Search
USPC ......... 257/E51–E51.052; 252/301.16–301.35
See application file for complete search history.

(56) References Cited

U.S. PATENT DOCUMENTS

| | | | |
|---|---|---|---|
| 6,821,643 | B1 | 11/2004 | Hu et al. |
| 2003/0166920 | A1 | 9/2003 | Lu et al. |
| 2007/0190355 | A1* | 8/2007 | Ikeda ................... C07D 239/26 428/690 |
| 2011/0278555 | A1* | 11/2011 | Inoue ................... C07D 209/82 257/40 |
| 2017/0104163 | A1* | 4/2017 | Lee ..................... H01L 51/0067 |

FOREIGN PATENT DOCUMENTS

| | | | |
|---|---|---|---|
| CN | 102971395 | A | 3/2013 |
| CN | 105916847 | A | 8/2016 |
| JP | 2007-223929 | A | 9/2007 |
| JP | 4106974 | B2 | 6/2008 |
| JP | 2008-280330 | A | 11/2008 |
| JP | 4474493 | B1 | 6/2010 |
| KR | 10-2007-0009074 | A | 1/2007 |
| KR | 10-2007-0030759 | A | 3/2007 |
| KR | 10-2009-0101954 | A | 9/2009 |
| KR | 10-2009-0130008 | A | 12/2009 |
| KR | 10-2010-0021908 | A | 2/2010 |
| KR | 10-0958641 | B1 | 5/2010 |
| KR | 10-2011-0049012 | A | 5/2011 |
| KR | 10-2012-0025006 | A | 3/2012 |
| KR | 10-2012-0082938 | A | 7/2012 |
| KR | 10-2013-0038218 | A | 4/2013 |
| WO | WO 2005/085387 | A1 | 9/2005 |
| WO | WO 2006/067976 | A1 | 6/2006 |
| WO | WO 2007/023840 | A1 | 3/2007 |
| WO | WO 2011-013843 | A | 2/2011 |
| WO | WO 2012/137958 | A1 | 10/2012 |

OTHER PUBLICATIONS

Provisional double patenting rejection over claims of the above-identified application; USPTO Office action dated Oct. 18, 2017, in U.S. Appl. No. 15/317,468.

Chinese Office Action dated Jan. 31, 2018, of the corresponding Chinese Patent Application No. 201480077673.5.

* cited by examiner

ORGANIC COMPOUND, COMPOSITION, ORGANIC OPTOELECTRONIC DIODE, AND DISPLAY DEVICE

CROSS REFERENCE TO RELATED APPLICATIONS

This is the U.S. national phase application based on PCT Application No. PCT/KR2014/006610, filed Jul. 21, 2014, which is based on Korean Patent Application No. 10-2014-0042630, filed Apr. 9, 2014, the entire contents of all of which are hereby incorporated by reference.

TECHNICAL FIELD

An organic compound, a composition, an organic optoelectronic diode, and a display device are disclosed.

BACKGROUND ART

An organic optoelectronic diode is a device that converts electrical energy into photoenergy, and vice versa.

An organic optoelectronic diode may be classified as follows in accordance with its driving principles. One is an optoelectronic diode where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode.

Performance of an organic light emitting diode may be affected by characteristics of the organic layer, and among them, may be mainly affected by characteristics of an organic material of the organic layer. Particularly, development for an organic material being capable of increasing hole and electron mobility and simultaneously increasing electrochemical stability is needed so that the organic light emitting diode may be applied to a large-size flat panel display.

DISCLOSURE

Technical Problem

One embodiment provides an organic compound being capable of realizing an organic optoelectronic diode having high efficiency and long life-span.

Another embodiment provides a composition for an organic optoelectronic diode including the organic compound.

Yet another embodiment provides an organic optoelectronic diode including the organic compound.

Still another embodiment provides a display device including the organic optoelectronic diode.

Technical Solution

According to an embodiment, an organic compound represented by Chemical Formula 1 and having a molecular weight of less than 750 is provided.

[Chemical Formula 1]

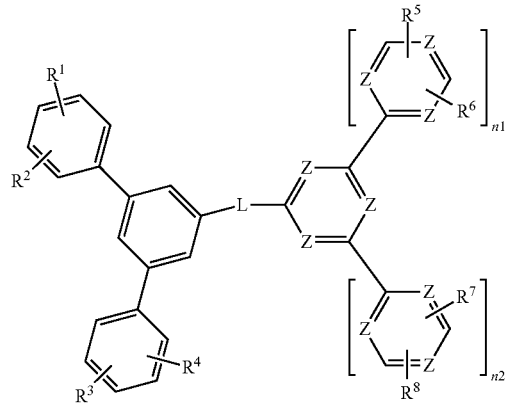

In Chemical Formula 1,

Z is independently N or $CR^a$, at least one of Z is N,

L is a substituted or unsubstituted phenylene group, a substituted or unsubstituted biphenylene group, or a substituted or unsubstituted terphenylene group, provided that L is not

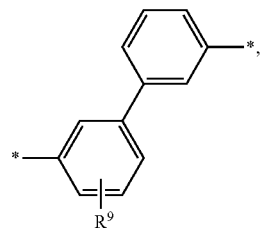

$R^1$ to $R^9$ and $R^a$ are independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, $R^1$ and $R^2$ are independently present or are linked to each other to form a ring, $R^3$ and $R^4$ are independently present or are linked to each other to form a ring, $R^5$, $R^6$, and $R^a$ are independently present or two of them are linked to each other to form a ring, $R^7$, $R^8$, and $R^a$ are independently present or two of them are linked to each other to form a ring, and n1 and n2 are independently 0 or 1.

According to another embodiment, a composition for an organic optoelectronic diode includes the organic compound as a first organic compound and at least one second organic compound having a carbazole moiety.

According to another embodiment, an organic optoelectronic diode includes an anode and a cathode facing each other, at least one organic layer between the anode and the cathode, wherein the organic layer includes the organic compound or the composition for an organic optoelectronic diode.

According to yet another embodiment, a display device including the organic optoelectronic diode is provided.

Advantageous Effects

An organic optoelectronic diode having high efficiency and long life-span may be realized.

BEST MODE

Figure 1:
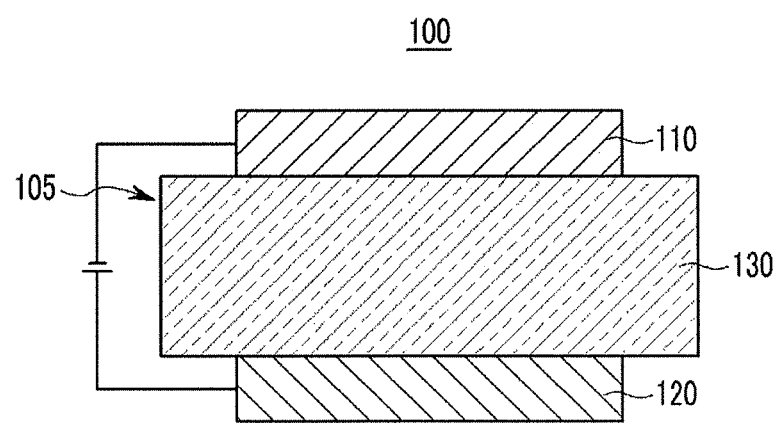
FIGS. 1 and 2 are cross-sectional views showing organic light emitting diodes according to an embodiment.

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heterocyclic group, a C1 to C20 alkoxy group, a fluoro group, a C1 to C10 trifluoroalkyl group such as a trifluoromethyl group, or a cyano group, instead of at least one hydrogen of a substituent or a compound.

In addition, two adjacent substituents of the substituted halogen, hydroxy group, an amino group, a substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heterocyclic group, C1 to C20 alkoxy group, fluoro group, C1 to C10 trifluoroalkyl group such as trifluoromethyl group and the like, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one hetero atom selected from the group consisting of N, O, S, P, and Si, and remaining carbons in one functional group.

In the present specification, "aryl group" refers to a cyclic substituent where all elements have p-orbitals, and these p-orbitals forms conjugation, and includes a monocyclic, polycyclic or fused ring polycyclic (i.e., rings sharing adjacent pairs of carbon atoms) functional group.

In the present specification, "heterocyclic group" refers to a group including at least one hetero atom selected from N, O, S, P and Si, and remaining carbons in a cyclic compound such as an aryl group or a cycloalkyl group. When the heterocyclic group is a fused ring, the heterocyclic entire ring or each ring may include at least one hetero atom.

More specifically, the substituted or unsubstituted C6 to C30 aryl group and/or the substituted or unsubstituted C2 to C30 heterocyclic group refer to a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, combinations thereof, or a fused form of combinations thereof, but are not limited thereto.

In the present specification, hole characteristics refer to characteristics to donate an electron and to form a hole when an electric field is applied, and characteristics that holes formed in the anode is easily injected into the emission layer and transported in the emission layer due to conductive characteristics according to HOMO level.

Electron characteristics refer to characteristics to accept an electron when an electric field is applied, and characteristics that electron formed in the cathode is easily injected into the emission layer and transported in the emission layer due to conductive characteristics according to LUMO level.

Hereinafter, an organic compound according to an embodiment is described.

An organic compound according to an embodiment is represented by Chemical Formula 1.

[Chemical Formula 1]

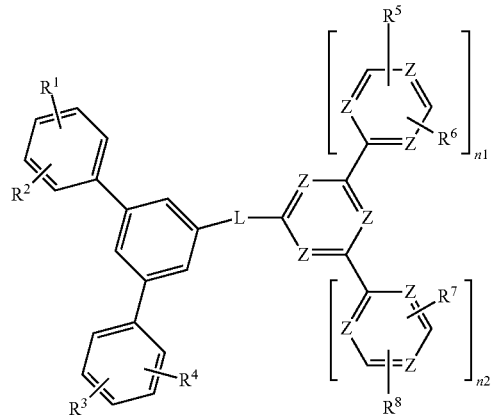

In Chemical Formula 1,

Z is independently N or CR$^a$, at least one of Z is N,

L is a substituted or unsubstituted phenylene group, a substituted or unsubstituted biphenylene group, or a substituted or unsubstituted terphenylene group, provided that L is not

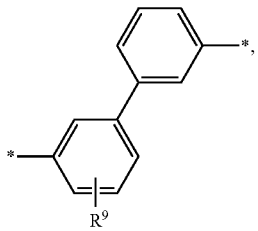

R$^1$ to R$^9$ and R$^a$ are independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, R$^1$ and R$^2$ are independently present or are linked to each other to form a ring, R$^3$ and R$^4$ are independently present or are linked to each other to form a ring, R$^5$, R$^6$, and R$^a$ are independently present or two of them are linked to each other to form a ring, R$^7$, R$^8$, and R$^a$ are independently present or two of them are linked to each other to form a ring, and n1 and n2 are independently 0 or 1.

The organic compound represented by Chemical Formula 1 respectively includes three or more substituted or unsubstituted aryl groups and a heteroaryl group having at least one nitrogen with an arylene group of a linking group (L) as the center.

Herein, the three or more substituted or unsubstituted aryl groups and the linking group (L) are respectively bonded at a meta position, and thus may exhibit steric hindrance characteristics and accordingly, reduce crystallization and improve efficiency and life-span characteristics by suppressing an interaction with neighboring molecules and resultantly.

In addition, the organic compound having a kinked terphenyl structure has a higher glass transition temperature (Tg) than a compound having a linearly-connected arylene structure and resultantly, may improve thermal characteristics and thus life-span characteristics.

The glass transition temperature (Tg) may be related to thermal stability of the organic compound and a device manufactured by using the same. In other words, when an organic compound having a high glass transition temperature (Tg) is applied in a form of a thin film to an organic light emitting diode, the organic compound may be prevented from degradation by the temperature in a subsequent process after depositing the organic compound, for example, an encapsulation process, securing life-span characteristics of the device.

The organic compound may have, for example, a glass transition temperature (Tg) of greater than or equal to about 70° C. and more effectively, greater than or equal to about 90° C. within the range. Within the range, the glass transition temperature (Tg) may be, for example, in a range of about 70° C. to 150° C. and specifically, in a range of about 90° C. to 130° C.

The organic compound has a structure of easily accepting electrons due to the ring including at least one nitrogen when an electric field is applied and resultantly, may decrease a driving voltage of an organic optoelectronic diode when applied thereto.

In addition, the organic compound includes a plurality of substituted or unsubstituted aryl group moiety easily accepting holes and a nitrogen-containing ring moiety easily accepting electrons and thus, has a bipolar structure and balances between hole and electron flows and resultantly, may improve efficiency of an organic optoelectronic diode when applied thereto.

In addition, the organic compound may exhibit excellent bipolar characteristics by appropriately localizing a plurality of substituted or unsubstituted aryl group moiety easily accepting a hole and a nitrogen-containing ring moiety easily accepting an electron with a linking group (L) as the center in the compound having the above bipolar structure and controlling a conjugation system flow. Accordingly, the life-span of an organic optoelectronic diode manufactured by applying the organic compound may be improved.

The organic compound may have a molecular weight of less than about 750. When it has a molecular weight within the range, the compound may be suppressed from being thermally decomposition at a high temperature during a deposition process and improve heat resistance. Within the range, it may be about 500 to 749, about 538 to 749, about 550 to 730, or about 600 to 700.

For example, in Chemical Formula 1, R$^1$ to R$^8$ and R$^a$ may independently be hydrogen, a substituted or unsubstituted phenyl group, a substituted or unsubstituted biphenyl group, or a substituted or unsubstituted naphthyl group.

For example, in Chemical Formula 1, L may be a unsubstituted phenylene group, unsubstituted biphenylene group or unsubstituted terphenylene group.

For example, in Chemical Formula 1, L may be a phenylene group substituted with a C6 to C12 aryl group, a biphenylene group substituted with a C6 to C12 aryl group, or a terphenylene group substituted with a C6 to C12 aryl group.

The organic compound may be for example represented by Chemical Formula 2 or 3 according to n1 and n2.

[Chemical Formula 2]

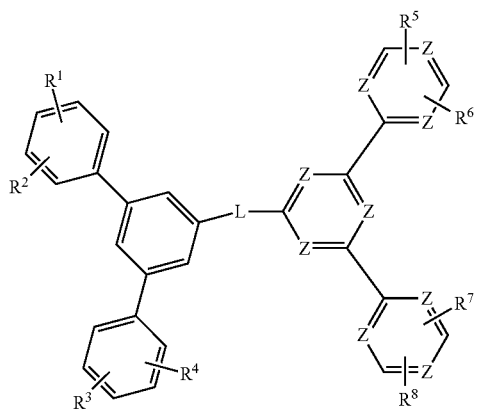

[Chemical Formula 3]
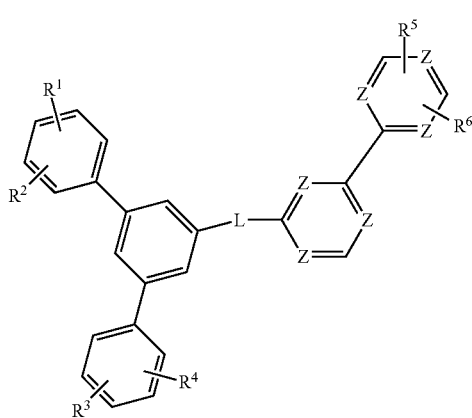
In Chemical Formula 2 or 3, Z, L, and $R^1$ to $R^8$ are the same as described above.
In Chemical Formulae 1 to 3, the L may be for example one of groups of Group 1.
[Group 1]
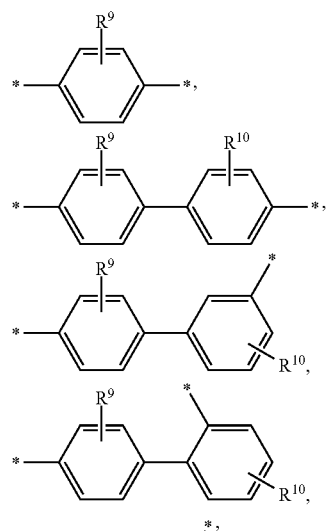
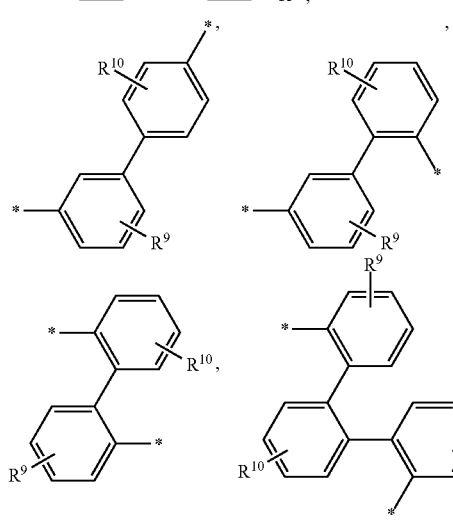
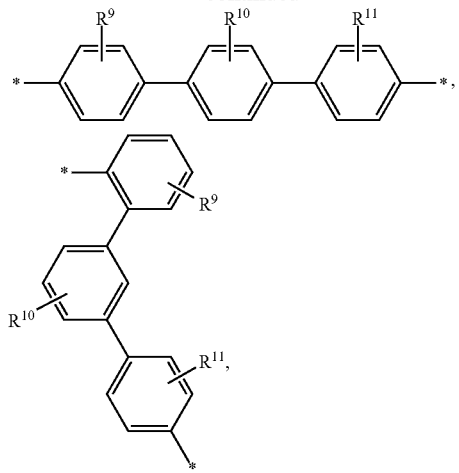
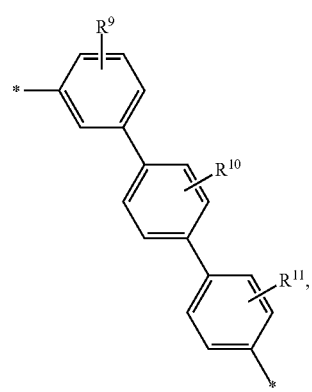
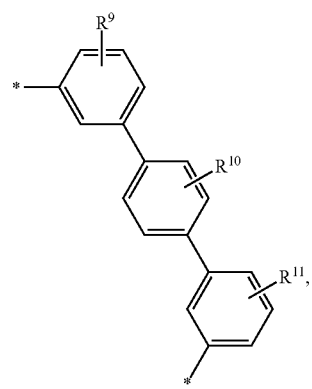
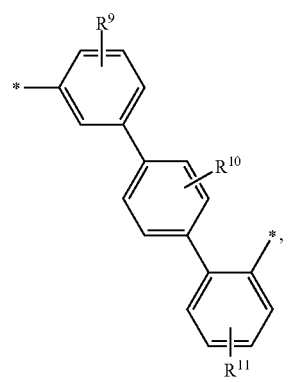

-continued

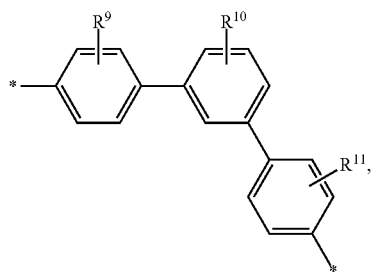

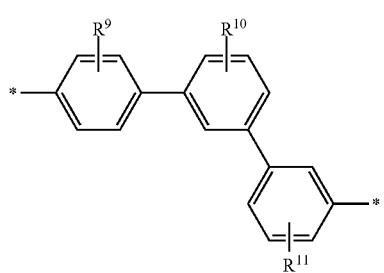

In Group 1, $R^9$ to $R^{11}$ are independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, and \* is a linking point.

For example, in the L of Group 1, $R^9$ to $R^{11}$ may independently be hydrogen.

The organic compound may be, for example compounds of Group 2, but is not limited thereto.

[Group 2]

1

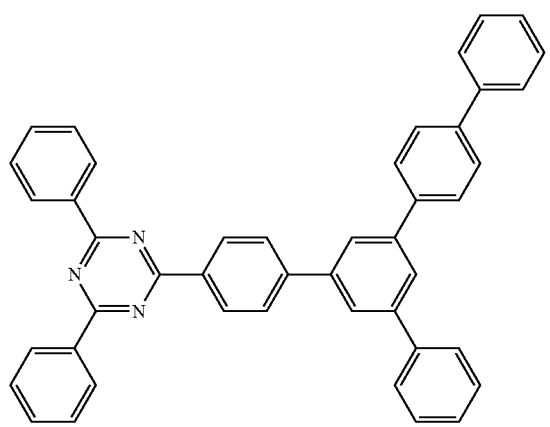

-continued

2

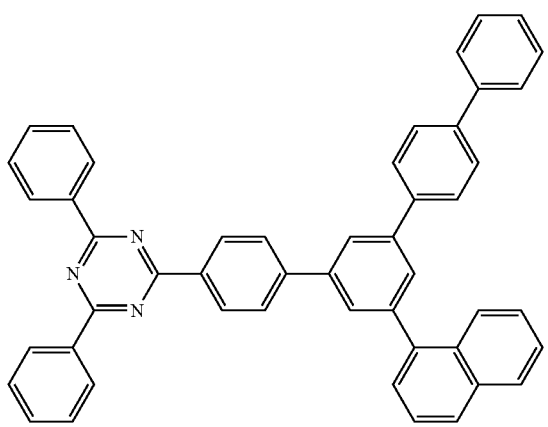

3

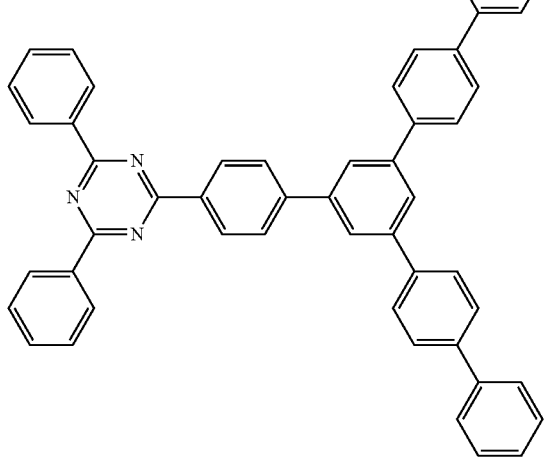

4

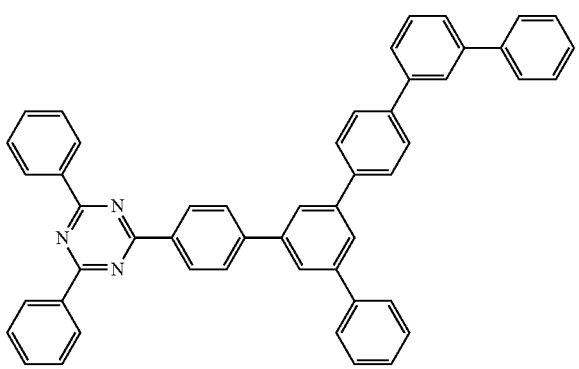

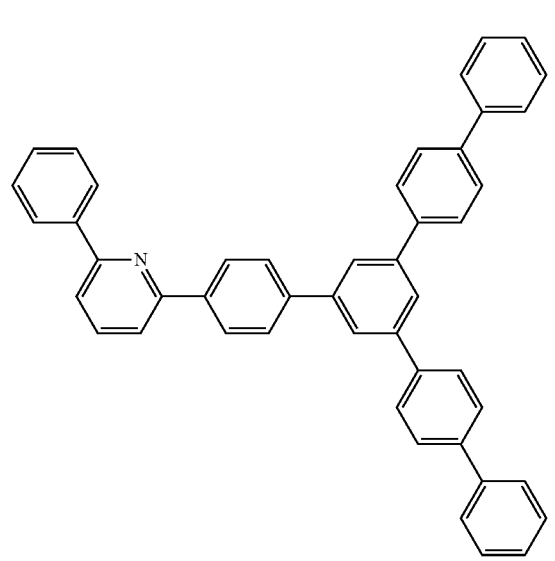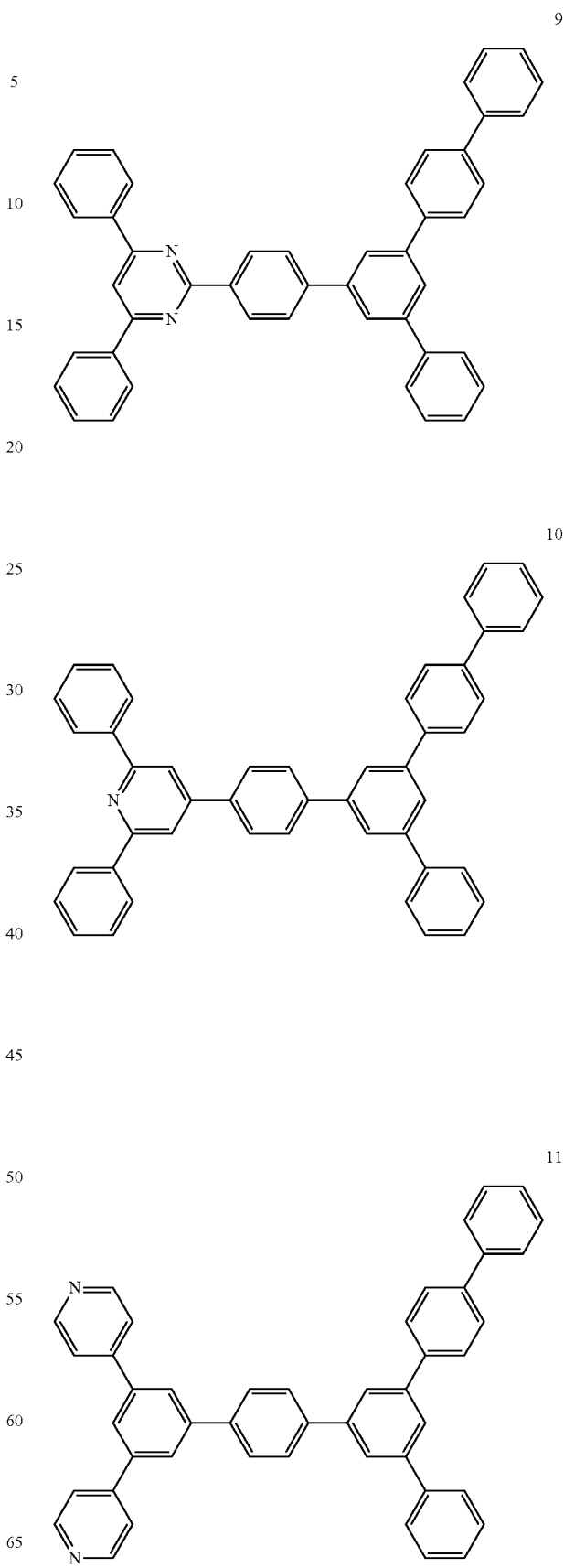

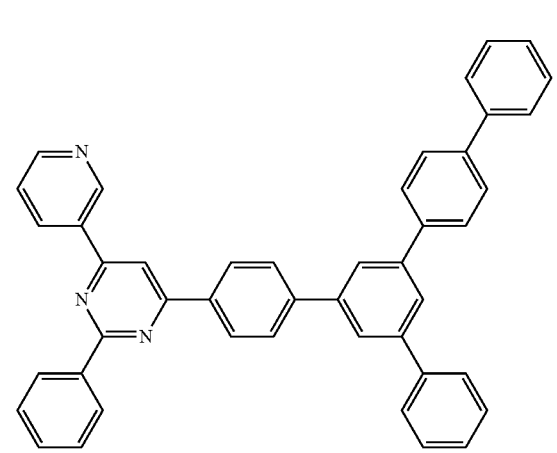
12
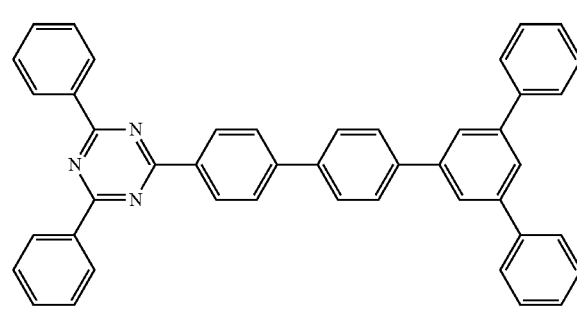
13
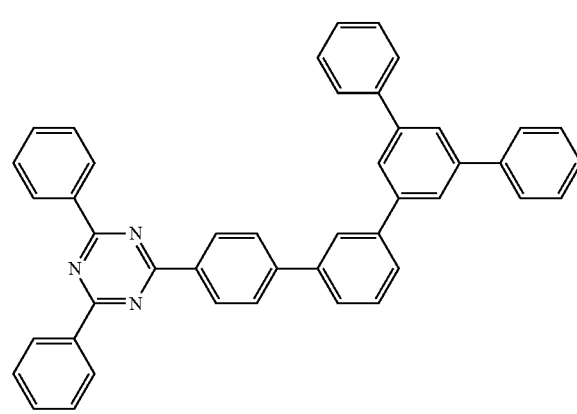
14
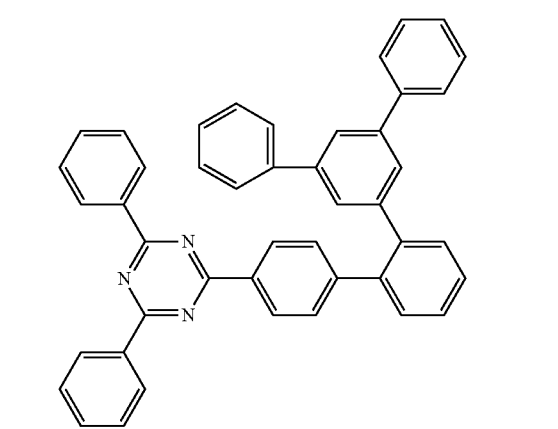
15
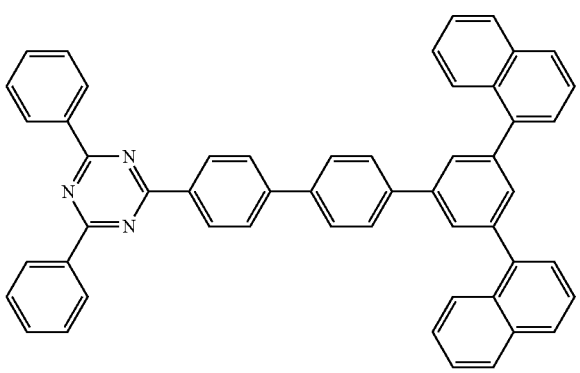
16
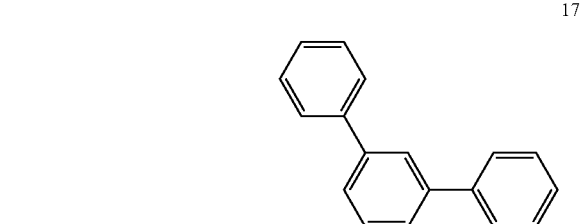
17
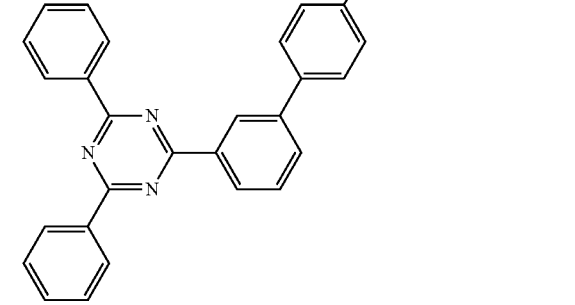
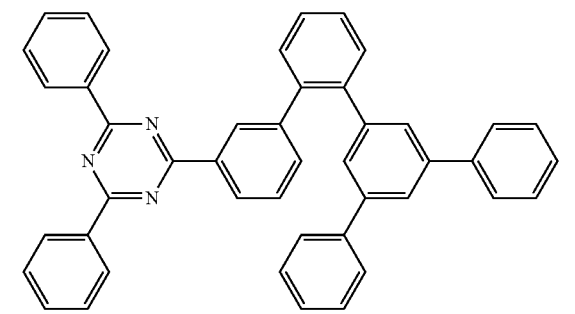
18

19
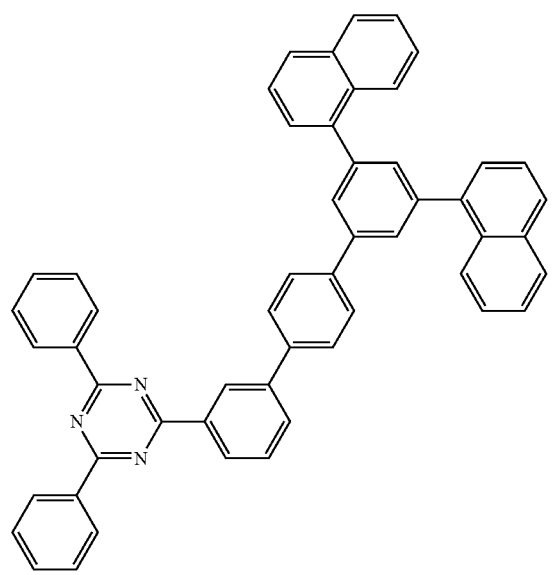
20
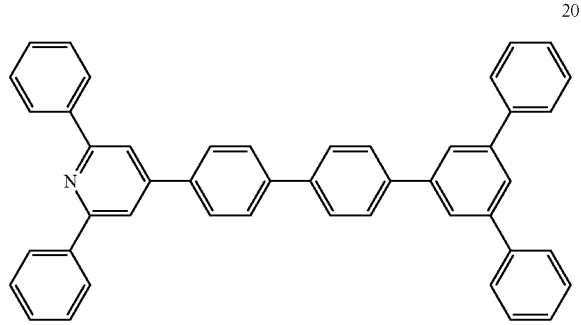
21
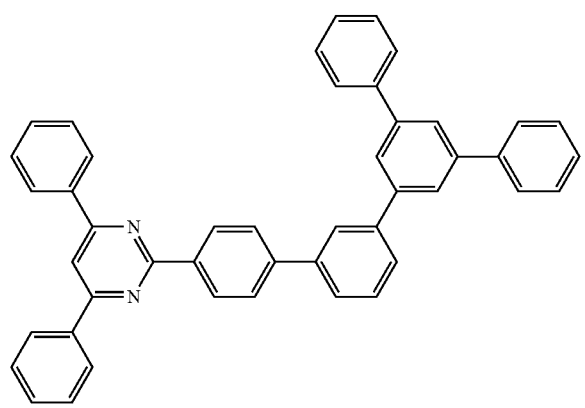
22
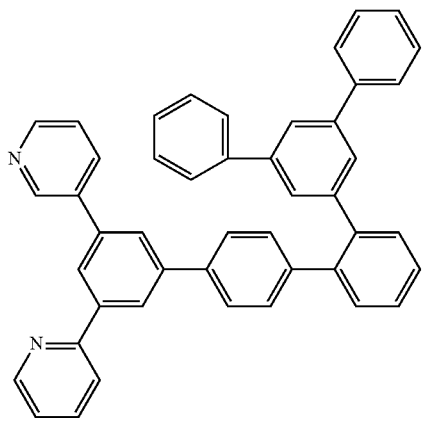
23
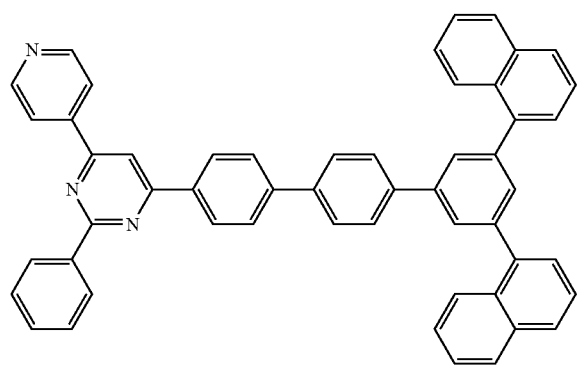
24
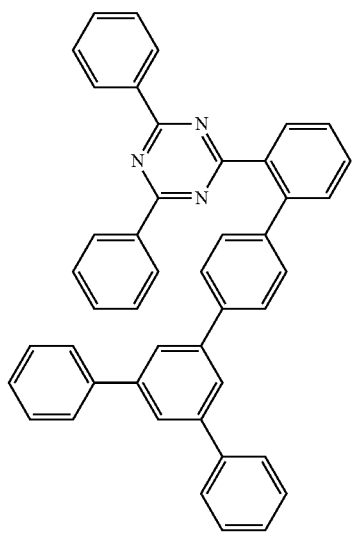

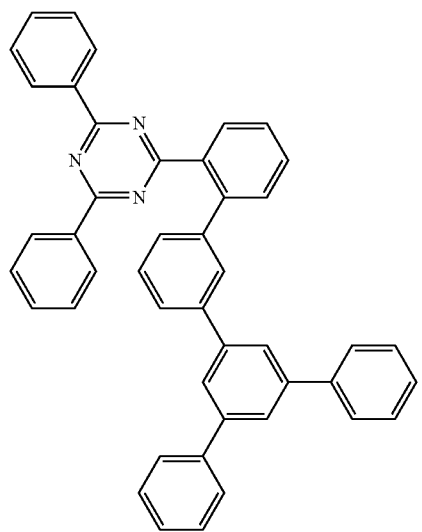
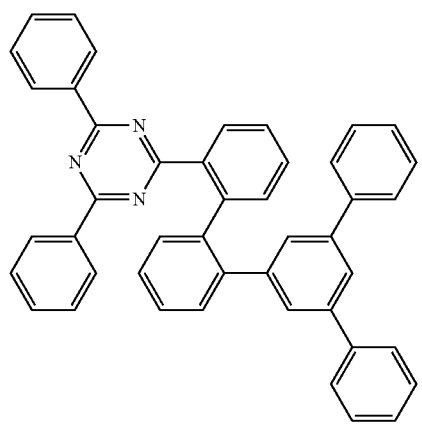
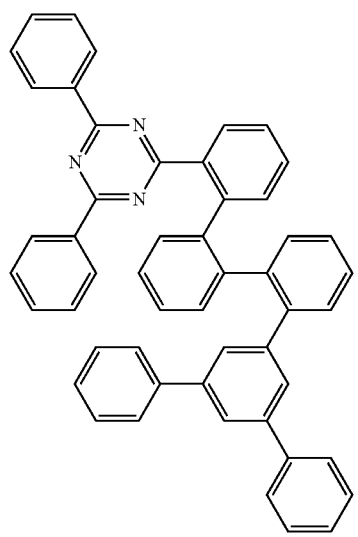
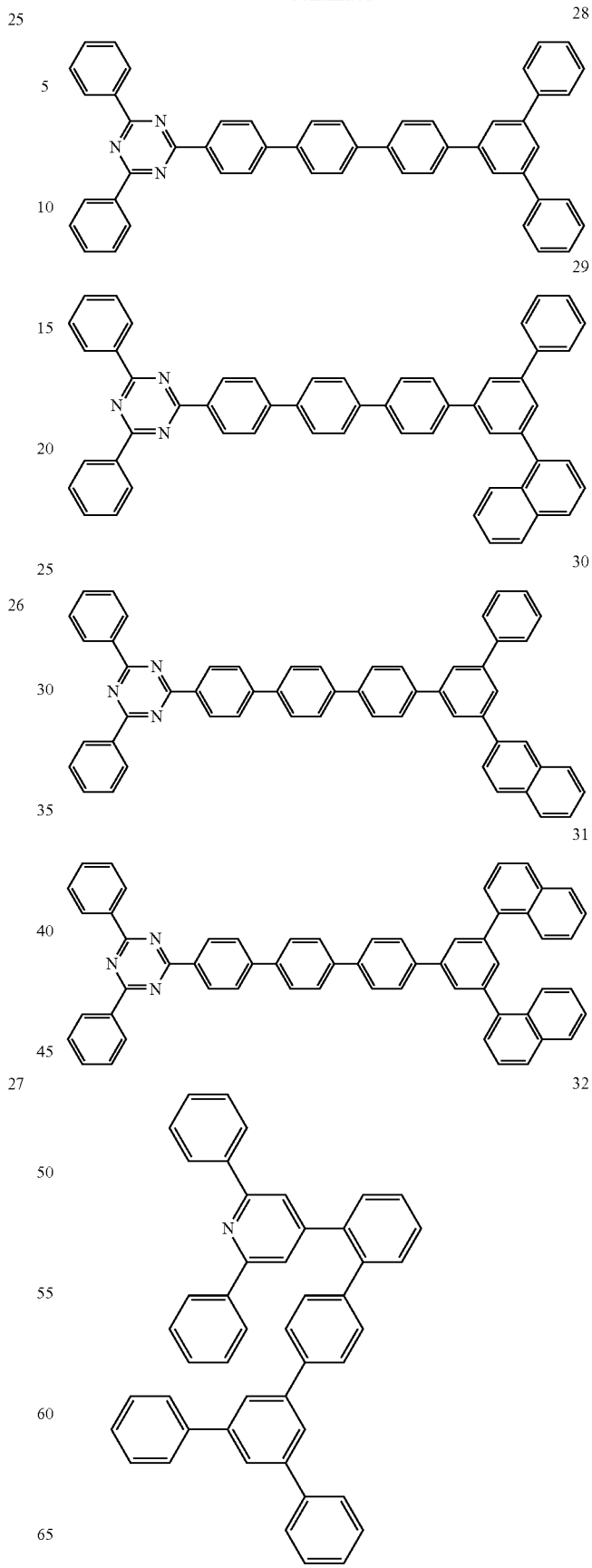

33
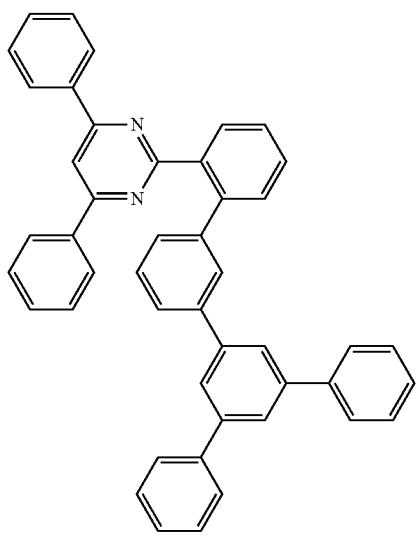
34
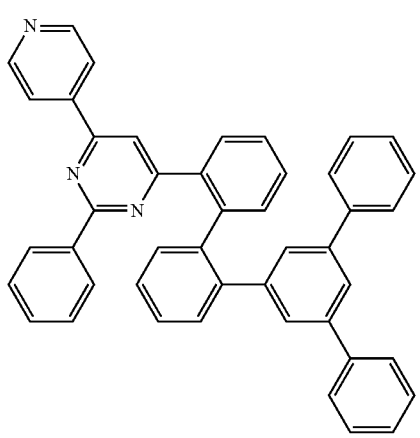
35
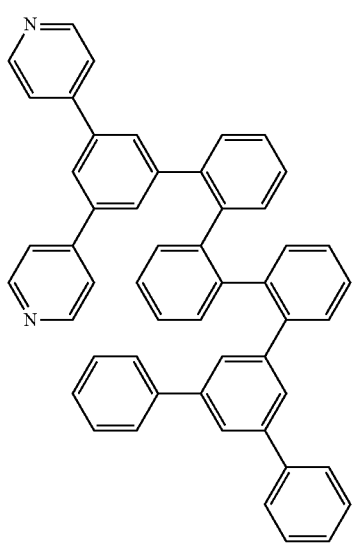
36
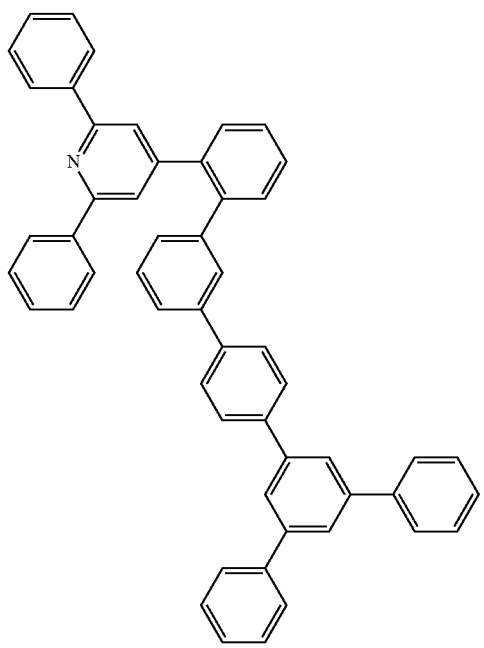
37

38

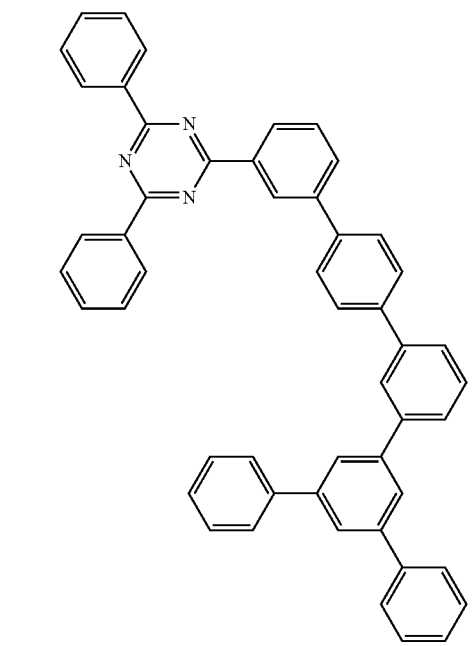

39

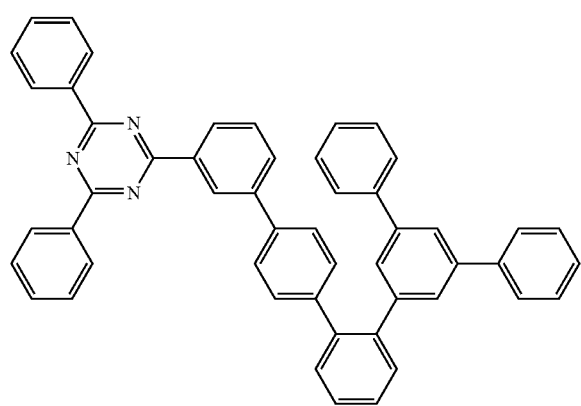

40

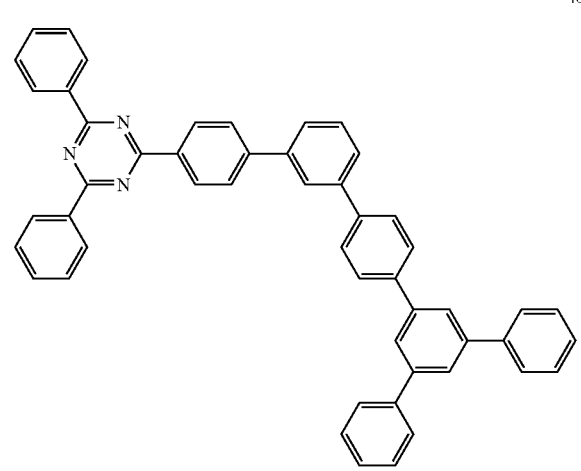

41

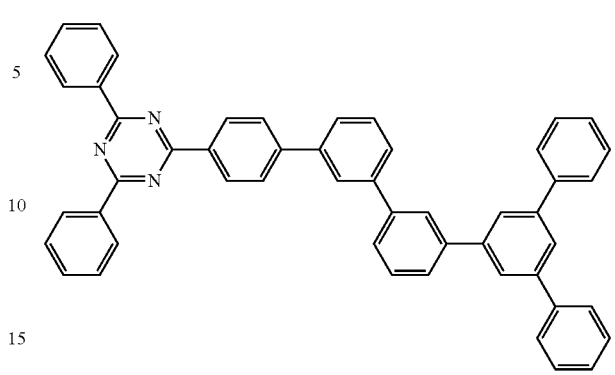

42

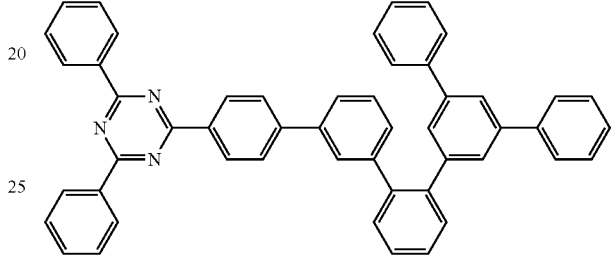

43

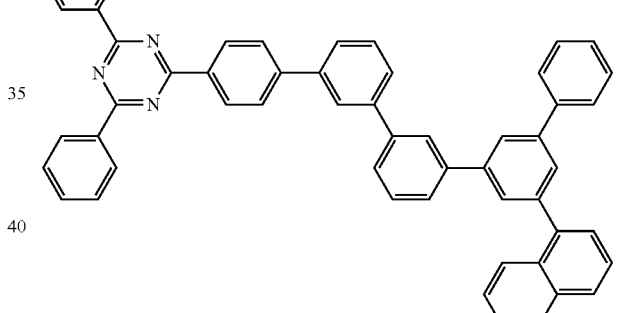

44

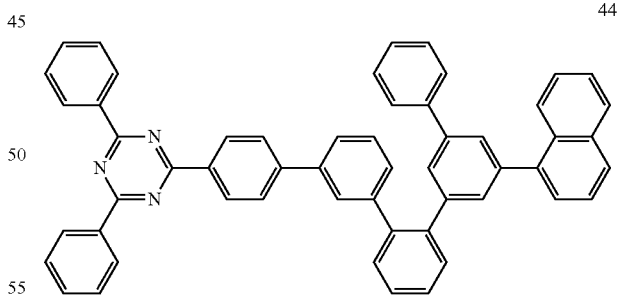

The organic compound may be applied to an organic optoelectronic diode.

The organic compound may be applied alone or with another organic compound to an organic optoelectronic diode. The organic compound may be applied in a form of a composition when it is used with another organic compound.

Hereinafter, an example of a composition for an organic optoelectronic diode including the organic compound is described.

The composition for an organic optoelectronic diode may be, for example a composition including the organic compound and at least one organic compound having a carbazole moiety. Hereinafter, the organic compound is referred to as a 'first organic compound' and the at least one organic compound including the carbazole moiety is referred to as a 'second organic compound.'

The second organic compound may be, for example a compound represented by Chemical Formula 4.

[Chemical Formula 4]

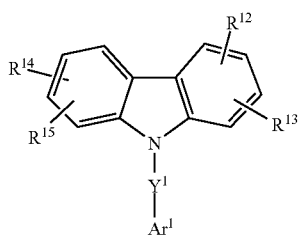

In Chemical Formula 4, $Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ is a substituted or unsubstituted C6 to C30 aryl group, a substituted or unsubstituted C2 to C30 heteroaryl group, or a combination thereof, $R^{12}$ to $R^{15}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, and at least one of $R^{12}$ to $R^{15}$ and $Ar^1$ includes one of a substituted or unsubstituted triphenylene group or a substituted or unsubstituted carbazole group.

The second organic compound represented by Chemical Formula 4 may be, for example represented by one of Chemical Formulae 4-I to 4-III:

[Chemical Formula 4-I]

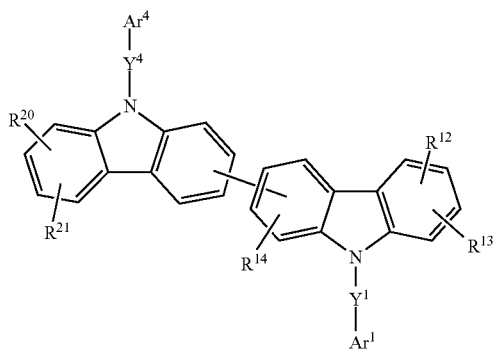

[Chemical Formula 4-II]

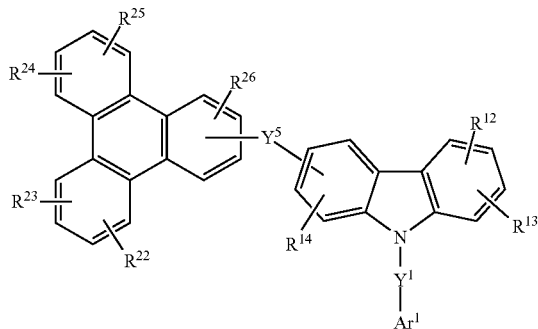

[Chemical Formula 4-III]

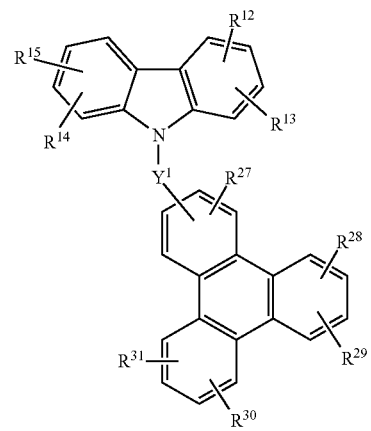

In Chemical Formulae 4-I to 4-III, $Y^1$, $Y^4$, and $Y^5$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ and $Ar^4$ are independently substituted or unsubstituted C6 to C30 aryl group, a substituted or unsubstituted C2 to C30 heteroaryl group, or a combination thereof, and $R^{12}$ to $R^{15}$ and $R^{20}$ to $R^{31}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof.

The second organic compound represented by Chemical Formula 4 may be, for example compounds of Group 3, but is not limited thereto.

[Group 3]
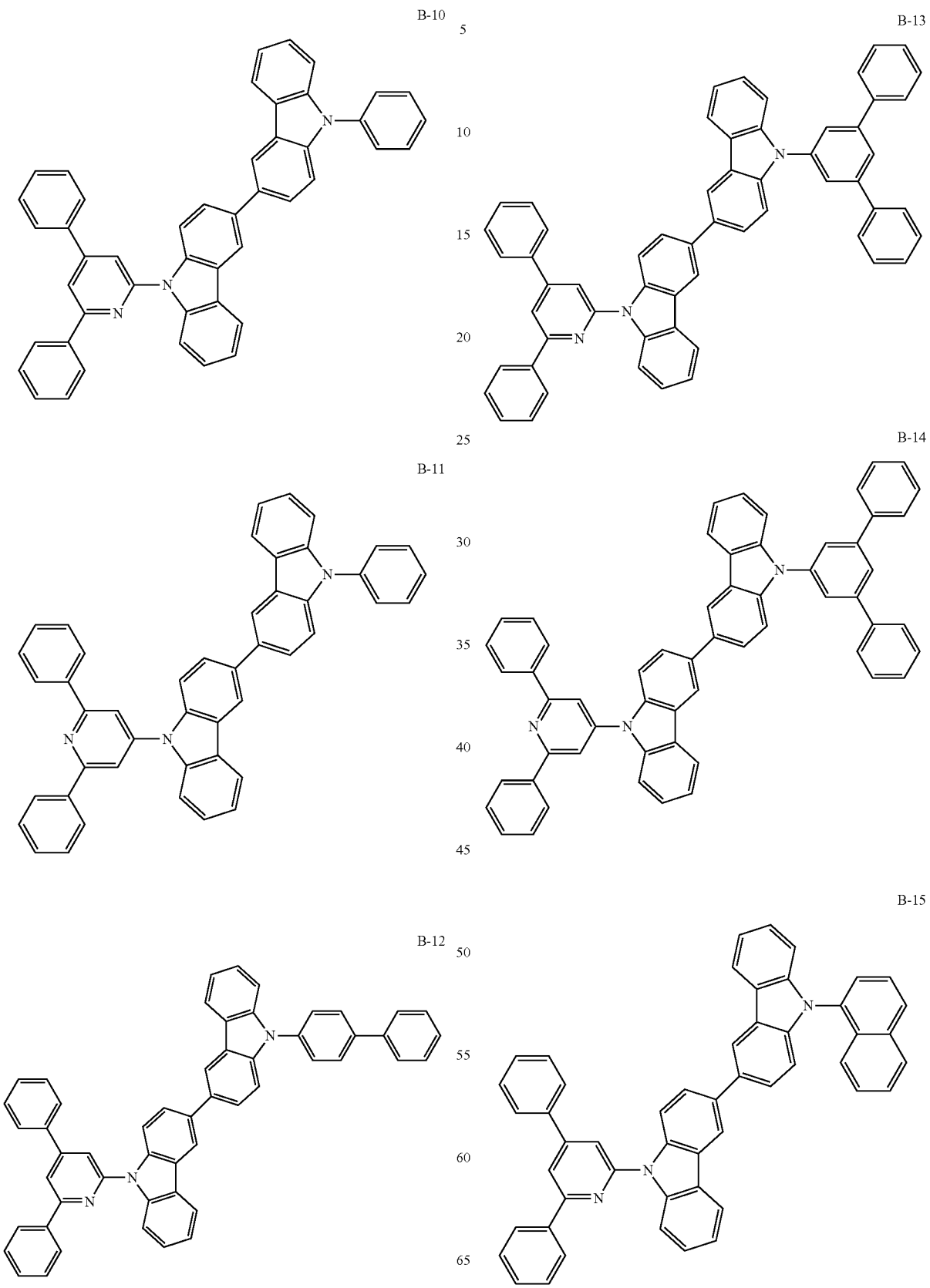

B-16
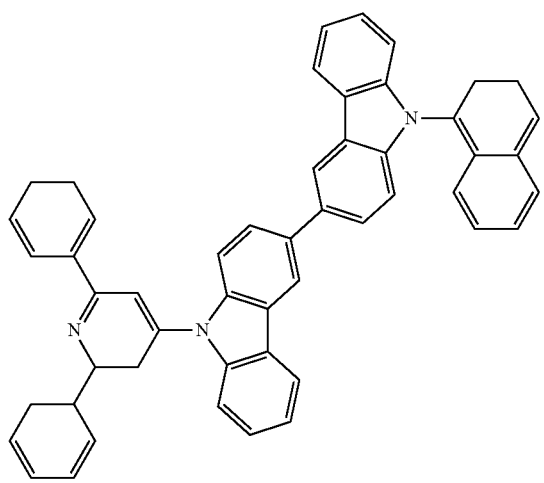
B-17
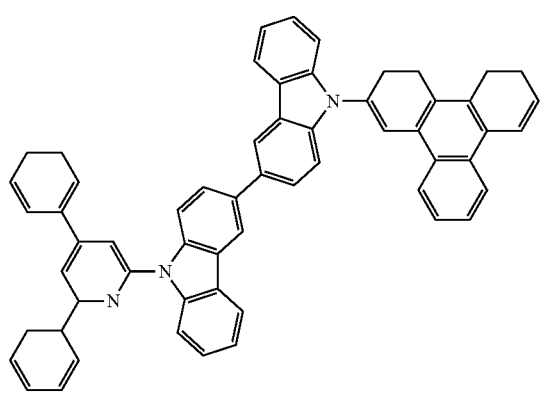
B-18
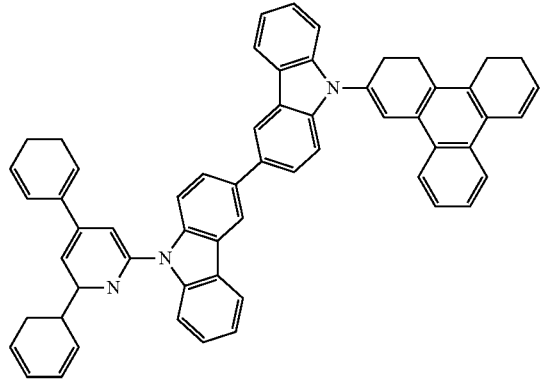
B-19
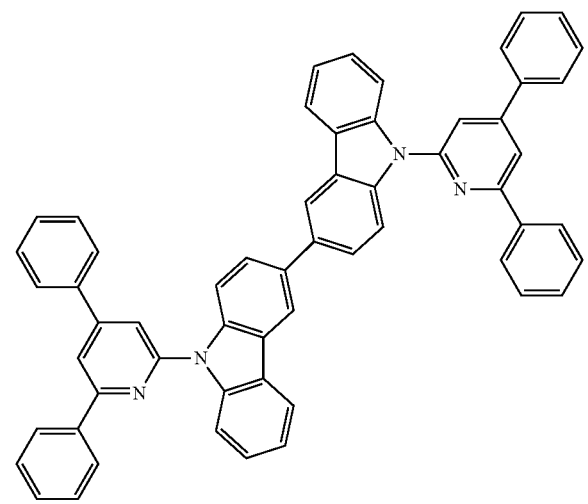
B-20
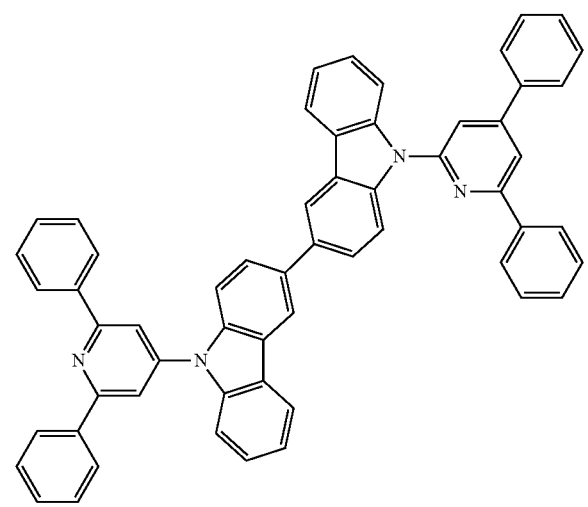
B-21
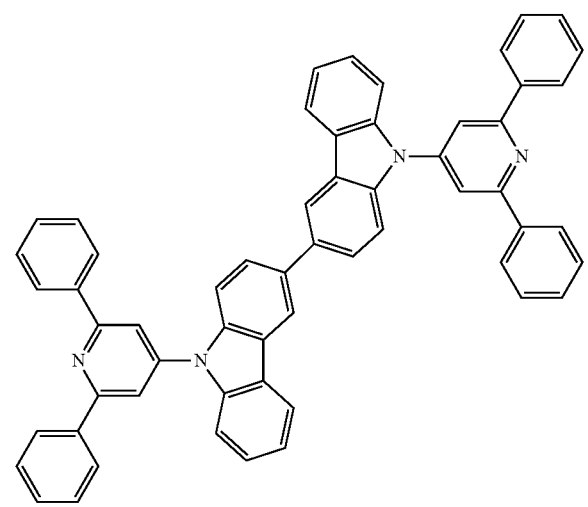

-continued
B-22
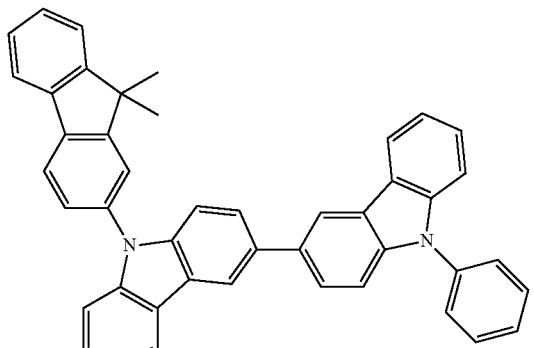
B-23
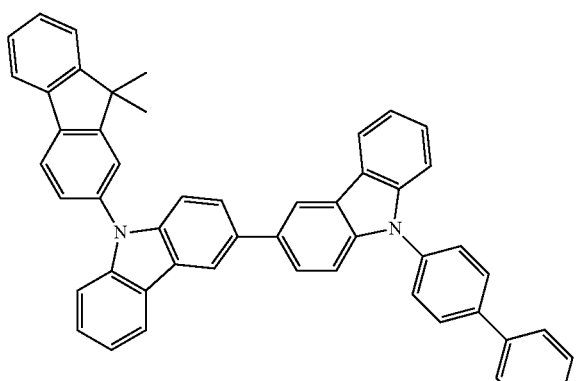
B-24
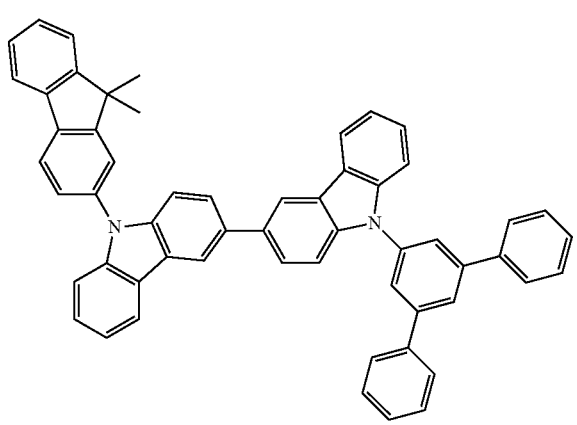
B-25
-continued
B-26
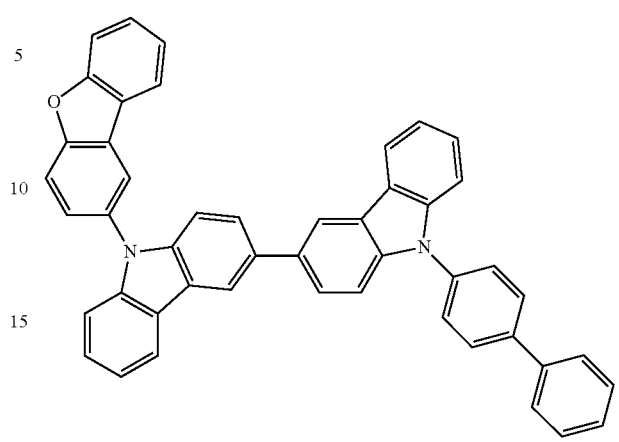
B-27
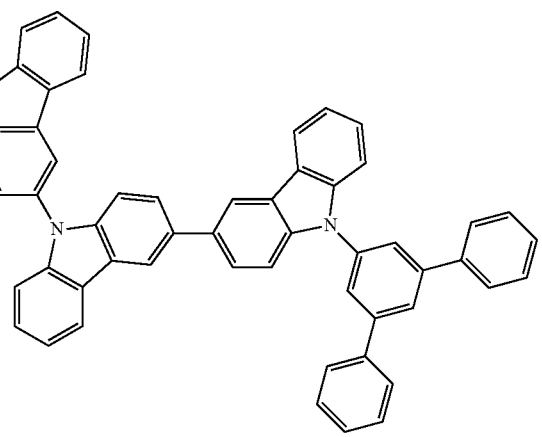
B-28
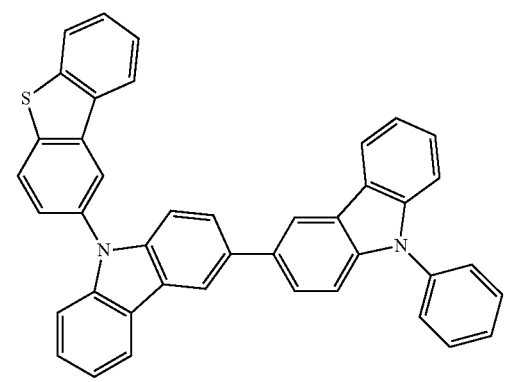

B-29
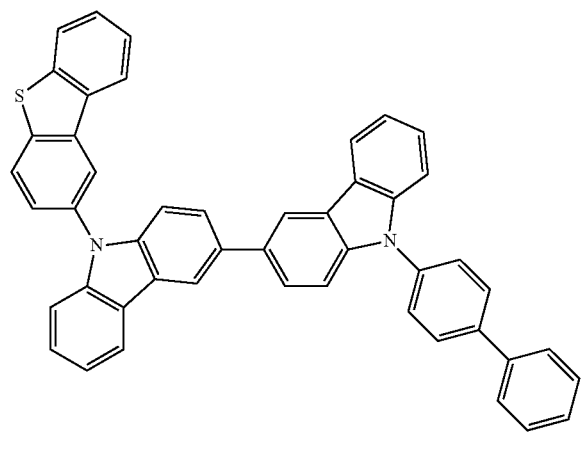
B-30
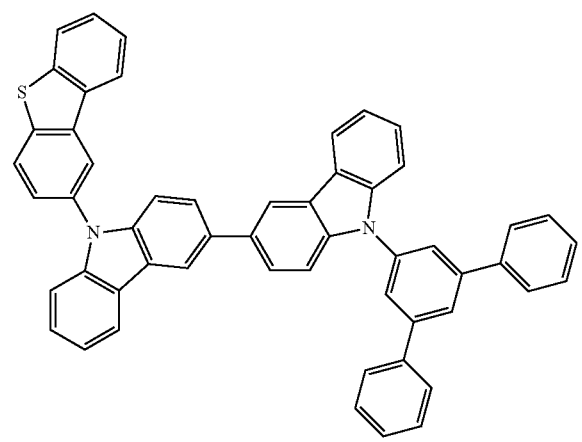
B-31
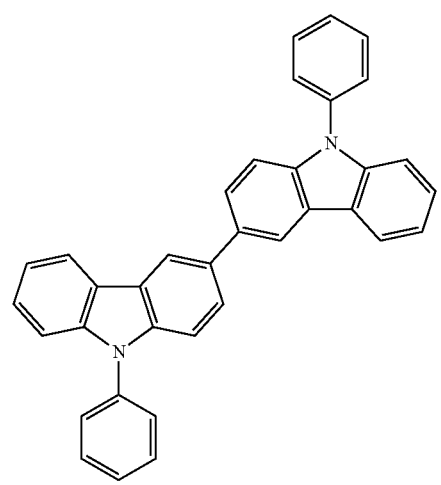
B-32
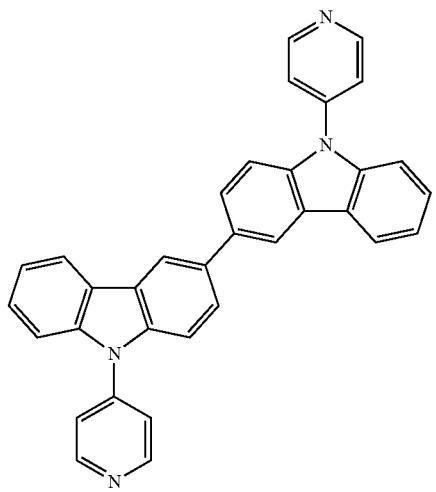
B-33
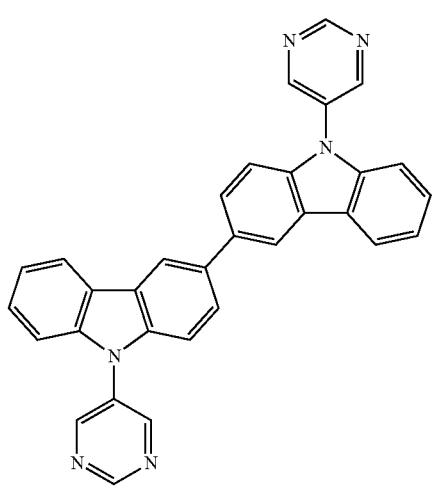
B-34
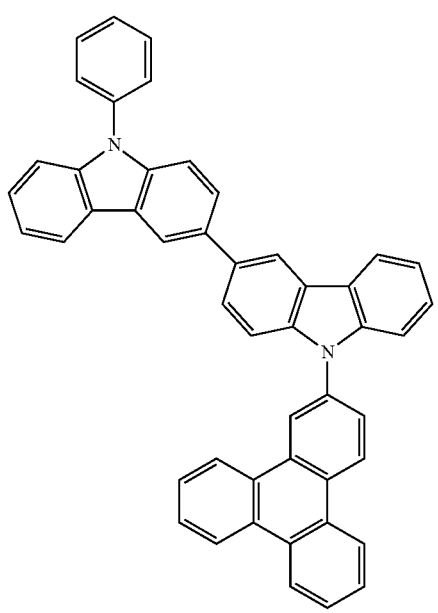

B-35
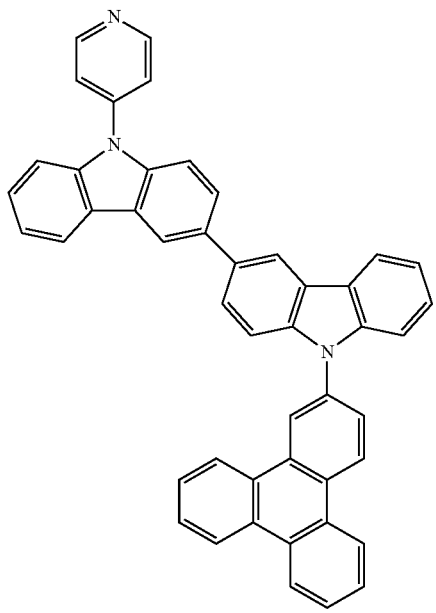
B-37
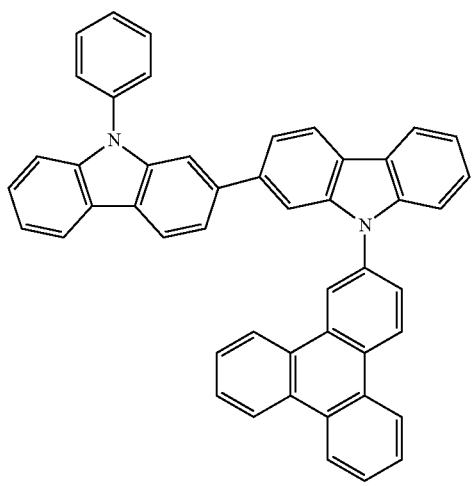
B-38
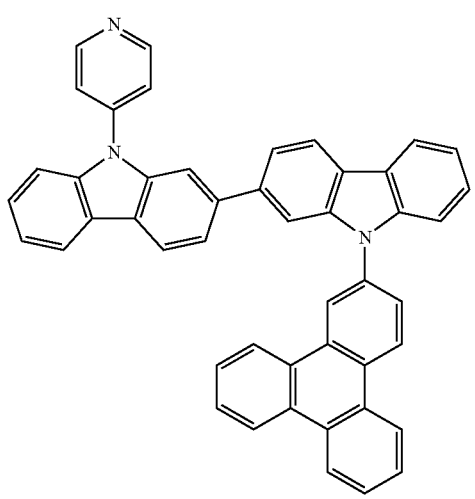
B-40
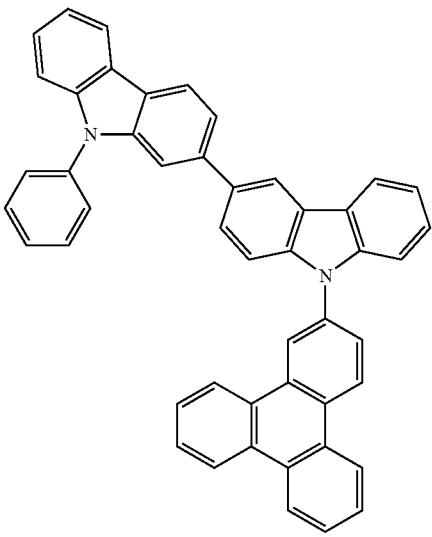
B-41
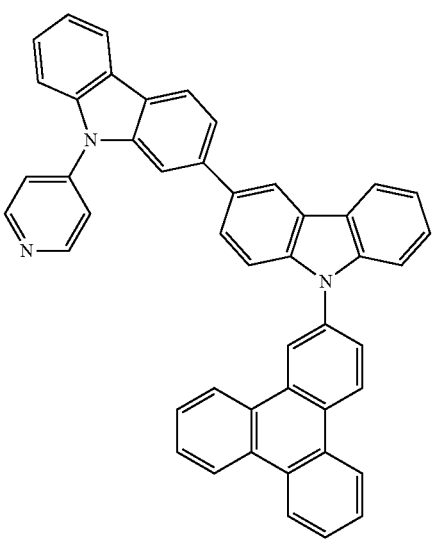

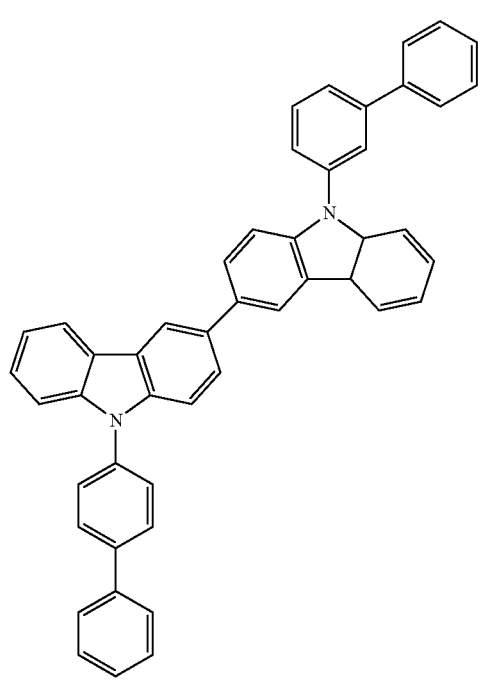
B-43
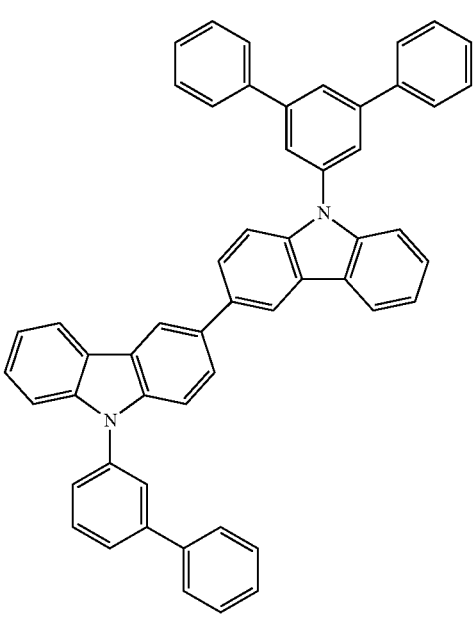
B-45
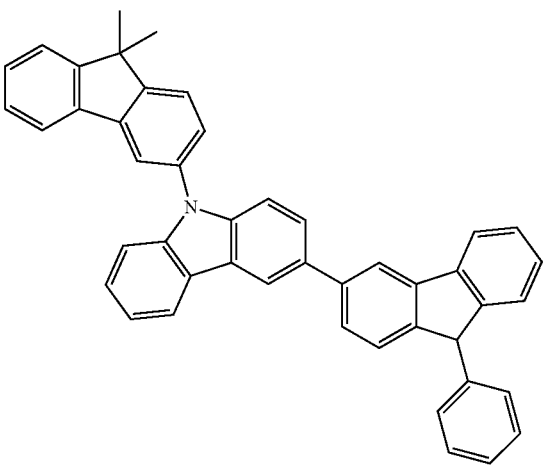
B-46
B-44

B-47
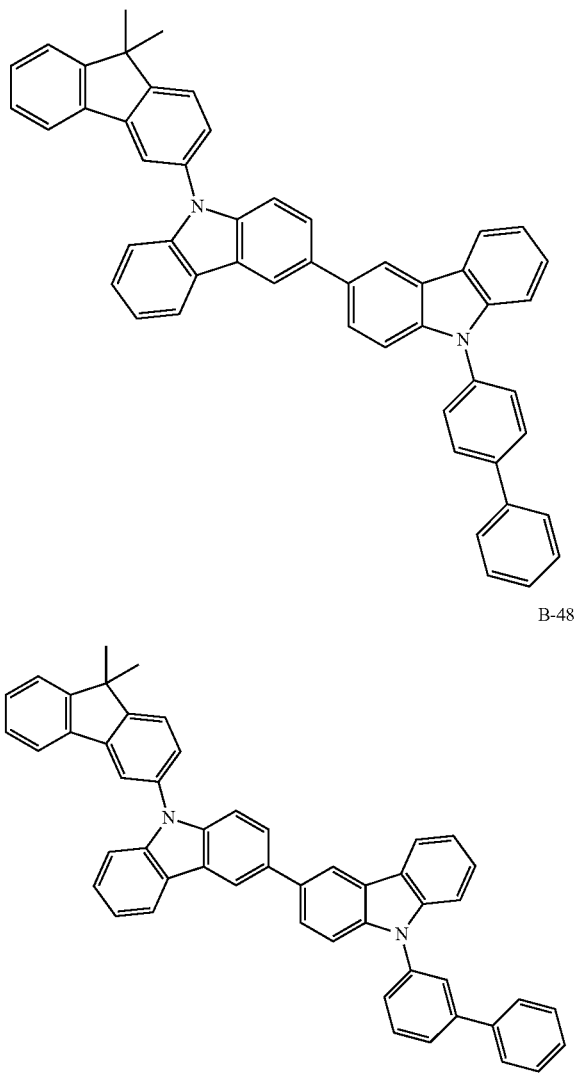
B-48
B-49
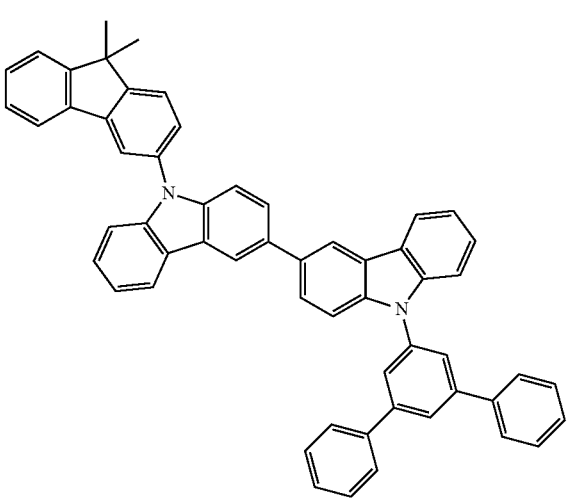
B-50
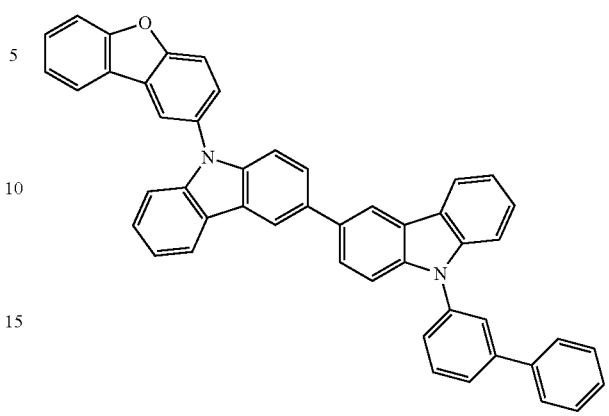
B-51
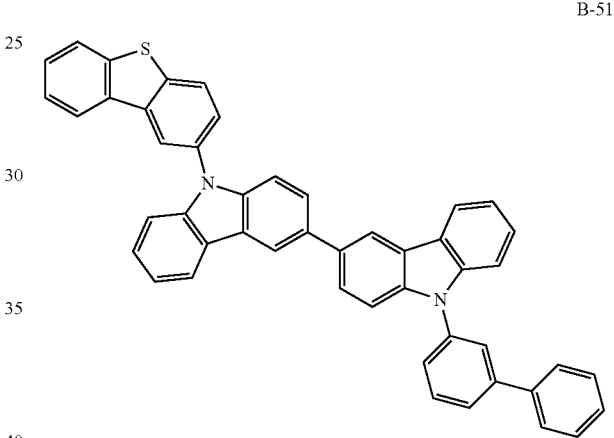
B-52
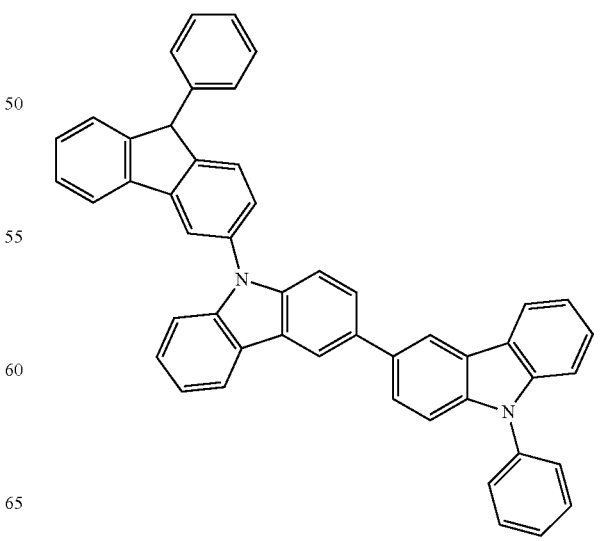

B-53
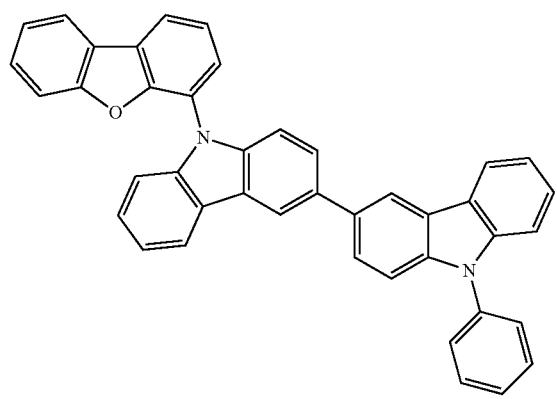
B-54
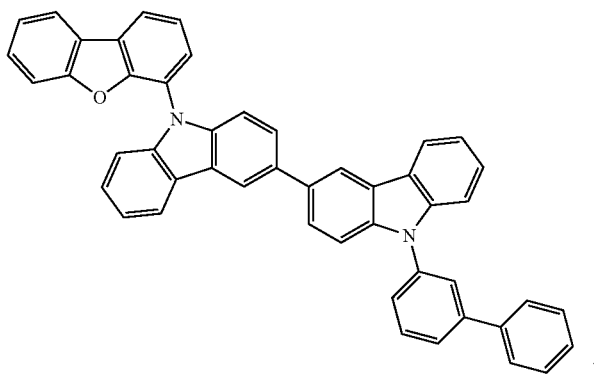
B-55
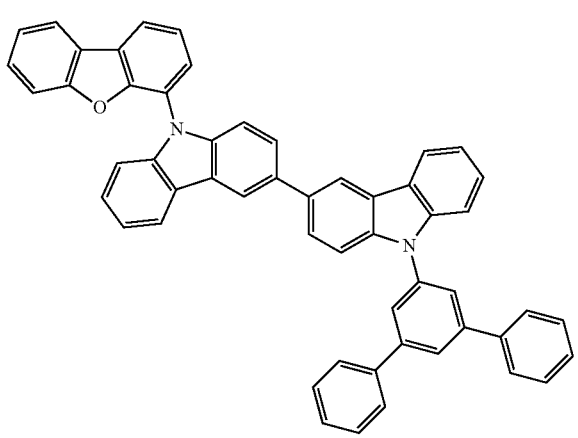
B-56
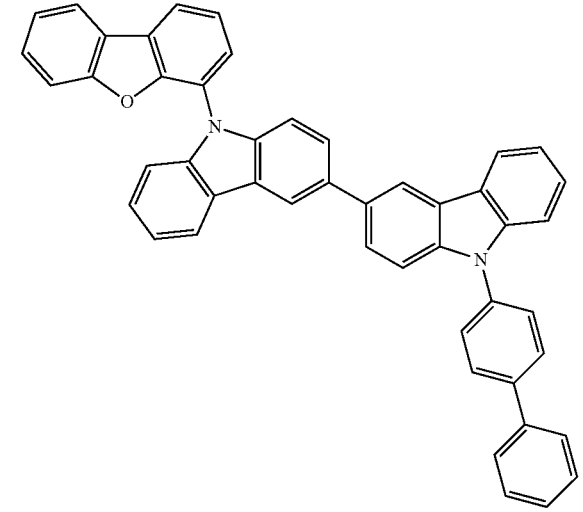
B-57
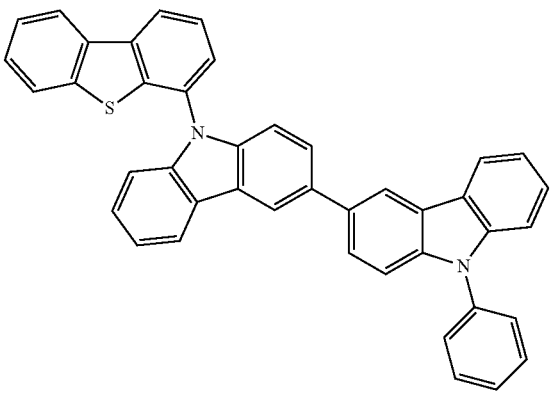
B-58
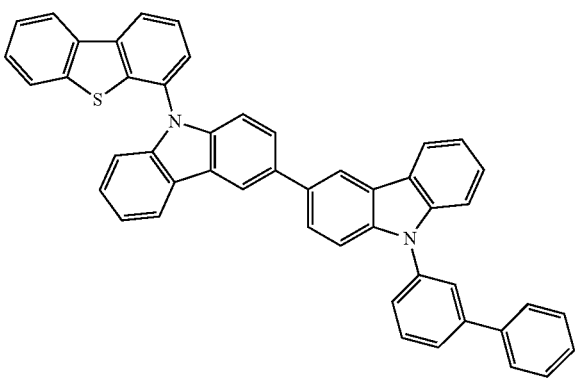

B-59
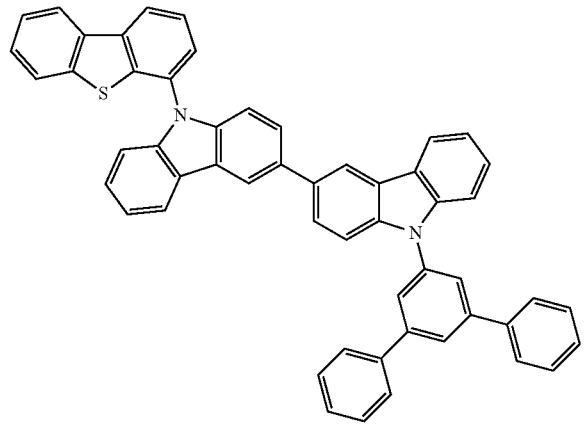
B-60
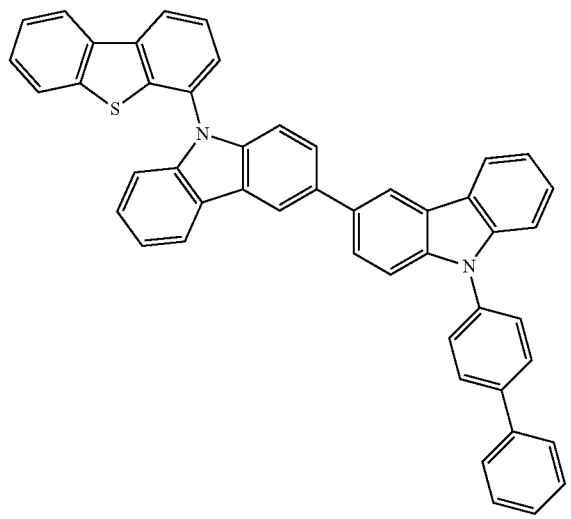
B-61
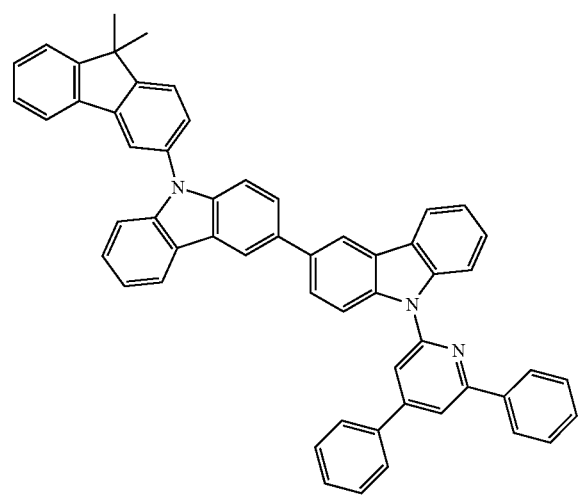
B-62
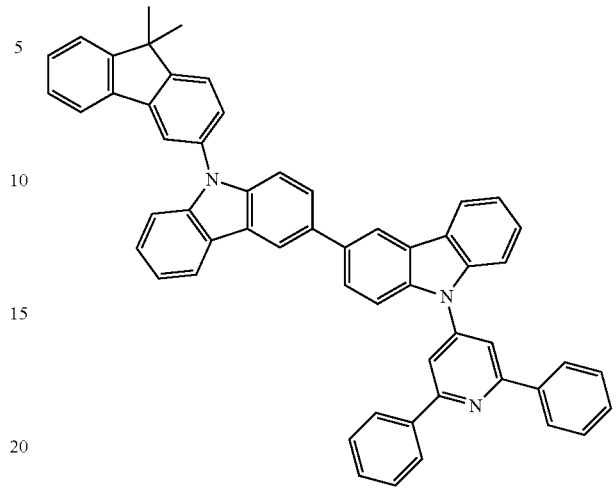
B-63
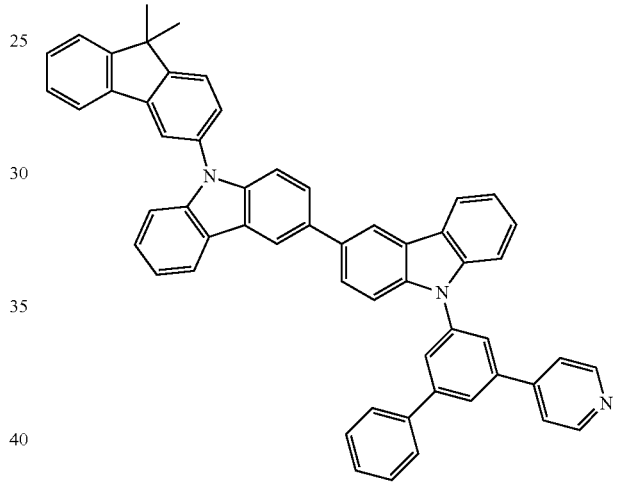
B-64
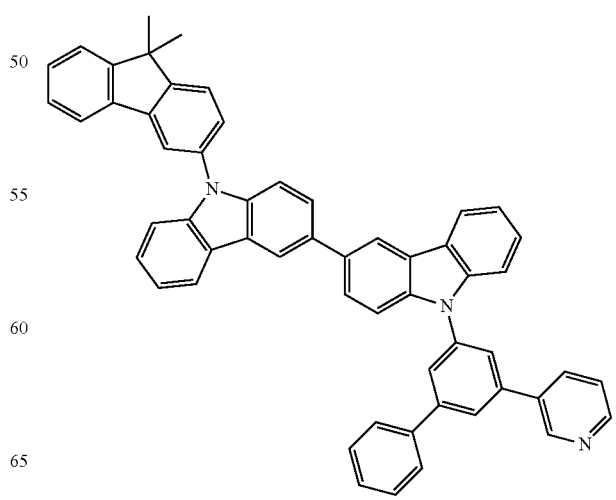

B-65
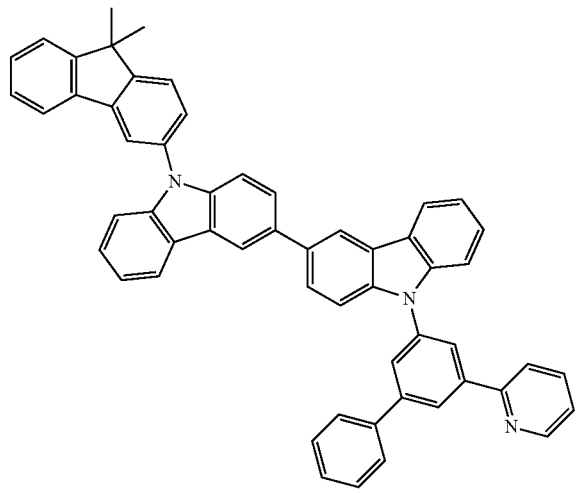
B-66
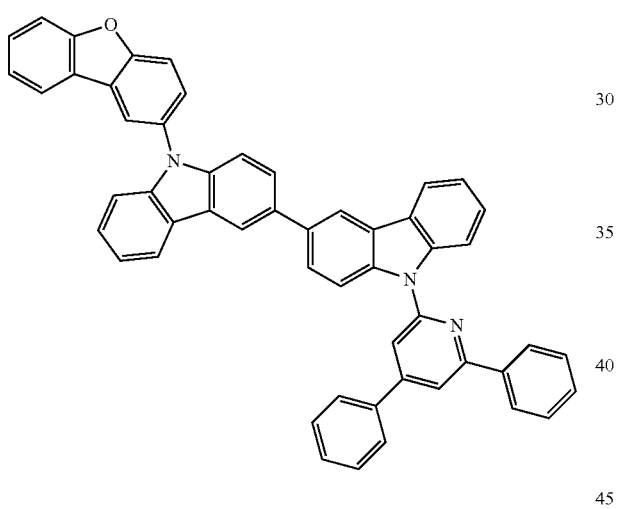
B-67
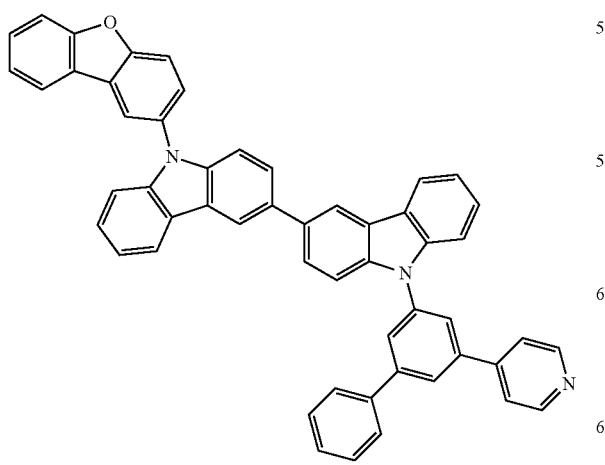
B-68
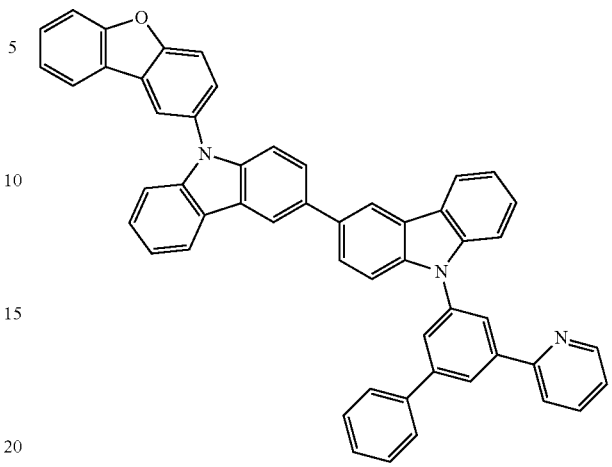
B-69
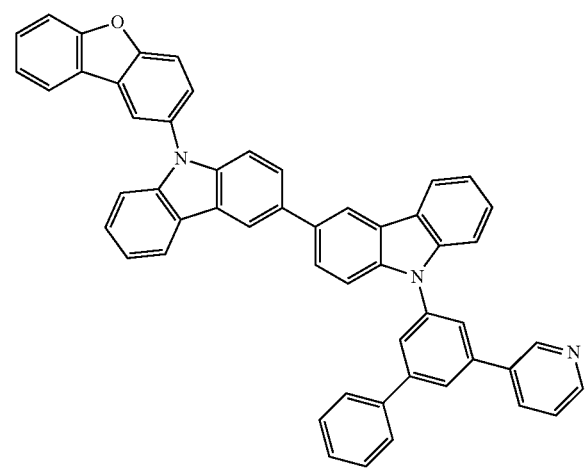
B-70
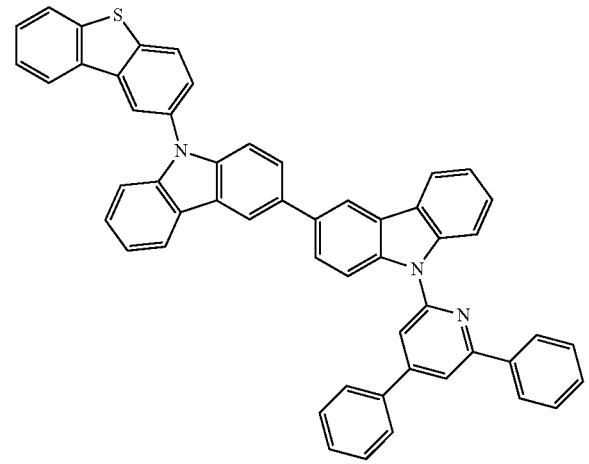

-continued
B-71
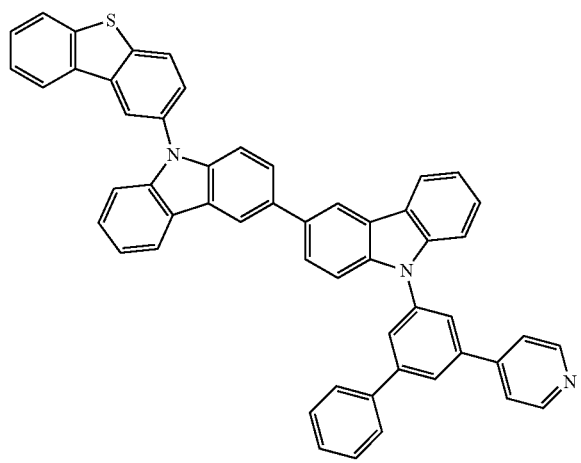
B-72
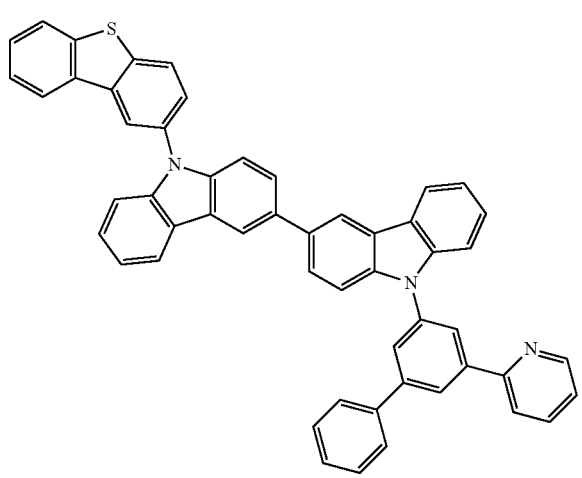
B-73
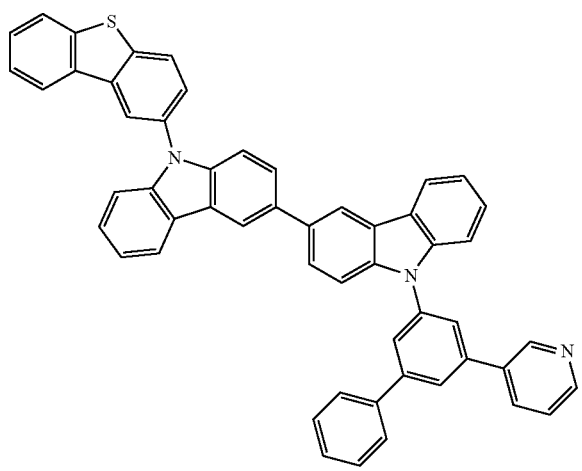
-continued
B-74
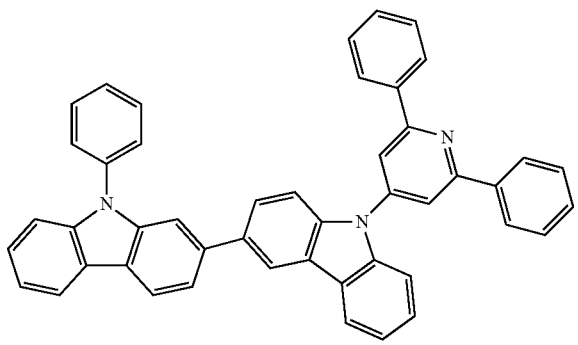
B-75
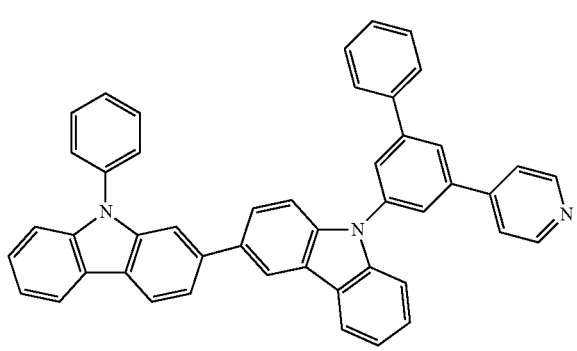
B-76
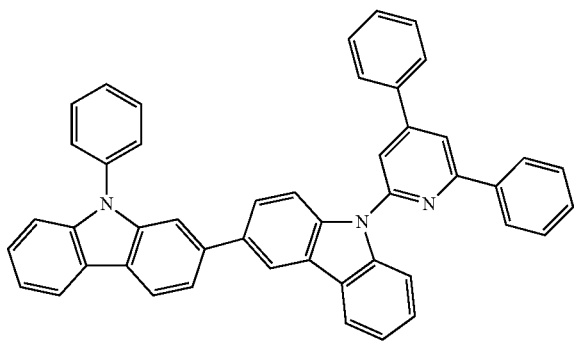
B-77
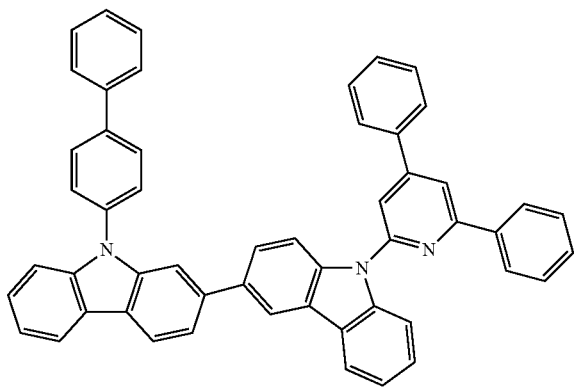

B-78
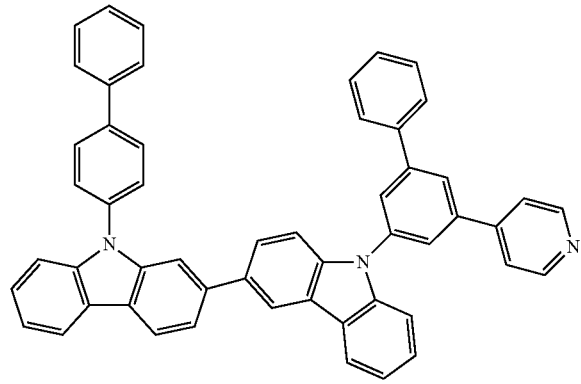
B-79
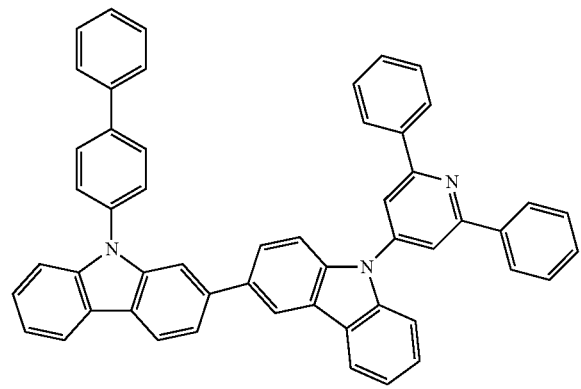
B-80
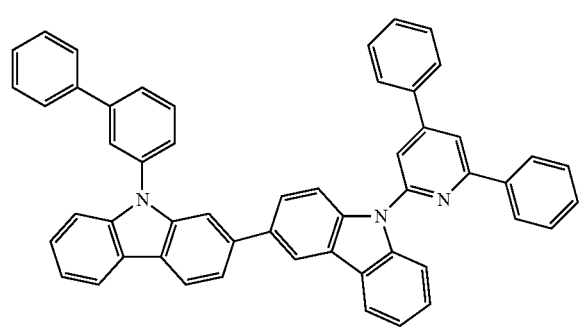
B-81
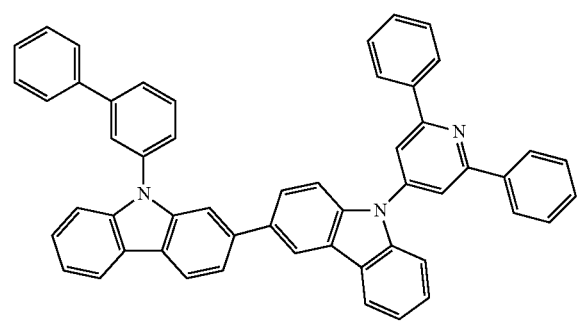
B-82
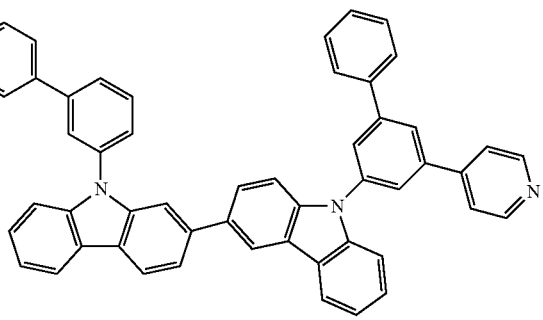
B-83
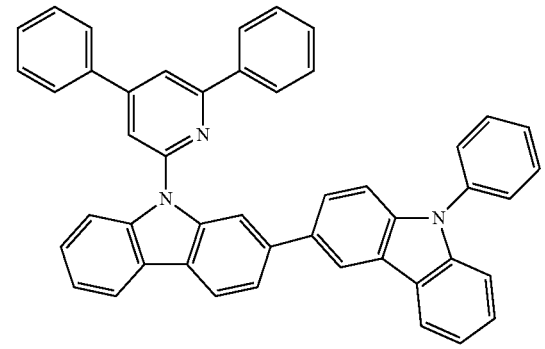
B-84
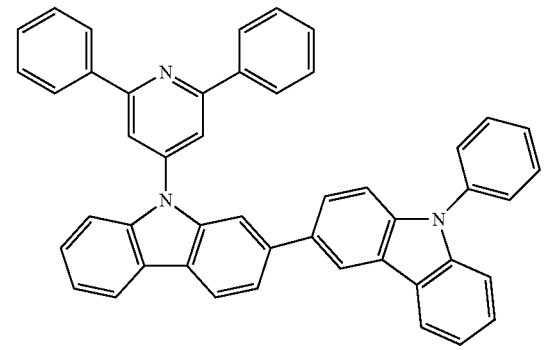
B-85
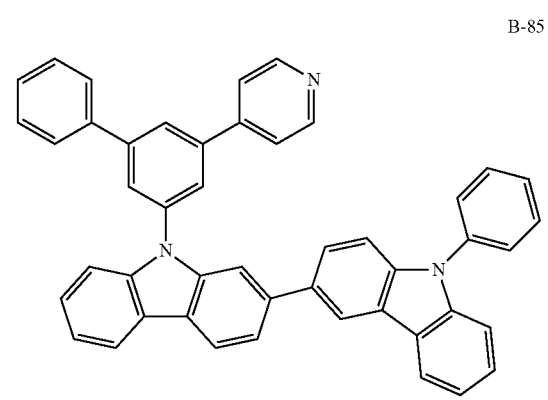

B-86
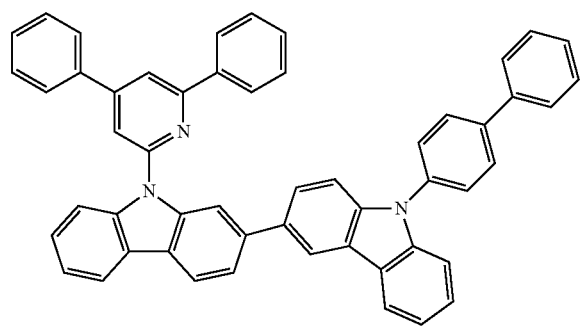
B-87
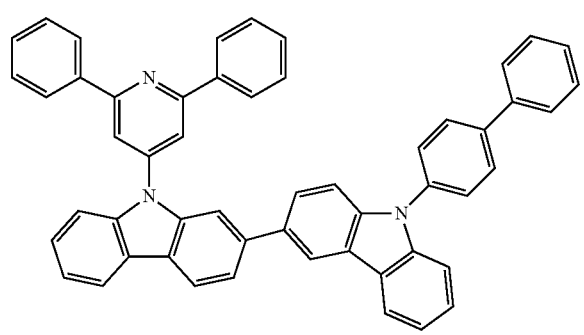
B-88
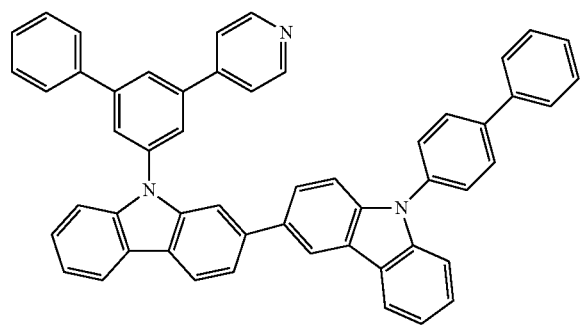
B-89
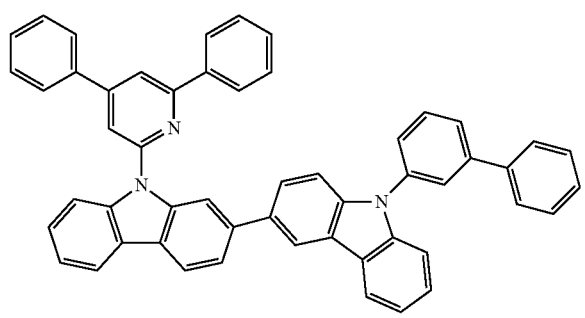
B-90
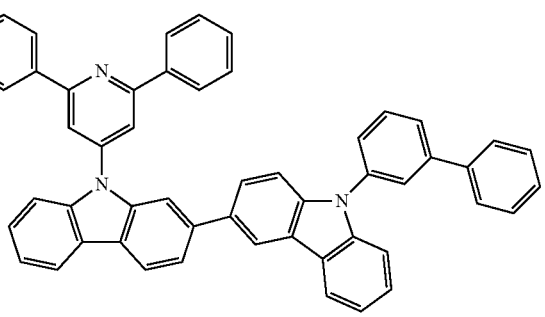
B-91
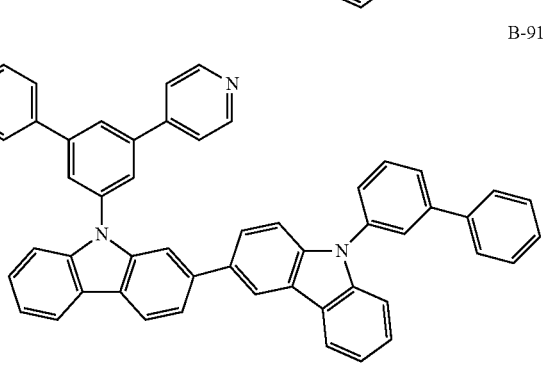
B-92
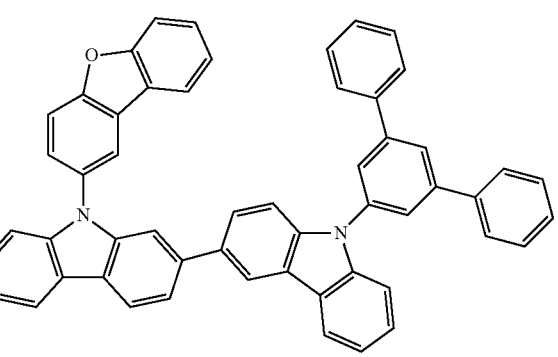
B-93
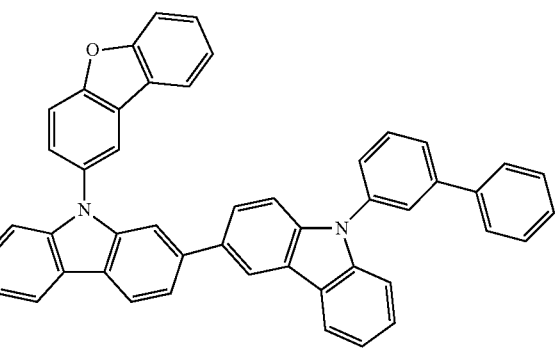

B-94
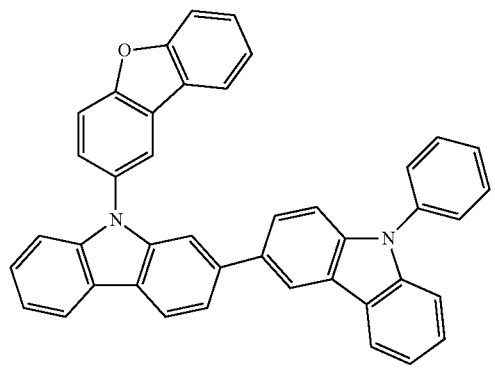
B-95
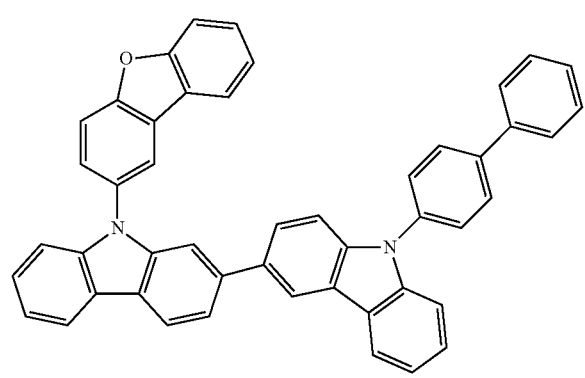
B-96
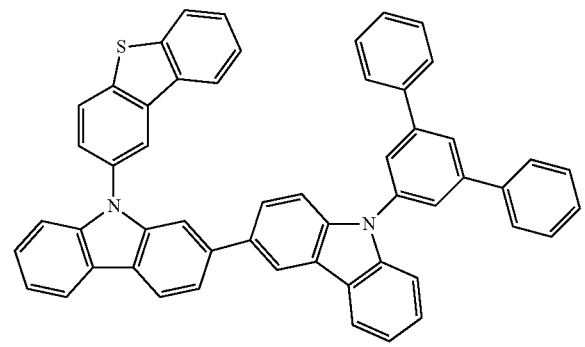
B-97
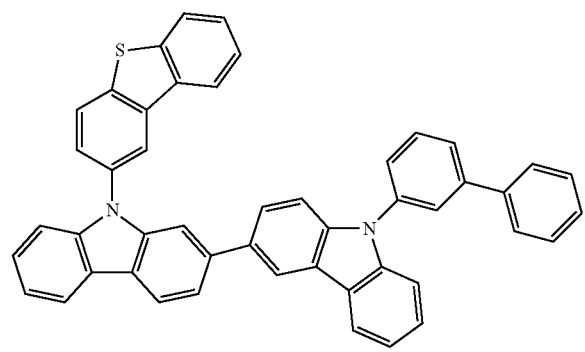
B-98
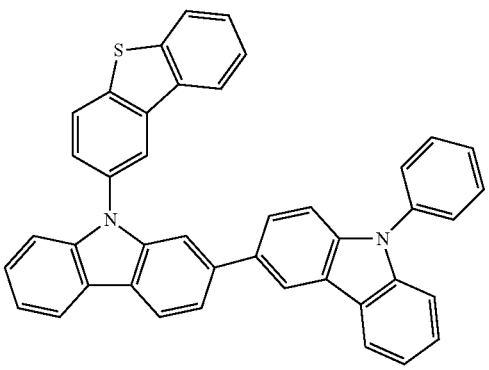
B-99
B-100
B-101
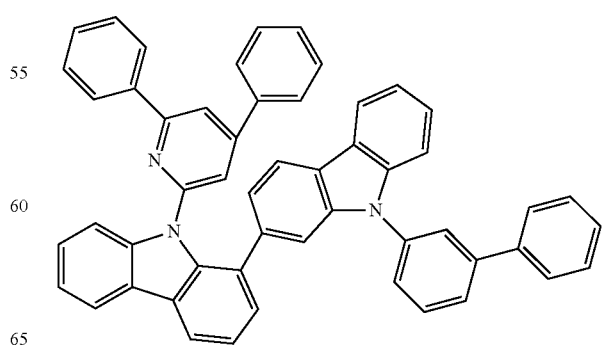

-continued
B-102
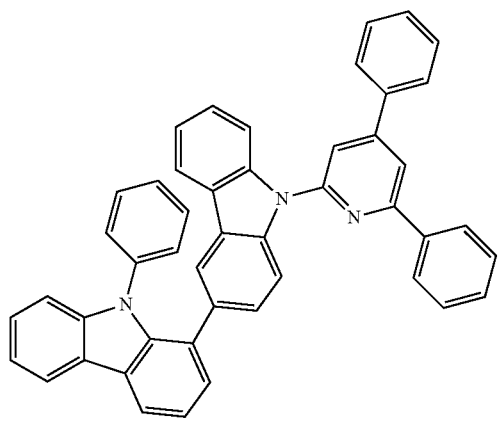
B-103
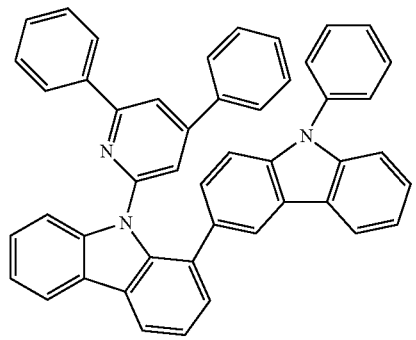
B-104
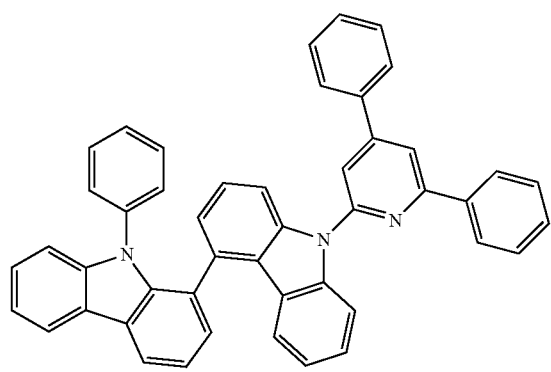
B-105
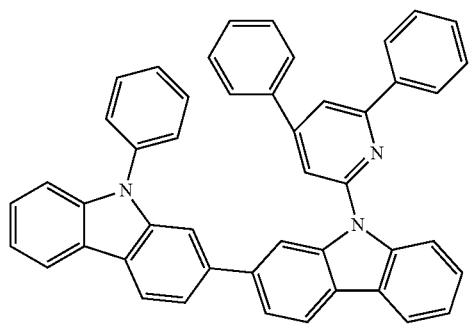
-continued
B-106
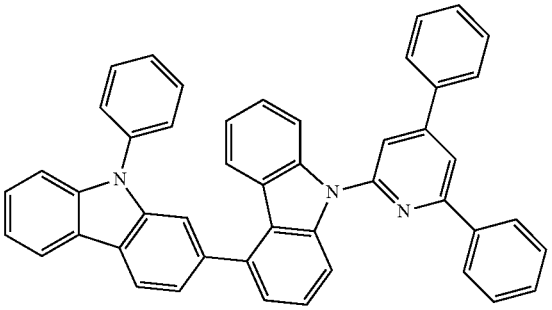
B-107
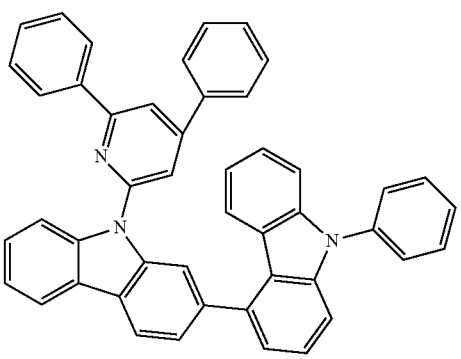
B-108
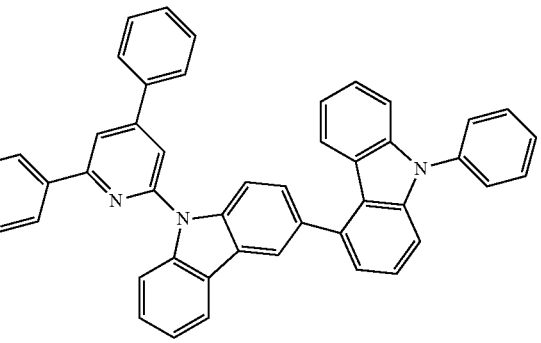
B-109
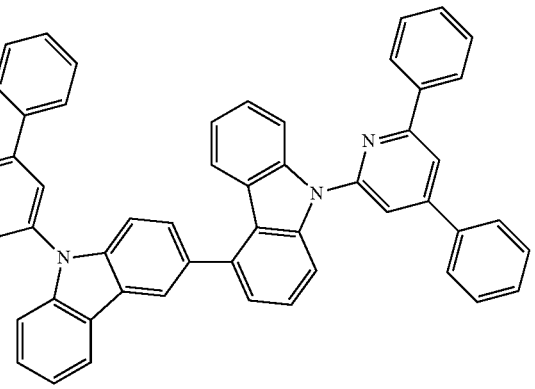

B-110
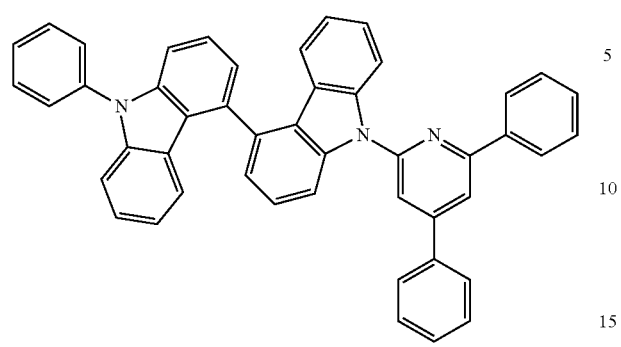
B-111
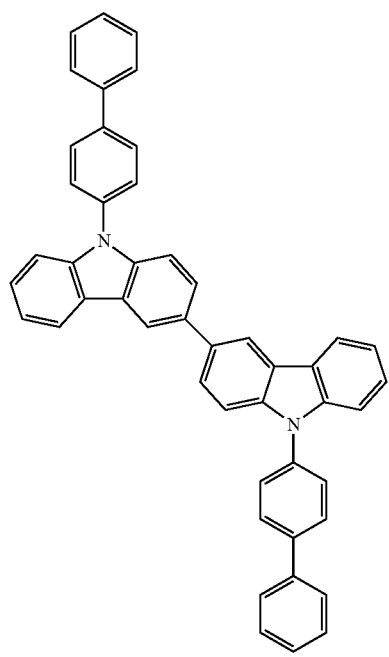
B-112
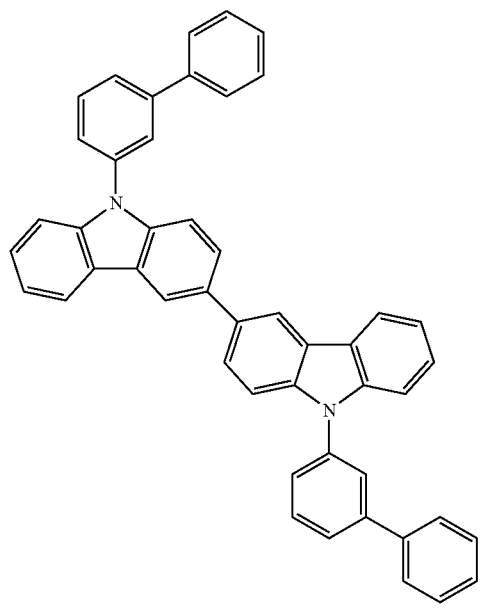
B-113
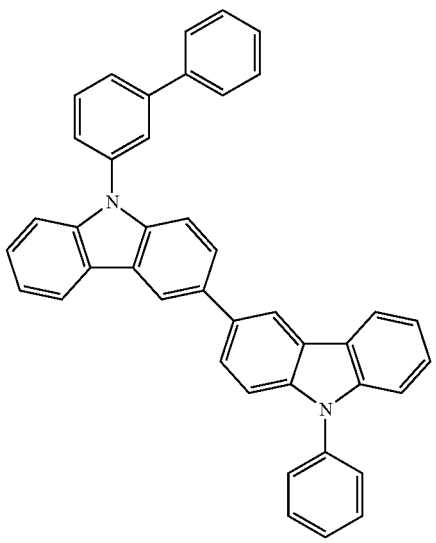
C-10
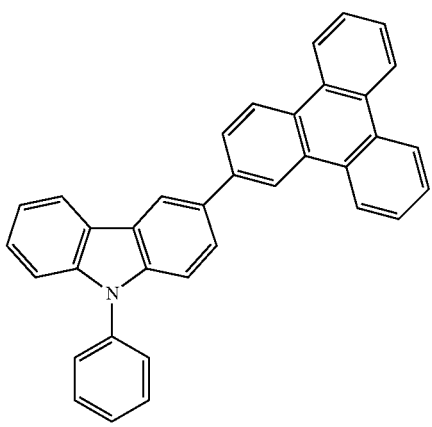
C-11
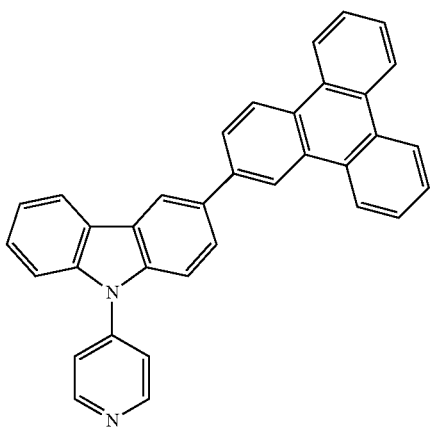

C-12
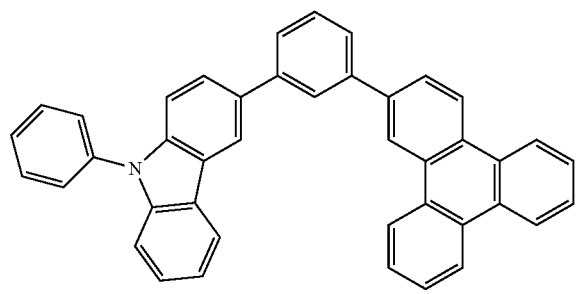
C-13
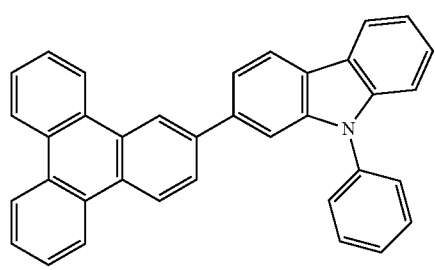
C-14
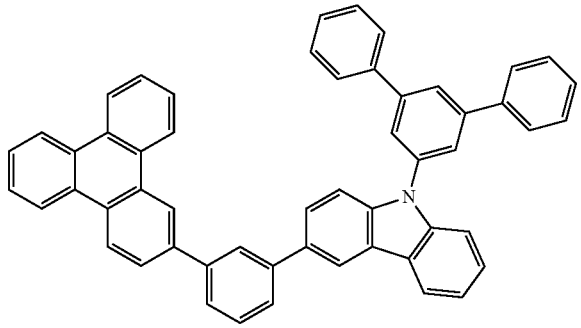
C-15
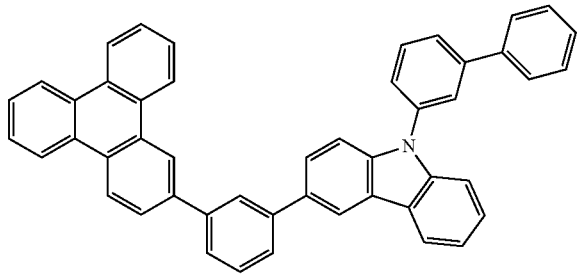
C-16
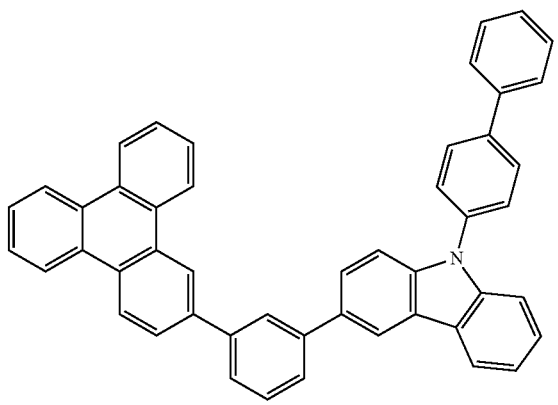
C-17
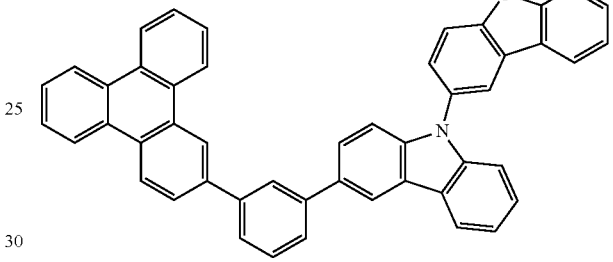
C-18
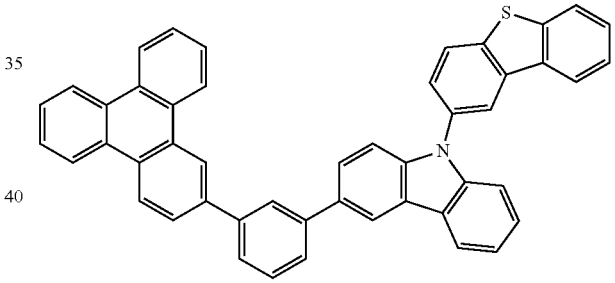
C-19
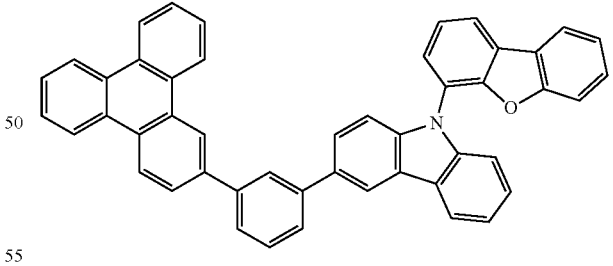
C-20
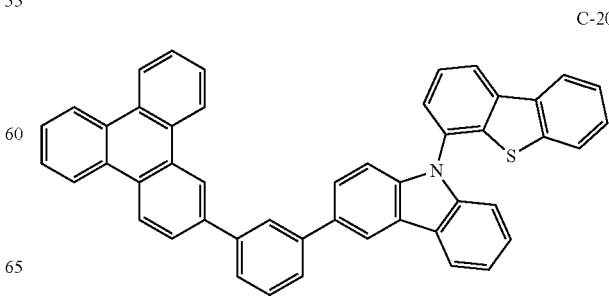

C-21
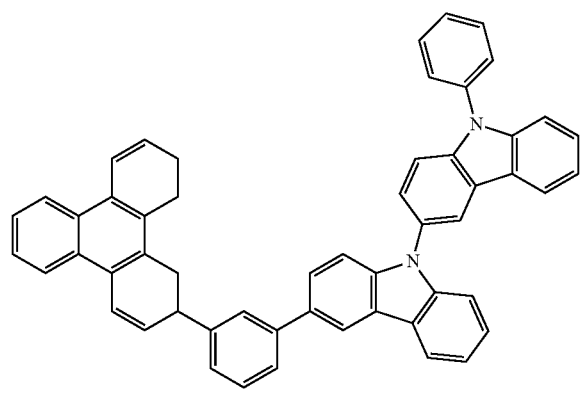
C-22
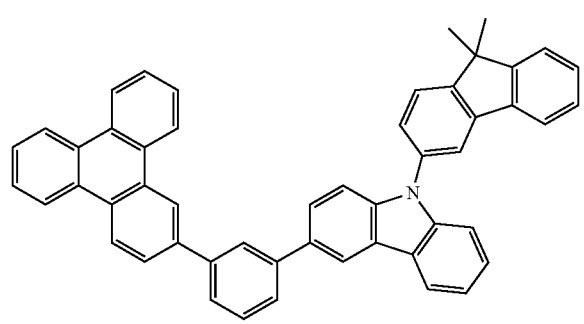
C-23
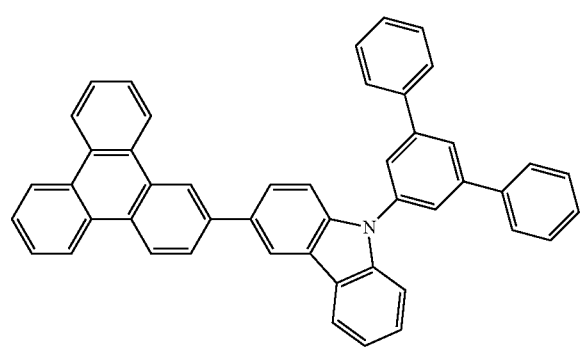
C-24
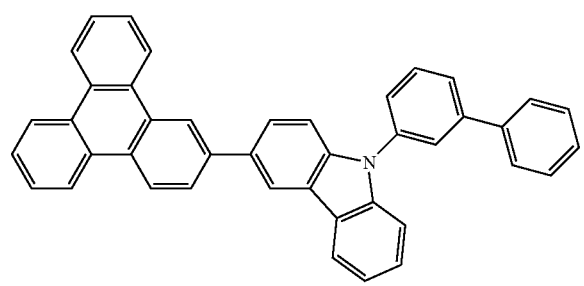
C-25
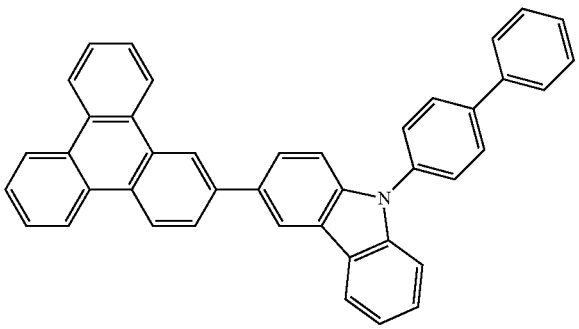
C-26
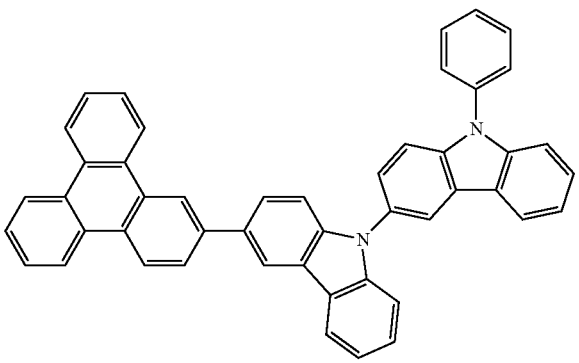
C-27
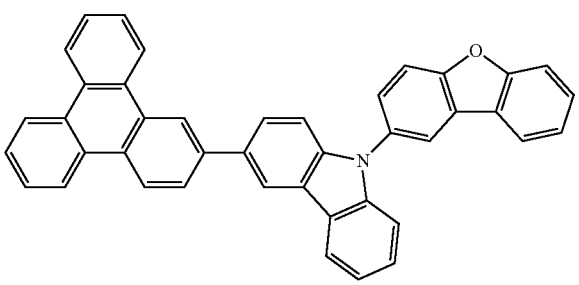
C-28
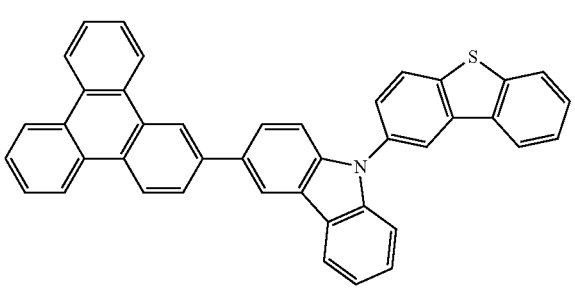
C-29
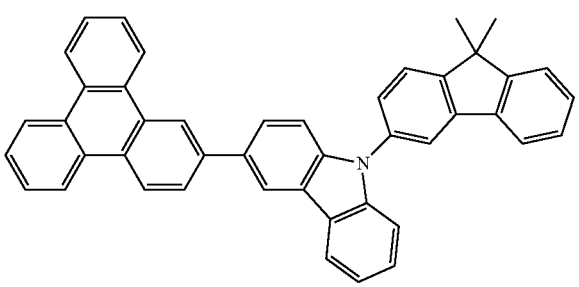

C-30
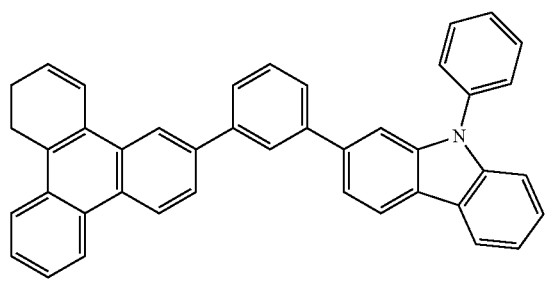
C-31
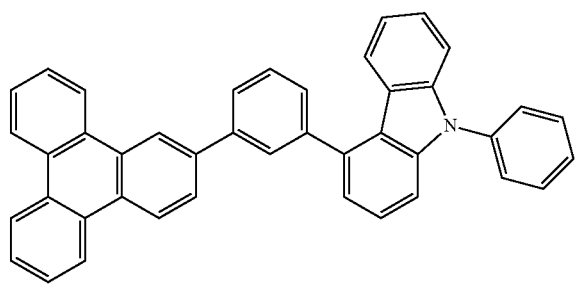
C-32
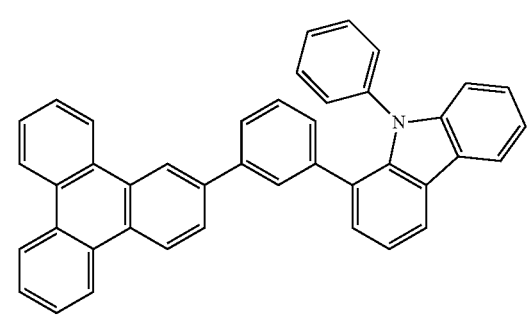
C-33
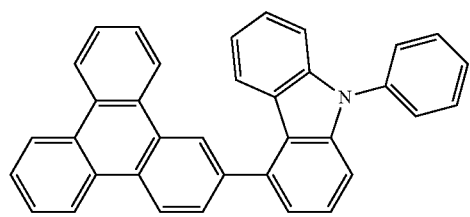
D-10
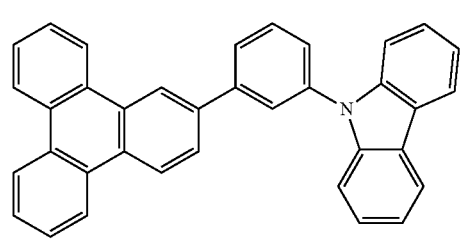
D-11
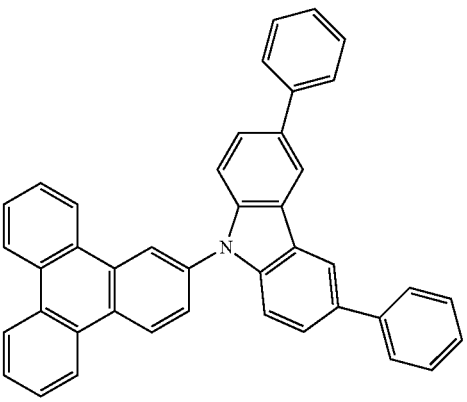
D-12
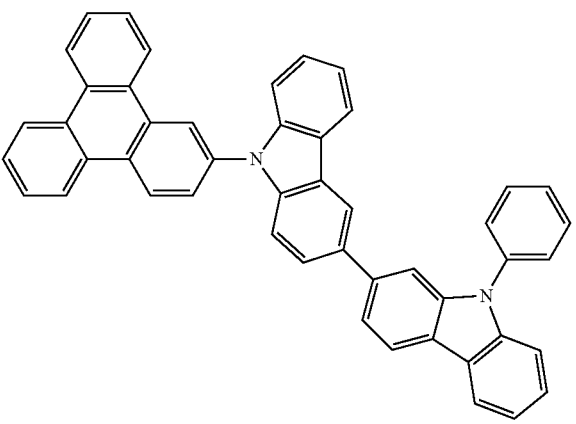
D-13
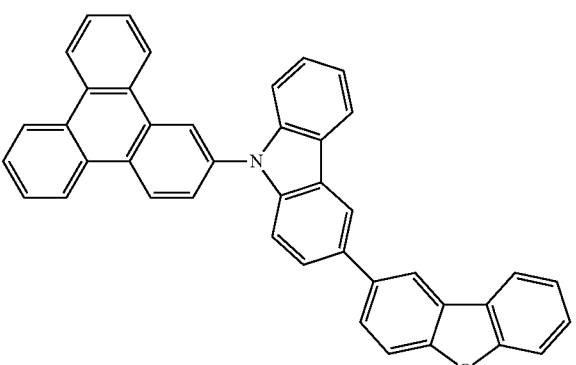
D-14
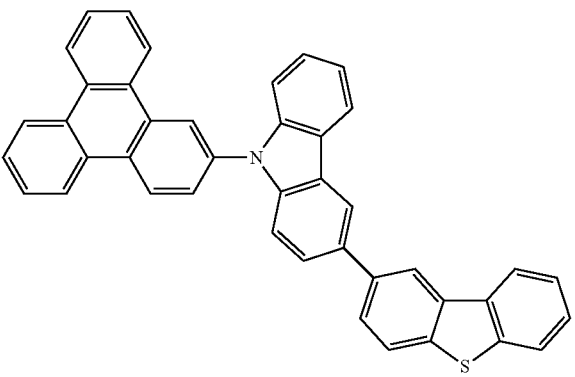

-continued
D-15
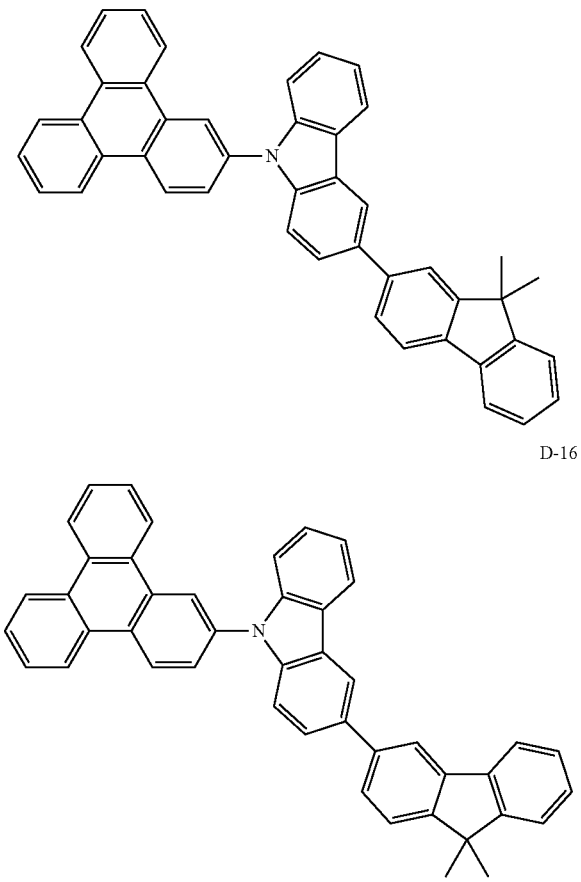
D-16
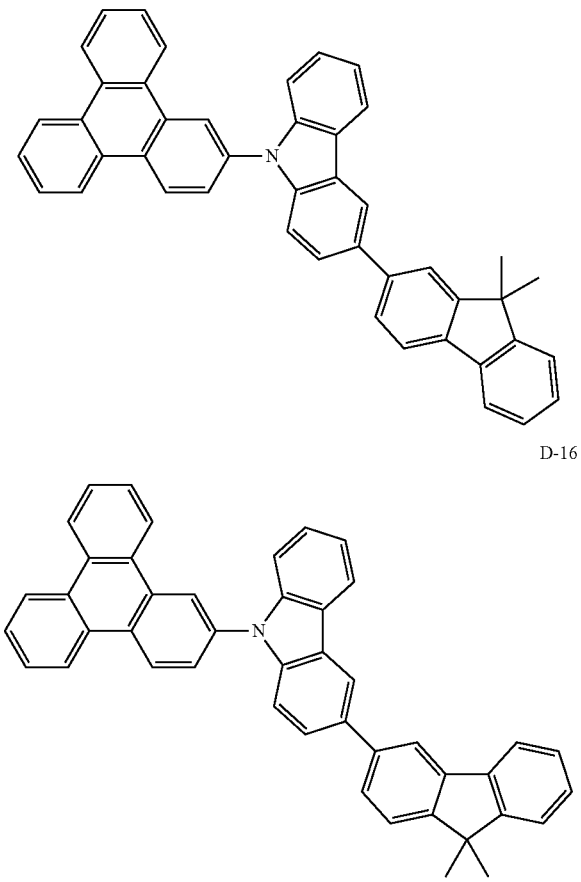
D-17
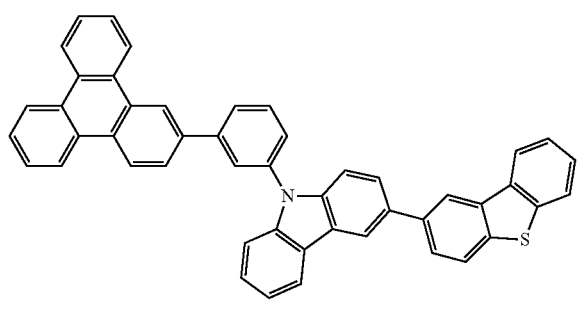
D-18
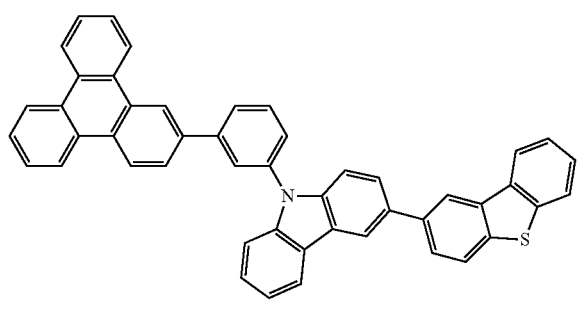
-continued
D-19
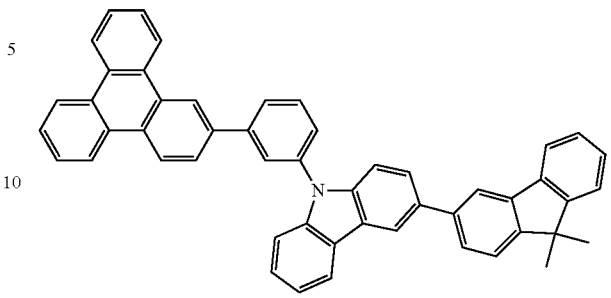
D-20
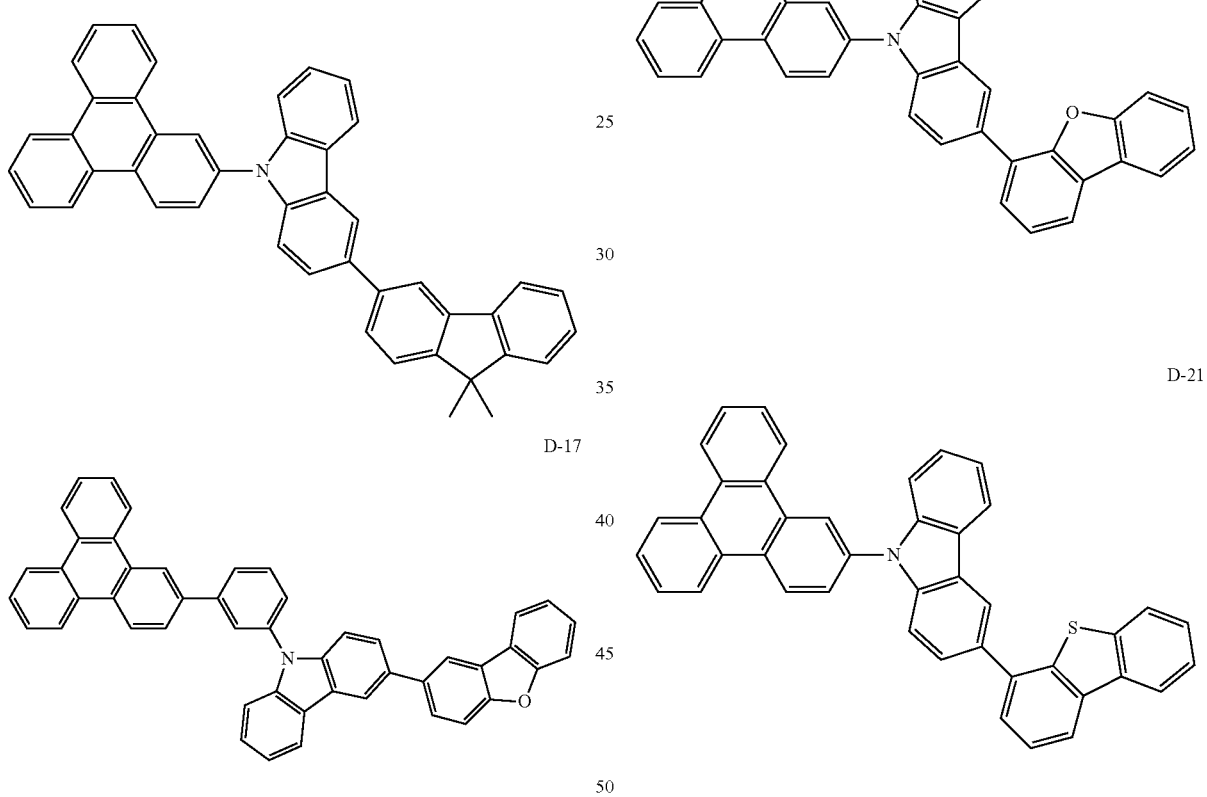
D-21
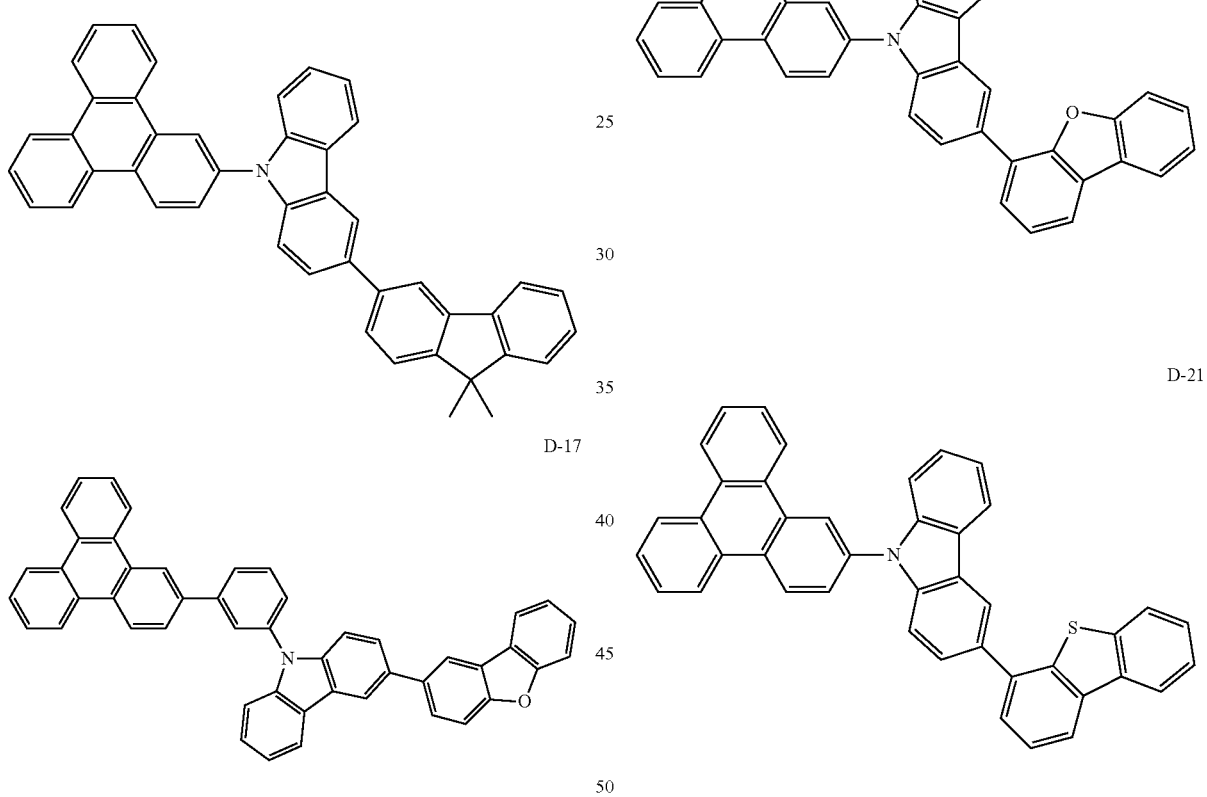
D-22
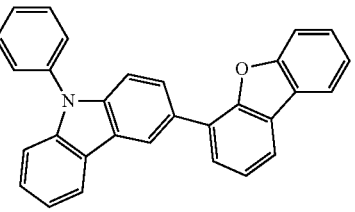

D-23
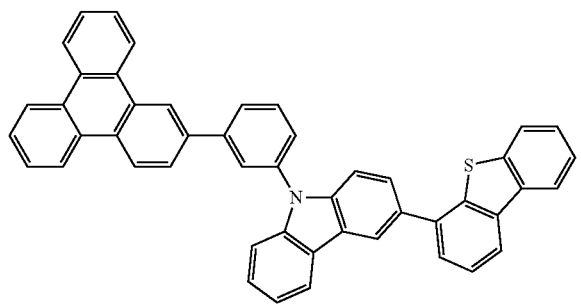
D-24
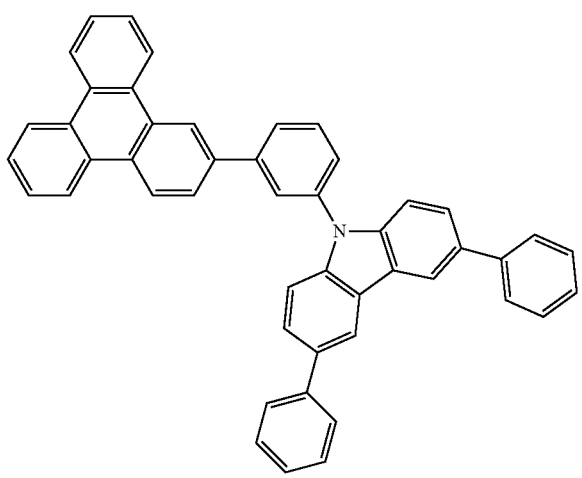
D-25
D-26
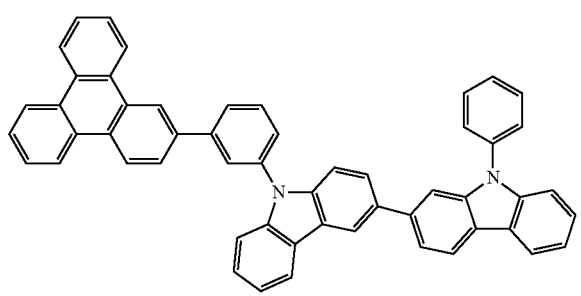
D-27
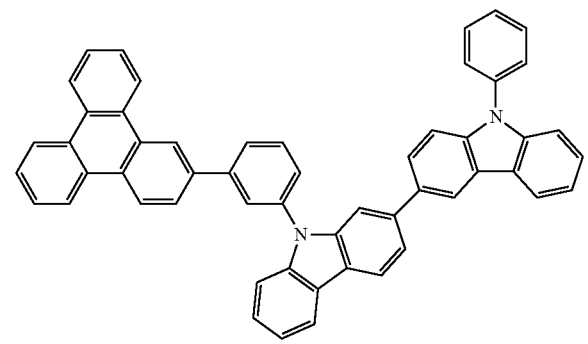
D-28
D-29
The second organic compound may be, for example a compound consisting of a combination of a moiety represented by Chemical Formula 5 and a moiety represented by Chemical Formula 6.
[Chemical Formula 5]
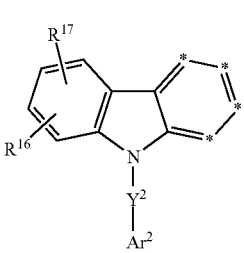

-continued

[Chemical Formula 6]

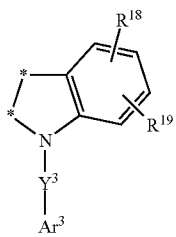

In Chemical Formula 5 or 6, $Y^2$ and $Y^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^2$ and $Ar^3$ are independently substituted or unsubstituted C6 to C30 aryl group, a substituted or unsubstituted C2 to C30 heteroaryl group, or a combination thereof, $R^{16}$ to $R^{19}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, two adjacent *'s of Chemical Formula 5 is combined with two *'s of Chemical Formula 6 to form a fused ring and in Chemical Formula 5, *'s not forming the fused ring are independently $CR^b$, and $R^b$ is hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof.

The organic compound consisting of the combination of the moiety represented by Chemical Formula 5 and the moiety represented by Chemical Formula 6 may be compounds of Group 4, but is not limited thereto.

[Group 4]

E-1

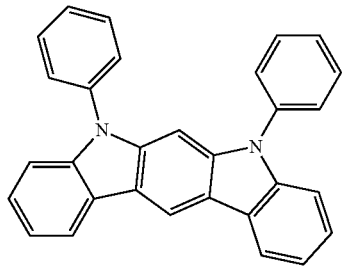

E-2

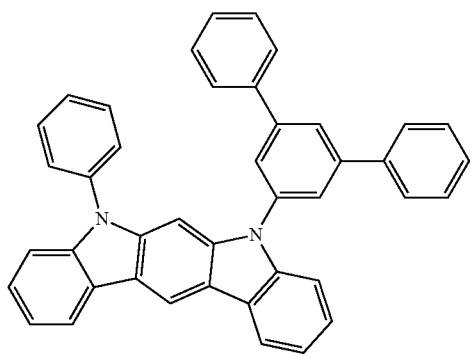

E-3

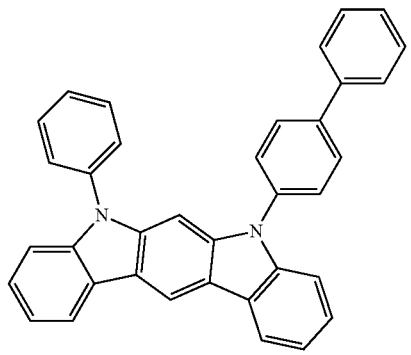

E-4

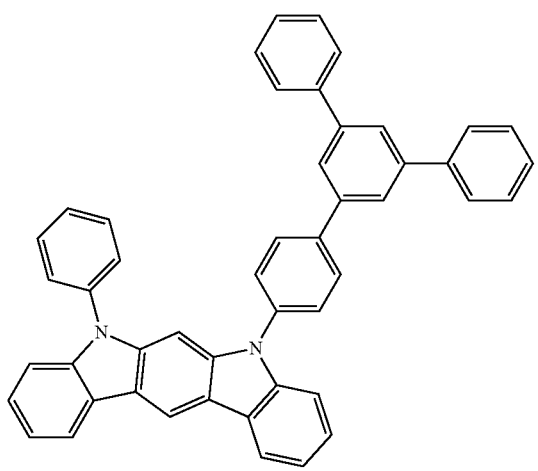

E-5

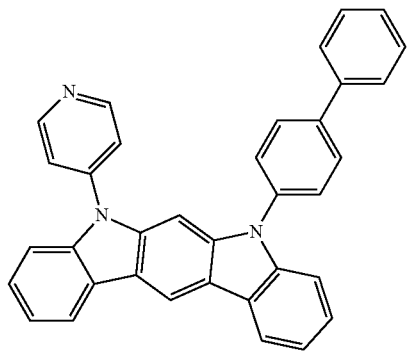

E-6

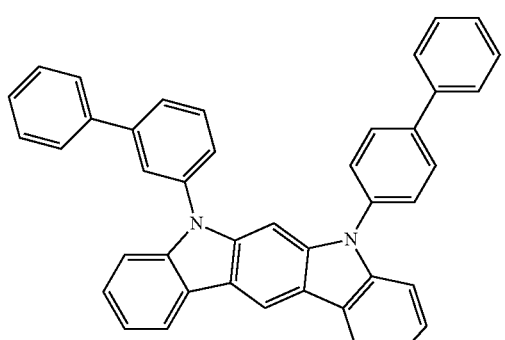

E-7
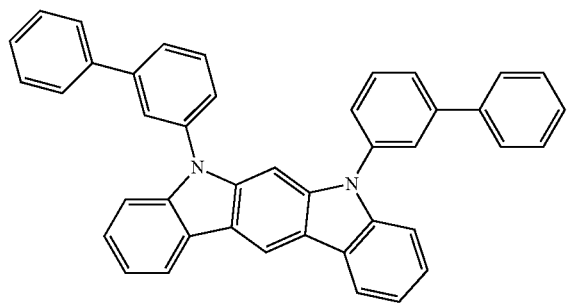
E-8
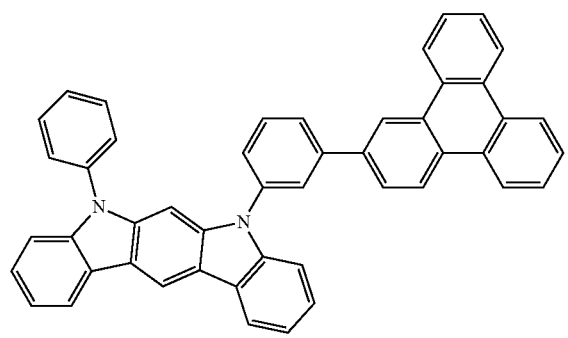
E-9
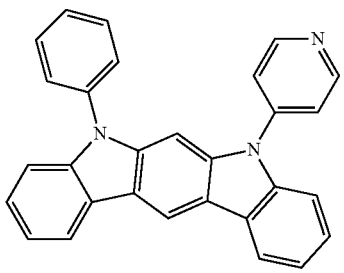
E-10
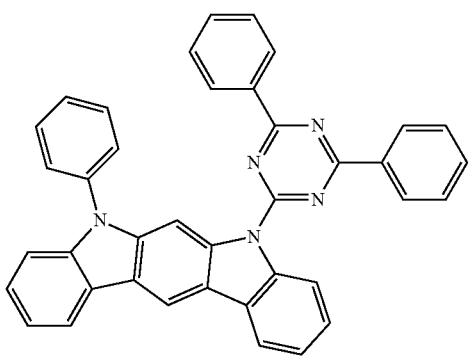
E-11
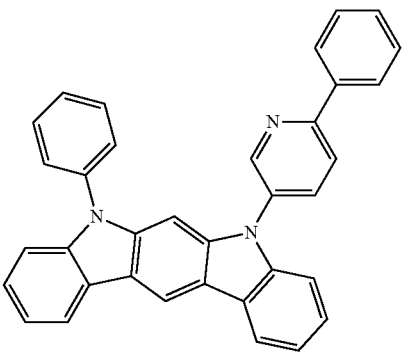
E-12
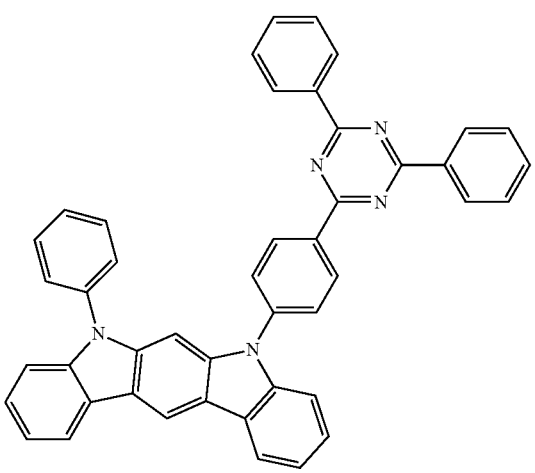
E-13
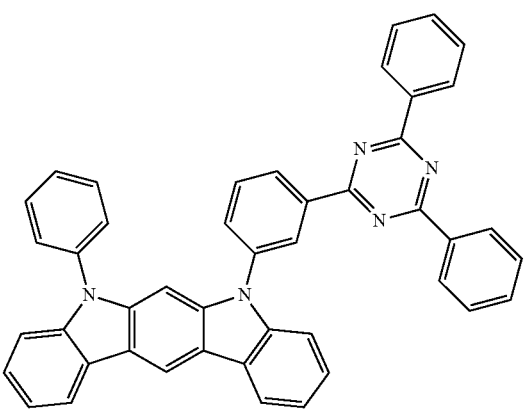
E-14
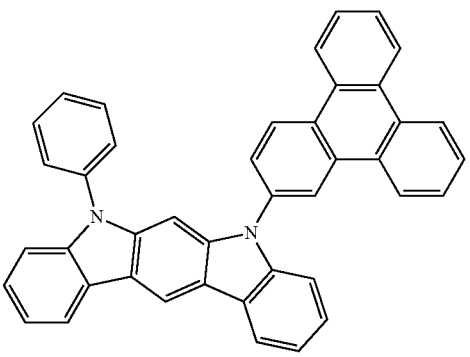

E-15
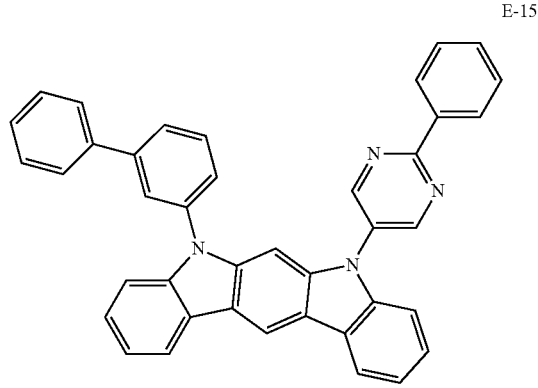
E-16
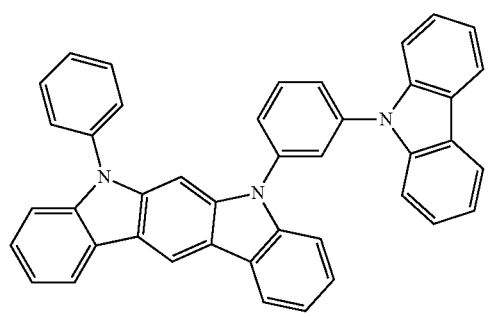
E-17
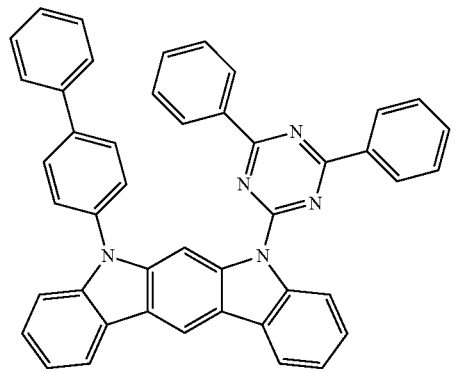
E-18
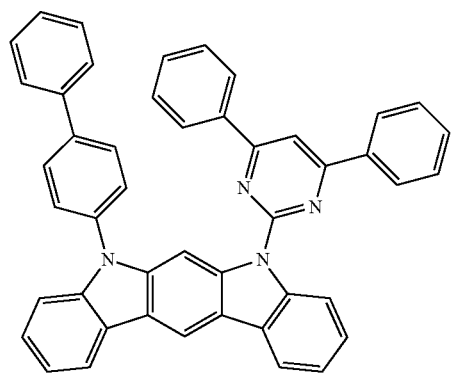
E-19
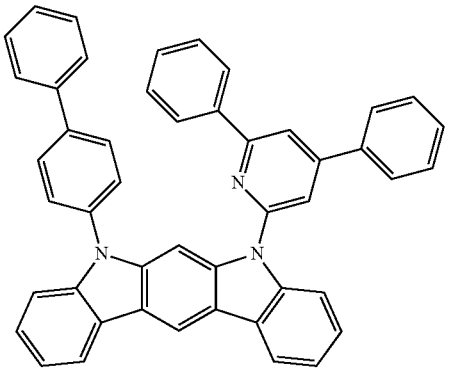
E-20
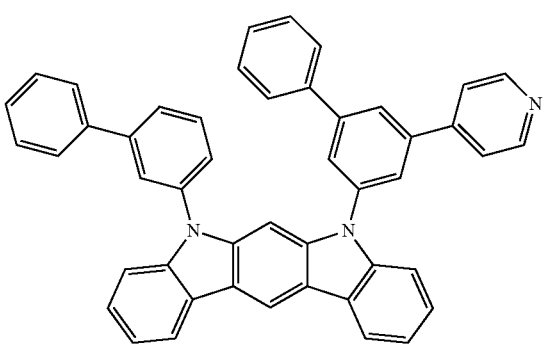
E-21
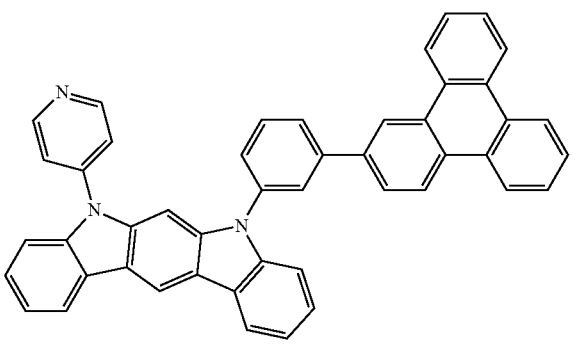
E-22
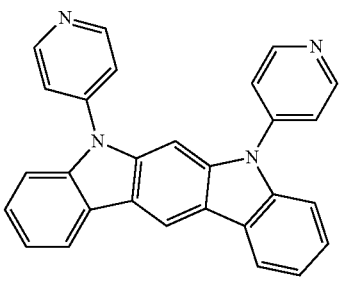

-continued
E-23
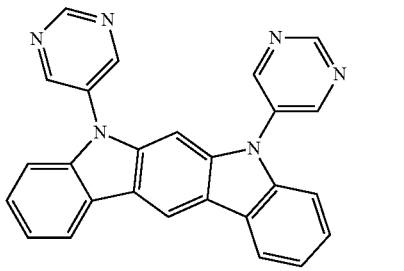
E-24
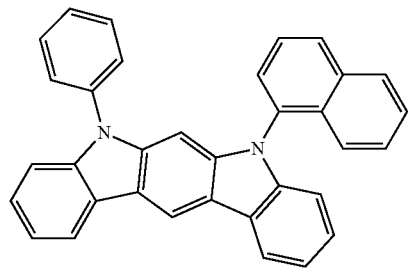
E-25
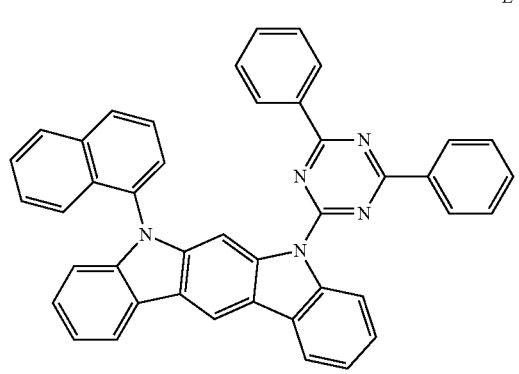
E-26
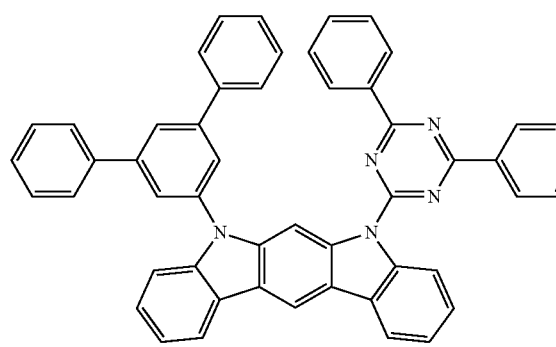
E-27
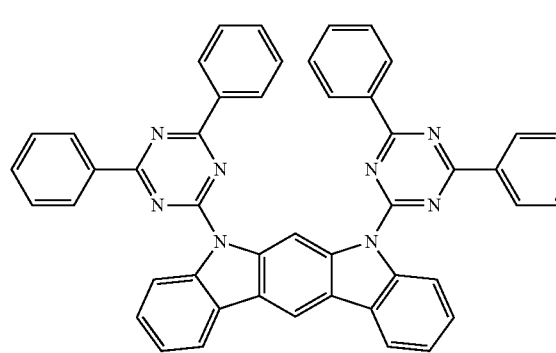
-continued
E-28
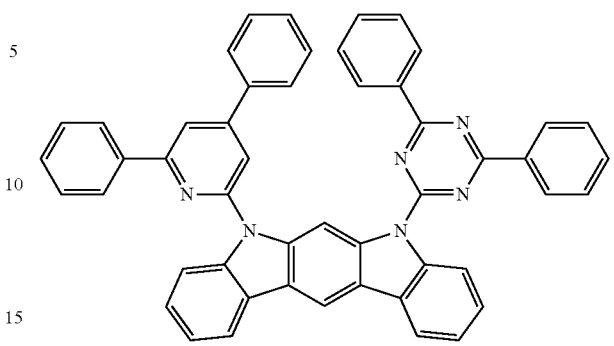
E-29
E-30
E-31
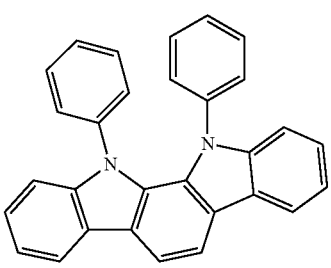

-continued
E-32
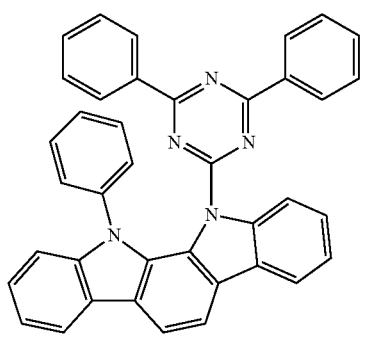
E-33
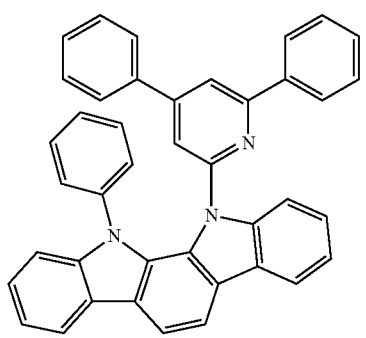
E-34
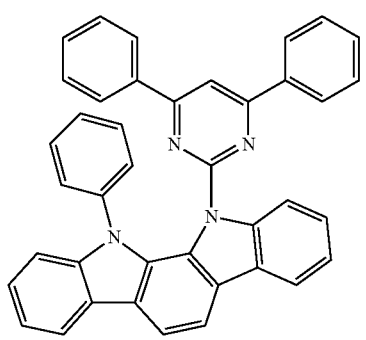
E-35
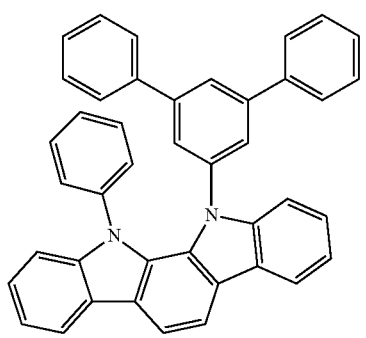
E-36
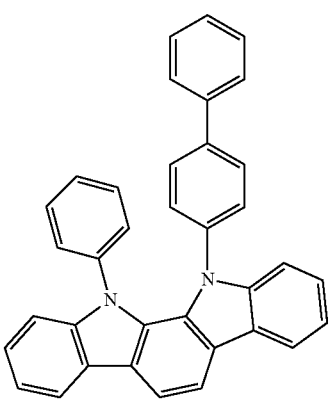
E-37
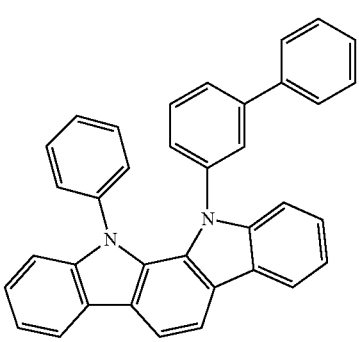
E-38
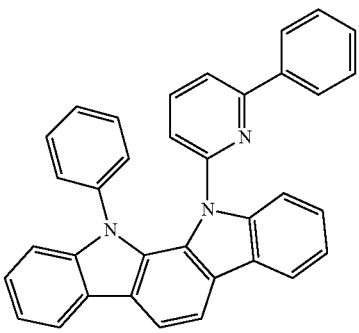
E-39
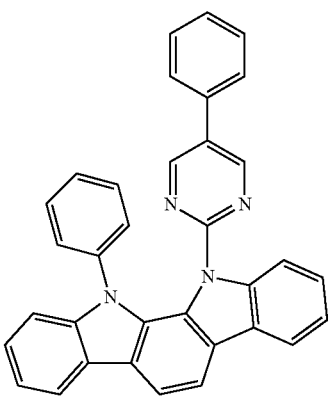

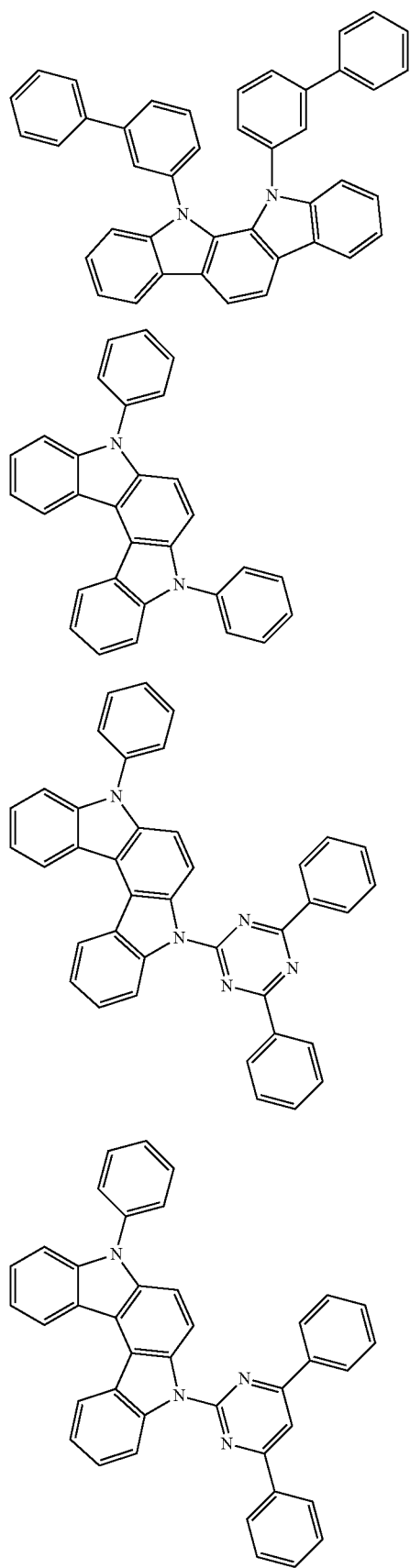
E-40
E-41
E-42
E-43
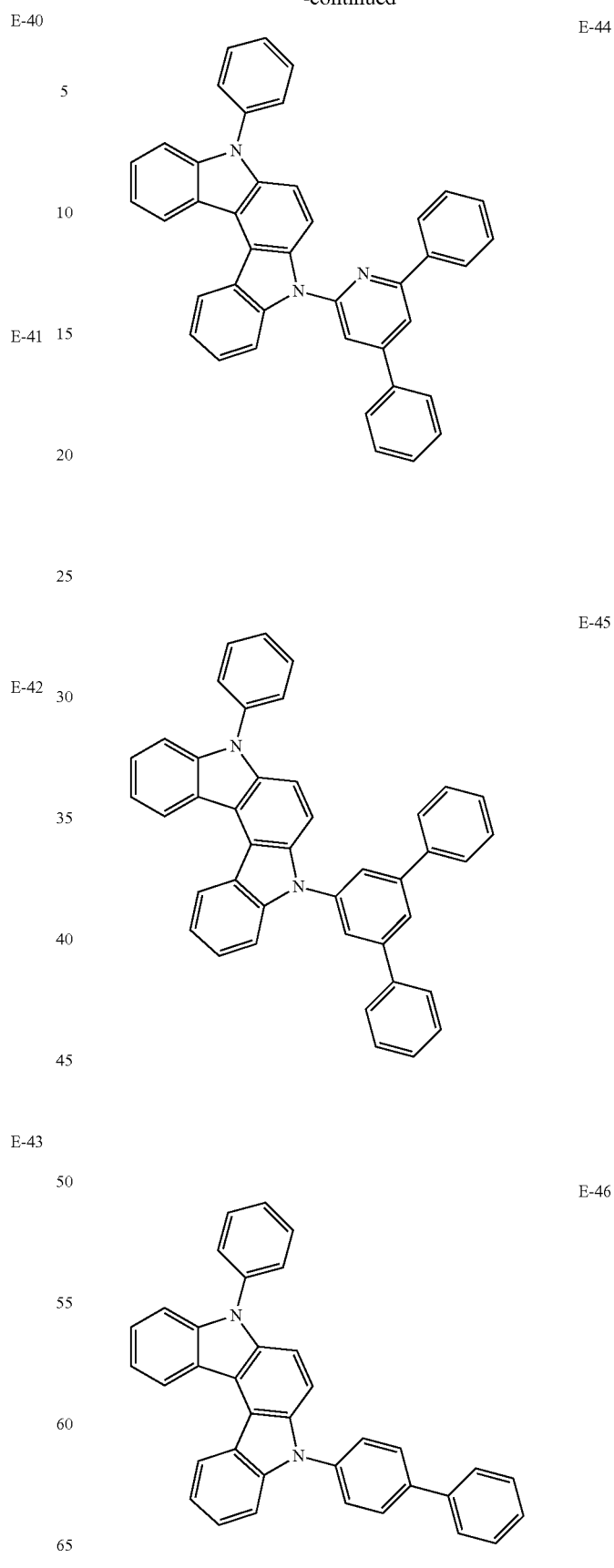
E-44
E-45
E-46

-continued
E-47
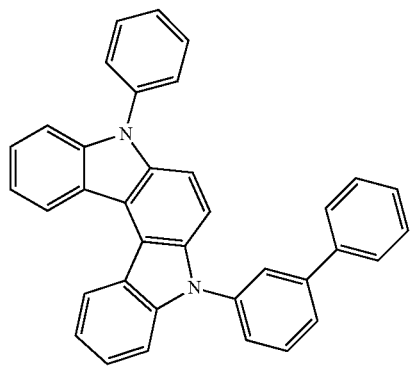
E-48
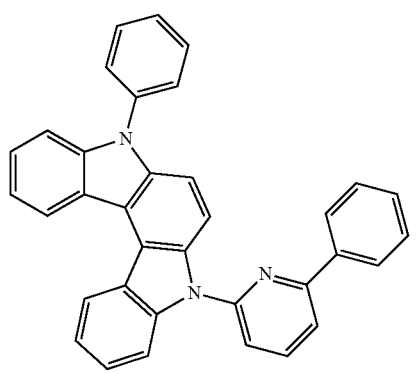
E-49
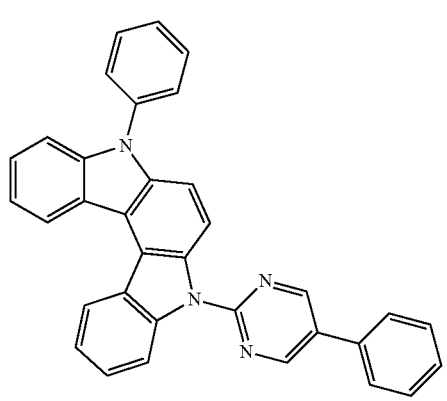
-continued
E-50
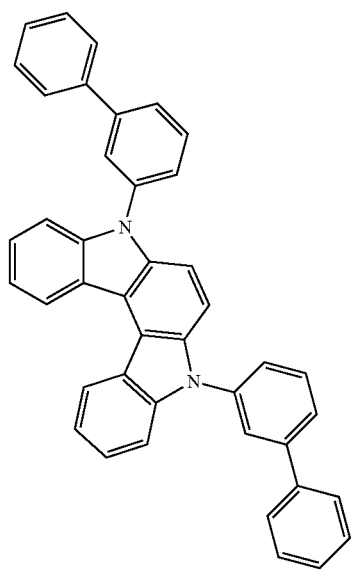
E-51
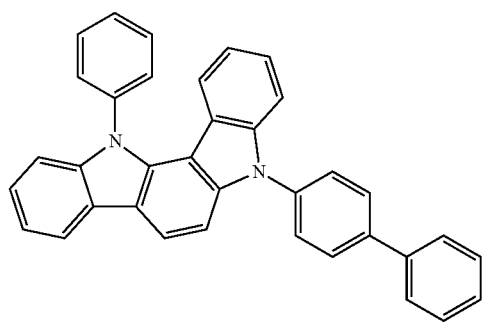
E-52
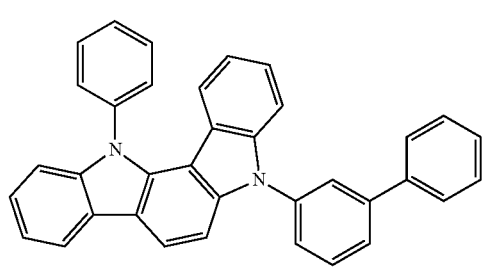
E-53
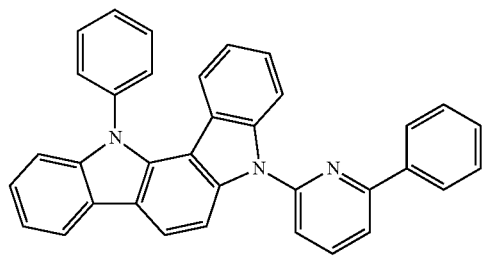

E-54
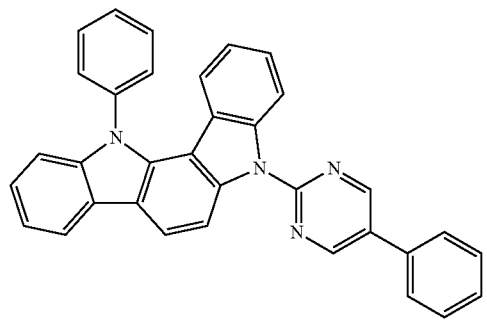
E-55
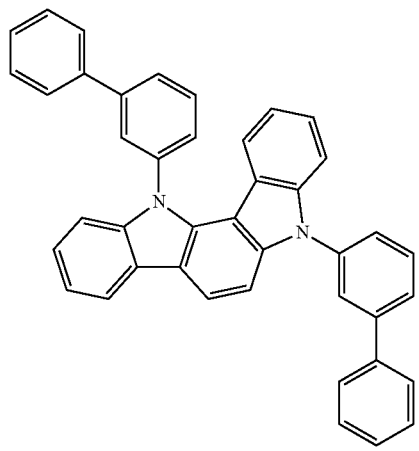
E-56
E-57
E-58
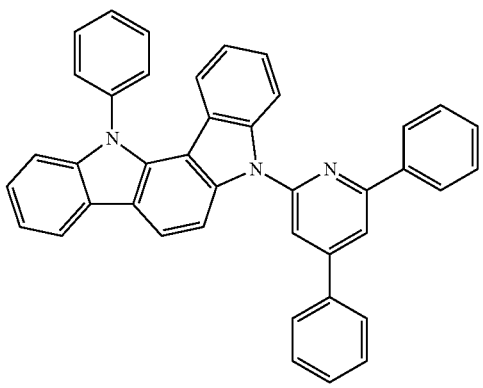
E-59
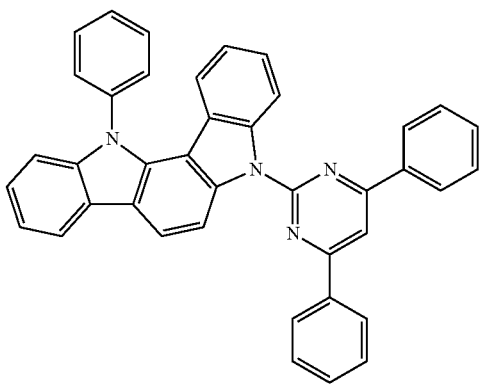
E-60
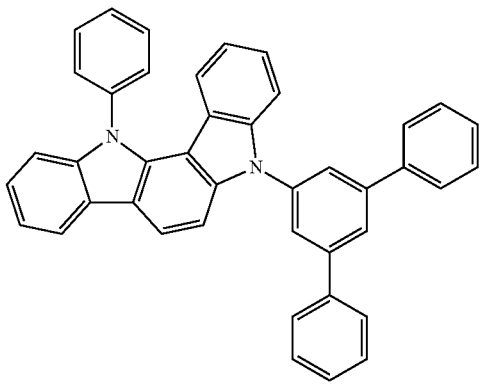

-continued

E-31 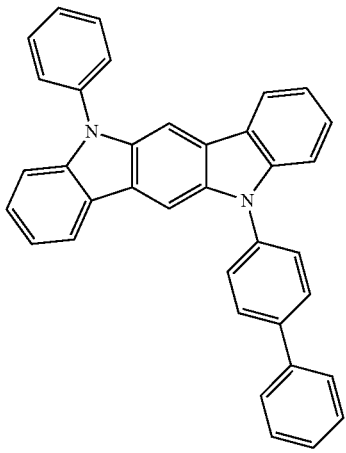

E-62 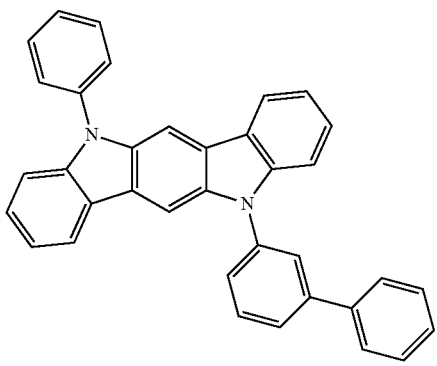

E-63 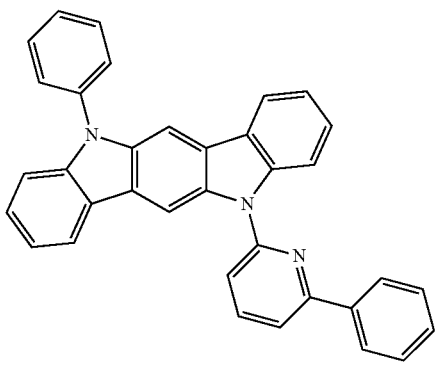

E-64 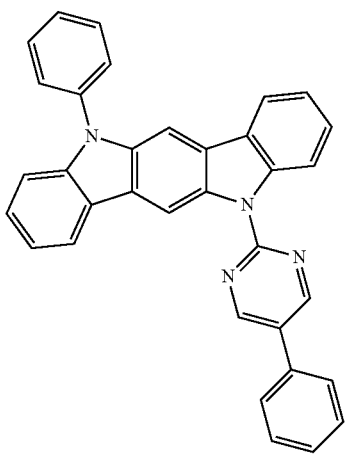

-continued

E-65 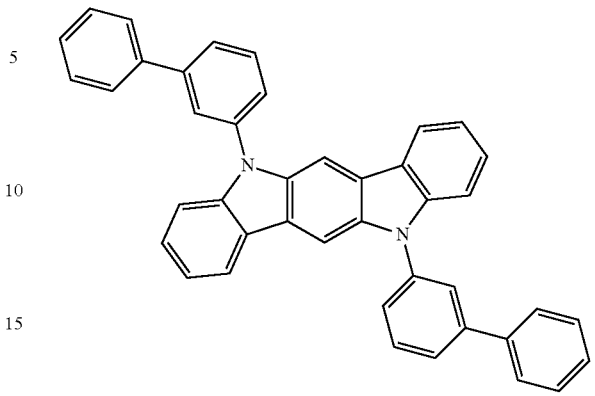

The second organic compound may include at least one of the compound represented by Chemical Formula 4 and a compound consisting of a moiety represented by Chemical Formula 5 and a moiety represented by Chemical Formula 6.

The composition may include the first organic compound and the second organic compound in a weight ratio of about 1:10 to about 10:1.

The composition may be applied to an organic layer of an organic optoelectronic diode, and the first organic compound and the second organic compound may function as a host. Herein, the first organic compound may be a compound having bipolar characteristics in which electron characteristics are relatively strong and the second organic compound may be a compound having bipolar characteristics in which hole characteristics are relatively strong, and when it is used with the first organic compound, to increase charge mobility and stability and thus luminous efficiency and life-span characteristics.

The composition may further include one or more organic compound in addition to the first organic compound and the second organic compound.

The composition may further include a dopant. The dopant may be a red, green, or blue dopant, for example a phosphorescent dopant.

The dopant is mixed with a host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd, or a combination thereof, and the L and X may be, for example a bidendate ligand.

The composition may be formed using a dry film formation method such as chemical vapor deposition (CVD) or a solution process.

Hereinafter, an organic optoelectronic diode to which the organic compound or the composition is applied is described.

The organic optoelectronic diode may be any device to convert electrical energy into photoenergy and vice versa without particular limitation, and may be, for example an organic photoelectric device, an organic light emitting diode, an organic solar cell, and an organic photo-conductor drum.

The organic optoelectronic diode includes an anode and a cathode facing each other, and at least one organic layer interposed between the anode and the cathode, wherein the organic layer includes the organic compound or the composition.

Herein, an organic light emitting diode as one example of an organic optoelectronic diode is described referring to drawings.

Figure 2:
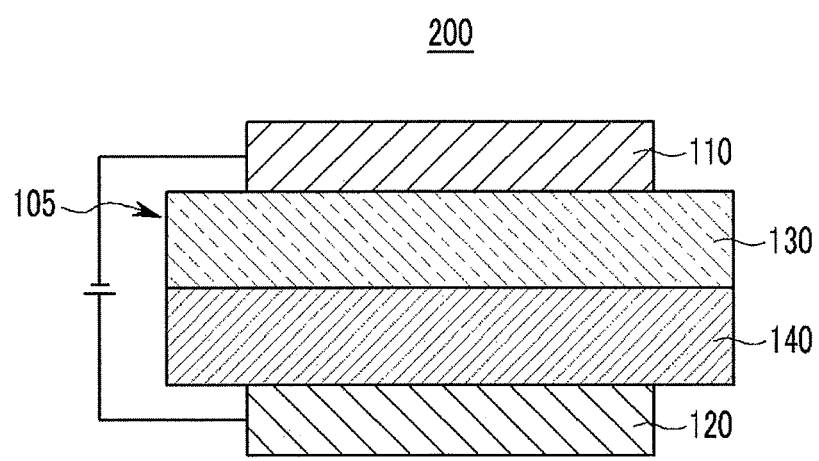

FIGS. 1 and 2 are cross-sectional views of each organic light emitting diode according to an embodiment.

Referring to FIG. 1, an organic light emitting diode 100 according to an embodiment includes an anode 120 and a cathode 110 facing each other and an organic layer 105 interposed between the anode 120 and the cathode 110.

The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO2 and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO$_2$/Al, LiF/Ca, LiF/Al, and BaF$_2$/Ca, but is not limited thereto.

The organic layer 105 includes an emission layer 130 including the organic compound or the composition.

The emission layer 130 may include, for example the organic compound alone, a mixture of at least two kinds of the organic compound or the composition.

Referring to FIG. 2, the organic light emitting diode 200 further include a hole auxiliary layer 140 as well as an emission layer 130. The hole auxiliary layer 140 increases hole injection and/or hole mobility between the anode 120 and the emission layer 230, and blocks electrons. The hole auxiliary layer 140 may be, for example a hole transport layer (HTL), a hole injection layer (HIL) and/or an electron blocking layer, and may include at least one layer.

In addition, in an embodiment of the present invention, in FIG. 1 or FIG. 2, the organic light emitting diode may further include an electron transport layer, an electron injection layer, a hole injection layer, and the like as the organic layer 105.

The organic light emitting diodes 100 and 200 may be manufactured by forming an anode or a cathode on a substrate, forming an organic layer in accordance with a dry coating method such as evaporation, sputtering, plasma plating, and ion plating, and forming a cathode or an anode thereon.

The organic light emitting diode may be applied to an organic light emitting display device.

MODE FOR INVENTION

Hereinafter, the embodiments are illustrated in more detail with reference to examples. These examples, however, are not in any sense to be interpreted as limiting the scope of the invention.

Synthesis of First Organic Compound

[Representative Synthesis Method]

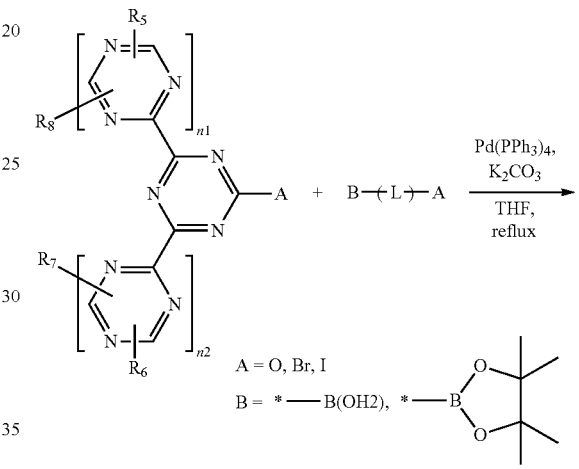

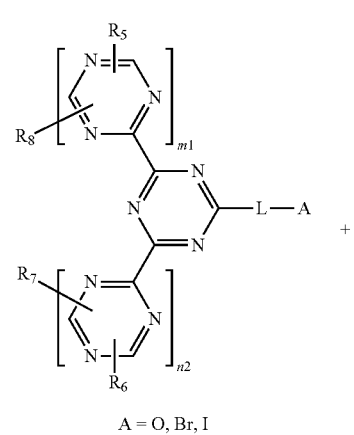

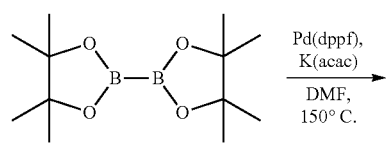

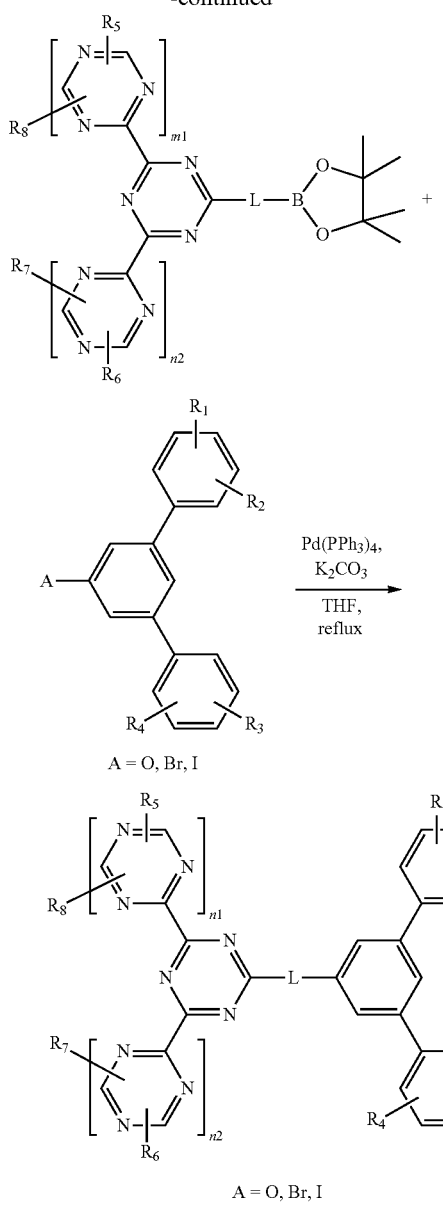

Synthesis of Intermediate

Synthesis Example 1: Synthesis of Intermediate I-1

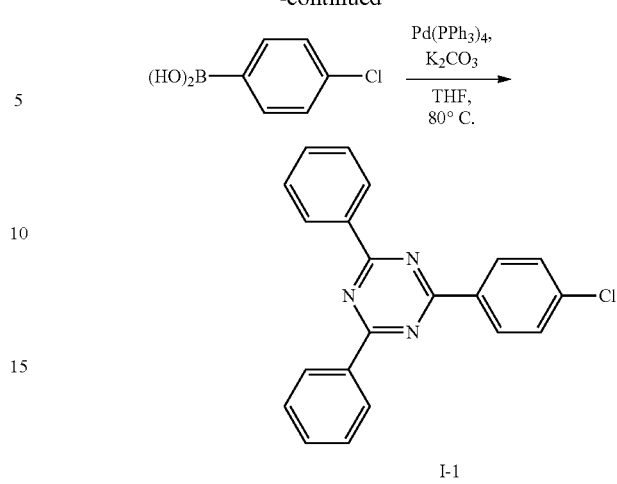

2-chloro-4,6-diphenyl-1,3,5-triazine of Shenzhen Gre-syn Chemical Technology Co., Ltd. (http://www.gre-syn.com/) (100 g, 374 mmol) was dissolved in 0.8 L of tetrahydrofuran (THF) under a nitrogen atmosphere, and 4-chlorophenylboronic acid (64.3 g, 411 mmol) and tetrakis(triphenylphosphine)palladium (4.32 g, 3.74 mmol) were added thereto and then stirred. Potassium carbonate saturated in water (129 g, 935 mmol) was added thereto, and the obtained mixture was heated and refluxed at 80° C. for 18 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound I-1 (118 g, 92%).

HRMS (70 eV, EI+): m/z calcd for C21H14C1N3: 343.0876, found: 343.

Elemental Analysis: C, 73%; H, 4%.

Synthesis Example 2: Synthesis of Intermediate I-2

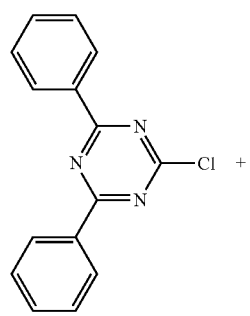

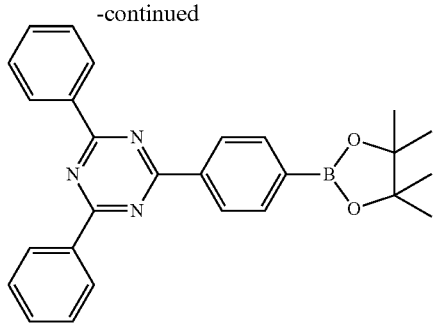

I-2

The compound I-1 (110 g, 320 mmol) was dissolved in 1.0 L of dimethylforamide (DMF) under a nitrogen atmosphere, and bis(pinacolato)diboron (97.5 g, 384 mmol), (1,1-bis(diphenylphosphine)ferrocene)dichloropalladium (II) (2.61 g, 3.20 mmol), and potassium acetate (113 g, 1,152 mmol) were added thereto, and the obtained mixture was heated and refluxed at 150° C. for 71 hours. When the reaction was complete, water was added to the reaction solution, and the mixture was filtered and dried in a vacuum oven. The obtained residue was separated and purified through flash column chromatography to obtain a compound I-2 (91.9 g, 66%).

HRMS (70 eV, EI+): m/z calcd for C27H26BN3O2: 435.2118, found: 435.

Elemental Analysis: C, 74%; H, 6%.

Synthesis Example 3: Synthesis of Intermediate I-3

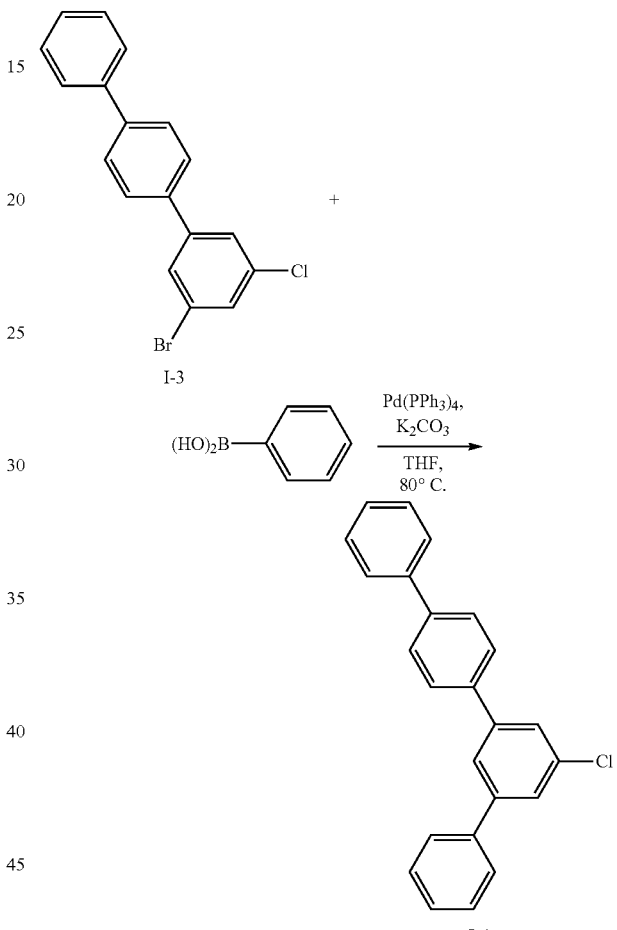

I-3

Biphenyl-4-ylboronic acid (100 g, 505 mmol) was dissolved in 1.3 L of tetrahydrofuran (THF) under a nitrogen atmosphere, and 1,3-dibromo-5-chlorobenzene (150 g, 555 mmol) and tetrakis(triphenylphosphine)palladium (5.05 g, 5.84 mmol) were added and stirred. Potassium carbonate saturated in water (174 g, 1,263 mmol) was added thereto, and the obtained mixture was heated and refluxed at 80° C. for 7 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound I-3 (149 g, 86%).

HRMS (70 eV, EI+): m/z calcd for C18H12BrCl: 343.0876, found: 343.

Elemental Analysis: C, 63%; H, 4%.

Synthesis Example 4: Synthesis of Intermediate I-4

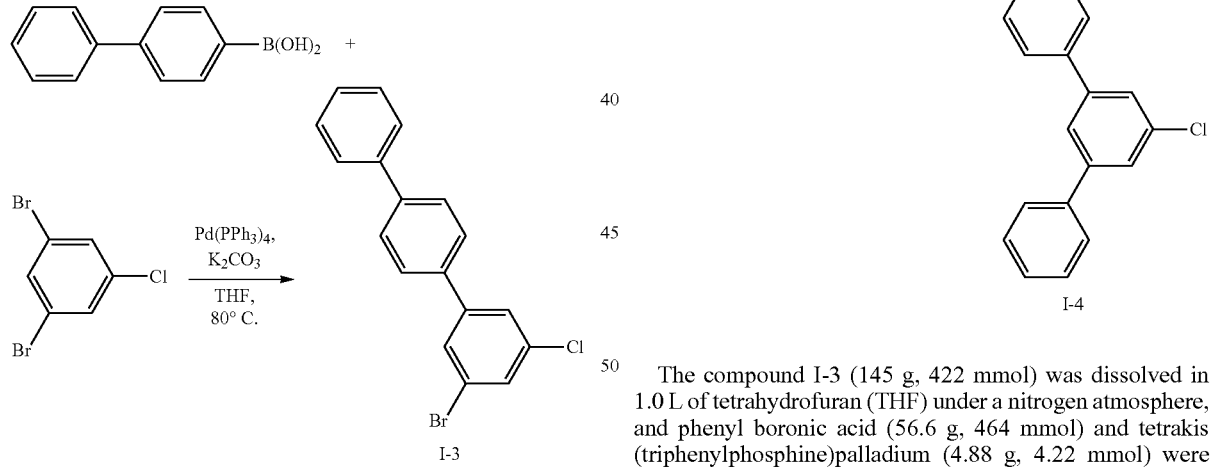

I-4

The compound I-3 (145 g, 422 mmol) was dissolved in 1.0 L of tetrahydrofuran (THF) under a nitrogen atmosphere, and phenyl boronic acid (56.6 g, 464 mmol) and tetrakis (triphenylphosphine)palladium (4.88 g, 4.22 mmol) were added thereto and stirred. Potassium carbonate saturated in water (146 g, 1,055 mmol) was added thereto, and the obtained mixture was heated and refluxed at 80° C. for 10 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound I-4 (134 g, 93%).

HRMS (70 eV, EI+): m/z calcd for C24H17Cl: 340.1019, found: 340.

Elemental Analysis: C, 85%; H, 5%.

Synthesis Example 5: Synthesis of Intermediate I-5

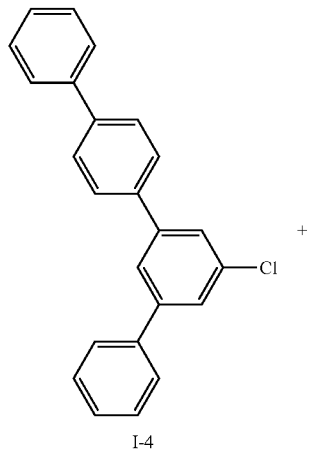

I-4

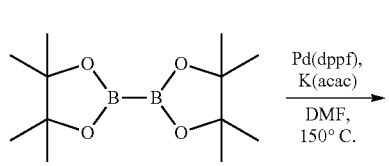

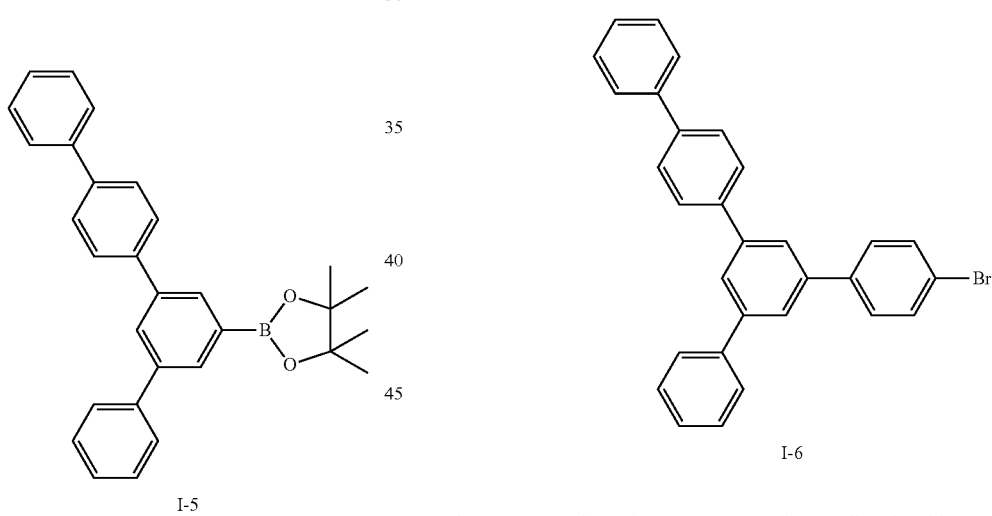

I-5

The compound I-4 (130 g, 381 mmol) was dissolved in 1.2 L of dimethylforamide (DMF) under a nitrogen atmosphere, and bis(pinacolato)diboron (116 g, 458 mmol), (1,1-bis(diphenylphosphine)ferrocene)dichloropalladium(II) (3.11 g, 3.81 mmol), and potassium acetate (112 g, 1,143 mmol) were added thereto, and the obtained mixture was heated and refluxed at 150° C. for 68 hours. When the reaction was complete, water was added to the reaction solution, and the mixture was filtered and dried in a vacuum oven. The obtained residue was separated and purified through flash column chromatography to obtain a compound I-5 (90.9 g, 70%).

HRMS (70 eV, EI+): m/z calcd for $C_{30}H_{29}BO_2$: 432.2261, found: 432.

Elemental Analysis: C, 83%; H, 7%.

Synthesis Example 6: Synthesis of Intermediate I-6

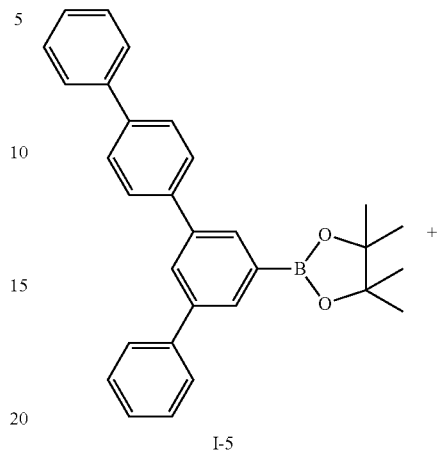

I-5

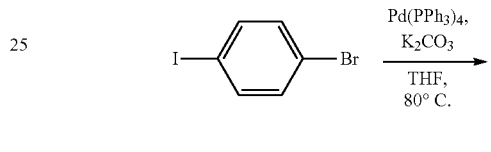

I-6

The compound I-5 (85 g, 197 mmol) was dissolved in 0.7 L of tetrahydrofuran (THF) under a nitrogen atmosphere, and 1-bromo-4-iodobenzene (61.2 g, 216 mmol) and tetrakis (triphenylphosphine)palladium (2.28 g, 1.97 mmol) were added thereto and then stirred. Potassium carbonate saturated in water (68.1 g, 493 mmol) was added thereto, and the obtained mixture was heated and refluxed at 80° C. for 12 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain a compound I-6 (81.8 g, 90%).

HRMS (70 eV, EI+): m/z calcd for $C_{30}H_{21}Br$: 460.0827, found: 460.

Elemental Analysis: C, 78%; H, 5%.

Synthesis Example 7: Synthesis of Intermediate I-7

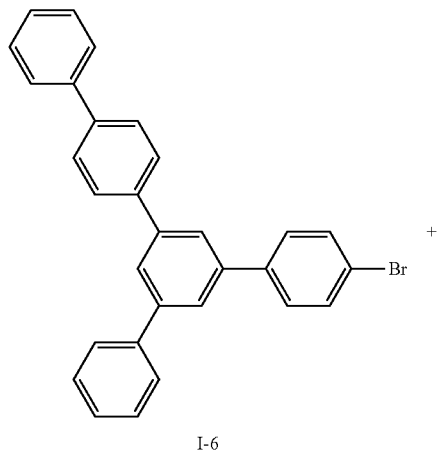

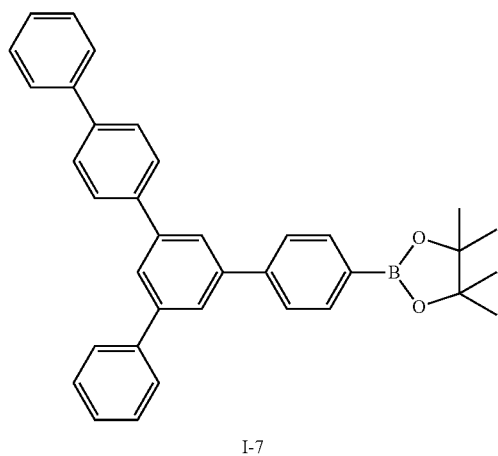

The compound I-6 (75 g, 163 mmol) was dissolved in 0.6 L of dimethylforamide (DMF) under a nitrogen atmosphere, bis(pinacolato)diboron (49.5 g, 195 mmol), (1,1-bis(diphenylphosphine)ferrocene)dichloropalladium(II) (1.33 g, 1.63 mmol), and potassium acetate (48.0 g, 489 mmol) were added thereto, and the obtained mixture was heated and refluxed at 150° C. for 8 hours. When the reaction was complete, water was added to the reaction solution, and the mixture was filtered and dried in a vacuum oven. The obtained residue was separated and purified through flash column chromatography to obtain a compound I-7 (67.1 g, 81%).

HRMS (70 eV, EI+): m/z calcd for C36H33BO2: 508.2574, found: 508.

Elemental Analysis: C, 85%; H, 7%.

Synthesis Example 8: Synthesis of Intermediate I-8

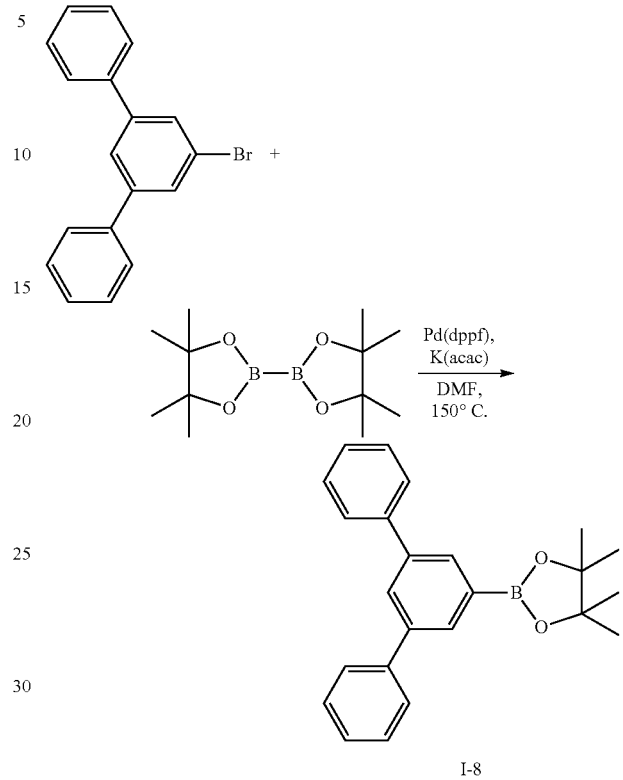

1-bromo-3,5-diphenylbenzene (100 g, 323 mmol) was dissolved in 1.0 L of dimethylforamide (DMF) under a nitrogen atmosphere, and bis(pinacolato)diboron (98.6 g, 388 mmol), (1,1-bis(diphenylphosphine)ferrocene)dichloropalladium(II) (2.64 g, 3.23 mmol), and potassium acetate (95.1 g, 969 mmol) were added thereto, and the obtained mixture was heated and refluxed at 150° C. for 10 hours. When the reaction was complete, water was added to the reaction solution, and the mixture was filtered and dried in a vacuum oven. The obtained residue was separated and purified through flash column chromatography to obtain a compound I-8 (97.8 g, 85%).

HRMS (70 eV, EI+): m/z calcd for C24H25BO2: 356.1948, found: 356.

Elemental Analysis: C, 81%; H, 7%.

Synthesis Example 9: Synthesis of Intermediate I-9

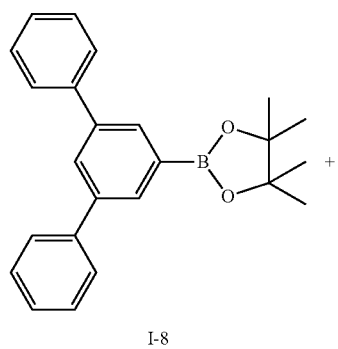

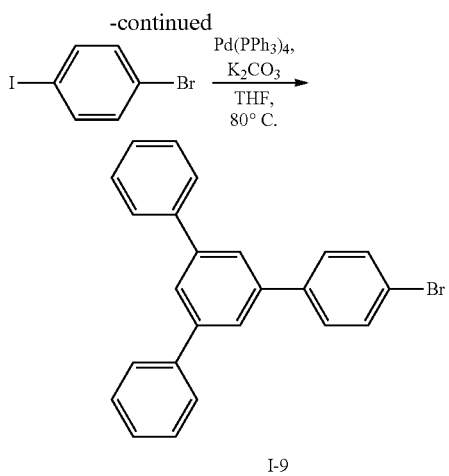

The compound I-8 (95 g, 267 mmol) was dissolved in 0.9 L of tetrahydrofuran (THF) under a nitrogen atmosphere, and 1-bromo-4-iodobenzene (83.0 g, 293 mmol) and tetrakis(triphenylphosphine)palladium (3.09 g, 2.67 mmol) were added thereto and then stirred. Potassium carbonate saturated in water (92.3 g, 668 mmol) was added thereto, and the mixture was heated and refluxed at 80° C. for 8 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound I-9 (89.5 g, 87%).

HRMS (70 eV, EI+): m/z calcd for C24H17Br: 384.0514, found: 384.

Elemental Analysis: C, 75%; H, 4%.

Synthesis Example 10: Synthesis of Intermediate I-10

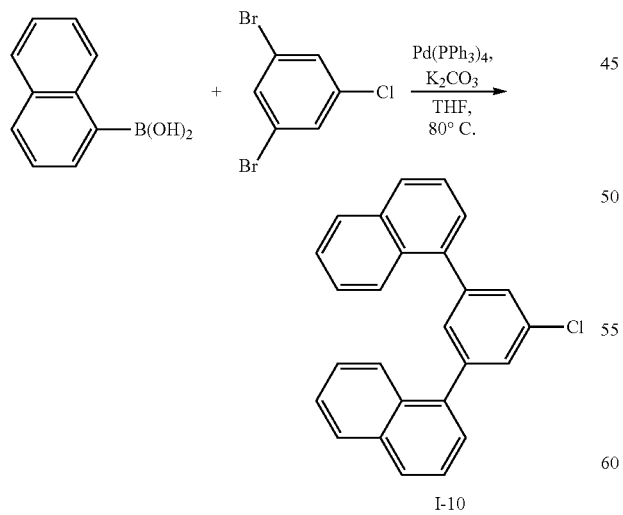

Naphthalen-1-yl boronic acid (134 g, 777 mmol) was dissolved in 1.1 L of tetrahydrofuran (THF) under a nitrogen atmosphere, and 1,3-dibromo-5-chlorobenzene (100 g, 370 mmol) and tetrakis(triphenylphosphine)palladium (8.98 g, 7.77 mmol) were added thereto and then stirred. Potassium carbonate saturated in water (268 g, 1,943 mmol) was added thereto, and the obtained mixture was heated and refluxed at 80° C. for 13 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound I-10 (249 g, 88%).

HRMS (70 eV, EI+): m/z calcd for C26H17Cl: 364.1019, found: 364.

Elemental Analysis: C, 86%; H, 5%.

Synthesis Example 11: Synthesis of Intermediate I-11

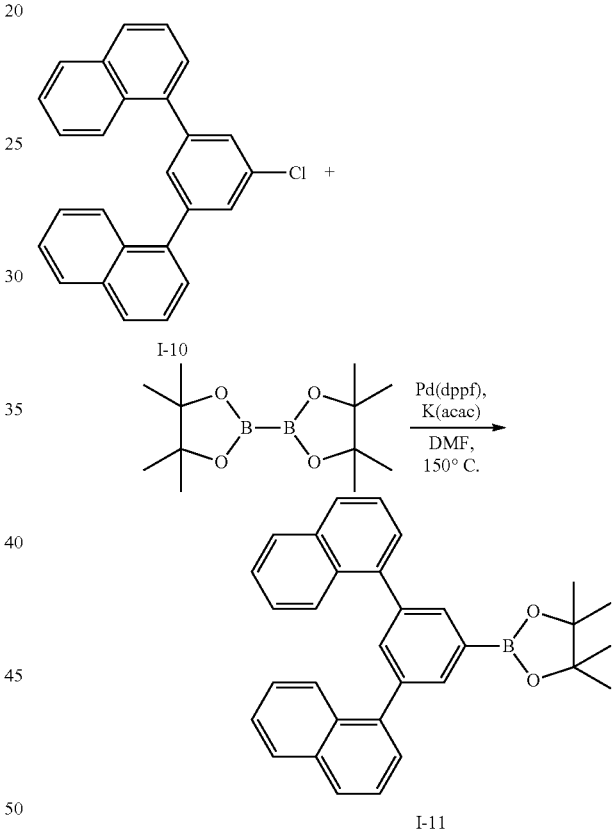

The compound I-10 (240 g, 658 mmol) was dissolved in 2.2 L of dimethylforamide (DMF) under a nitrogen atmosphere, bis(pinacolato)diboron (200 g, 789 mmol), (1,1'-bis(diphenylphosphine)ferrocene)dichloropalladium(II) (5.37 g, 6.58 mmol), and potassium acetate (194 g, 1,974 mmol) were added thereto, and the obtained mixture was heated and refluxed at 150° C. for 57 hours. When the reaction was complete, water was added to the reaction solution, and the mixture was filtered and dried in a vacuum oven. The obtained residue was separated and purified through flash column chromatography to obtain a compound I-11 (183 g, 61%).

HRMS (70 eV, EI+): m/z calcd for C32H29BO2: 456.2261, found: 456.

Elemental Analysis: C, 84%; H, 6%.

Synthesis Example 12: Synthesis of Intermediate I-12

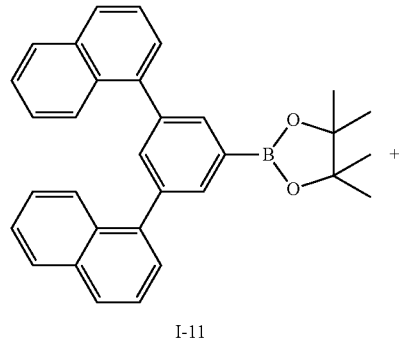

I-11

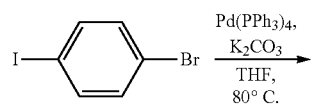

Pd(PPh₃)₄, K₂CO₃
THF,
80° C.

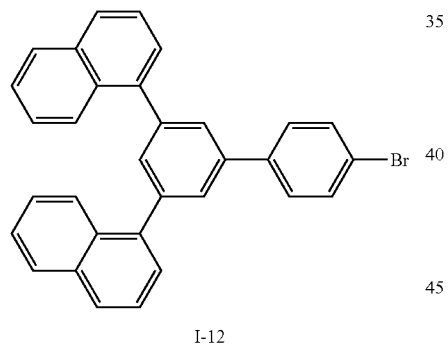

I-12

The compound I-11 (180 g, 394 mmol) was dissolved in 1.5 L of tetrahydrofuran (THF) under a nitrogen atmosphere, and 1-bromo-4-iodobenzene (123 g, 434 mmol) and tetrakis (triphenylphosphine)palladium (4.55 g, 3.94 mmol) were added thereto and then stirred. Potassium carbonate saturated in water (136 g, 985 mmol) was added thereto, and the obtained mixture was heated and refluxed at 80° C. for 10 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound I-12 (191 g, 90%).

HRMS (70 eV, EI+): m/z calcd for $C_{32}H_{21}Br$: 484.0827, found: 484.

Elemental Analysis: C, 79%; H, 4%.

Synthesis Example 13: Synthesis of Intermediate I-13

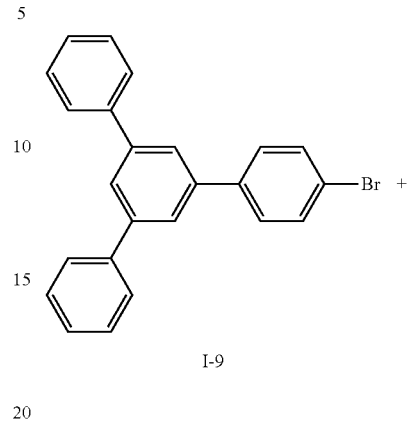

I-9

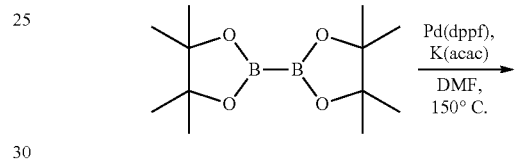

Pd(dppf), K(acac)
DMF,
150° C.

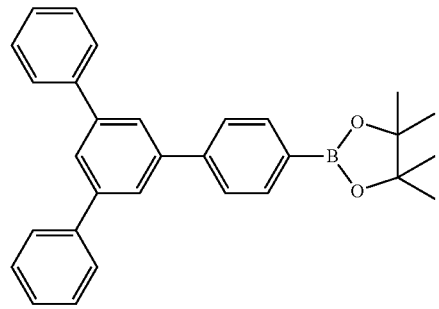

I-13

The compound I-9 (100 g, 260 mmol) was dissolved 0.9 L of dimethylforamide (DMF) under a nitrogen atmosphere, and bis(pinacolato)diboron (79.1 g, 311 mmol), (1,1'-bis (diphenylphosphine)ferrocene)dichloropalladium (II) (2.12 g, 2.60 mmol), and potassium acetate (76.5 g, 780 mmol) were added thereto, and the obtained mixture was heated and refluxed at 150° C. for 13 hours. When the reaction was complete, water was added to the reaction solution, and the mixture was filtered and dried in a vacuum oven. The obtained residue was separated and purified through flash column chromatography to obtain a compound I-13 (78.7 g, 70%).

HRMS (70 eV, EI+): m/z calcd for $C_{30}H_{29}BO_2$: 432.2261, found: 432.

Elemental Analysis: C, 83%; H, 7%.

Synthesis Example 14: Synthesis of Intermediate I-14

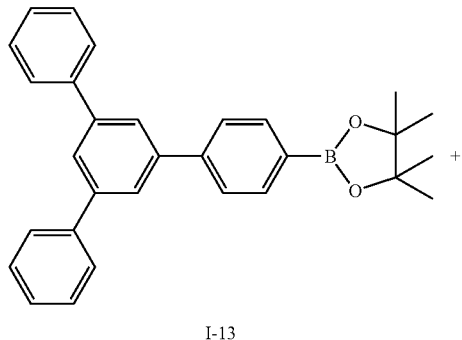

I-13

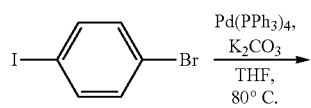

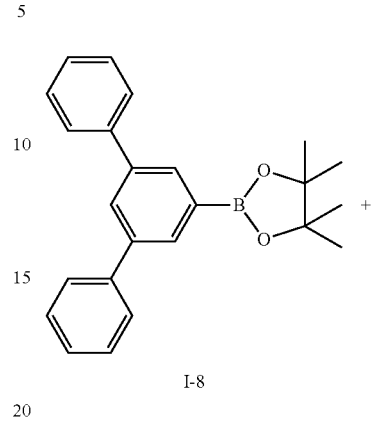

I-8

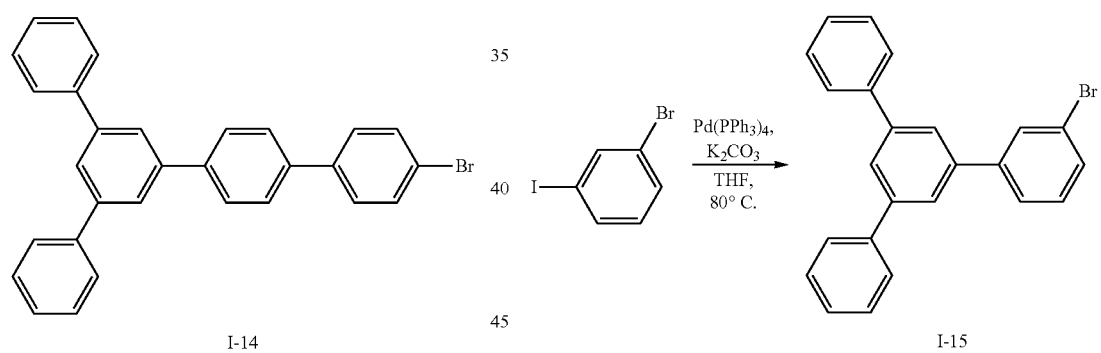

Synthesis Example 15: Synthesis of Intermediate I-15

The compound I-13 (75 g, 173 mmol) was dissolved in 0.65 L of tetrahydrofuran (THF) under a nitrogen atmosphere, and 1-bromo-4-iodobenzene (54.0 g, 191 mmol) and tetrakis(triphenylphosphine)palladium (2.0 g, 1.73 mmol) were added thereto and then stirred. Potassium carbonate saturated in water (59.8 g, 433 mmol) was added thereto, and the obtained mixture was heated and refluxed at 80° C. for 16 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain a compound I-14 (72.6 g, 91%).

HRMS (70 eV, EI+): m/z calcd for C30H21Br: 460.0827, found: 460.

Elemental Analysis: C, 78%; H, 5%.

The compound I-8 (50 g, 140 mmol) was dissolved in 0.45 L of tetrahydrofuran (THF) under a nitrogen atmosphere, and 1-bromo-3-iodobenzene (43.7 g, 154 mmol) and tetrakis(triphenylphosphine)palladium (1.62 g, 1.40 mmol) were added thereto and then stirred. Potassium carbonate saturated in water (48.4 g, 350 mmol) was added thereto, and the obtained mixture was heated and refluxed at 80° C. for 12 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain a compound I-15 (41.5 g, 77%).

HRMS (70 eV, EI+): m/z calcd for C24H17Br: 384.0514, found: 384.

Elemental Analysis: C, 75%; H, 4%.

Synthesis Example 16: Synthesis of Intermediate I-16

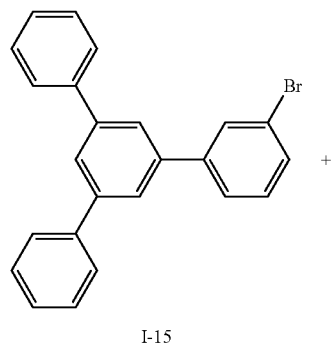

I-15

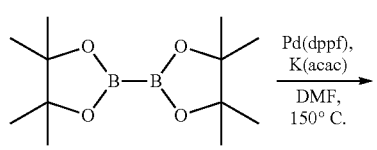

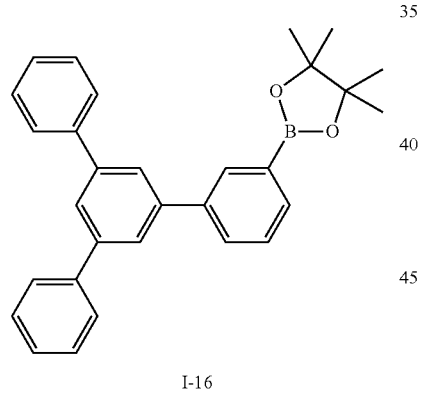

I-16

The compound I-15 (40 g, 104 mmol) was dissolved in 0.35 L of dimethylforamide (DMF) under a nitrogen atmosphere, bis(pinacolato)diboron (31.6 g, 125 mmol), (1,1'-bis(diphenylphosphine)ferrocene)dichloropalladium(II) (0.85 g, 1.04 mmol), and potassium acetate (30.6 g, 312 mmol) were added thereto, and the obtained mixture was heated and refluxed at 150° C. for 10 hours. When the reaction was complete, water was added to the reaction solution, and the mixture was filtered and dried in a vacuum oven. The obtained residue was separated and purified through flash column chromatography to obtain a compound I-16 (33.7 g, 75%).

HRMS (70 eV, EI+): m/z calcd for C30H29BO2: 432.2261, found: 432.

Elemental Analysis: C, 83%; H, 7%.

Synthesis Example 17: Synthesis of Intermediate I-17

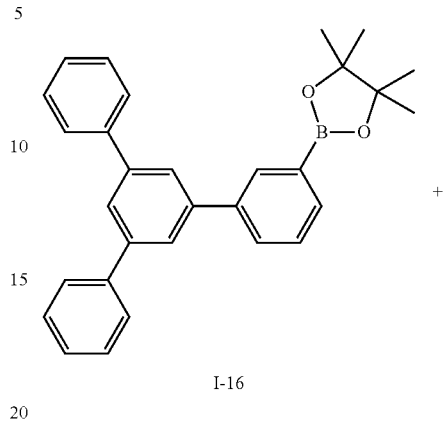

I-16

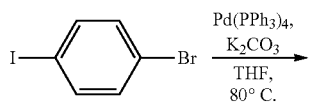

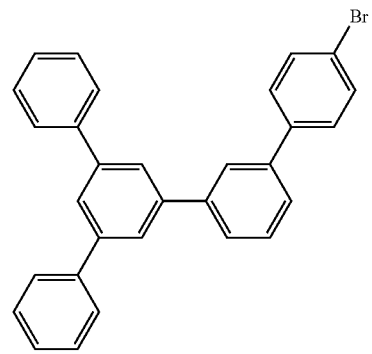

I-17

The compound I-16 (30 g, 69.4 mmol) was dissolved in 0.26 L of tetrahydrofuran (THF) under a nitrogen atmosphere, and 1-bromo-4-iodobenzene (21.6 g, 76.3 mmol) and tetrakis(triphenylphosphine)palladium (0.80 g, 0.69 mmol) were added thereto and then stirred. Potassium carbonate saturated in water (24.0 g, 174 mmol) was added thereto, and the obtained mixture was heated and refluxed at 80° C. for 8 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound I-17 (25.6 g, 80%).

HRMS (70 eV, EI+): m/z calcd for C30H21Br: 460.0827, found: 460.

Elemental Analysis: C, 78%; H, 5%.

Synthesis Example 18: Synthesis of Intermediate I-18

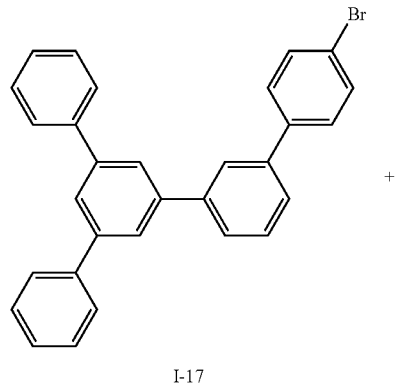

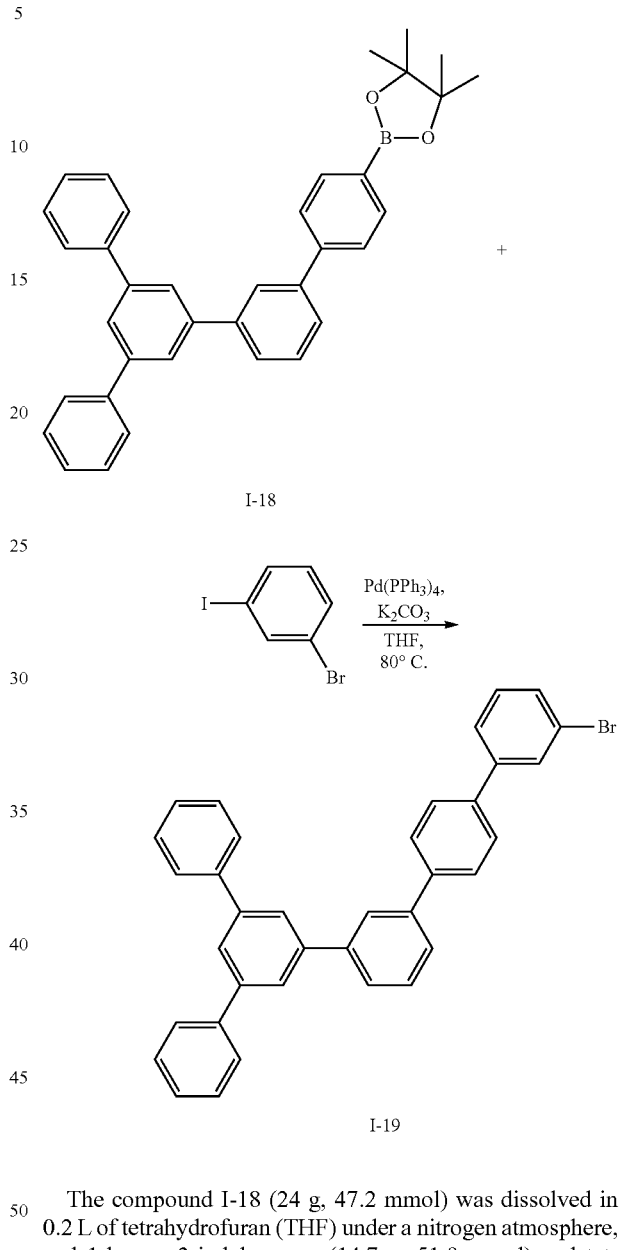

The compound I-17 (25 g, 54.2 mmol) was dissolved in 0.2 L of dimethylforamide (DMF) under a nitrogen atmosphere, and bis(pinacolato)diboron (16.5 g, 65.0 mmol), (1,1'-bis(diphenylphosphine)ferrocene)dichloropalladium (II) (0.44 g, 0.54 mmol), and potassium acetate (16.0 g, 163 mmol) were added thereto, and the obtained mixture was heated and refluxed at 150° C. for 9 hours. When the reaction was complete, water was added to the reaction solution, and the mixture was filtered and dried in a vacuum oven. The obtained residue was separated and purified through flash column chromatography to obtain a compound I-18 (24.5 g, 89%).

HRMS (70 eV, EI+): m/z calcd for C36H33BO2: 508.2574, found: 508.

Elemental Analysis: C, 85%; H, 7%.

Synthesis Example 19: Synthesis of Intermediate I-19

The compound I-18 (24 g, 47.2 mmol) was dissolved in 0.2 L of tetrahydrofuran (THF) under a nitrogen atmosphere, and 1-bromo-3-iodobenzene (14.7 g, 51.9 mmol) and tetrakis(triphenylphosphine)palladium (0.54 g, 0.47 mmol) were added thereto and then stirred. Potassium carbonate saturated in water (16.3 g, 118 mmol) was added thereto, and the obtained mixture was heated and refluxed at 80° C. for 12 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound I-19 (21.3 g, 84%).

HRMS (70 eV, EI+): m/z calcd for C36H25Br: 536.1140, found: 536.

Elemental Analysis: C, 80%; H, 5%.

Synthesis Example 20: Synthesis of Intermediate I-20

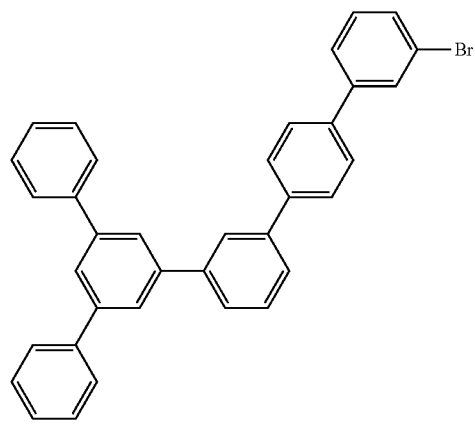

I-19

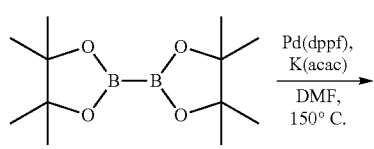

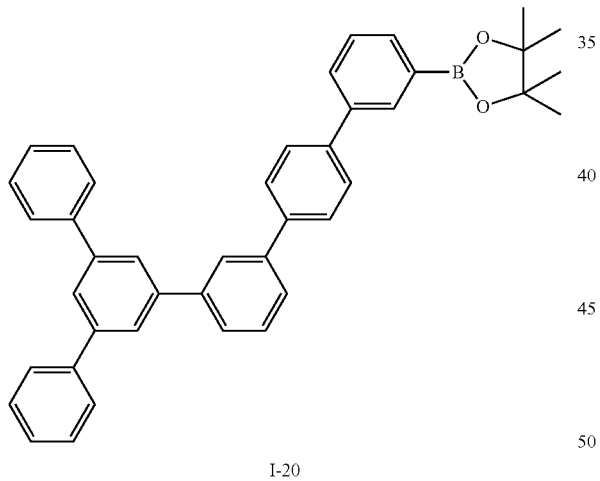

I-20

The compound I-19 (20 g, 37.2 mmol) was dissolved in 0.16 L of dimethylforamide (DMF) under a nitrogen atmosphere, and bis(pinacolato)diboron (11.3 g, 44.7 mmol), (1,1'-bis(diphenylphosphine)ferrocene)dichloropalladium(II) (0.30 g, 0.37 mmol), and potassium acetate (11.0 g, 112 mmol) were added thereto, and the obtained mixture was heated and refluxed at 150° C. for 15 hours. When the reaction was complete, water was added to the reaction solution, and the mixture was filtered and dried in a vacuum oven. The obtained residue was separated and purified through flash column chromatography to obtain a compound I-20 (18.5 g, 85%).

HRMS (70 eV, EI+): m/z calcd for C42H37BO2: 584.2887, found: 584.

Elemental Analysis: C, 86%; H, 6%.

Synthesis Example 21: Synthesis of Intermediate I-21

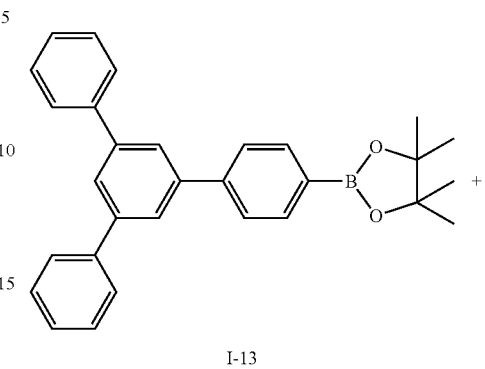

I-13

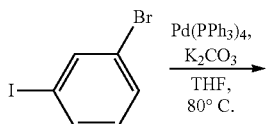

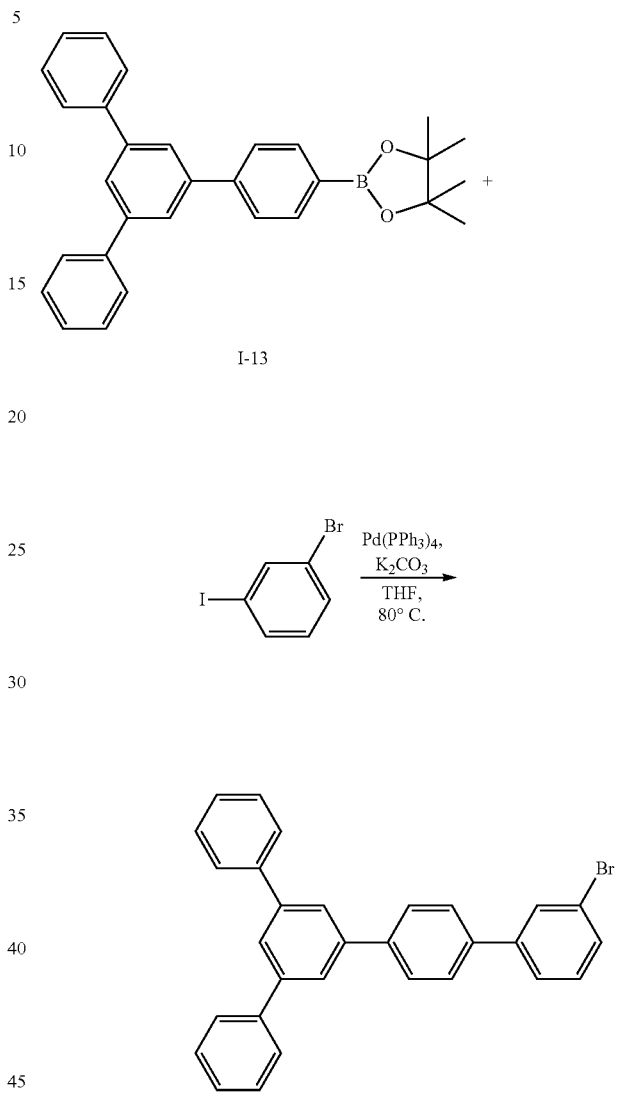

I-21

The compound I-13 (50 g, 116 mmol) was dissolved in 0.43 L of tetrahydrofuran (THF) under a nitrogen atmosphere, and 1-bromo-3-iodobenzene (36.0 g, 127 mmol) and tetrakis(triphenylphosphine)palladium (1.34 g, 1.16 mmol) were added thereto and then stirred. Potassium carbonate saturated in water (40.1 g, 290 mmol) was added thereto, and the obtained mixture was heated and refluxed at 80° C. for 10 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound I-21 (46.6 g, 87%).

HRMS (70 eV, EI+): m/z calcd for C30H21Br: 460.0827, found: 460.

Elemental Analysis: C, 78%; H, 5%.

Synthesis Example 22: Synthesis of Intermediate I-22

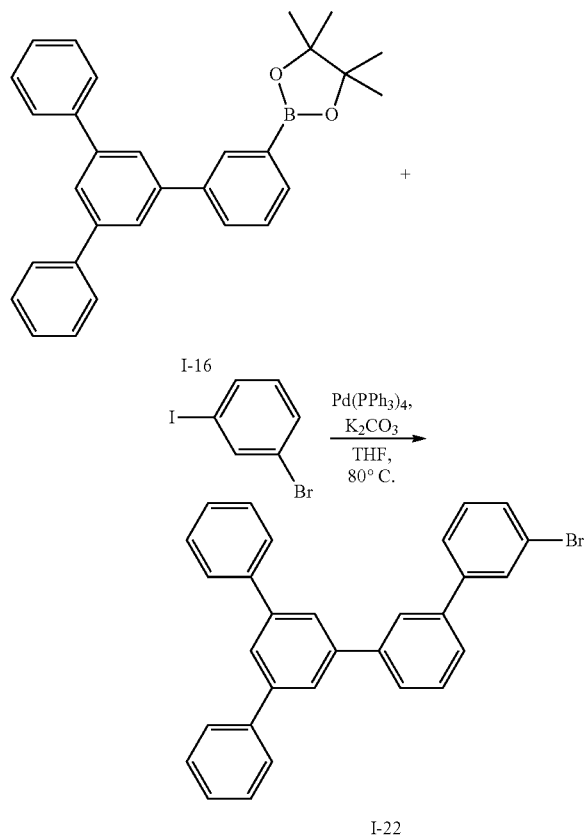

The compound I-16 (30 g, 69.4 mmol) was dissolved in 0.26 L of tetrahydrofuran (THF) under a nitrogen atmosphere, and 1-bromo-3-iodobenzene (21.6 g, 76.3 mmol) and tetrakis(triphenylphosphine)palladium (0.80 g, 0.69 mmol) were added thereto and then stirred. Potassium carbonate saturated in water (24.0 g, 174 mmol) was added thereto, and the obtained mixture was heated and refluxed at 80° C. for 10 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound I-22 (27.2 g, 85%).

HRMS (70 eV, EI+): m/z calcd for C30H21Br: 460.0827, found: 460.

Elemental Analysis: C, 78%; H, 5%.

Synthesis Example 23: Synthesis of Intermediate I-23

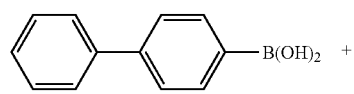

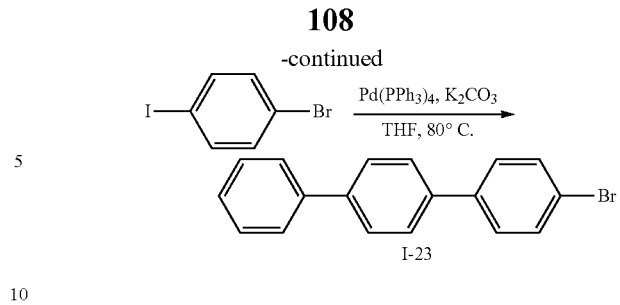

Biphenyl-4-ylboronic acid (100 g, 505 mmol) was dissolved in 1.5 L of tetrahydrofuran (THF) under a nitrogen atmosphere, and 1-bromo-4-iodobenzene (157 g, 555 mmol) and tetrakis(triphenylphosphine)palladium (58.4 g, 5.05 mmol) were added thereto and then stirred. Potassium carbonate saturated in water (174 g, 1,262 mmol) was added thereto, and the obtained mixture was heated and refluxed at 80° C. for 6 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound I-23 (141 g, 90%).

HRMS (70 eV, EI+): m/z calcd for C18H13Br: 308.0201, found: 308.

Elemental Analysis: C, 70%; H, 4%.

Synthesis Example 24: Synthesis of Intermediate I-24

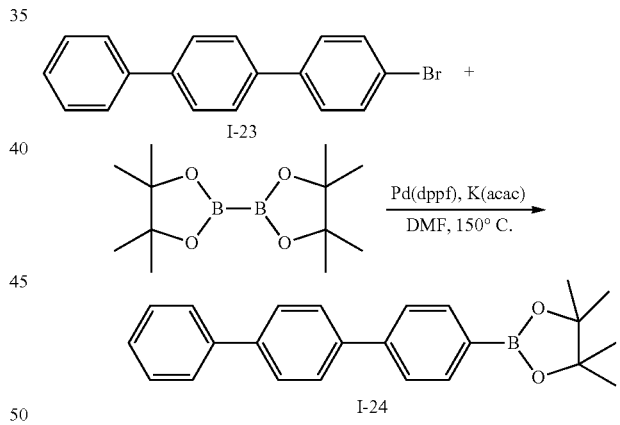

The compound I-23 (120 g, 388 mmol) was dissolved in 1.2 L of dimethylforamide (DMF) under a nitrogen atmosphere, and bis(pinacolato)diboron (118 g, 466 mmol) and (1,1'-bis(diphenylphosphine)ferrocene)dichloropalladium (II) (3.17 g, 3.88 mmol), and potassium acetate (114 g, 1,164 mmol) were added thereto, and the obtained mixture was heated and refluxed at 150° C. for 4 hours. When the reaction was complete, water was added to the reaction solution, and the mixture was filtered and dried in a vacuum oven. The obtained residue was separated and purified through flash column chromatography to obtain a compound I-24 (124 g, 90%).

HRMS (70 eV, EI+): m/z calcd for C24H25BO2: 356.1948, found: 356.

Elemental Analysis: C, 81%; H, 7%.

Synthesis Example 25: Synthesis of Intermediate I-25

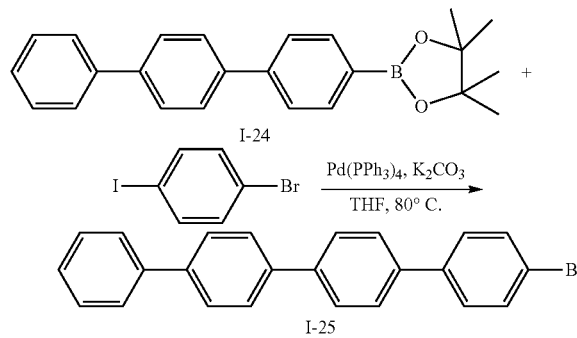

The compound I-24 (120 g, 337 mmol) was dissolved in 1.3 L of tetrahydrofuran (THF) under a nitrogen atmosphere, and 1-bromo-4-iodobenzene (105 g, 371 mmol) and tetrakis (triphenylphosphine)palladium (3.89 g, 3.37 mmol) were added thereto and then stirred. Potassium carbonate saturated in water (116 g, 843 mmol) was added thereto, and the obtained mixture was heated and refluxed at 80° C. for 10 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound I-25 (108 g, 83%).

HRMS (70 eV, EI+): m/z calcd for C24H17Br: 384.0514, found: 384.

Elemental Analysis: C, 75%; H, 4%.

Synthesis Example 26: Synthesis of Intermediate I-26

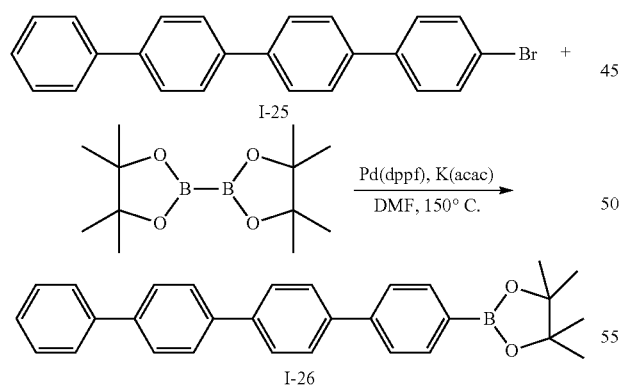

The compound I-25 (75 g, 195 mmol) was dissolved in 0.67 L of dimethylforamide (DMF) under a nitrogen atmosphere, and bis(pinacolato)diboron (59.3 g, 234 mmol), (1,1'-bis(diphenylphosphine)ferrocene)dichloropalladium (II) (1.59 g, 1.95 mmol), and potassium acetate (57.4 g, 585 mmol) were added thereto, and the obtained mixture was heated and refluxed at 150° C. for 6 hours. When the reaction was complete, water was added to the reaction solution, and the mixture was filtered and dried in a vacuum oven. The obtained residue was separated and purified through flash column chromatography to obtain a compound I-26 (63.2 g, 75%).

HRMS (70 eV, EI+): m/z calcd for C30H29BO2: 432.2261, found: 432.

Elemental Analysis: C, 83%; H, 7%.

Synthesis Example 27: Synthesis of Intermediate I-27

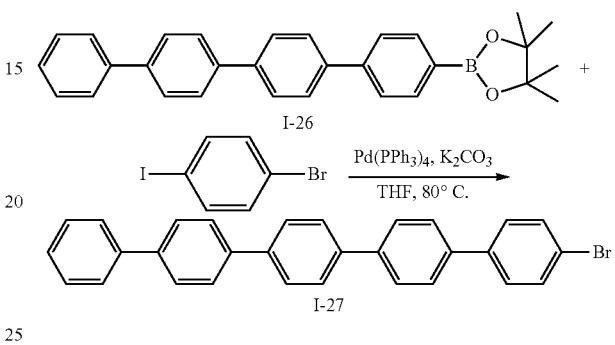

The compound I-26 (60 g, 139 mmol) was dissolved in 0.5 L of tetrahydrofuran (THF) under a nitrogen atmosphere, and 1-bromo-4-iodobenzene (43.2 g, 153 mmol) and tetrakis (triphenylphosphine)palladium (1.61 g, 1.39 mmol) were added thereto and then stirred. Potassium carbonate saturated in water (48.0 g, 348 mmol) was added thereto, and the obtained mixture was heated and refluxed at 80° C. for 8 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound I-27 (51.3 g, 80%).

HRMS (70 eV, EI+): m/z calcd for C30H21Br: 460.0827, found: 460.

Elemental Analysis: C, 78%; H, 5%.

Synthesis Example 28: Synthesis of Intermediate I-28

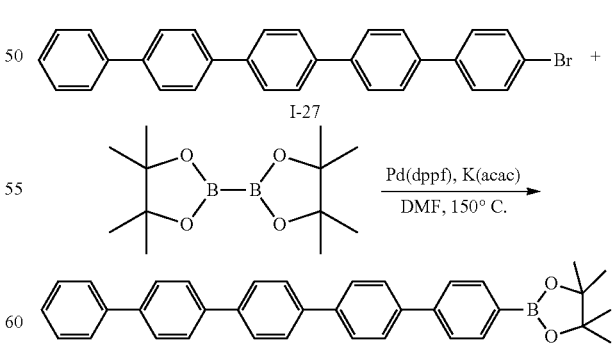

The compound I-27 (25 g, 54.2 mmol) was dissolved in 0.21 L of dimethylforamide (DMF) under a nitrogen atmosphere, and bis(pinacolato)diboron (16.5 g, 65.0 mmol), (1,1'-bis(diphenylphosphine)ferrocene)dichloropalladium (II) (0.44 g, 0.54 mmol), and potassium acetate (16.0 g, 163 mmol) were added thereto, and the obtained mixture was heated and refluxed at 150° C. for 12 hours. When the reaction was complete, water was added to the reaction solution, and the mixture was filtered and dried in a vacuum oven. The obtained residue was separated and purified through flash column chromatography to obtain a compound I-28 (19.6 g, 71%).

HRMS (70 eV, EI+): m/z calcd for C36H33BO2: 508.2574, found: 508.

Elemental Analysis: C, 85%; H, 7%.

Synthesis Example 29: Synthesis of Intermediate I-29

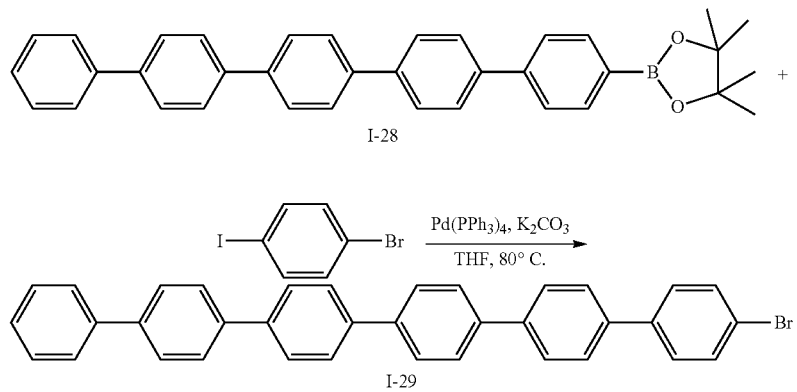

The compound I-28 (19 g, 37.4 mmol) was dissolved in 0.15 L of tetrahydrofuran (THF) under a nitrogen atmosphere, and 1-bromo-4-iodobenzene (11.6 g, 41.1 mmol) and tetrakis(triphenylphosphine)palladium (0.43 g, 0.37 mmol) were added thereto and then stirred. Potassium carbonate saturated in water (12.9 g, 93.5 mmol) was added thereto, and the obtained mixture was heated and refluxed at 80° C. for 15 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound I-29 (13.1 g, 65%).

HRMS (70 eV, EI+): m/z calcd for C36H25Br: 536.1140, found: 536.

Elemental Analysis: C, 80%; H, 5%.

Final Compound

Synthesis Example 30: Synthesis of Compound 1

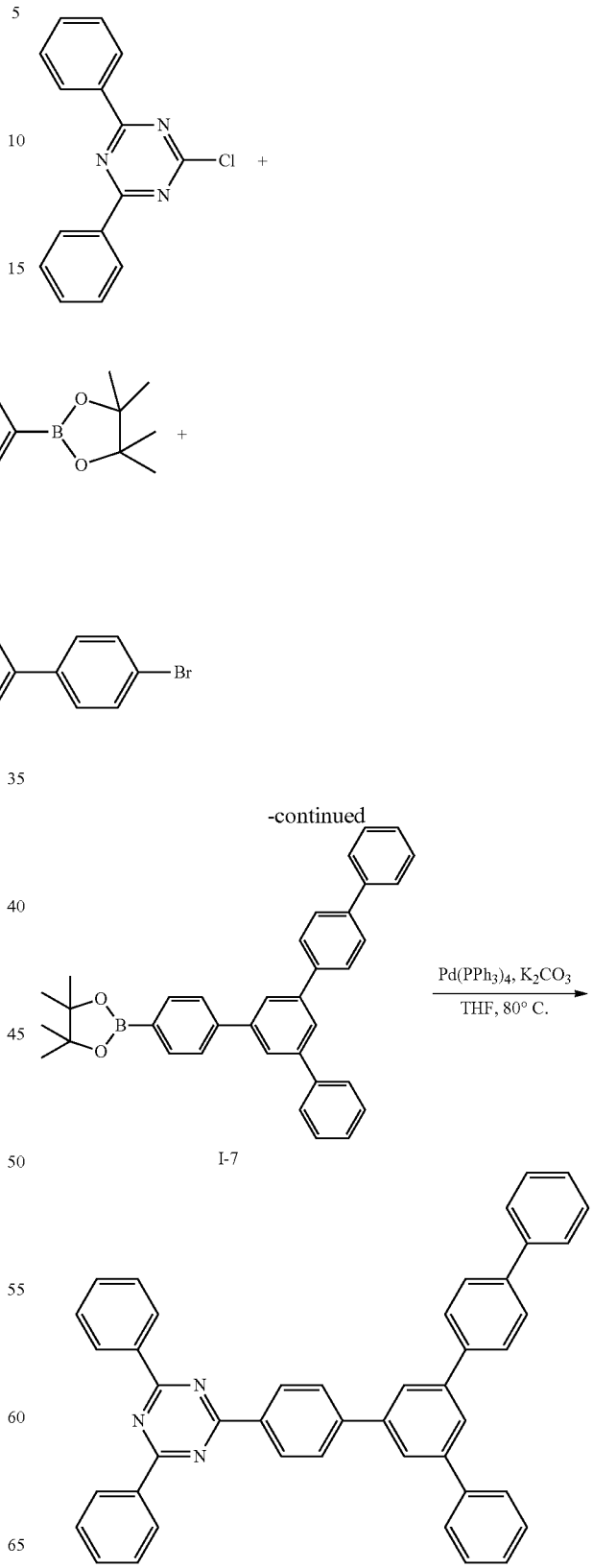

2-chloro-4,6-diphenyl-1,3,5-triazine of Shenzhen Gre-syn Chemical Technology Co., Ltd. (http://www.gre-syn.com/) (20 g, 74.7 mmol) was dissolved in 0.25 L of tetrahydrofuran (THF) under a nitrogen atmosphere, and the compound I-7 (38.0 g, 74.7 mmol) and tetrakis(triphenylphosphine)palladium (0.87 g, 0.75 mmol) were added thereto and then stirred. Potassium carbonate saturated in water (25.8 g, 187 mmol) was added thereto, and the obtained mixture was heated and refluxed at 80° C. for 17 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain a compound 1 (41.3 g, 90%).

HRMS (70 eV, EI+): m/z calcd for C45H31N3: 613.2518, found: 613.

Elemental Analysis: C, 88%; H, 5%.

Synthesis Example 31: Synthesis of Compound 9

2-chloro-4,6-diphenylpyrimidine of Shenzhen Gre-syn Chemical Technology Co., Ltd. (http://www.gre-syn.com/) (20 g, 75.0 mmol) was dissolved in 0.3 L of tetrahydrofuran (THF) under a nitrogen atmosphere, and the compound I-7 (38.1 g, 75.0 mmol) and tetrakis(triphenylphosphine)palladium (0.87 g, 0.75 mmol) were added thereto and then stirred. Potassium carbonate saturated in water (25.9 g, 188 mmol) was added thereto, and the obtained mixture was heated and refluxed at 80° C. for 15 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain a compound 9 (43.2 g, 94%).

HRMS (70 eV, EI+): m/z calcd for C46H32N2: 612.2565, found: 612.

Elemental Analysis: C, 90%; H, 5%.

Synthesis Example 32: Synthesis of Compound 10

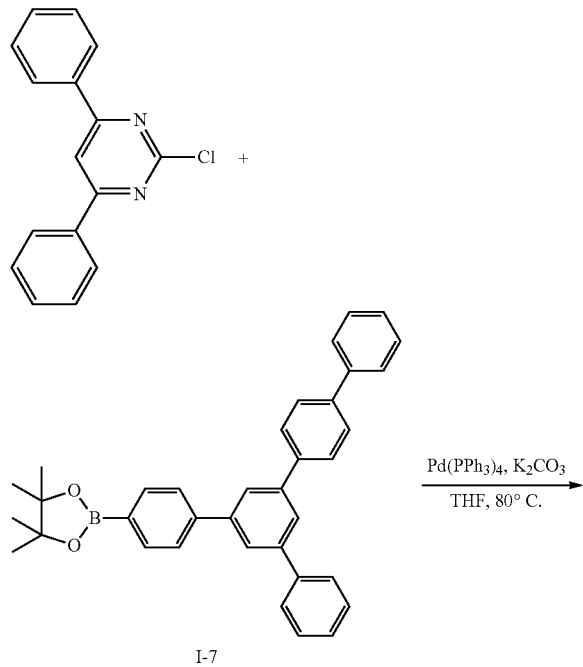

4-chloro-2,6-diphenylpyridine of Shenzhen Gre-syn Chemical Technology Co., Ltd. (http://www.gre-syn.com/) (20 g, 75.3 mmol) was dissolved in 0.3 L of tetrahydrofuran (THF) under a nitrogen atmosphere, and the compound I-7 (38.3 g, 75.3 mmol) and tetrakis(triphenylphosphine)palladium (0.87 g, 0.75 mmol) were added thereto and then stirred. Potassium carbonate saturated in water (26.0 g, 188 mmol) was added thereto, and the obtained mixture was heated and refluxed at 80° C. for 18 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound 10 (41.0 g, 89%).

HRMS (70 eV, EI+): m/z calcd for C47H33N: 611.2613, found: 611.

Elemental Analysis: C, 92%; H, 5%.

Synthesis Example 33: Synthesis of Compound 13

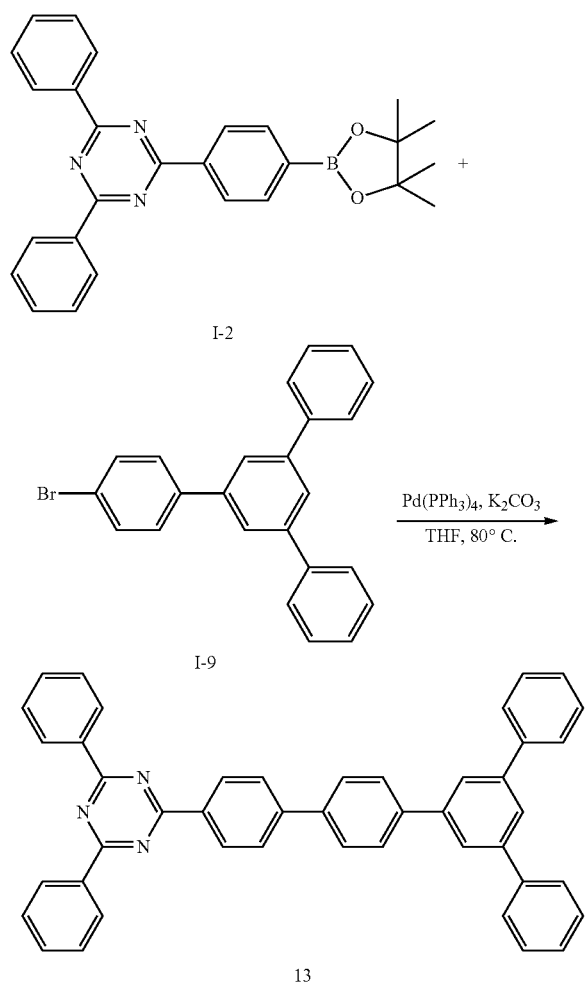

thereto and then stirred. Potassium carbonate saturated in water (15.9 g, 115 mmol) was added thereto, and the obtained mixture was heated and refluxed at 80° C. for 12 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound 13 (23.7 g, 84%).

HRMS (70 eV, EI+): m/z calcd for C45H31N3: 613.2518, found: 613.

Elemental Analysis: C, 88%; H, 5%.

Synthesis Example 34: Synthesis of Compound 16

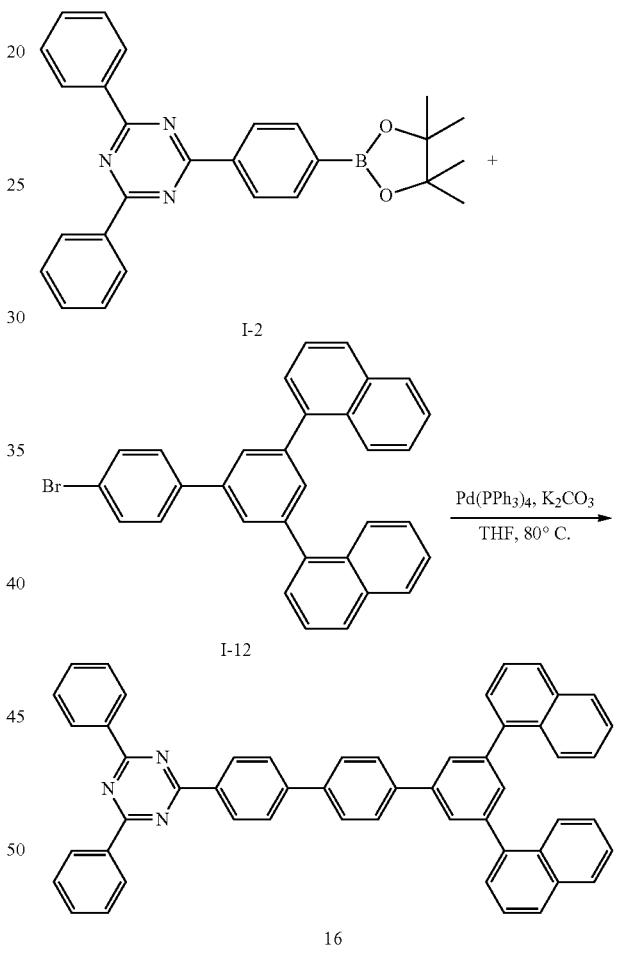

The compound I-2 (20 g, 45.9 mmol) was dissolved in 0.2 L of tetrahydrofuran (THF) under a nitrogen atmosphere, the compound I-9 (17.7 g, 45.9 mmol) and tetrakis(triphenylphosphine)palladium (0.53 g, 0.46 mmol) were added The compound I-2 (20 g, 45.9 mmol) was dissolved in 0.2 L of tetrahydrofuran (THF) 0.2 L under a nitrogen atmosphere, and the compound I-12 (22.3 g, 45.9 mmol) and tetrakis(triphenylphosphine)palladium (0.53 g, 0.46 mmol) were added thereto and then stirred. Potassium carbonate saturated in water (15.9 g, 115 mmol) was added thereto, and the obtained mixture was heated and refluxed at 80° C. for 15 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound 16 (27.9 g, 85%).

HRMS (70 eV, EI+): m/z calcd for C53H35N3: 713.2831, found: 713.

Elemental Analysis: C, 89%; H, 5%.

Synthesis Example 35: Synthesis of Compound 28

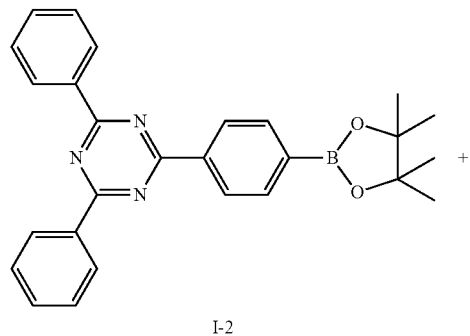

Synthesis Example 36: Synthesis of Compound 38

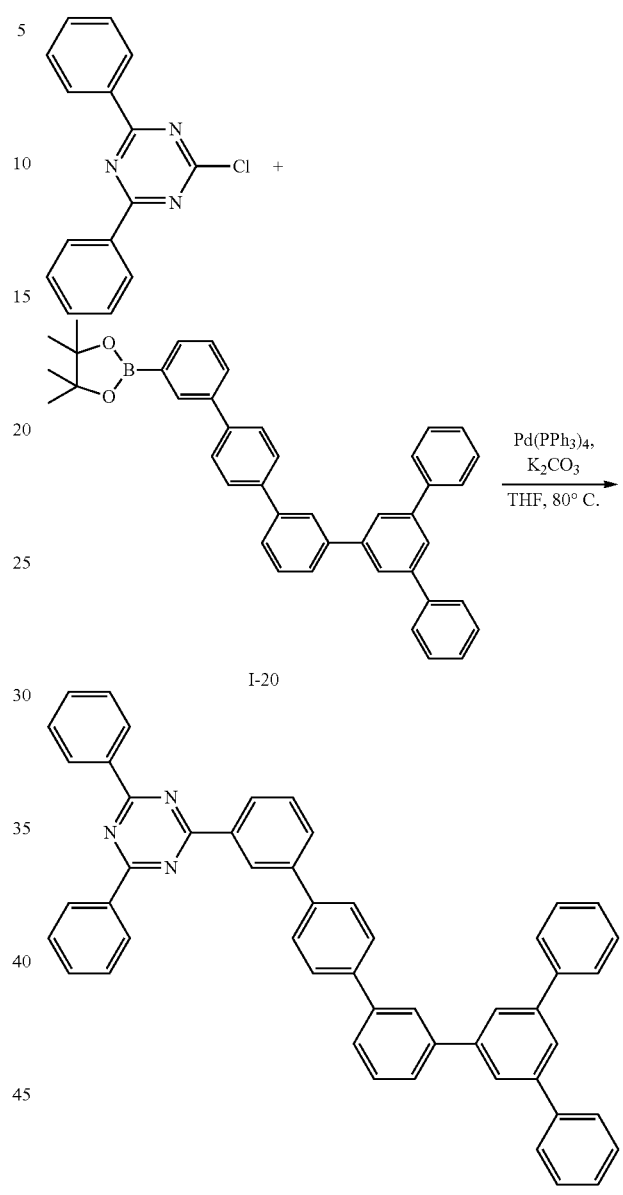

The compound I-2 (20 g, 45.9 mmol) was dissolved in 0.2 L of tetrahydrofuran (THF) under a nitrogen atmosphere, and the compound I-14 (21.2 g, 45.9 mmol) and tetrakis(triphenylphosphine)palladium (0.53 g, 0.46 mmol) were added thereto and then stirred. Potassium carbonate saturated in water (15.9 g, 115 mmol) was added thereto, and the obtained mixture was heated and refluxed at 80° C. for 15 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound 28 (25.6 g, 81%).

HRMS (70 eV, EI+): m/z calcd for C51H35N3: 689.2831, found: 689.

Elemental Analysis: C, 89%; H, 5%.

2-chloro-4,6-diphenyl-1,3,5-triazine of Shenzhen Gresyn Chemical Technology Co., Ltd. (http://www.gre-syn.com/) (6.87 g, 25.7 mmol) was dissolved in 0.11 L of tetrahydrofuran (THF) under a nitrogen atmosphere, and the compound I-20 (15.0 g, 25.7 mmol) and tetrakis(triphenylphosphine)palladium (0.30 g, 0.26 mmol) were added thereto and then stirred. Potassium carbonate saturated in water (8.88 g, 64.3 mmol) was added thereto, and the obtained mixture was heated and refluxed at 80° C. for 20 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound 38 (17.0 g, 96%).

HRMS (70 eV, EI+): m/z calcd for C51H35N3: 689.2831, found: 689.

Elemental Analysis: C, 89%; H, 5%.

Synthesis Example 37: Synthesis of Compound 40

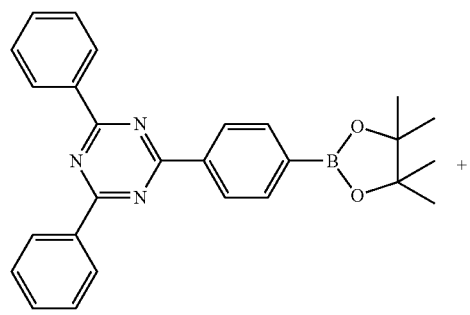

I-2

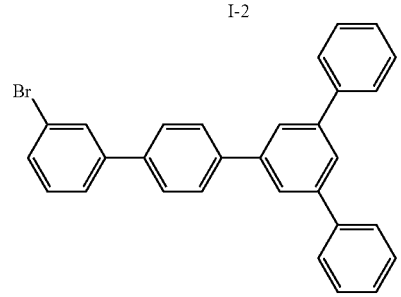

I-21

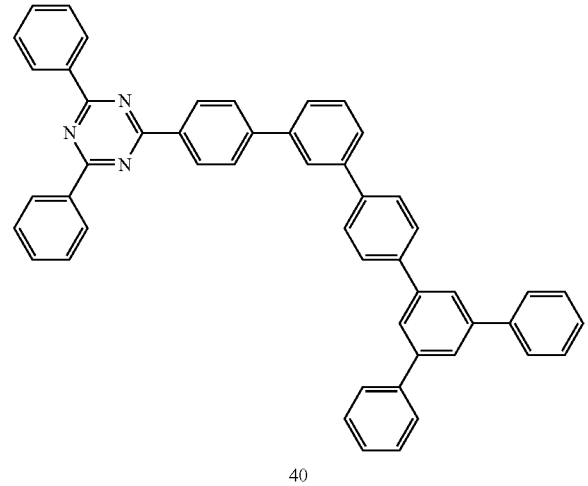

40

The compound I-2 (20 g, 45.9 mmol) was dissolved in 0.2 L of tetrahydrofuran (THF) under a nitrogen atmosphere, and the compound I-21 (21.2 g, 45.9 mmol) and tetrakis (triphenylphosphine)palladium (0.53 g, 0.46 mmol) were added thereto and then stirred. Potassium carbonate saturated in water (15.9 g, 115 mmol) was added thereto, and the obtained mixture was heated and refluxed at 80° C. for 17 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound 40 (25.3 g, 80%).

HRMS (70 eV, EI+): m/z calcd for C51H35N3: 689.2831, found: 689.

Elemental Analysis: C, 89%; H, 5%.

Synthesis Example 38: Synthesis of Compound 41

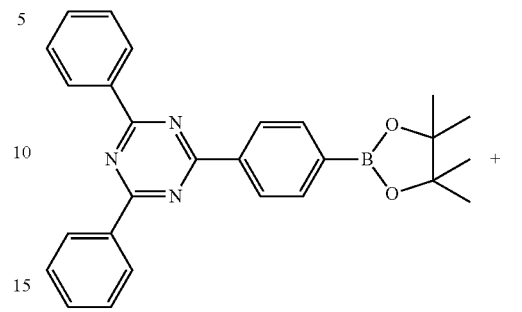

I-2

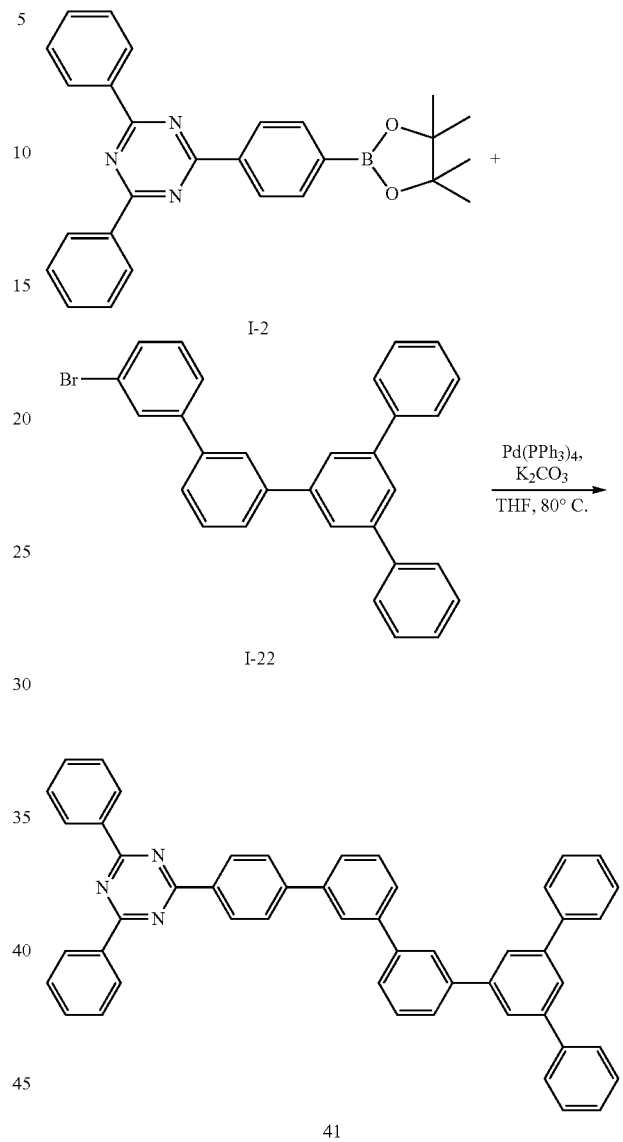

The compound I-2 (20 g, 45.9 mmol) was dissolved in 0.2 L of tetrahydrofuran (THF) under a nitrogen atmosphere, and the compound I-22 (21.2 g, 45.9 mmol) and tetrakis (triphenylphosphine)palladium (0.53 g, 0.46 mmol) were added thereto and then stirred. Potassium carbonate saturated in water (15.9 g, 115 mmol) was added thereto, and the obtained mixture was heated and refluxed at 80° C. for 15 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound 41 (27.2 g, 86%).

HRMS (70 eV, EI+): m/z calcd for C51H35N3: 689.2831, found: 689.

Elemental Analysis: C, 89%; H, 5%.

Comparative Synthesis Example 1: Synthesis of Compound Host 1

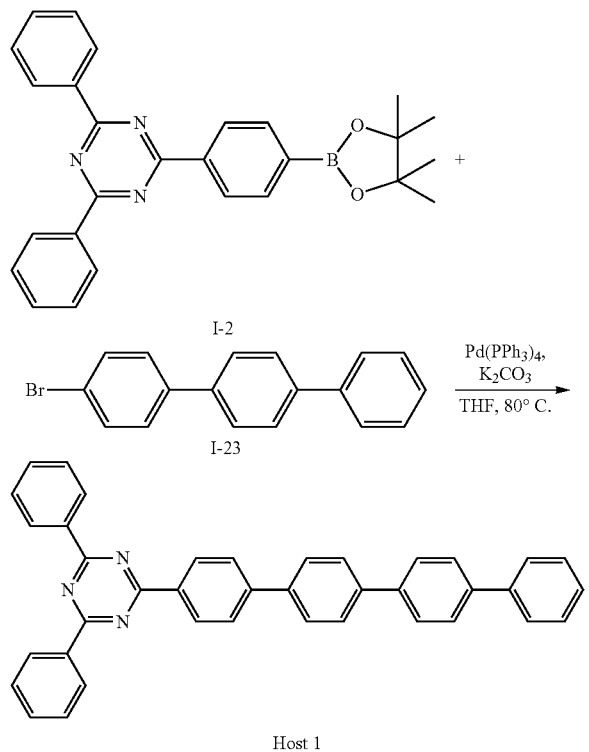

Host 1

The compound I-2 (20 g, 45.9 mmol) was dissolved in 0.17 L of tetrahydrofuran (THF) under a nitrogen atmosphere, and the compound I-23 (14.2 g, 45.9 mmol) and tetrakis(triphenylphosphine)palladium (0.53 g, 0.46 mmol) were added thereto and then stirred. Potassium carbonate saturated in water (15.9 g, 115 mmol) was added thereto, and the obtained mixture was heated and refluxed at 80° C. for 12 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound Host 1 (21.0 g, 85%).

HRMS (70 eV, EI+): m/z calcd for C39H27N3: 537.2205, found: 537.

Elemental Analysis: C, 87%; H, 5%.

Comparative Synthesis Example 2: Synthesis of Compound Host 2

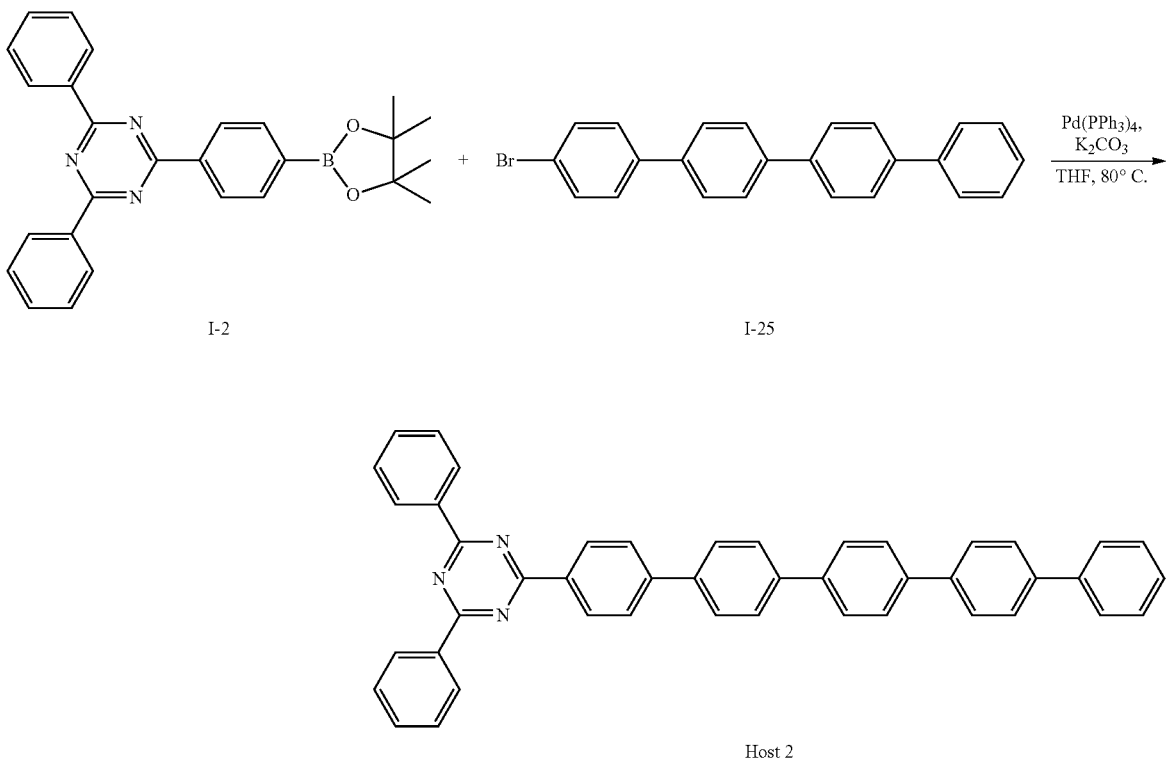

Host 2

The compound I-2 (20 g, 45.9 mmol) was dissolved in 0.11 L of tetrahydrofuran (THF) under a nitrogen atmosphere, and the compound I-25 (17.7 g, 45.9 mmol) and tetrakis(triphenylphosphine)palladium (0.53 g, 0.46 mmol) were added thereto and then stirred. Potassium carbonate saturated in water (15.9 g, 115 mmol) was added thereto, and the obtained mixture was heated and refluxed at 80° C. for 10 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound Host 2 (22.3 g, 79%).

HRMS (70 eV, EI+): m/z calcd for C45H31N3: 613.2518, found: 613.

Elemental Analysis: C, 88%; H, 5%.

Comparative Synthesis Example 3: Synthesis of Compound Host 3

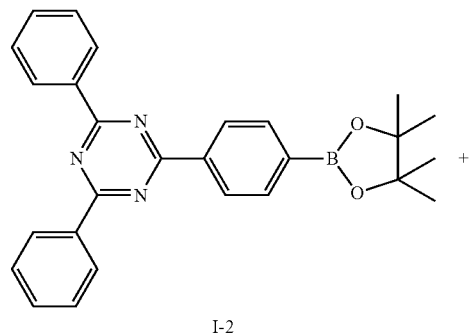
I-2

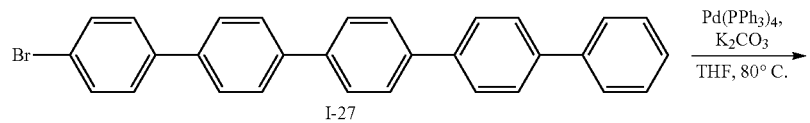
I-27

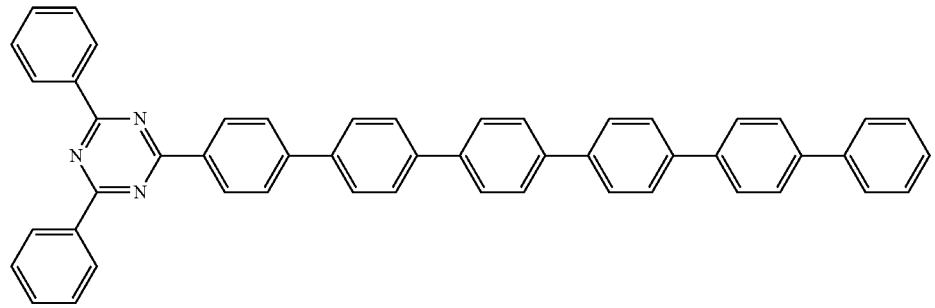
Host 3

The compound I-2 (20 g, 45.9 mmol) was dissolved in 0.21 L of tetrahydrofuran (THF) under a nitrogen atmosphere, and the compound I-27 (21.2 g, 45.9 mmol) and tetrakis(triphenylphosphine)palladium (0.53 g, 0.46 mmol) were added thereto and then stirred. Potassium carbonate saturated in water (15.9 g, 115 mmol) was added thereto, and the obtained mixture was heated and refluxed at 80° C. for 14 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound Host 3 (23.1 g, 73%).

HRMS (70 eV, EI+): m/z calcd for C51H35N3: 689.2831, found: 689.

Elemental Analysis: C, 89%; H, 5%.

Comparative Synthesis Example 4: Synthesis of Compound Host 4

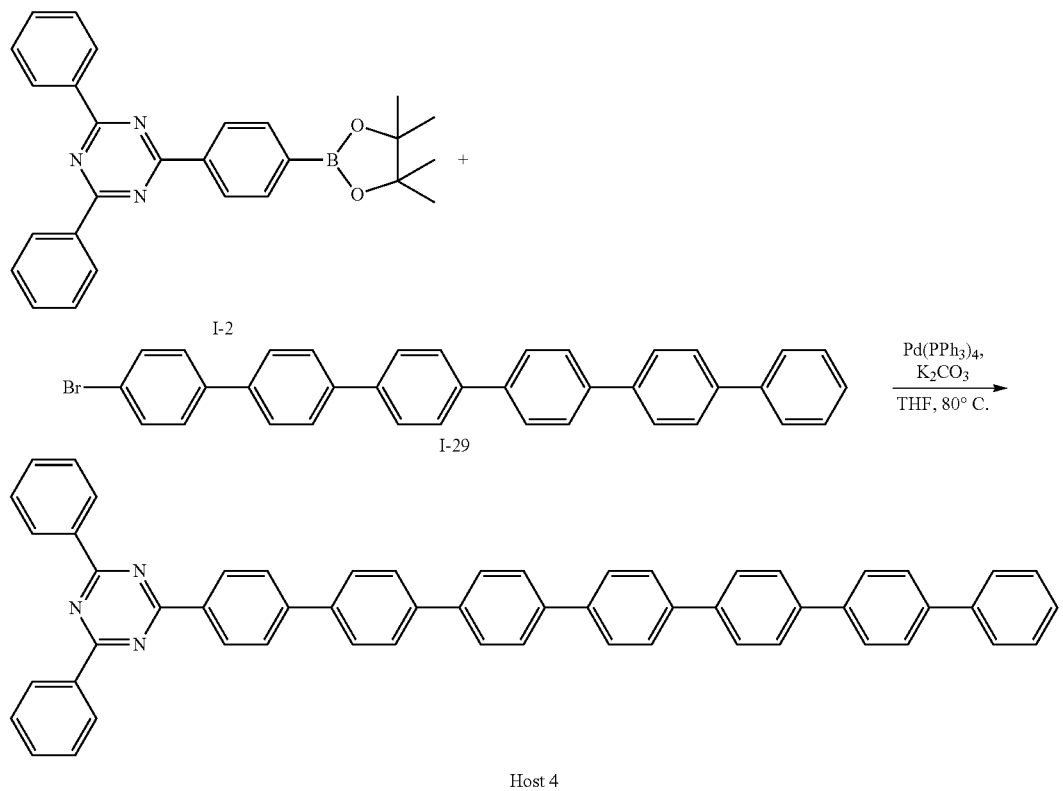

The compound I-2 (10 g, 23.0 mmol) was dissolved in 0.21 L of tetrahydrofuran (THF) under a nitrogen atmosphere, and the compound I-29 (12.4 g, 23.0 mmol) and tetrakis(triphenylphosphine)palladium (0.27 g, 0.23 mmol) were added thereto and then stirred. Potassium carbonate saturated in water (8.0 g, 58.0 mmol) was added thereto, and the obtained mixture was heated and refluxed at 80° C. for 12 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound Host 4 (11.8 g, 67%).

HRMS (70 eV, EI+): m/z calcd for C57H39N3: 765.3144, found: 765.

Elemental Analysis: C, 89%; H, 5%.

Manufacture of Organic Light Emitting Diode

Example 1

An organic light emitting diode was manufactured by using the compound 1 of Synthesis Example 30 as a host and Ir(PPy)$_3$ as a dopant.

As for an anode, 1000 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of a sheet resistance into a size of 50 mm×50 mm×0.7 mm, ultrasonic wave-cleaning them in acetone, isopropylalcohol, and pure water for 15 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) (80 nm) under a vacuum degree 650×10$^{-7}$ Pa at a deposition rate of 0.1 to 0.3 nm/s. Subsequently, A 300 Å-thick emission layer was formed by using the compound 1 of Synthesis Example 30 under the same vacuum deposition condition, and herein, a phosphorescent dopant of Ir(PPy)$_3$ was simultaneously deposited. Herein, the phosphorescent dopant was deposited to be 7 wt % based on 100 wt % of the total weight of the emission layer by adjusting the deposition rate.

On the emission layer, a 50 Å-thick hole blocking layer was formed by depositing bis(2-methyl-8-quinolinolate)-4-(phenylphenolato)aluminium (BAlq) under the same vacuum deposition condition. Subsequently, a 200 Å-thick electron transport layer (ETL) was formed by depositing Alq3 under the same vacuum deposition condition. On the electron transport layer (ETL), a cathode is formed by sequentially depositing LiF and Al to manufacture an organic photoelectric device.

The organic photoelectric device has a structure of ITO/NPB (80 nm)/EML (compound 1 (93 wt %)+Ir(PPy)$_3$ (7 wt %), 30 nm)/Balq (5 nm)/Alq3 (20 nm)/LiF (1 nm)/Al (100 nm).

Example 2

An organic light emitting diode was manufactured according to the same method as Example 1 except that the compound 9 of Synthesis Example 31 was used instead of the compound 1 of Synthesis Example 30.

Example 3

An organic light emitting diode was manufactured according to the same method as Example 1 except that the compound 10 of Synthesis Example 32 was used instead of the compound 1 of Synthesis Example 30.

Example 4

An organic light emitting diode was manufactured according to the same method as Example 1 except that the compound 13 of Synthesis Example 33 was used instead of the compound 1 of Synthesis Example 30.

Example 5

An organic light emitting diode was manufactured according to the same method as Example 1 except that the compound 16 of Synthesis Example 34 was used instead of the compound 1 of Synthesis Example 30.

Example 6

An organic light emitting diode was manufactured according to the same method as Example 1 except that the compound 28 of Synthesis Example 35 was used instead of the compound 1 of Synthesis Example 30.

Example 7

An organic light emitting diode was manufactured according to the same method as Example 1 except that the compound 38 of Synthesis Example 36 was used instead of the compound 1 of Synthesis Example 30.

Example 8

An organic light emitting diode was manufactured according to the same method as Example 1 except that the compound 40 of Synthesis Example 37 was used instead of the compound 1 of Synthesis Example 30.

Example 9

An organic light emitting diode was manufactured according to the same method as Example 1 except that the compound 41 of Synthesis Example 38 was used instead of the compound 1 of Synthesis Example 30.

Comparative Example 1

An organic light emitting diode was manufactured according to the same method as Example 1 except that CBP was used instead of the compound 1 of Synthesis Example 30.

Comparative Example 2

An organic light emitting diode was manufactured according to the same method as Example 1 except that HOST 1 of Comparative Synthesis Example 1 was used instead of the compound 1 of Synthesis Example 30.

Comparative Example 3

An organic light emitting diode was manufactured according to the same method as Example 1 except that HOST 2 of Comparative Synthesis Example 2 was used instead of the compound 1 of Synthesis Example 30.

Comparative Example 4

An organic light emitting diode was manufactured according to the same method as Example 1 except that HOST 3 of Comparative Synthesis Example 3 was used instead of the compound 1 of Synthesis Example 30.

Comparative Example 5

An organic light emitting diode was manufactured according to the same method as Example 1 except that HOST 4 of Comparative Synthesis Example 4 was used instead of the compound 1 of Synthesis Example 30.

The structures of NPB, BAlq, CBP, and Ir(PPy)$_3$ used to manufacture the organic light emitting diodes are as follows.

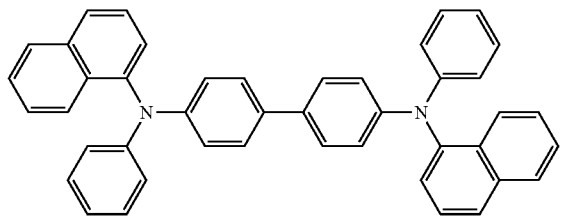

[NPB]

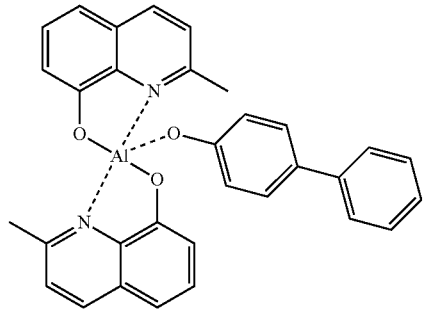

[BAlq]

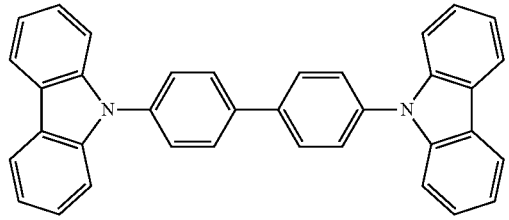

[CBP]

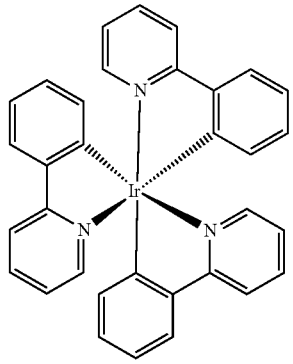

[Ir(PPy)$_3$]

Evaluation 1

Current density and luminance changes depending on a voltage and luminous efficiency of each organic light emitting diode according to Examples 1 to 9 and Comparative Examples 1 to 5 were measured.

The measurements were specifically performed in the following methods, and the results are shown in Table 1.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm2) was calculated by using the luminance, current density, and voltages (V) from the items (1) and (2).

(4) Measurement of Life-Span

Life-span was obtained by measuring time taken until current efficiency (cd/A) decreased down to 90% while luminance (cd/m2) was maintained at 5000 cd/m$^2$.

TABLE 1

| No. | Compounds | Driving voltage (V) | Color (EL color) | Efficiency (cd/A) | 90% life-span (h) at 5000 cd/m$^2$ |
|---|---|---|---|---|---|
| Example 1 | compound 1 | 3.8 | Green | 85.1 | 1,000 |
| Example 2 | compound 9 | 4.0 | Green | 83.5 | 950 |
| Example 3 | compound 10 | 4.2 | Green | 80.5 | 860 |
| Example 4 | compound 13 | 3.9 | Green | 85.2 | 1,190 |
| Example 5 | compound 16 | 4.3 | Green | 93.0 | 1,250 |
| Example 6 | compound 28 | 4.0 | Green | 88.1 | 1,420 |
| Example 7 | compound 38 | 4.4 | Green | 82.6 | 1,930 |
| Example 8 | compound 40 | 4.2 | Green | 83.5 | 1,670 |
| Example 9 | compound 41 | 4.5 | Green | 81.0 | 2,000 |
| Comparative Example 1 | CBP | 4.8 | Green | 31.4 | 40 |
| Comparative Example 2 | HOST 1 | 4.6 | Green | 95.1 | 80 |
| Comparative Example 3 | HOST 2 | 3.9 | Green | 99.7 | 210 |
| Comparative Example 4 | HOST 3 | 5.0 | Green | 95.5 | 60 |
| Comparative Example 5 | HOST 4 | 5.3 | Green | 69.5 | 10 |

Referring to 1, the organic light emitting diodes according to Examples 1 to 9 exhibited equivalent or excellent driving voltage and efficiency and also, exhibited remarkably improved life-span characteristics compared with the organic light emitting diodes according to Comparative Examples 1 to 5.

Evaluation 2

Each deposition temperature, glass transition temperature (Tg), and purities at room temperature and a high temperature of the compound 28 of Synthesis Example 35, the compound 38 of Synthesis Example 36, the compound 40 of Synthesis Example 37, the compound 41 of Synthesis Example 38, the HOST1 of Comparative Synthesis Example 1, the HOST2 of Comparative Synthesis Example 2, the HOST3 of Comparative Synthesis Example 3, and the HOST4 of Comparative Synthesis Example 4 was measured.

The measurements were specifically performed in the following methods, and the results are shown in Table 2.

(1) Deposition Temperature (° C.)

A deposition temperature indicates a temperature at which a host of an emission layer was deposited during manufacture of the organic light emitting diode according to Example 1 and specifically, a 1 Å-thick emission layer per 1 second (A/sec) was deposited.

(2) Glass Transition Temperature (Tg)

An energy input difference was measured as a function of a temperature by changing temperatures of a sample and a reference with a DSC1 equipment made by Metter teledo Inc.

(3) Purity at Room Temperature (%)

HPLC made by Waters (Model No.: Alliance e2695—4 gradient pump) and PDA (Model No.: 2994) made by Waters were used. As for a column, Symmetry C18 (3.9×150 mm, 5 μm) was used.

(4) Purity at High Temperature (%)

1 g of sample taken from the compounds was put in a glass vessel, filled with nitrogen, and the glass vessel was closed and sealed. The glass vessel was stored in a 200° C. oven for 200 hours, and the purity of the compound sample at a high temperature was measured in the same method as purity at room temperature.

TABLE 2

| Nos. | Deposition temperature (° C.) | Tg (° C.) | Purity at room temperature (%) | Purity at high temperature (%) | Deposition temperature (° C.) |
|---|---|---|---|---|---|
| Compound 28 | 208.2 | 117 | 100 | 99.98 | 0.02 |
| Compound 38 | 205.3 | 109 | 100 | 99.99 | 0.01 |
| Compound 40 | 203.9 | 107 | 100 | 99.99 | 0.01 |
| Compound 41 | 204.0 | 105 | 100 | 99.98 | 0.02 |
| HOST 1 | 190.8 | 61.0 | 100 | 99.95 | 0.05 |
| HOST 2 | 210.1 | 66.5 | 100 | 99.95 | 0.05 |
| HOST 3 | 230.5 | 76.3 | 100 | 98.83 | 1.17 |
| HOST 4 | 253.2 | 88.5 | 100 | 98.50 | 1.5 |

Referring to Table 2, the compound 28 according to Synthesis Example 35, the compound 38 according to Synthesis Example 36, the compound 40 according to Synthesis Example 37, and the compound 41 according to Synthesis Example 38 had a high glass transition temperature (Tg) of greater than or equal to about 90° C., but HOST's 1, 2, 3 and 4 had a lower glass transition temperature (Tg) than the temperature.

The glass transition temperature (Tg) may be related to thermal stability of the compounds and a device manufactured by using the same. In other words, when the compounds are applied in a form of a thin film to an organic light emitting diode, the thin film may be expected to be damaged and thus sharply reduce life-span of the organic light emitting diode in a subsequent process after depositing the compounds, for example, an encapsulation process around the glass transition temperature (Tg) or at a higher temperature than the glass transition temperature (Tg).

In order to compensate the glass transition temperature (Tg) of HOST 1, when the number of phenyl group is increased like HOST2, HOST 3, and HOST 4, the glass transition temperature (Tg) is not much increased, but their deposition temperatures are rather increased, deteriorating thermal stability of the compounds. In other words, since the HOST 1 and the HOST 2 have a low glass transition temperature (Tg), a thin film formed thereof may be expected to be damaged in a subsequent process, and the HOST 3 and the HOST 4 have a much increased deposition temperature and an influence on purity at a high temperature ant thus may be expected to sharply deteriorate life-span of a device.

On the other hand, the compound 28 according to Synthesis Example 35, the compound 38 according to Synthesis Example 36, the compound 40 according to Synthesis Example 37, and the compound 41 according to Synthesis Example 38 have a high glass transition temperature (Tg) but not much high deposition temperature and thus may improve high temperature stability.

Synthesis of Second Organic Compound
Synthesis of Intermediate

Synthesis Example 1 of Second Organic Compound: Synthesis of Intermediate I-30

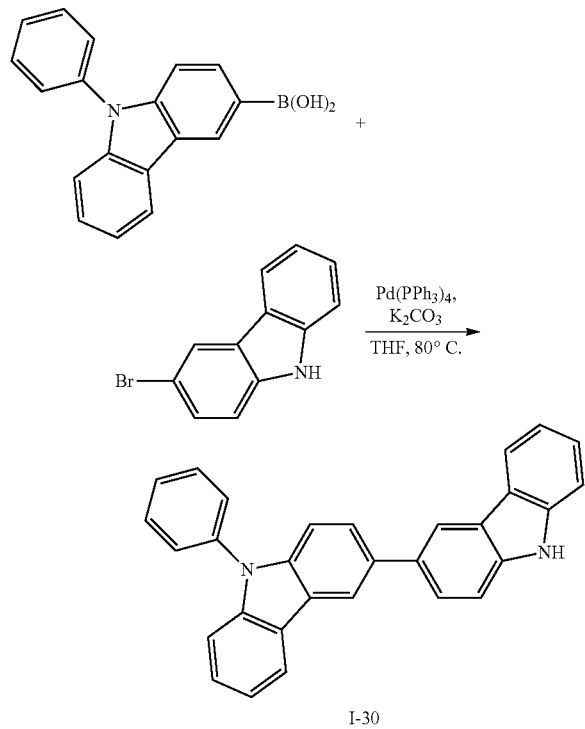

9-phenyl-9H-carbazol-3-ylboronic acid (100 g, 348 mmol) was dissolved in 0.93 L of tetrahydrofuran (THF) under a nitrogen atmosphere, and a 3-bromo-9H-carbazole (85.6 g, 348 mmol) and tetrakis(triphenylphosphine)palladium (4.02 g, 3.48 mmol) were added thereto and then stirred. Potassium carbonate saturated in water (120 g, 870 mmol) was added thereto, and the obtained mixture was heated and refluxed at 80° C. for 10 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound I-30 (85.3 g, 60%).

HRMS (70 eV, EI+): m/z calcd for C30H20N2: 408.1626, found: 408.

Elemental Analysis: C, 88%; H, 5%.

Synthesis Example 2 of Synthesis of Second Organic Compound: Synthesis of Intermediate I-31

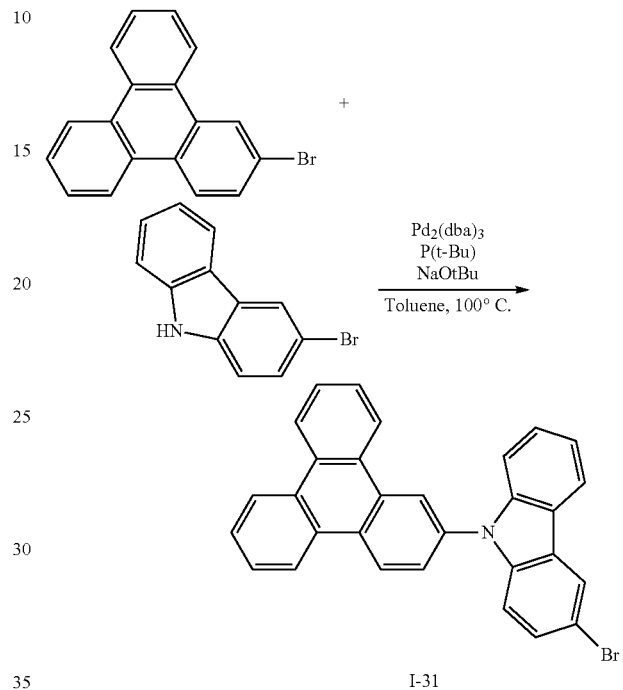

2-bromotriphenylene (100 g, 326 mmol) was dissolved in 0.18 L of toluene under a nitrogen atmosphere, and 3-bromo-9H-carbazole (80.1 g, 326 mmol), tris(diphenylideneacetone)dipalladium(o) (2.99 g, 3.26 mmol), tris-tert butylphosphine (2.64 g, 13.0 mmol), and sodium tert-butoxide (37.6 g, 391 mmol) were sequentially added, and the obtained mixture was heated and refluxed at 100° C. for 15 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound I-31 (109 g, 71%).

HRMS (70 eV, EI+): m/z calcd for C30H18BrN: 471.0623, found: 471.

Elemental Analysis: C, 76%; H, 4%.

Synthesis Example 3 of Second Organic Compound: Synthesis of Intermediate I-32

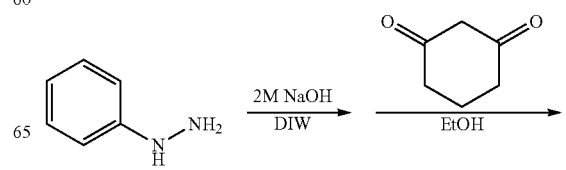

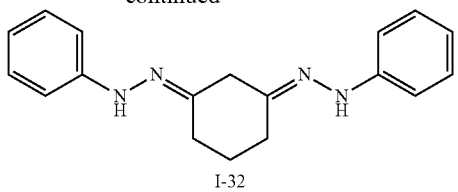

I-32

Phenylhydrazine hydrochloride (100 g, 925 mmol) was dissolved in 0.5 L of distilled water under a nitrogen atmosphere, and a 2 M NaOH aqueous solution was added thereto. Then, a solid produced therein was filtered to obtain phenylhydrazine. Subsequently, cyclohexane-1,3-dione (51.8 g, 462 mmol) dissolved in 1.0 L of ethanol was slowly added to the phenylhydrazine, and the mixture was reacted for 20 minutes. When the reaction was complete, ice water was added thereto. Then, a solid produced therein was filtered, while washed with ethanol. The solid was dried under a reduced pressure to obtain a compound I-32 (108 g, 40%).

HRMS (70 eV, EI+): m/z calcd for C18H20N4: 292.1688, found: 292.

Elemental Analysis: C, 74%; H, 7%.

Synthesis Example 4 of Second Organic Compound: Synthesis of Intermediate I-33

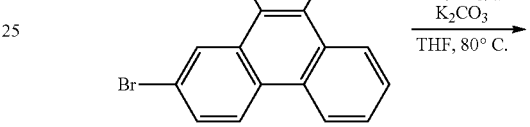

I-32

I-33

The compound I-32 (100 g, 342 mmol) was slowly added to 0.5 L of a mixed solution of acetic acid and sulfuric acid (1:4) under a nitrogen atmosphere at 0° C. After stirring the mixture for 5 minutes, the mixture was heated up to 50° C. and then, slowly heated up to 110° C. After 20 minutes, the heated mixture was cooled down to room temperature and stirred for 12 hours. Then, 0.5 L of ethanol was added thereto, and a solid produced therein was filtered under a reduced pressure and neutralized. The neutralized solid was dried under a reduced pressure to obtain the compound I-33 (43.8 g, 50%).

HRMS (70 eV, EI+): m/z calcd for C18H12N2: 256.1000, found: 256.

Elemental Analysis: C, 84%; H, 5%.

Synthesis of Final Compound

Synthesis Example 5 of Second Organic Compound: Synthesis of Compound B-1

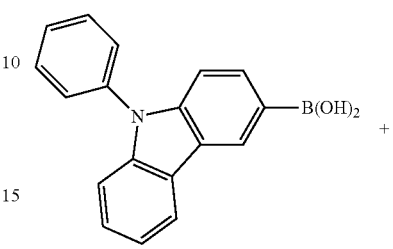

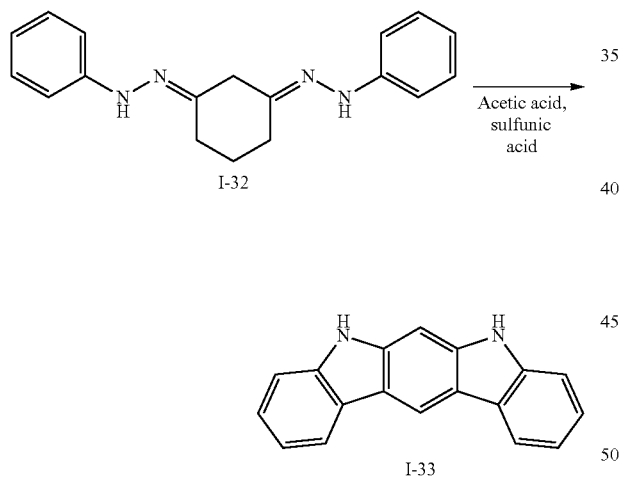

B-1

9-phenyl-9H-carbazol-3-ylboronic acid (20 g, 69.7 mmol) was dissolved in 0.21 L of tetrahydrofuran (THF) under a nitrogen atmosphere, and 2-bromotriphenylene (21.4 g, 69.7 mmol) and tetrakis(triphenylphosphine)palladium (0.81 g, 0.70 mmol) were added thereto and then stirred. Potassium carbonate saturated in water (24.1 g, 174 mmol) was added thereto, and the obtained mixture was heated and refluxed at 80° C. for 8 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain a compound B-1 (29.5 g, 90%).

HRMS (70 eV, EI+): m/z calcd for C36H23N: 469.1830, found: 469.

Elemental Analysis: C, 92%; H, 5%.

Synthesis Example 6 of Second Organic Compound: Synthesis of Compound B-10

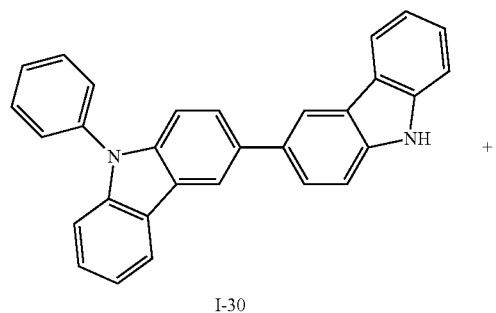

I-30

+

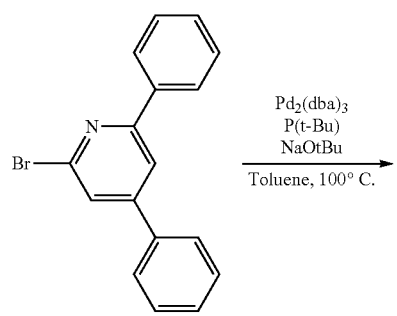

Pd₂(dba)₃
P(t-Bu)
NaOtBu
———————→
Toluene, 100° C.

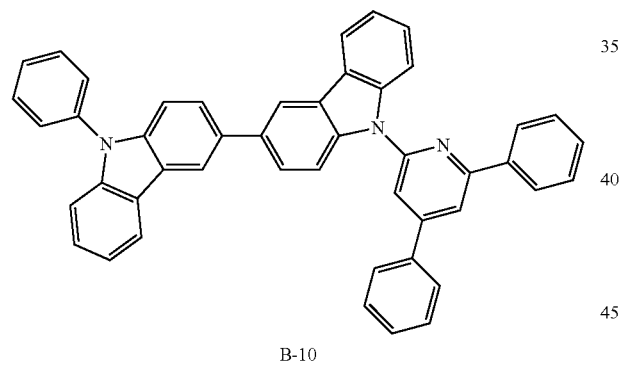

B-10

A compound I-30 (20 g, 49.0 mmol) was dissolved in 0.18 L of toluene under a nitrogen atmosphere, 2-bromo-4,6-diphenylpyridine of Amadis Chemical Co., Ltd. (http://www.amadischem.com/) (15.1 g, 49.0 mmol), tris(diphenylideneacetone)dipalladium(o) (0.45 g, 0.49 mmol), tris-tert butylphosphine (0.40 g, 1.96 mmol), and sodium tert-butoxide (5.65 g, 58.8 mmol) were sequentially added and the obtained mixture was heated and refluxed at 100° C. for 18 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound B-10 (31.3 g, 77%).

HRMS (70 eV, EI+): m/z calcd for C47H31N3: 637.2518, found: 637.

Elemental Analysis: C, 89%; H, 5%.

Synthesis Example 7 of Second Organic Compound: Synthesis of Compound B-31

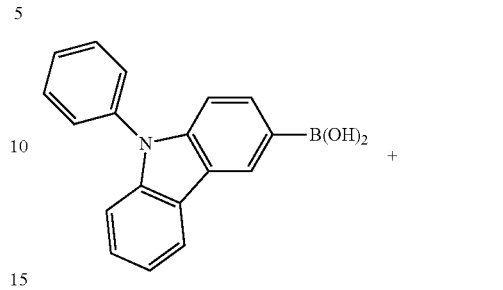

+

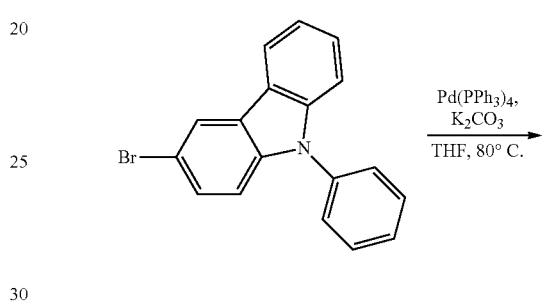

Pd(PPh₃)₄,
K₂CO₃
———————→
THF, 80° C.

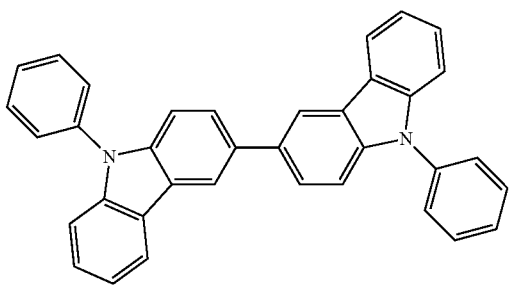

B-31

9-phenyl-9H-carbazol-3-ylboronic acid (20 g, 69.7 mmol) was dissolved in 0.21 L of tetrahydrofuran (THF) under a nitrogen atmosphere, and 3-bromo-9-phenyl-9H-carbazole (22.5 g, 69.7 mmol) and tetrakis(triphenylphosphine)palladium (0.81 g, 0.70 mmol) were added thereto and then stirred. Potassium carbonate saturated in water (24.1 g, 174 mmol) was added thereto, and the obtained mixture was heated and refluxed at 80° C. for 12 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain a compound B-31 (31.1 g, 92%).

HRMS (70 eV, EI+): m/z calcd for C36H24N2: 484.1939, found: 484.

Elemental Analysis: C, 89%; H, 5%.

Synthesis Example 8 of Second Organic Compound: Synthesis of Compound B-34

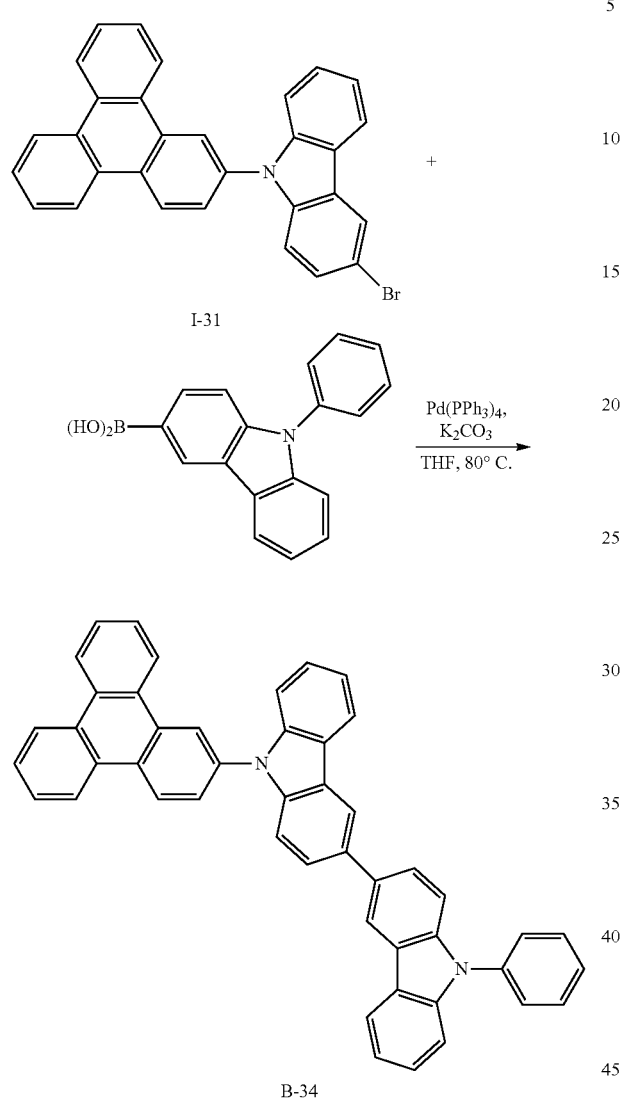

A compound I-31 (20 g, 42.3 mmol) was dissolved in 0.16 L of tetrahydrofuran (THF) under a nitrogen atmosphere, and 9-phenyl-9H-carbazol-3-ylboronic acid (12.1 g, 42.3 mmol) and tetrakis(triphenylphosphine)palladium (0.49 g, 0.42 mmol) were added thereto and then stirred. Potassium carbonate saturated in water (14.7 g, 106 mmol) was added thereto, and the obtained mixture was heated and refluxed at 80° C. for 16 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain a compound B-34 (22.8 g, 85%).

HRMS (70 eV, EI+): m/z calcd for $C_{48}H_{30}N_2$: 634.2409, found: 634.

Elemental Analysis: C, 91%; H, 5%.

Synthesis Example 9 of Second Organic Compound: Synthesis of Compound B-43

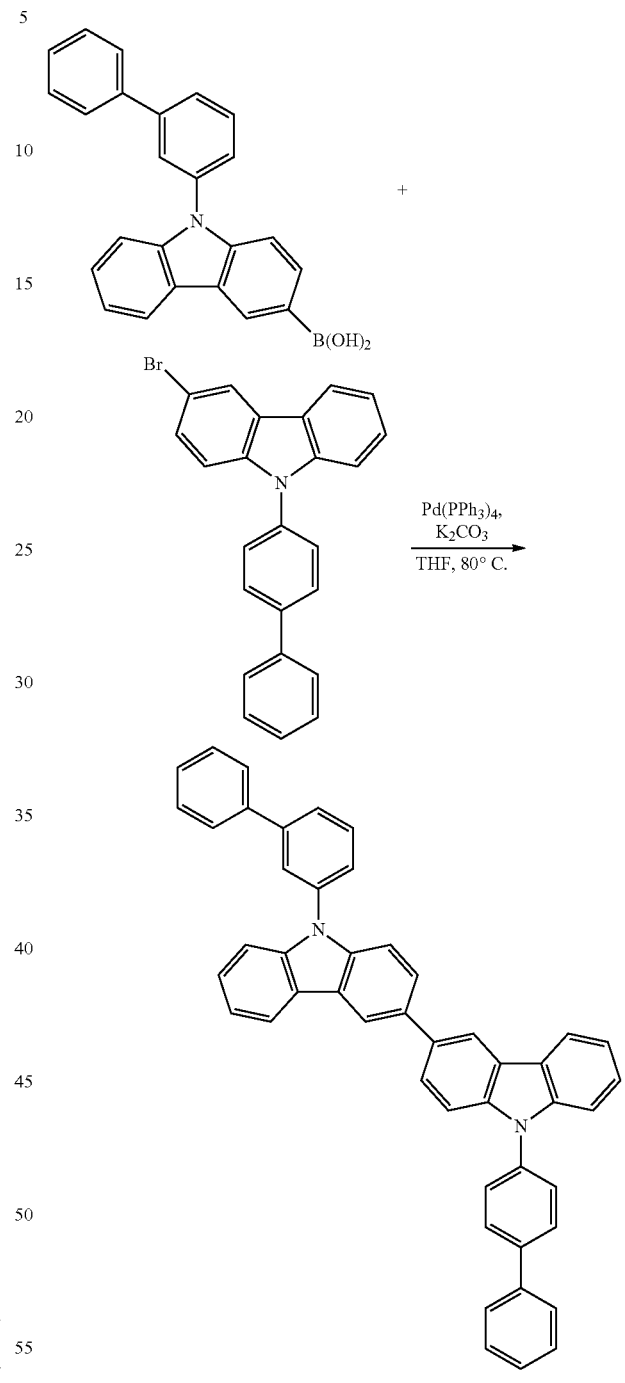

9-(biphenyl-3-yl)-9H-carbazol-3-ylboronic acid of Amadis Chemical Co., Ltd. (http://www.amadischem.com/) (20 g, 55.1 mmol) was dissolved in 0.21 L of tetrahydrofuran (THF) 0.21 L under a nitrogen atmosphere, 9-(biphenyl-4-yl)-3-bromo-9H-carbazole of Amadis Chemical Co., Ltd. (21.9 g, 55.1 mmol) and tetrakis(triphenylphosphine)palladium (0.64 g, 0.55 mmol) were added thereto and then stirred. Potassium carbonate saturated in water (19.0 g, 138 mmol) was added thereto, and the obtained mixture was heated and refluxed at 80° C. for 18 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound B-43 (33.7 g, 96%).

HRMS (70 eV, EI+): m/z calcd for C48H32N2: 636.2565, found: 636.

Elemental Analysis: C, 91%; H, 5%.

Synthesis Example 10 of Second Organic Compound: Synthesis of Compound E-1

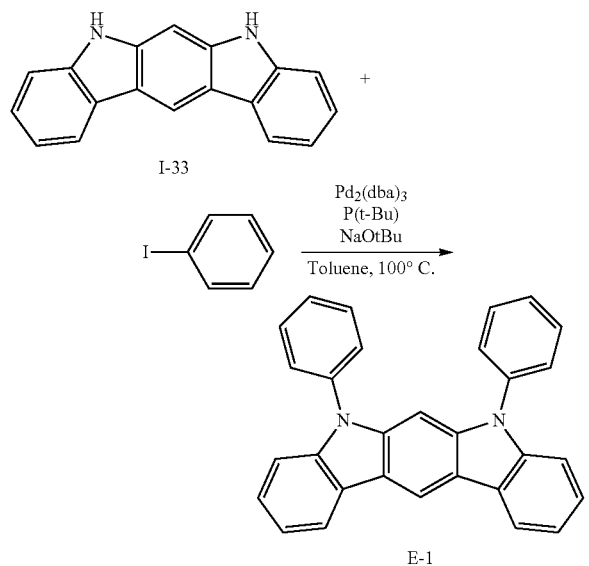

A compound I-33 (20 g, 78.0 mmol) was dissolved in 0.26 L of toluene under a nitrogen atmosphere, and iodobenzene (31.8 g, 156 mmol), tris(diphenylideneacetone)dipalladium (o) (0.71 g, 0.78 mmol), tris-tert butylphosphine (0.63 g, 3.12 mmol), and sodium tert-butoxide (8.99 g, 93.6 mmol) were sequentially added, and the obtained mixture was heated and refluxed at 100° C. for 10 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain a compound E-1 (25.5 g, 80%).

HRMS (70 eV, EI+): m/z calcd for C30H20N2: 408.1626, found: 408.

Elemental Analysis: C, 88%; H, 5%.
Manufacture of Organic Light Emitting Diode

Example 10

ITO (indium tin oxide) was coated to be 1500 Å thick on a glass substrate, and the coated glass was ultrasonic wave-washed with a distilled water. After washing with distilled water, the washed glass substrate was ultrasonic wave-washed with a solvent such as isopropyl alcohol, acetone, methanol, and the like was moved to a plasma cleaner to clean the substrate by using oxygen plasma for 10 minutes and moved to a vacuum depositor. This ITO transparent electrode was used as an anode, N4,N4'-diphenyl-N4,N4'-bis (9-phenyl-9H-carbazol-3-yl)biphenyl-4,4'-diamine (compound A) was vacuum-deposited on the ITO substrate to form a 700 Å-thick hole injection layer, 1,4,5,8,9,11-hexaazatriphenylene-hexacarbonitrile (HAT-CN) (compound B) was deposited in a 50 Å thickness on the injection layer, and N-(biphenyl-4-yl)-9,9-dimethyl-N-(4-(9-phenyl-9H-carbazol-3-yl)phenyl)-9H-fluoren-2-amine (compound C) was deposited in a 1020 Å thickness to form a hole transport layer. The compound 41 of Synthesis Example 38 and the compound B-1 of Synthesis Example 5 of Second Organic Compound were simultaneously used as a host, and 10 wt % of tris(2-phenylpyridine)iridium (III) [Ir(ppy)$_3$] was doped by vacuum deposition to form a 400 Å-thick emission layer on the hole transport layer. Herein, the compound 41 and the compound B-1 were used in a ratio of 4:1. Subsequently, on the emission layer, 8-(4-(4,6-di(naphthalen-2-yl)-1,3,5-triazin-2-yl)phenyl)quinolone (compound D) and Liq were simultaneously vacuum-deposited in a ratio of 1:1 to form a 300 Å-thick electron transport layer, and 15 Å Liq and 1200 Å Al were sequentially vacuum-deposited on the electron transport layer to form a cathode to manufacture an organic light emitting diode.

The organic light emitting diode has a structure including five-layered organic thin layers, and specifically the following structure.

The structure is ITO/Compound A 700 Å/Compound B 50 Å/Compound C 1020 Å/EML [Compound 41:Compound B-1:Ir(ppy)3=X:X:10%] 400 Å/compound D:Liq 300 Å/Liq 15 Å/Al 1200 Å. (X=a weight ratio)

Example 11

An organic light emitting diode was manufactured according to the same method as Example 10 except that the compound 41 and compound B-1 were used in a ratio of 1:1.

Example 12

An organic light emitting diode was manufactured according to the same method as Example 10 except that the compound 41 and compound B-1 were used in a ratio of 1:4.

Example 13

An organic light emitting diode was manufactured according to the same method as Example 10 except that the compound B-10 of Synthesis Example 6 of Second Organic Compound was used instead of the compound B-1.

Example 14

An organic light emitting diode was manufactured according to the same method as Example 13 except that the compound 41 and compound B-10 were used in a ratio of 1:1.

Example 15

An organic light emitting diode was manufactured according to the same method as Example 13 except that the compound 41 and compound B-10 were used in a ratio of 1:4.

Example 16

An organic light emitting diode was manufactured according to the same method as Example 10 except that the compound B-31 of Synthesis Example 7 of Second Organic Compound was used instead of the compound B-1.

Example 17

An organic light emitting diode was manufactured according to the same method as Example 16 except that the compound 41 and compound B-31 were used in a ratio of 1:1.

Example 18

An organic light emitting diode was manufactured according to the same method as Example 10 except that the compound B-34 of Synthesis Example 8 of Second Organic Compound was used instead of the compound B-1.

Example 19

An organic light emitting diode was manufactured according to the same method as Example 18 except that the compound 41 and compound B-34 were used in a ratio of 1:1.

Example 20

An organic light emitting diode was manufactured according to the same method as Example 10 except that the compound B-43 of Synthesis Example 9 of Second Organic Compound was used instead of the compound B-1.

Example 21

An organic light emitting diode was manufactured according to the same method as Example 10 except that the compound E-1 of Synthesis Example 10 of Second Organic Compound was used instead of the compound B-1.

Comparative Example 6

An organic light emitting diode was manufactured according to the same method as Example 10 except that CBP alone was used as a single host instead of two kinds of host including the compound 41 and the compound B-1.

Comparative Example 7

An organic light emitting diode was manufactured according to the same method as Example 10 except that compound B-1 alone was used as a single host instead of two kinds of host including the compound 41 and the compound B-1.

Comparative Example 8

An organic light emitting diode was manufactured according to the same method as Example 10 except that compound B-10 alone was used as a single host instead of two kinds of host including the compound 41 and the compound B-1.

Comparative Example 9

An organic light emitting diode was manufactured according to the same method as Example 10 except that compound B-31 alone was used as a single host instead of two kinds of host including the compound 41 and the compound B-1.

Comparative Example 10

An organic light emitting diode was manufactured according to the same method as Example 10 except that compound B-34 alone was used as a single host instead of two kinds of host including the compound 41 and the compound B-1.

Comparative Example 11

An organic light emitting diode was manufactured according to the same method as Example 10 except that compound B-43 alone was used as a single host instead of two kinds of host including the compound 41 and the compound B-1.

Comparative Example 12

An organic light emitting diode was manufactured according to the same method as Example 10 except that compound E-1 alone was used as a single host instead of two kinds of host including the compound 41 and the compound B-1.

Evaluation 3

Luminous efficiency and life-span characteristics of each organic light emitting diode according to Examples 10 to 21 and Comparative Examples 6 to 12 were measured.

The measurements were specifically performed in the following method, and the results are shown in Table 3.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm2) were calculated by using the luminance, current density, and voltages (V) from the items (1) and (2).

(4) Measurement of Life-Span

Life-span was obtained by measuring time taken until current efficiency (cd/A) decreased down to 97% while luminance (cd/m$^2$) was maintained at 6000 cd/m$^2$.

TABLE 3

| | First host | Second host | First host:Second host | Luminous efficiency (cd/A) | Life-span T97 (h) |
|---|---|---|---|---|---|
| Example 10 | compound 41 | B-1 | 4:1 | 42.5 | 520 |
| Example 11 | compound 41 | B-1 | 1:1 | 47.5 | 525 |
| Example 12 | compound 41 | B-1 | 1:4 | 48.5 | 370 |
| Example 13 | compound 41 | B-10 | 4:1 | 42.5 | 460 |
| Example 14 | compound 41 | B-10 | 1:1 | 50.0 | 520 |
| Example 15 | compound 41 | B-10 | 1:4 | 47.0 | 330 |

TABLE 3-continued

| | First host | Second host | First host:Second host | Luminous efficiency (cd/A) | Life-span T97 (h) |
|---|---|---|---|---|---|
| Example 16 | compound 41 | B-31 | 4:1 | 51.0 | 395 |
| Example 17 | compound 41 | B-31 | 1:1 | 55.0 | 300 |
| Example 18 | compound 41 | B-34 | 4:1 | 44.0 | 780 |
| Example 19 | compound 41 | B-34 | 1:1 | 49.0 | 1,000 |
| Example 20 | compound 41 | B-43 | 4:1 | 47.0 | 1,150 |
| Example 21 | compound 41 | E-1 | 4:1 | 46.5 | 1,200 |
| Comparative Example 6 | | CBP | — | 19.3 | 0.5 |
| Comparative Example 7 | | B-1 | — | 16.5 | 10 |
| Comparative Example 8 | | B-10 | — | 37.5 | 10 |
| Comparative Example 9 | | B-31 | — | 2.5 | 0 |
| Comparative Example 10 | | B-34 | — | 18.3 | 0 |
| Comparative Example 11 | | B-43 | — | 2.8 | 10 |
| Comparative Example 12 | | E-1 | — | 1.4 | 30 |

Referring to 3, the organic light emitting diodes according to Examples 10 to 21 exhibited remarkably improved characteristics of luminous efficiency and life-span characteristics compared with the organic light emitting diodes according to Comparative Examples 6 to 12.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: cathode
120: anode
130: emission layer
140: hole auxiliary layer

The invention claimed is:

1. An organic compound represented by Chemical Formula 1 and having a molecular weight of less than 750:

[Chemical Formula 1]

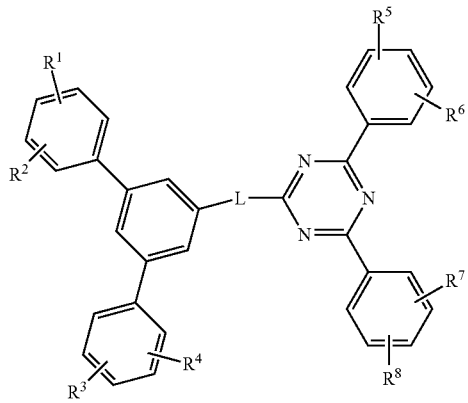

wherein, in Chemical Formula 1,
L is represented by one of the groups listed in Group 1, below,

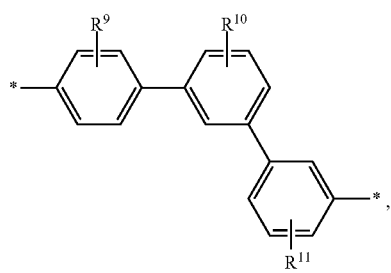

in which $R^9$ to $R^{11}$ are hydrogen and * is a linking point, $R^1$ to $R^8$ are hydrogen.

2. A composition for an organic optoelectronic diode, comprising:
   the first organic compound according to claim 1, and
   at least one second organic compound having a carbazole moiety.

3. The composition for an organic optoelectronic diode of claim 2, wherein the second organic compound comprises at least one of a compound represented by Chemical Formula 4 and a compound consisting of a combination of a moiety represented by Chemical Formula 5 and a moiety represented by Chemical Formula 6:

[Chemical Formula 4]

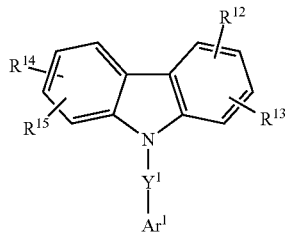

wherein, in Chemical Formula 4,
$Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, Ar$^1$ is a substituted or unsubstituted C6 to C30 aryl group, a substituted or unsubstituted C2 to C30 heteroaryl group, or a combination thereof, R$^{12}$ to R$^{15}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, and at least one of R$^{12}$ to R$^{15}$ and Ar$^1$ includes one of a substituted or unsubstituted triphenylene group or a substituted or unsubstituted carbazole group,

[Chemical Formula 5]

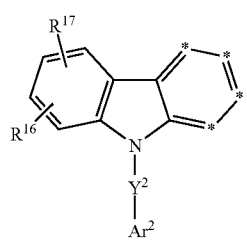

[Chemical Formula 6]

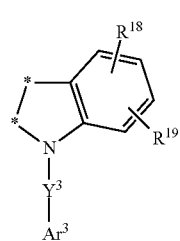

wherein, in Chemical Formulae 5 and 6,

Y$^2$ and Y$^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, Ar$^2$ and Ar$^3$ are independently substituted or unsubstituted C6 to C30 aryl group, a substituted or unsubstituted C2 to C30 heteroaryl group, or a combination thereof, R$^{16}$ to R$^{19}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, two adjacent *'s of Chemical Formula 5 is combined with two *'s of Chemical Formula 6 to form a fused ring and in Chemical Formula 5, *'s not forming the fused ring are independently CR$^b$, and R$^b$ is hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof.

4. The composition for an organic optoelectronic diode of claim 3, wherein the second organic compound represented by Chemical Formula 4 is represented by one of Chemical Formulae 4-I to 4-III:

[Chemical Formula 4-I]

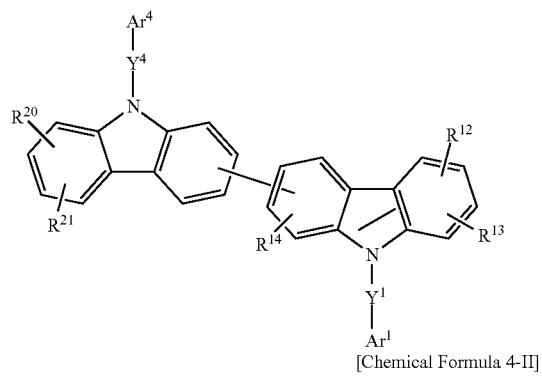

[Chemical Formula 4-II]

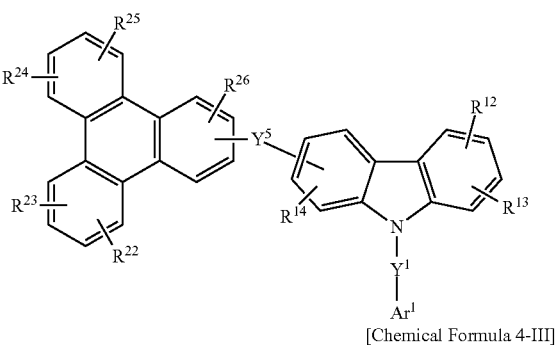

[Chemical Formula 4-III]

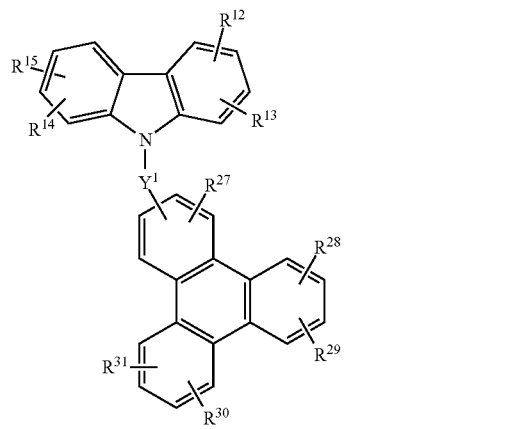

wherein, in Chemical Formulae 4-I to 4-III,

Y$^1$, Y$^4$, and Y$^5$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, Ar$^1$ and Ar$^4$ are independently substituted or unsubstituted C6 to C30 aryl group, a substituted or unsubstituted C2 to C30 heteroaryl group, or a combination thereof, and R$^{12}$ to R$^{15}$ and R$^{20}$ to R$^{31}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof.

5. The composition for an organic optoelectronic diode of claim 3, wherein the second organic compound represented by Chemical Formula 4 is selected from compounds listed in Group 3:

[Group 3]
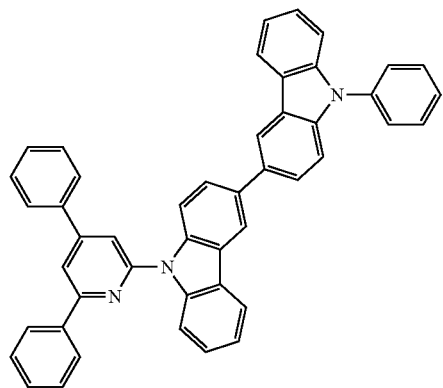
B-10
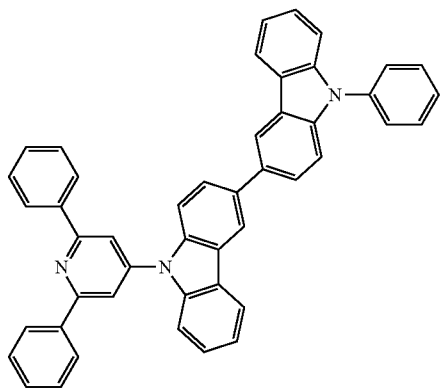
B-11
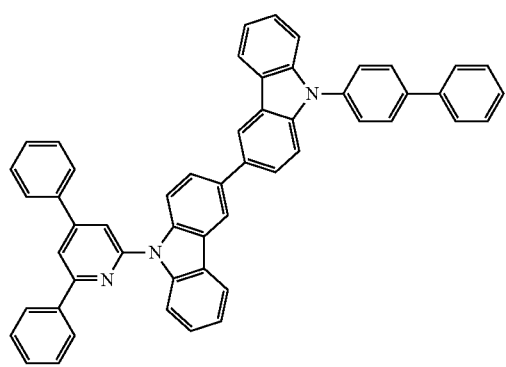
B-12
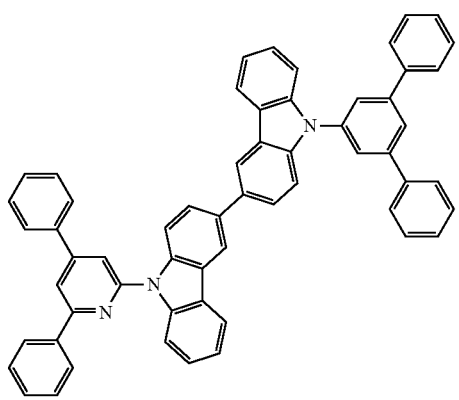
B-13
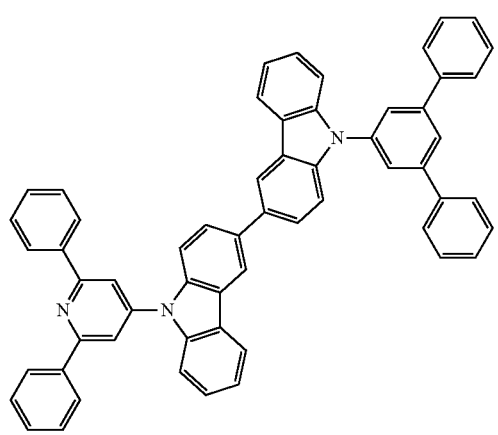
B-14
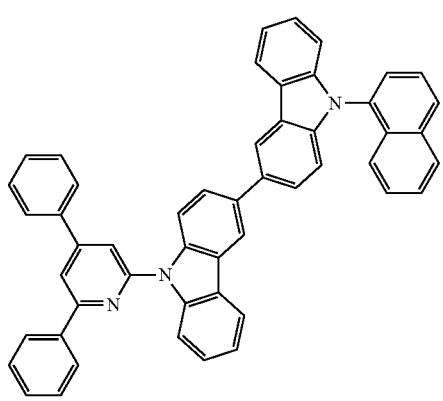
B-15

-continued
B-16
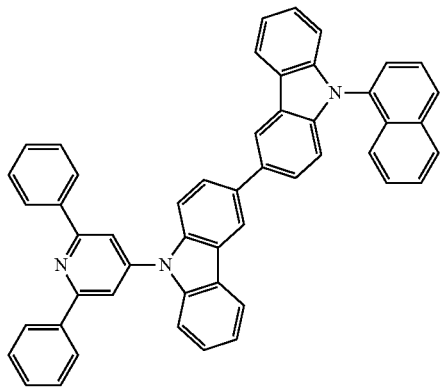
B-17
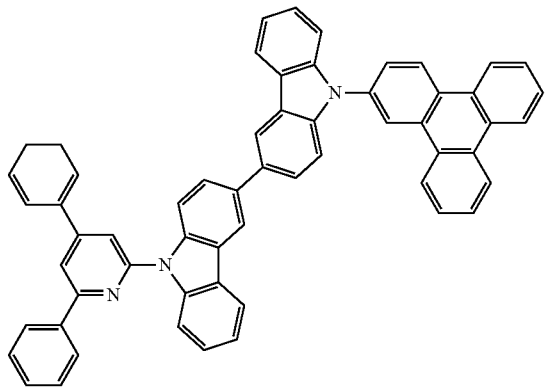
B-18
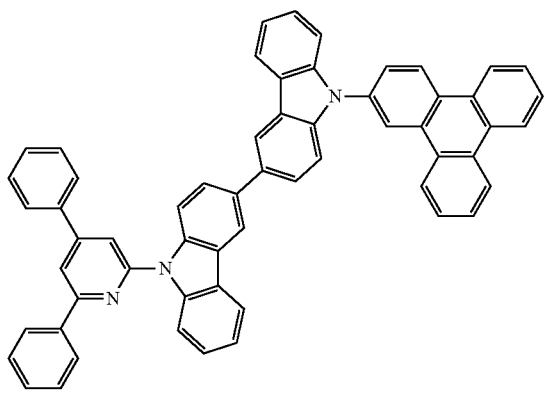
B-19
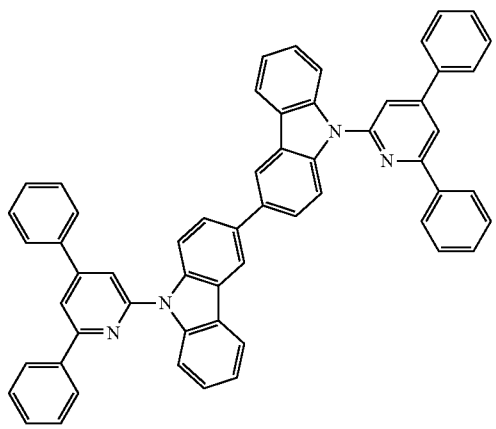
B-20
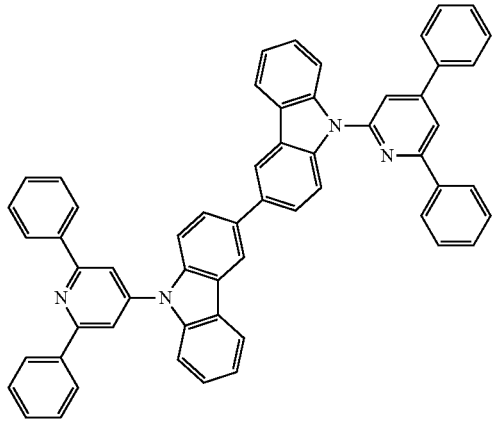
B-21
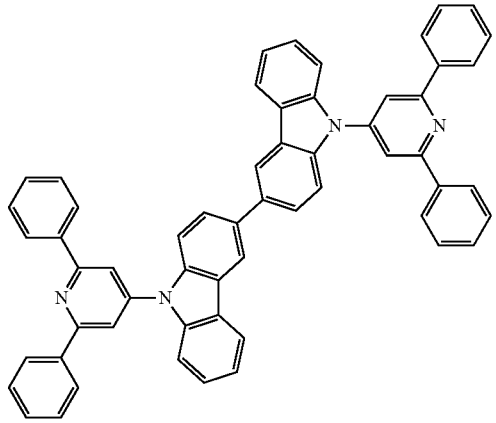
B-22
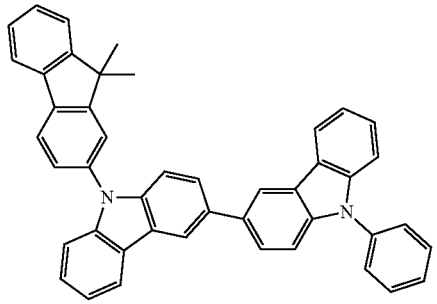
B-23
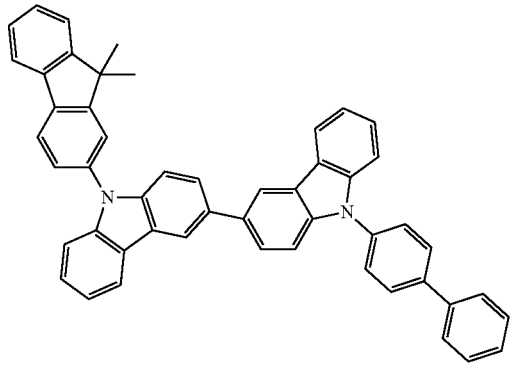

-continued
B-24
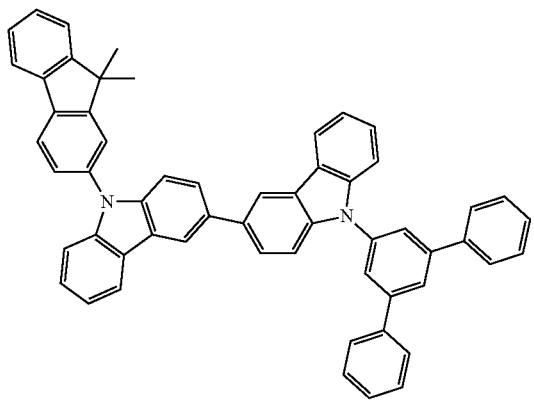
B-25
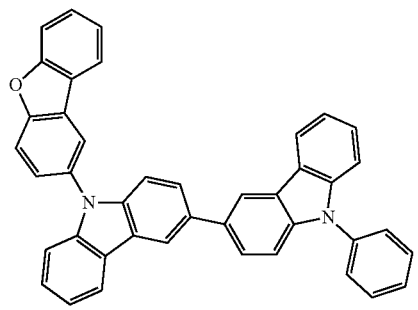
B-26
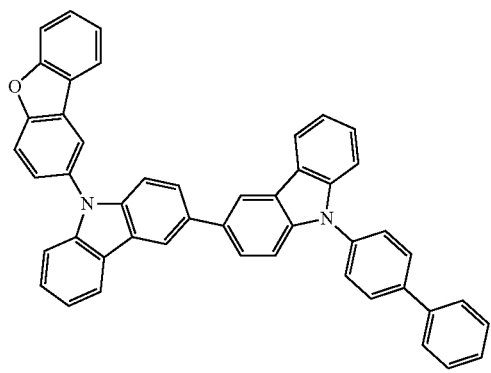
B-27
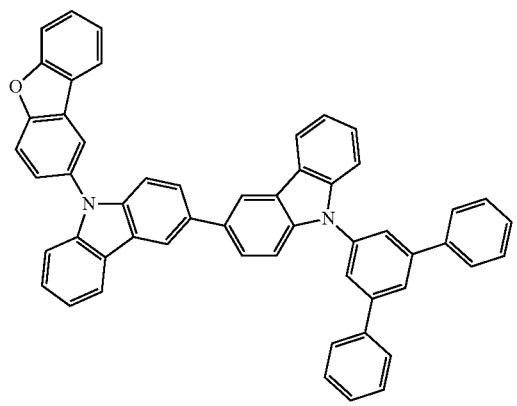
B-28
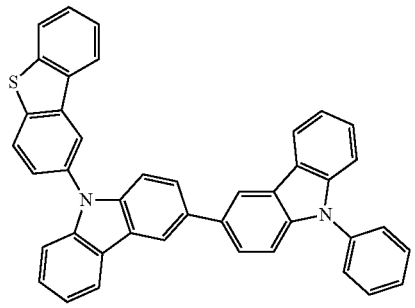
B-29
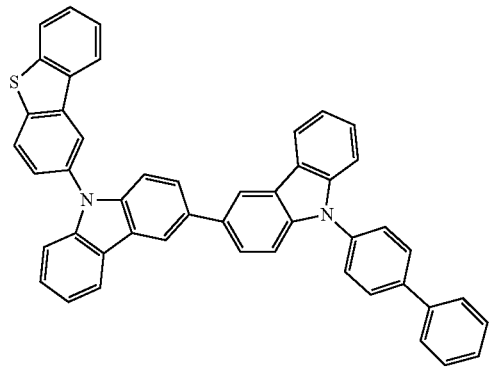
B-30
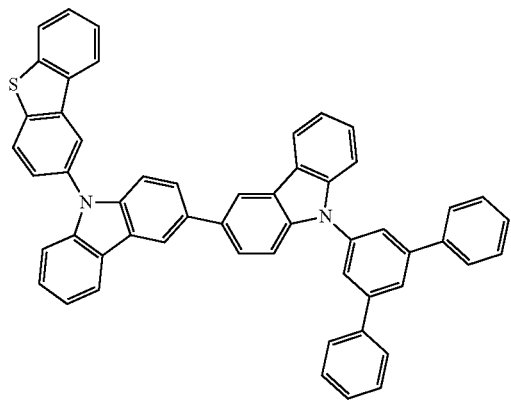
B-31
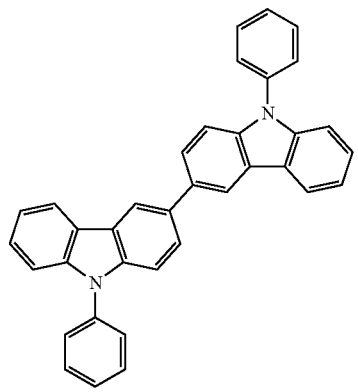

-continued
B-32
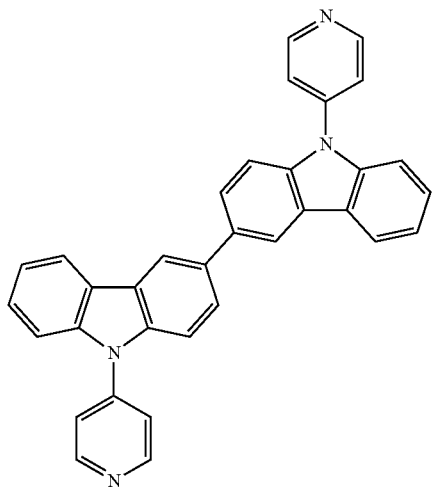
B-33
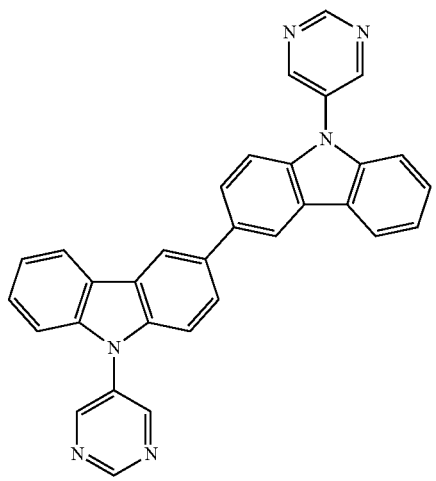
B-34
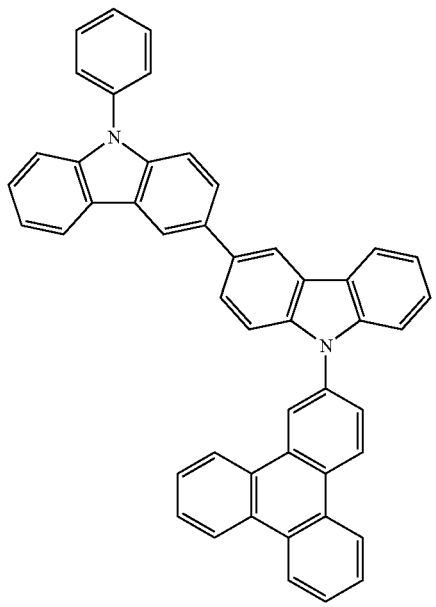
B-35
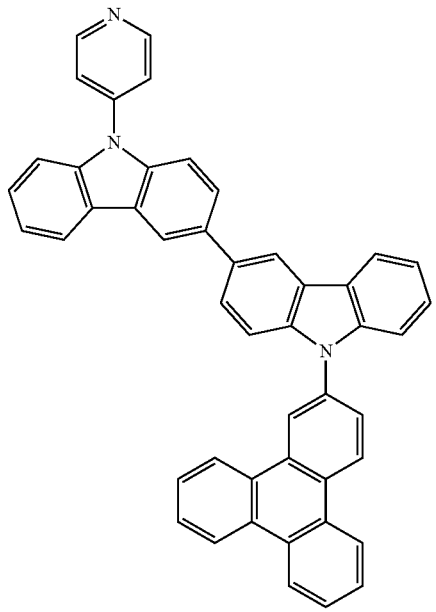
B-37
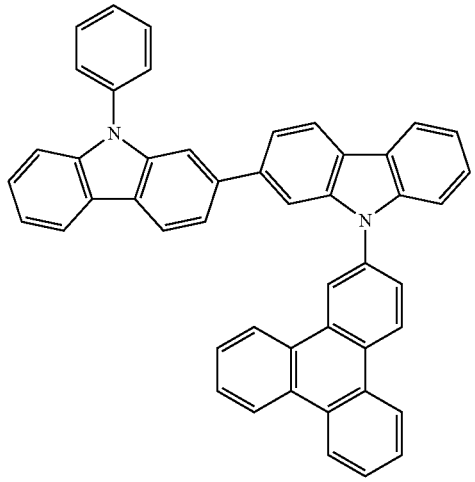
B-38
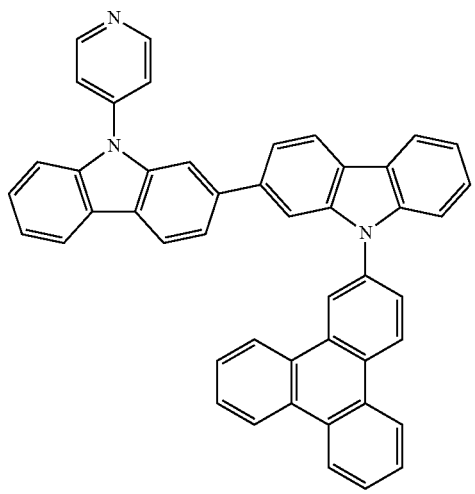

-continued
B-40
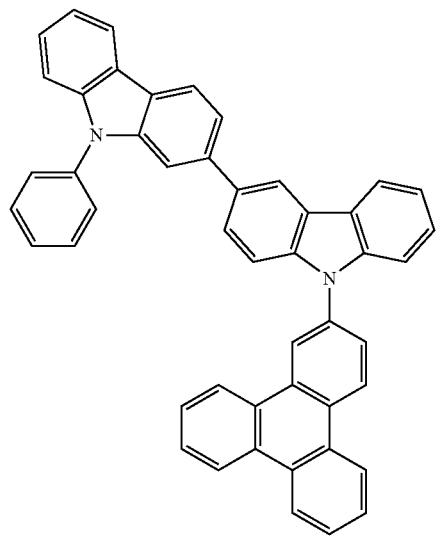
B-41
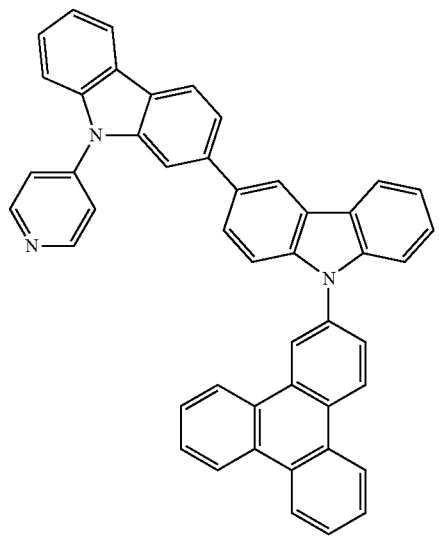
B-43
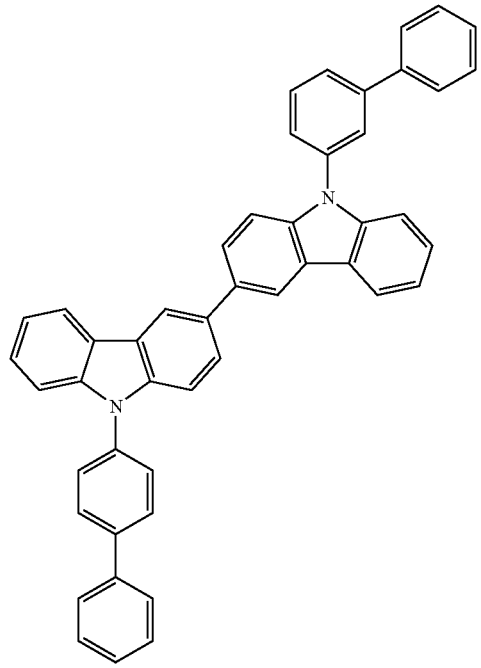
B-44
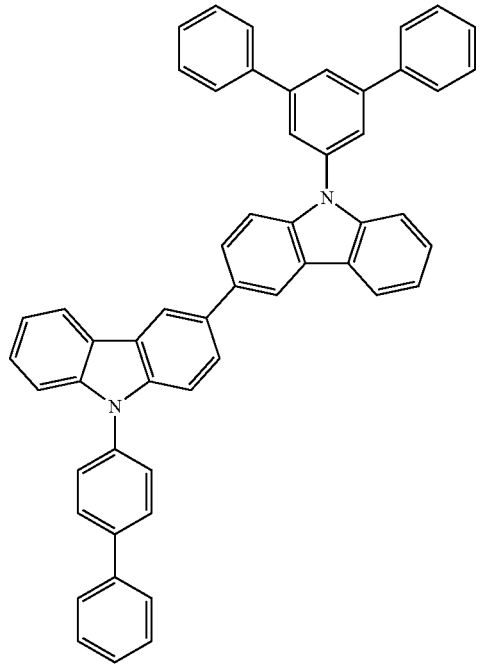

-continued
B-45
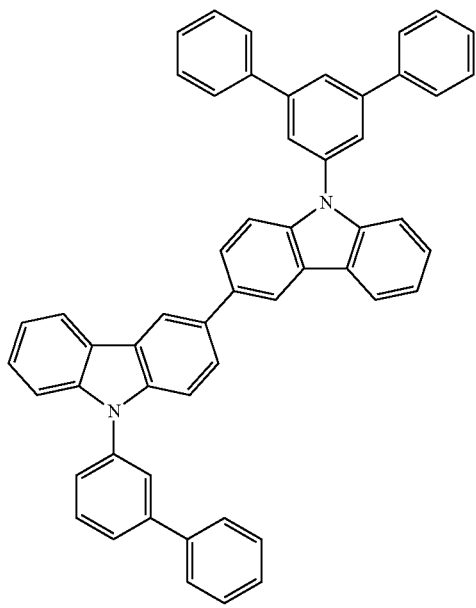
B-46
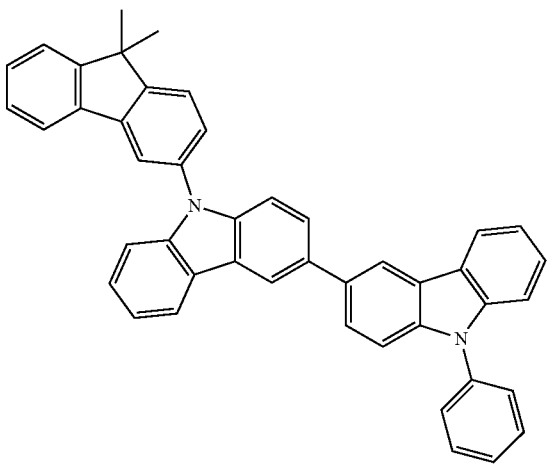
B-47
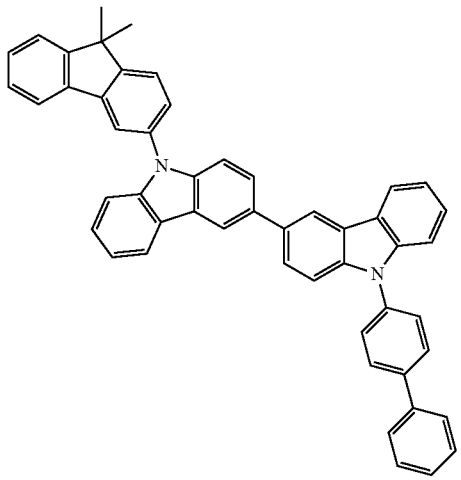
B-48
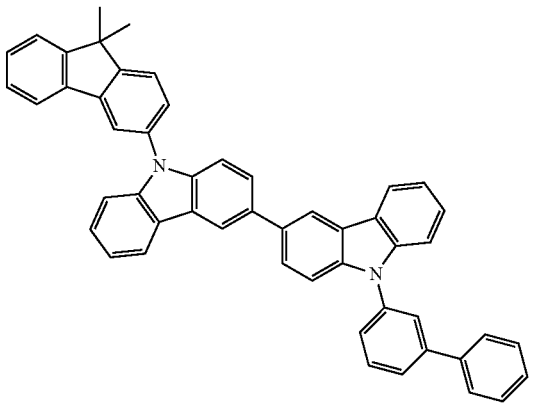
B-49
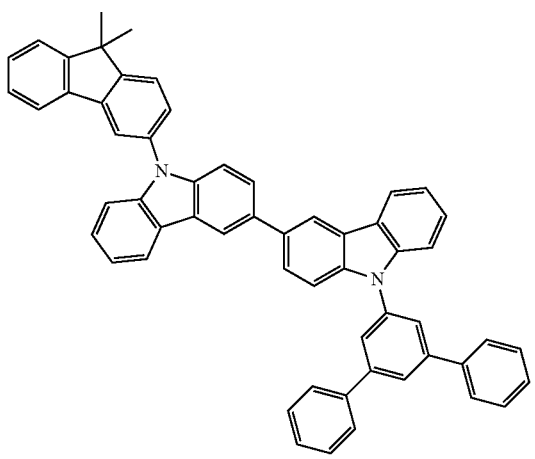
B-50
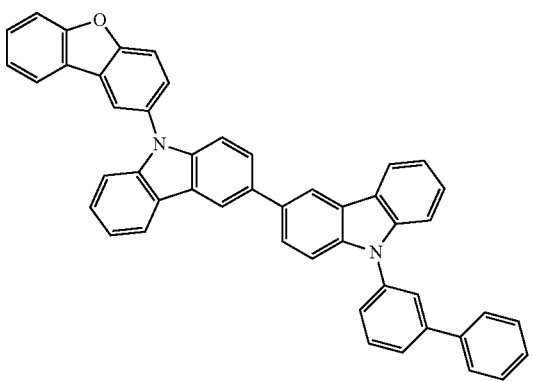

-continued
B-51
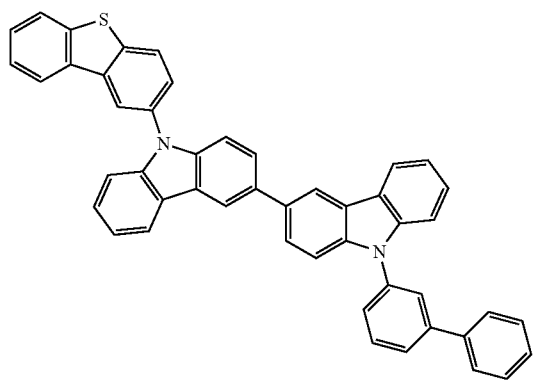
B-52
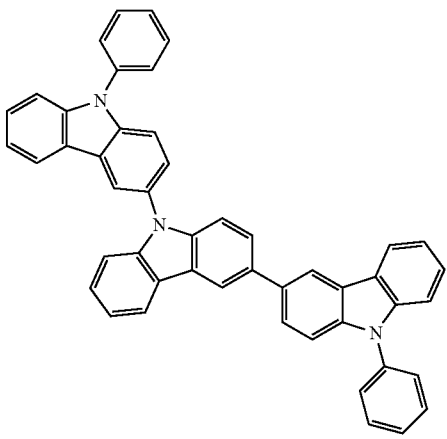
B-53
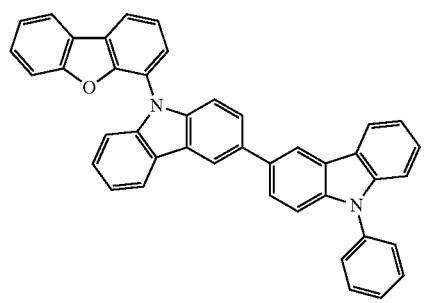
B-54
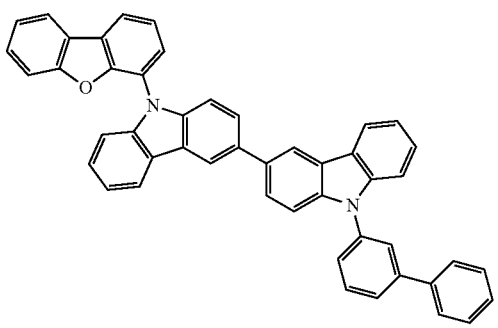
B-55
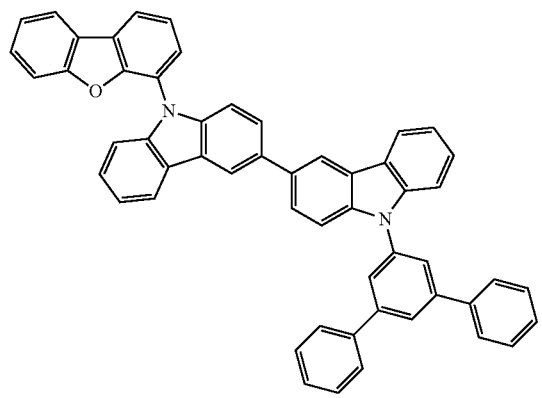
B-56
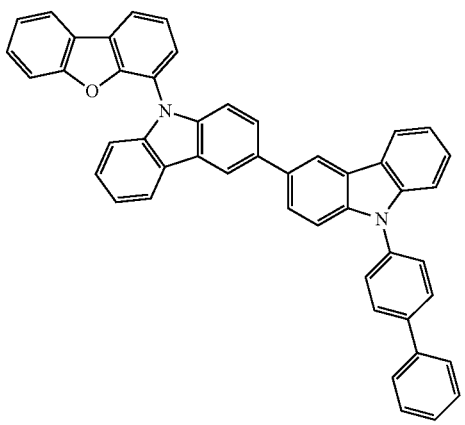
B-57
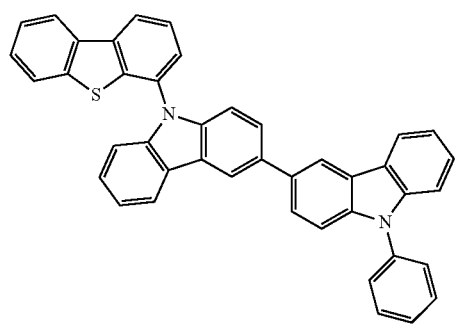
B-58
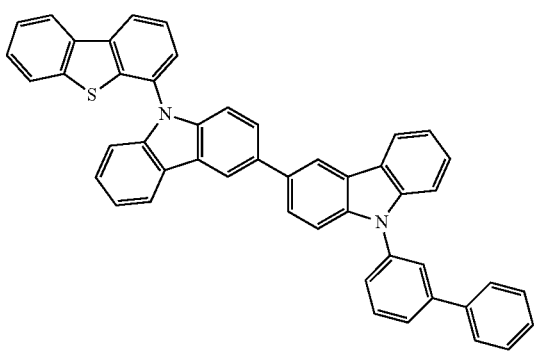

-continued
B-59
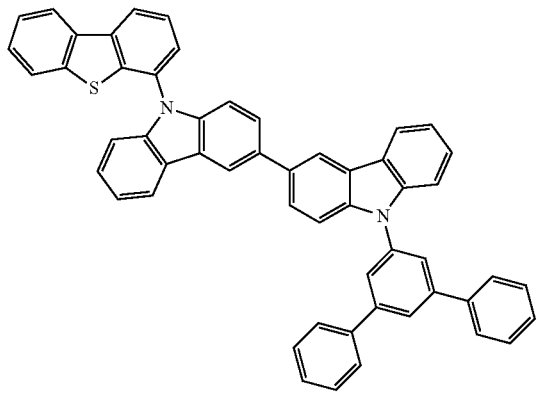
B-60
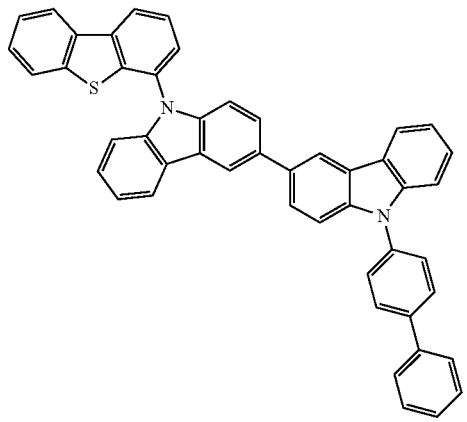
B-61
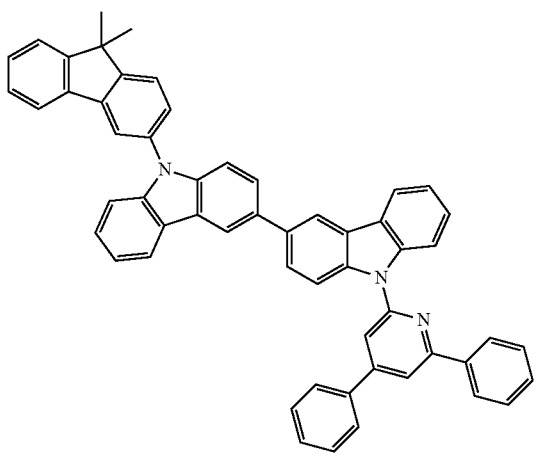
B-62
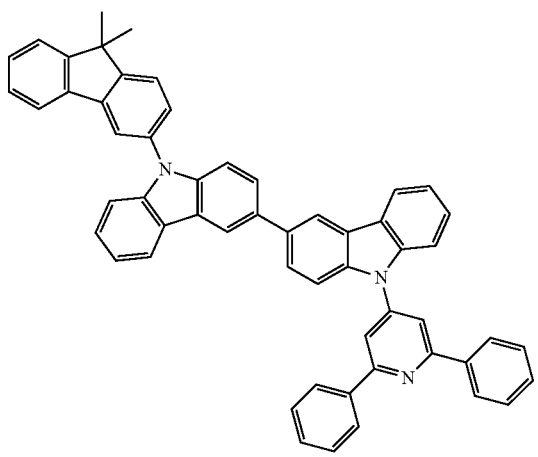
B-63
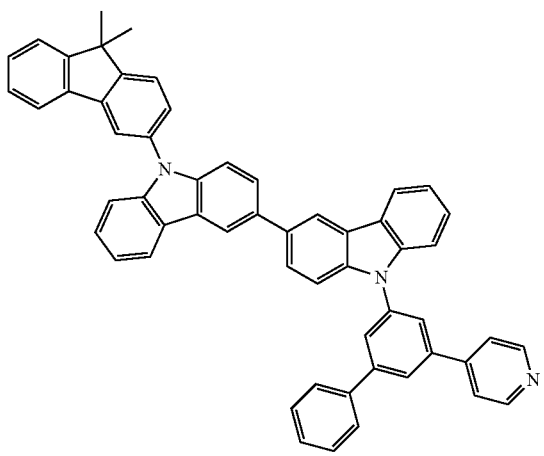
B-64
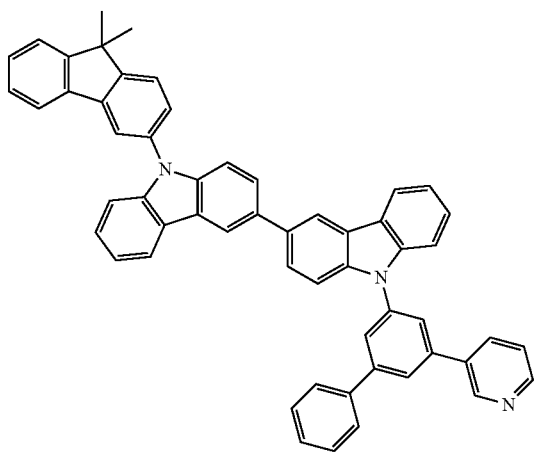

-continued
B-65
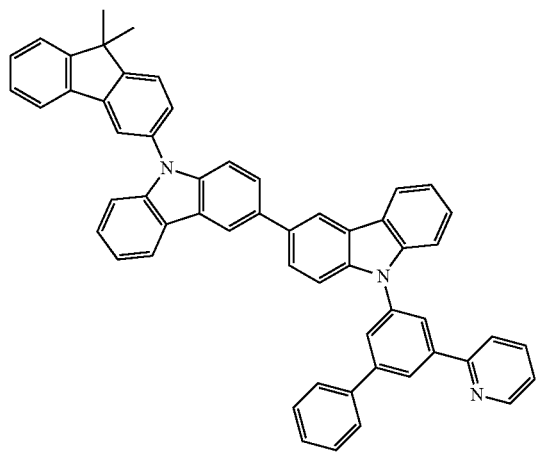
B-66
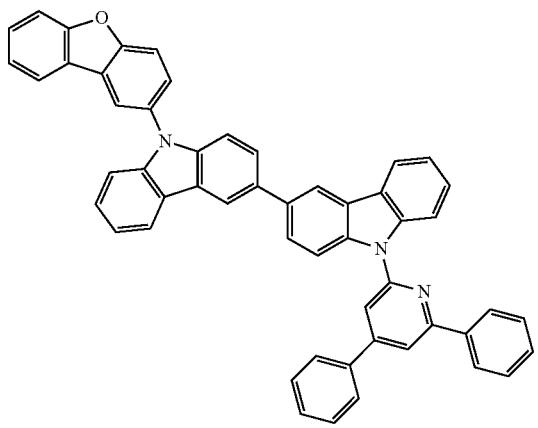
B-67
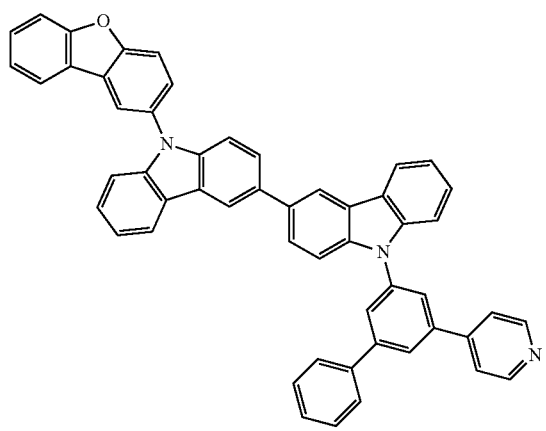
B-68
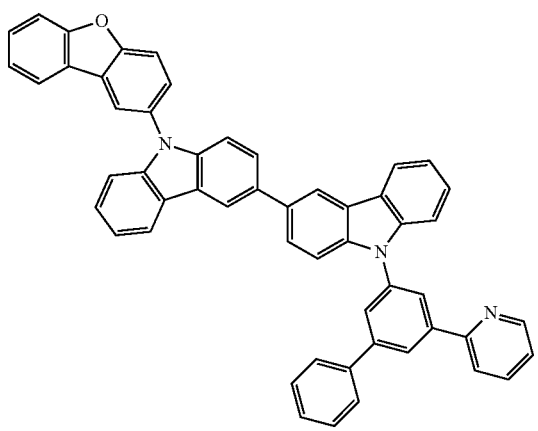
B-69
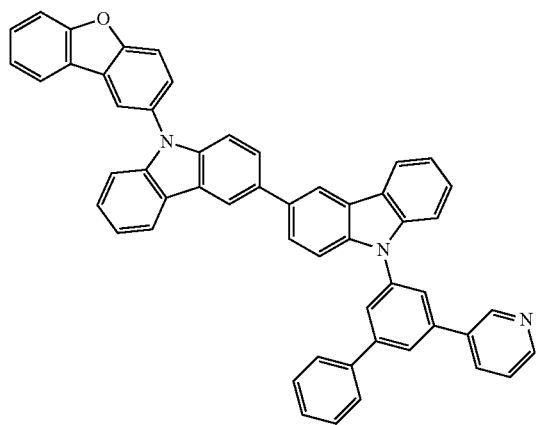
B-70
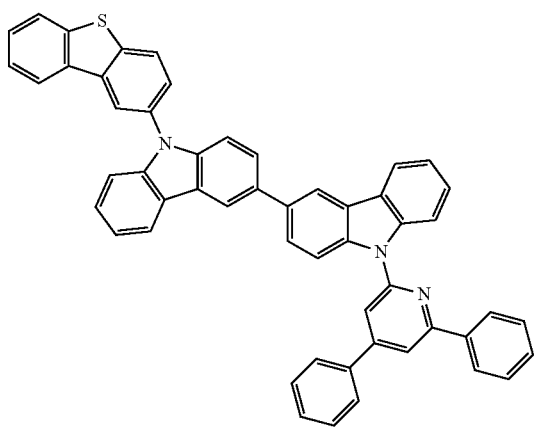

-continued
B-71
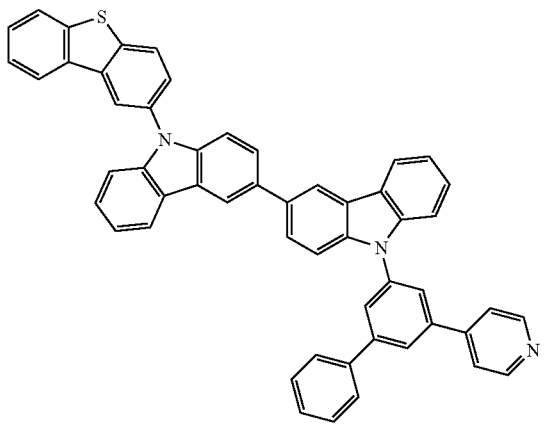
B-72
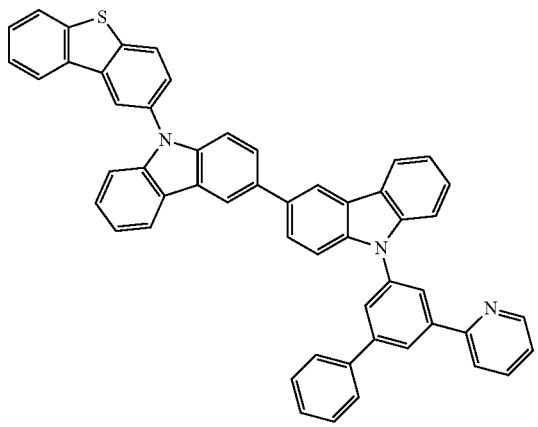
B-73
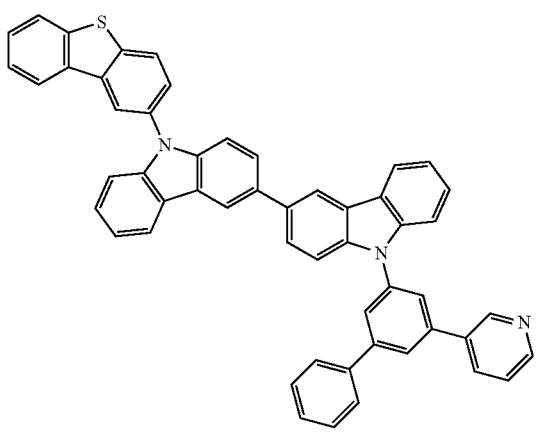
B-74
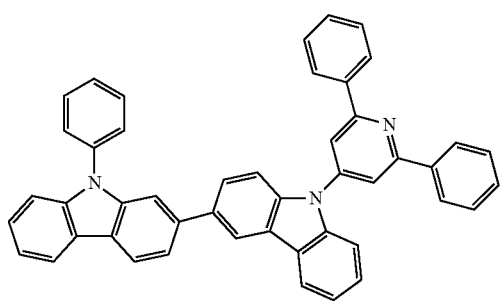
B-75
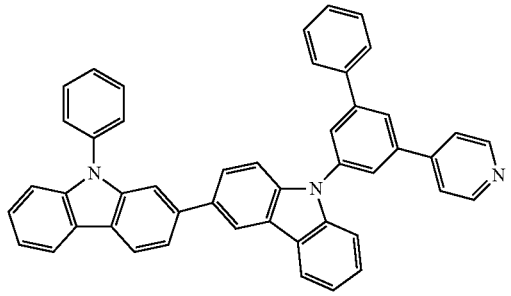
B-76
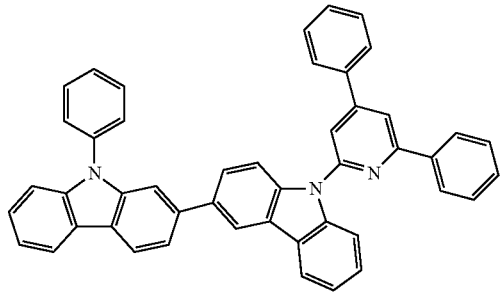
B-77
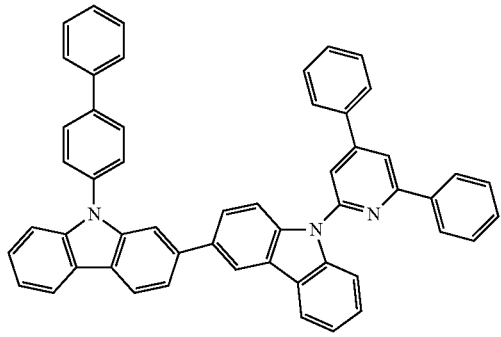
B-78
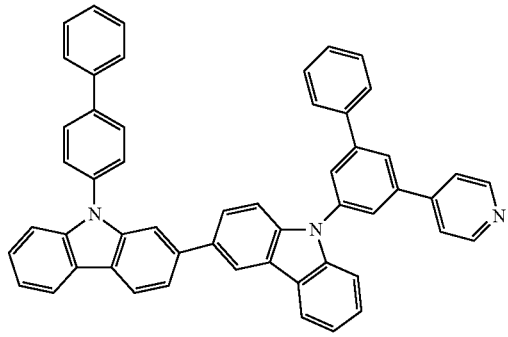

-continued
B-79
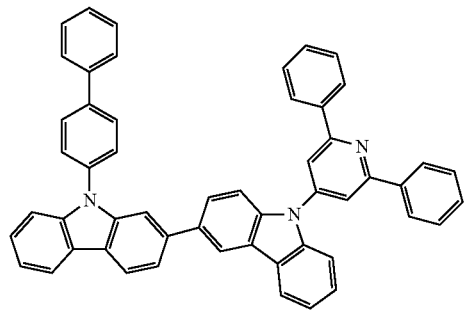
B-80
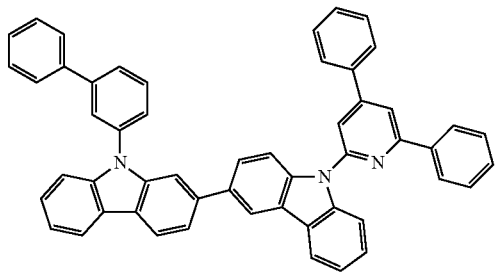
B-81
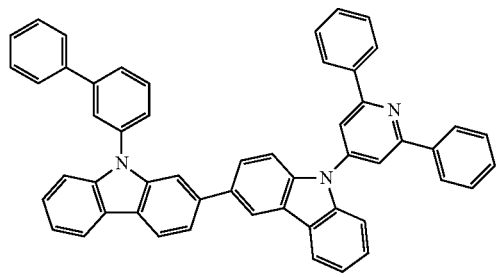
B-82
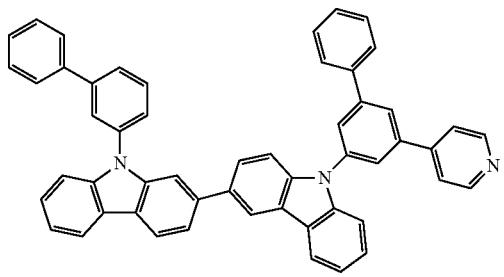
B-83
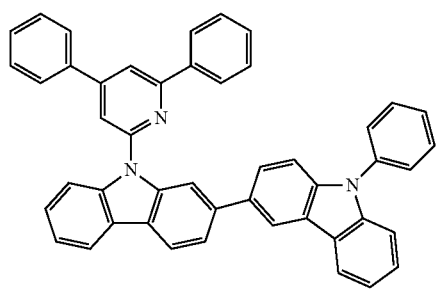
B-84
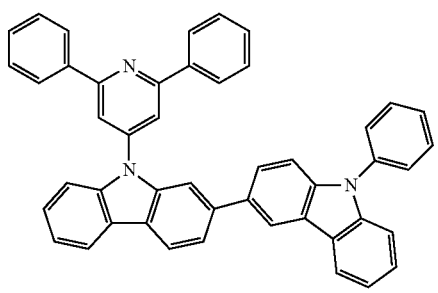
B-85
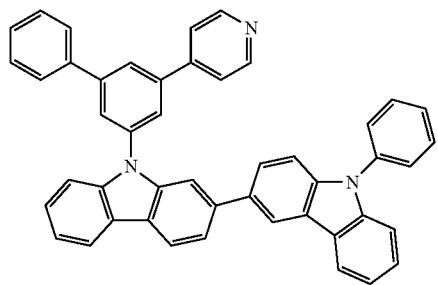
B-86
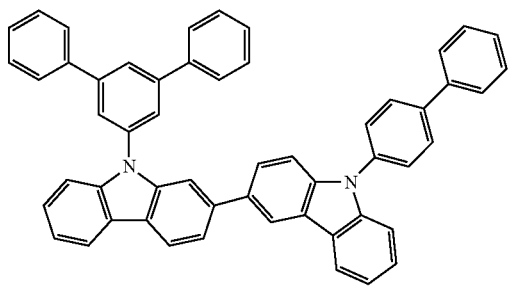
B-87
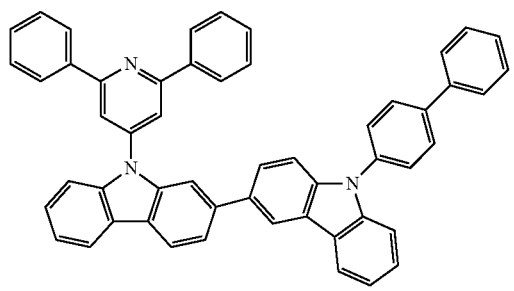
B-88
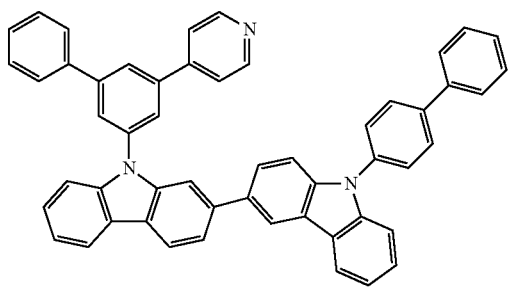

-continued
B-89
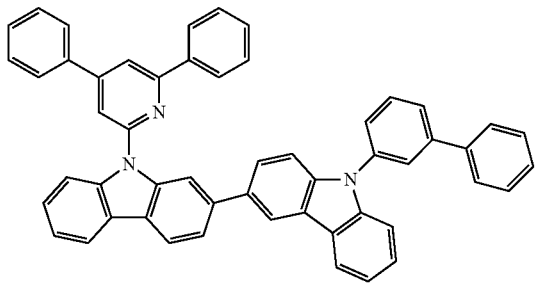
B-90
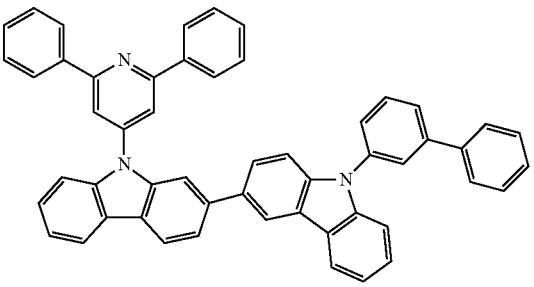
B-91
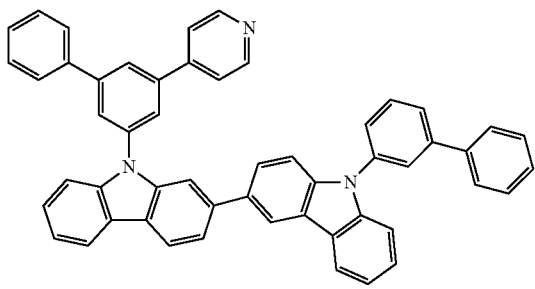
B-92
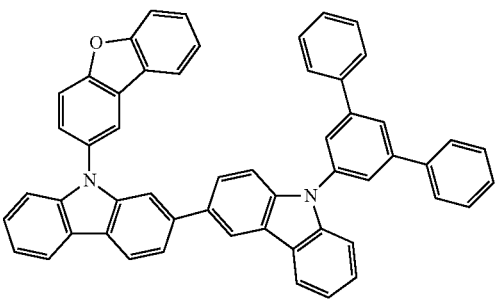
B-93
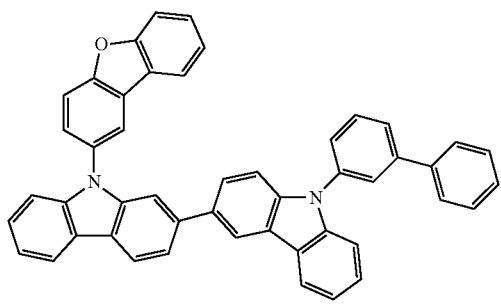
B-94
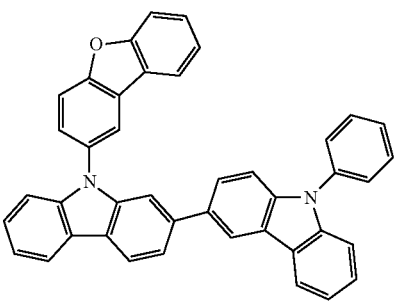
B-95
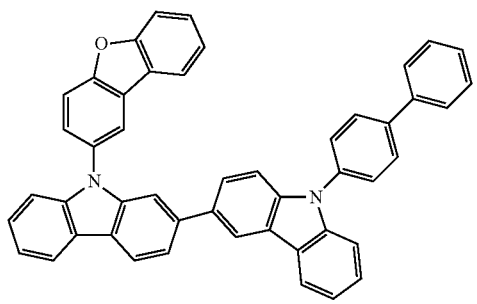
B-96
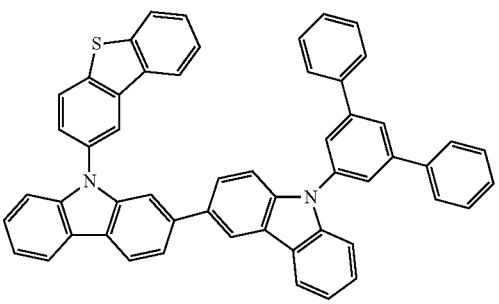
B-97
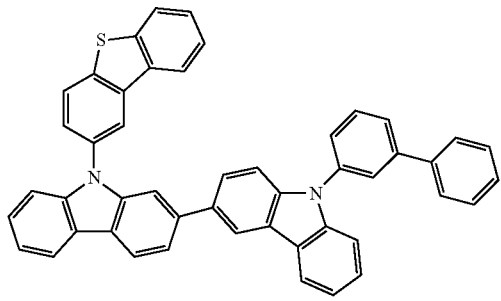
B-98
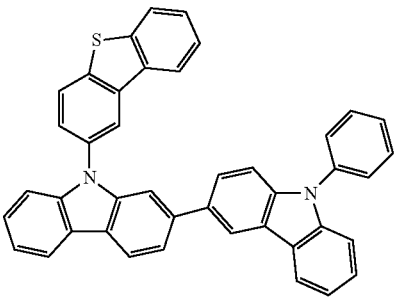

-continued
B-99
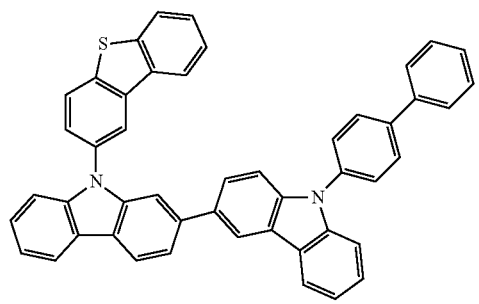
B-100
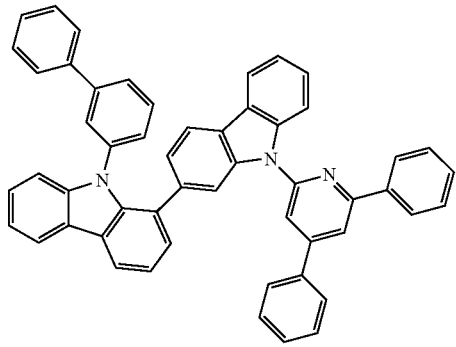
B-101
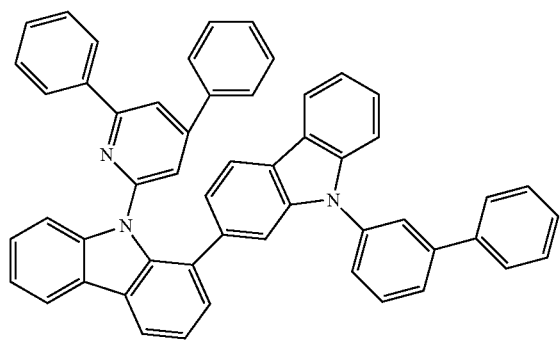
B-102
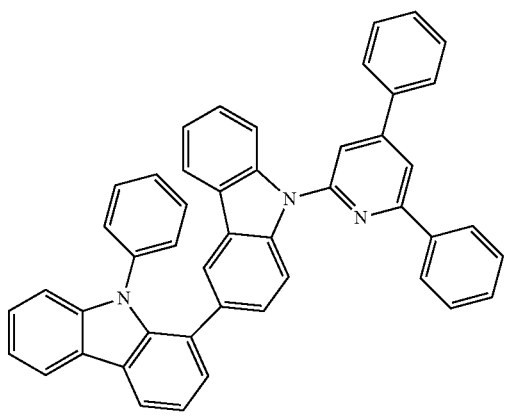
B-103
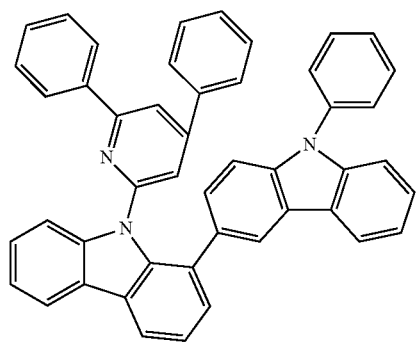
B-104
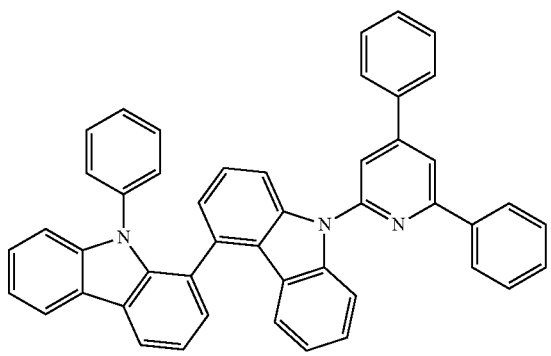
B-105
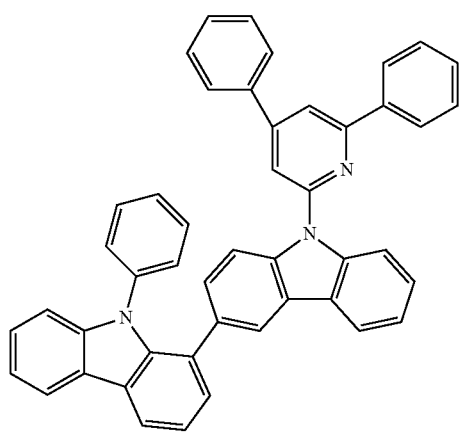
B-106
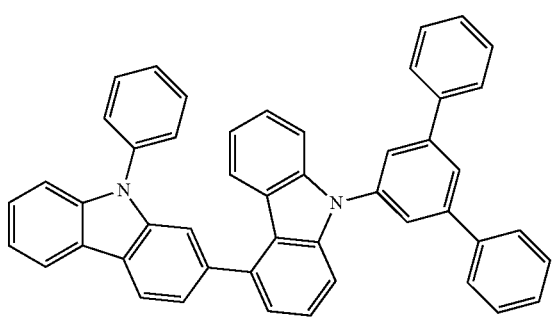

-continued
B-107
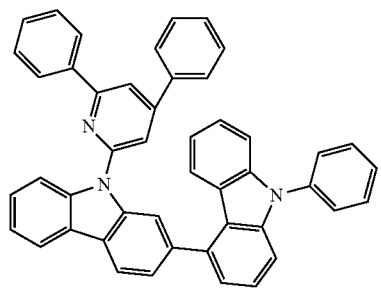
B-108
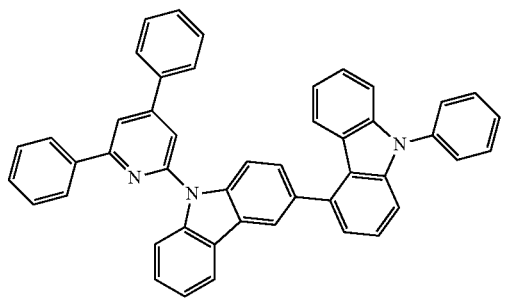
B-109
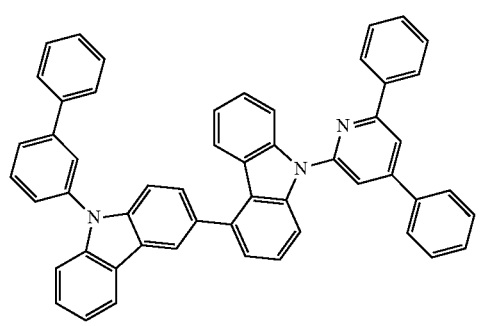
B-110
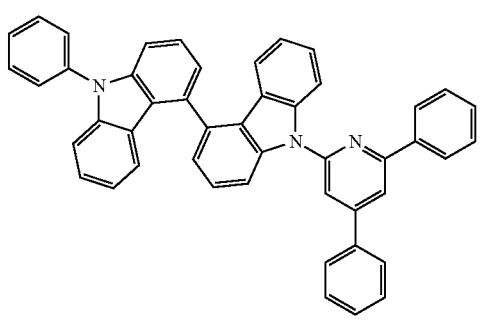
B-111
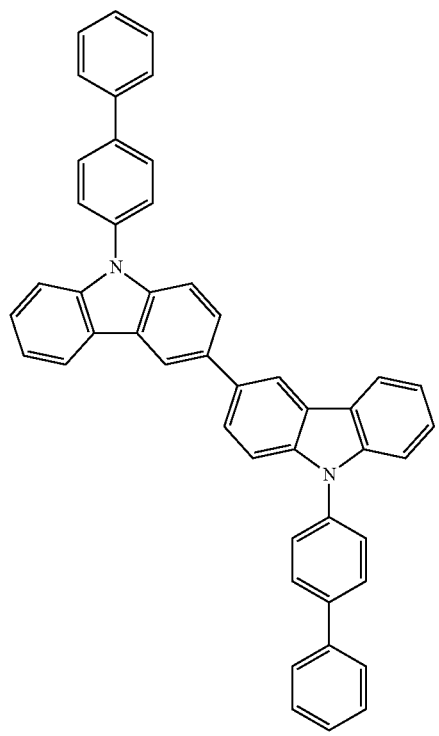
B-112
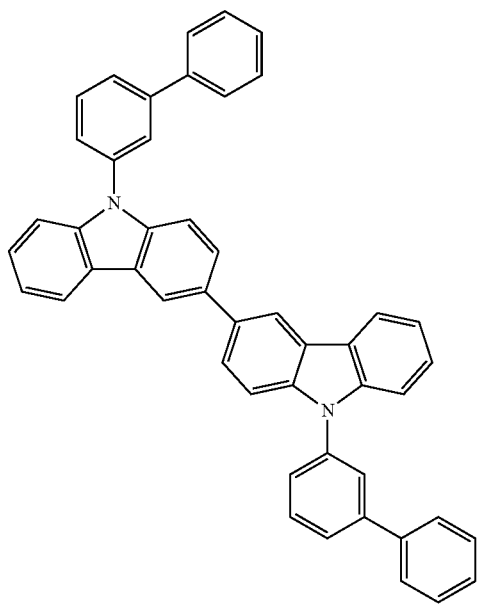

-continued
B-113
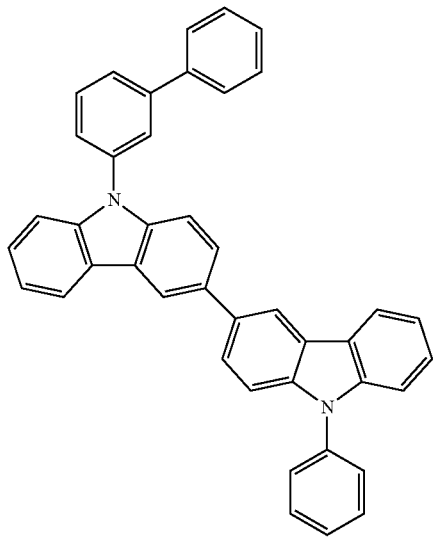
C-10
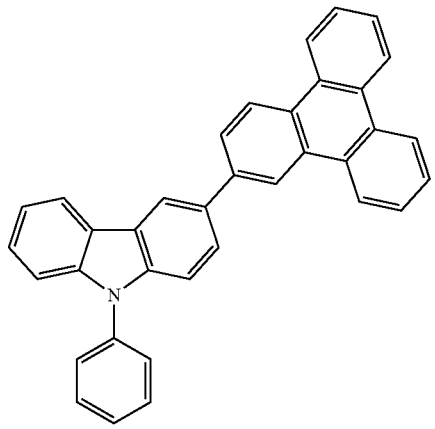
C-11
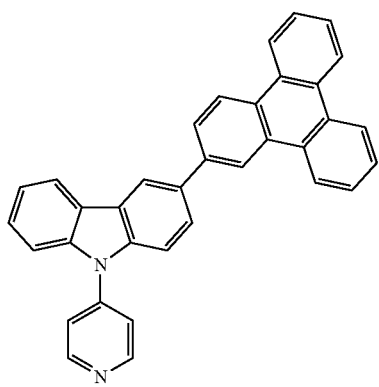
C-12
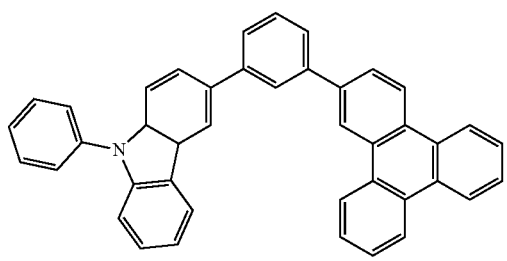
C-13
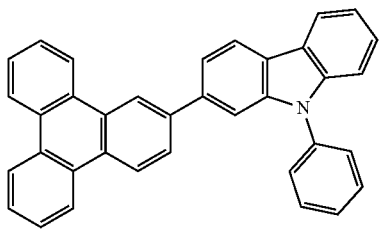
C-14
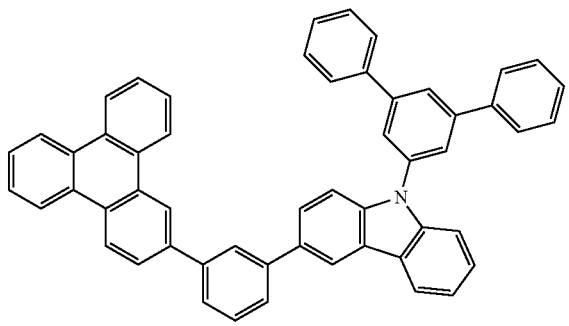
C-15
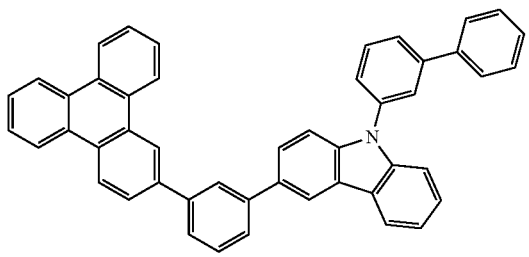
C-16
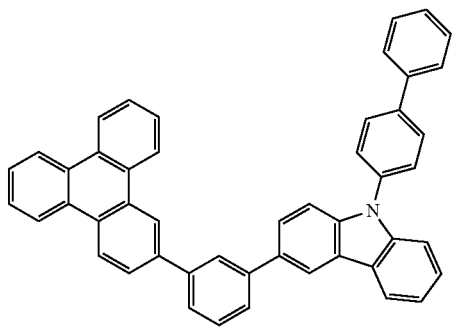

-continued
C-17
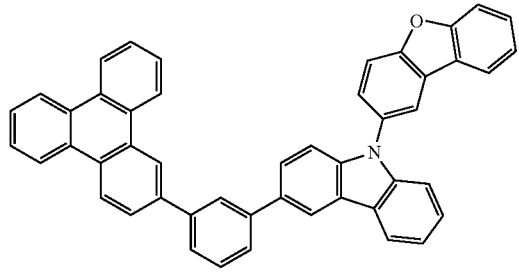
C-18
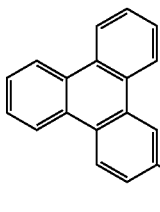
C-19
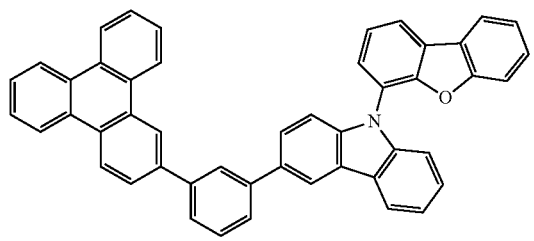
C-20
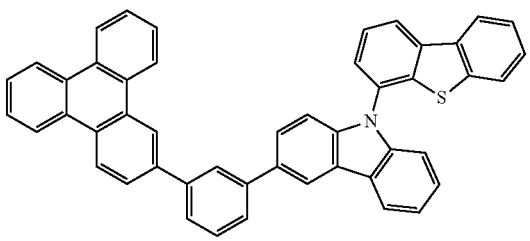
C-21
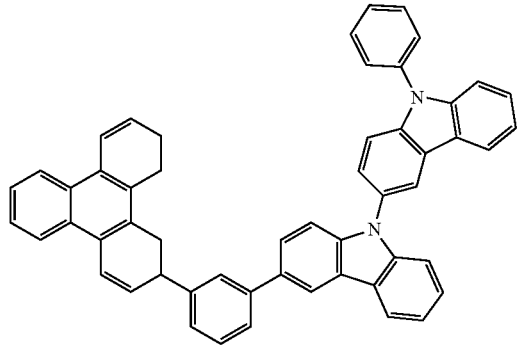
C-22
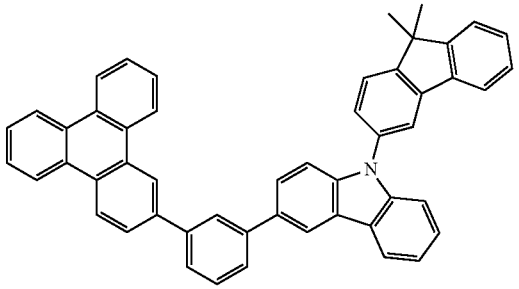
C-23
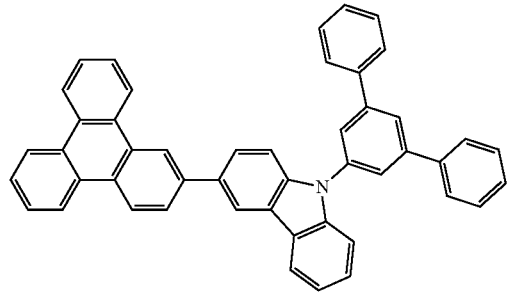
C-24
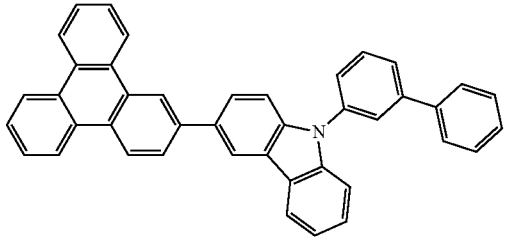
C-25
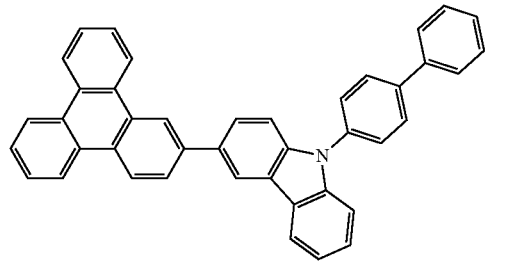
C-26
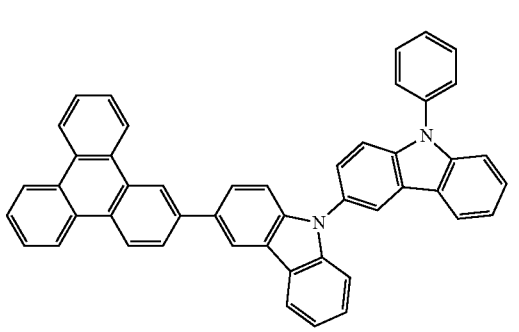

-continued
C-27
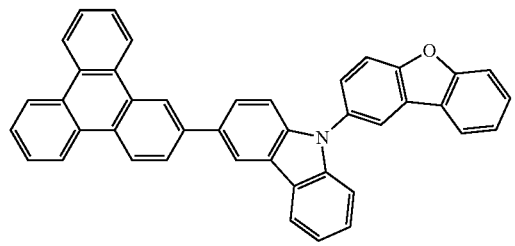
C-28
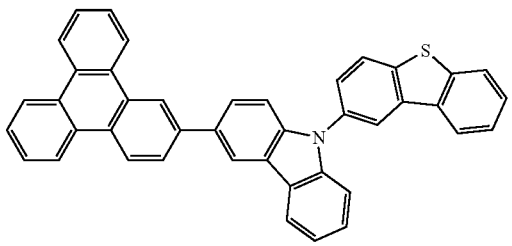
C-29
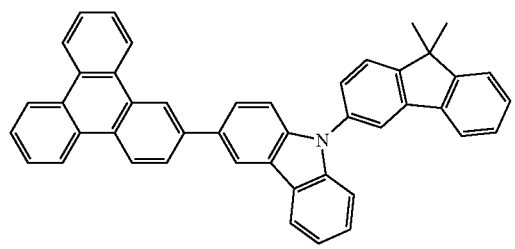
C-30
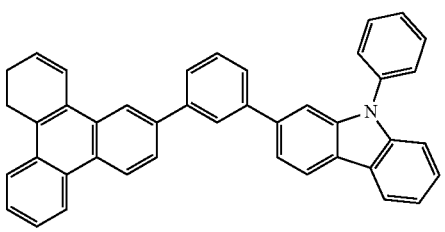
C-31
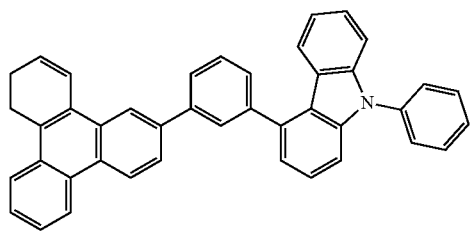
C-32
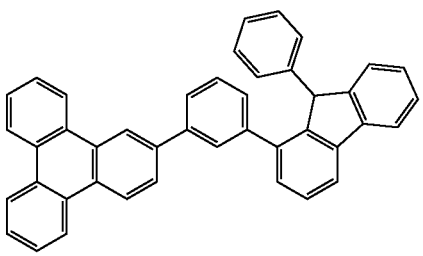
C-33
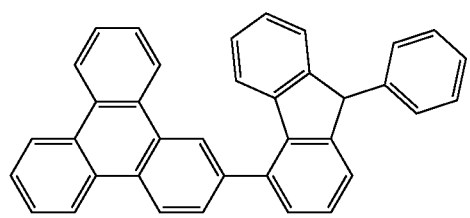
D-10
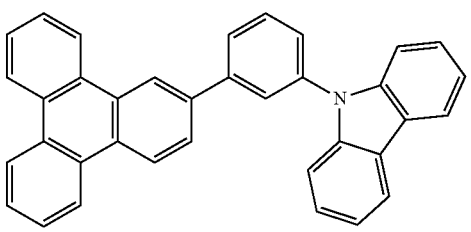
D-11
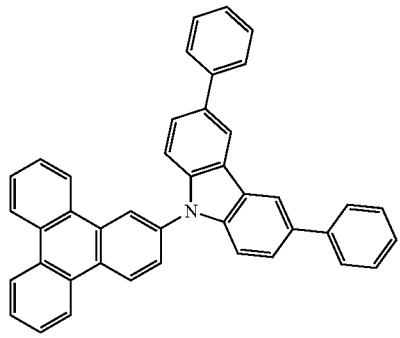
D-12
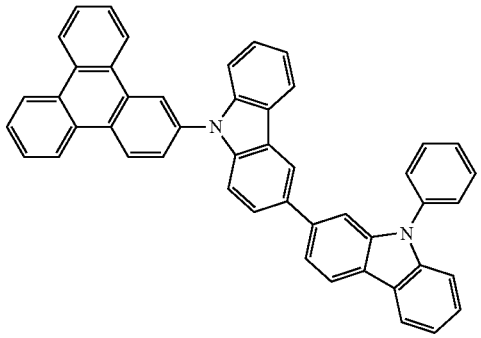

-continued
D-13
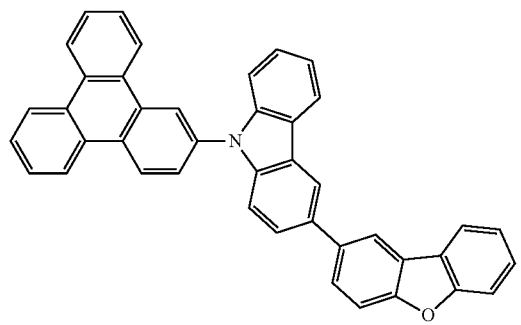
D-14
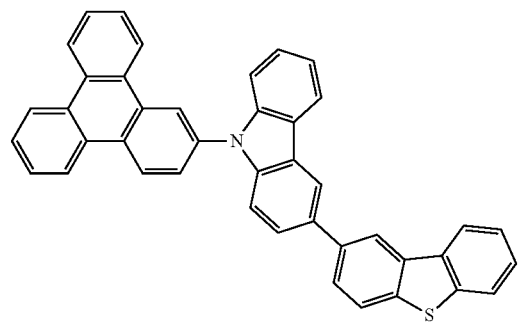
D-15
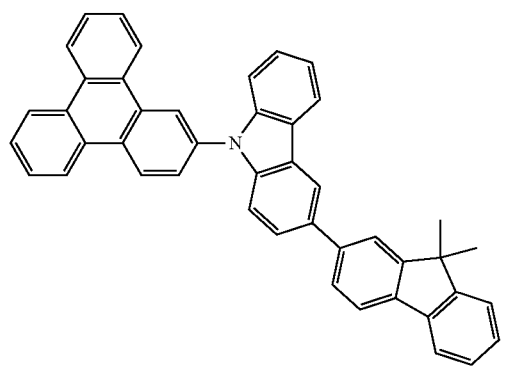
D-16
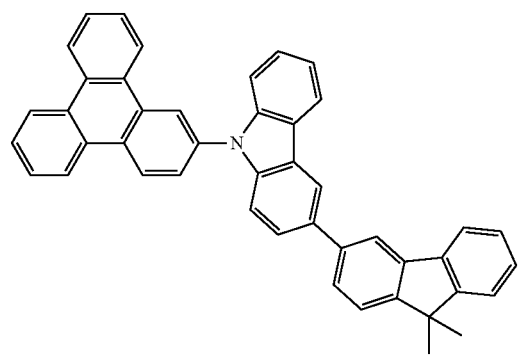
D-17
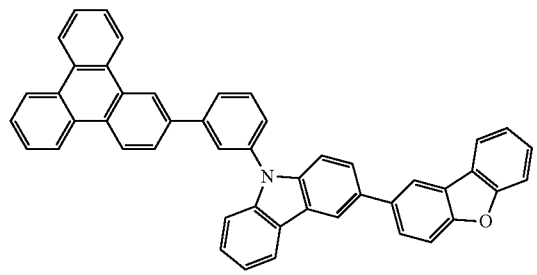
D-18
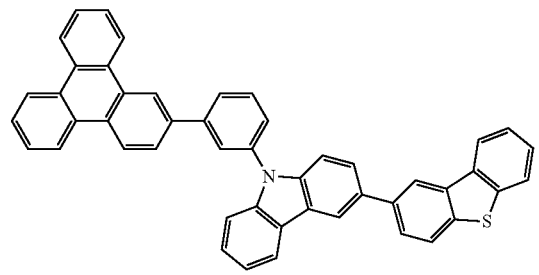
D-19
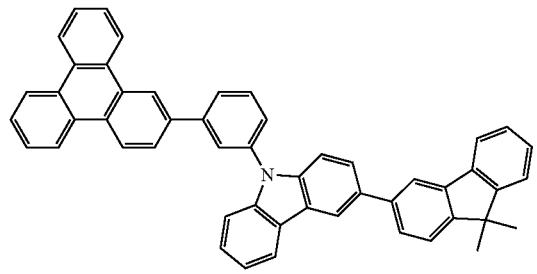
D-20
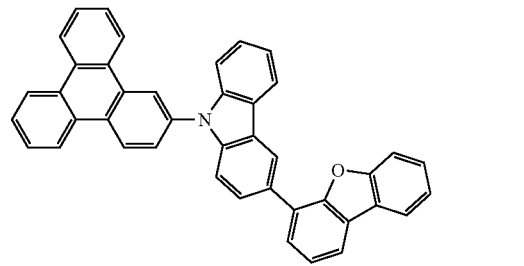
D-21
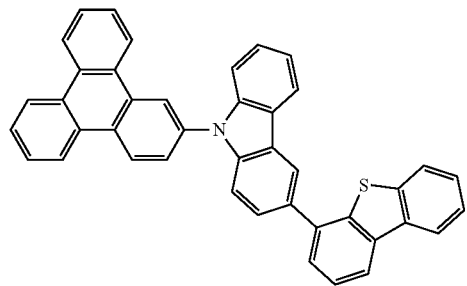
D-22
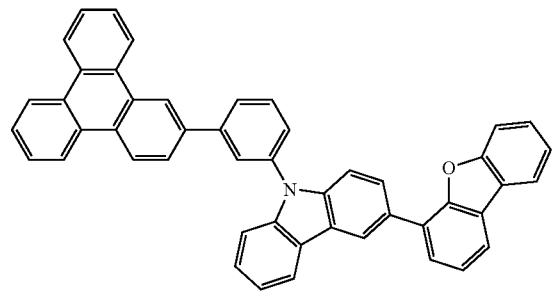

-continued
D-23
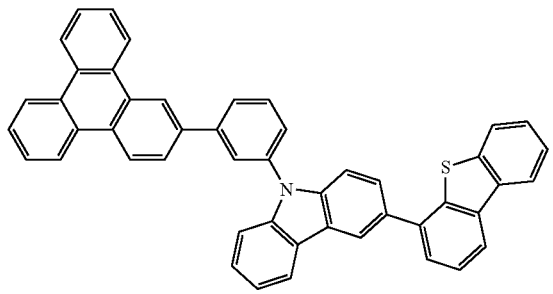
D-24
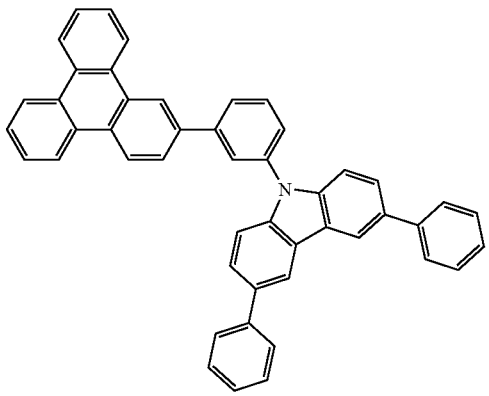
D-25
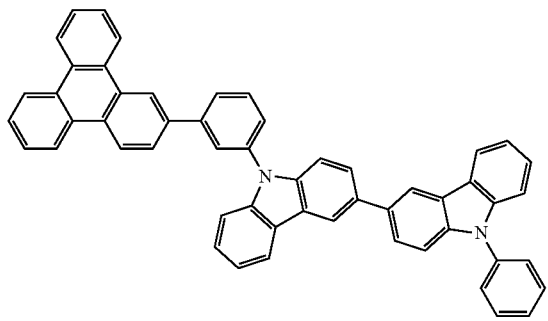
D-26
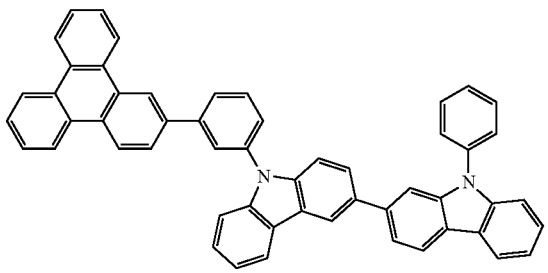
D-27
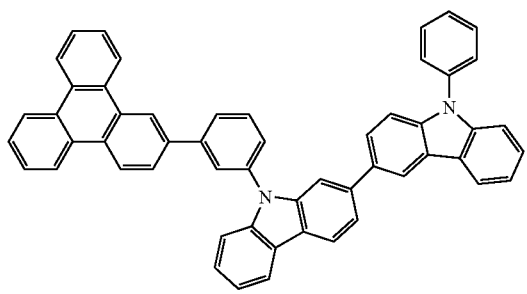
D-28
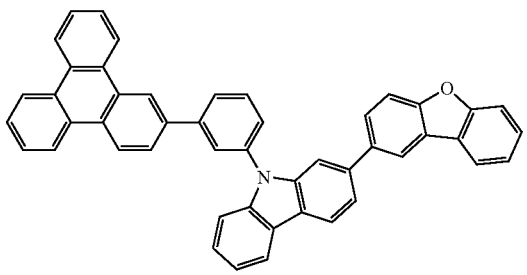
D-29
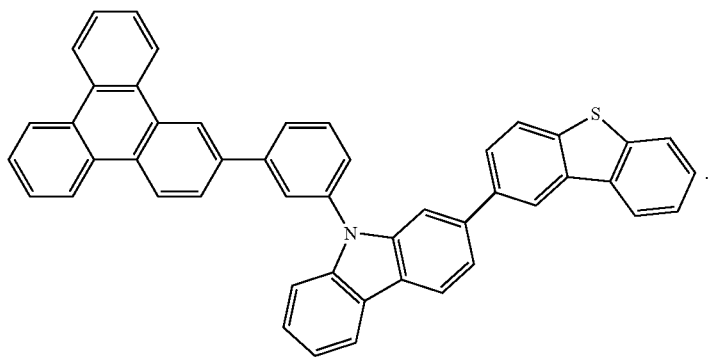

6. The composition for an organic optoelectronic diode of claim 3, wherein the compound consisting of the moiety represented by Chemical Formula 5 and the moiety represented by Chemical Formula 6 is selected from the compounds listed in Group 4:
[Group 4]
E-1
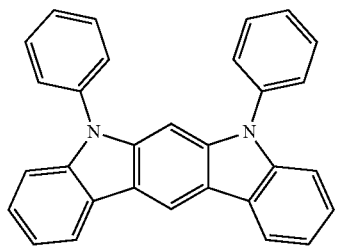
E-2
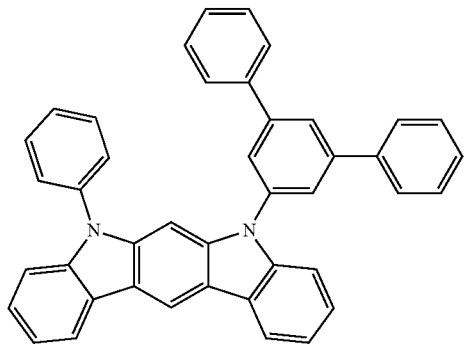
E-3
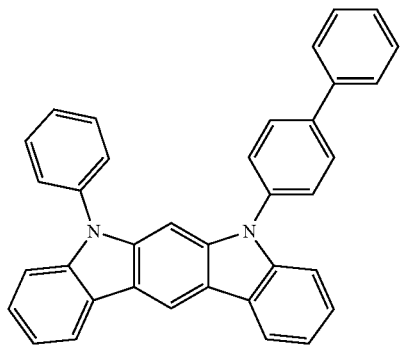
E-4
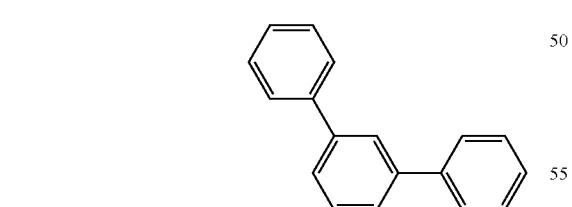
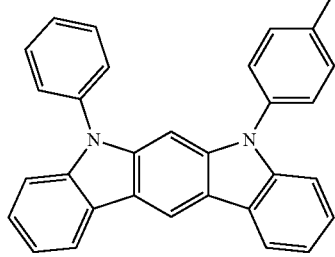
E-5
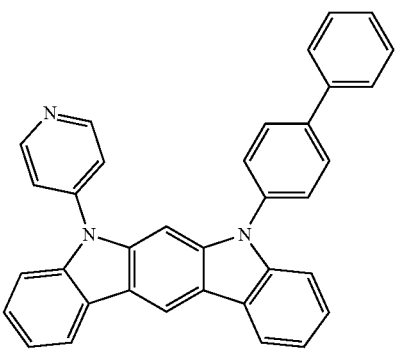
E-6
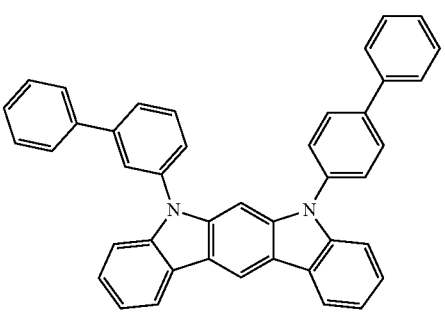
E-7
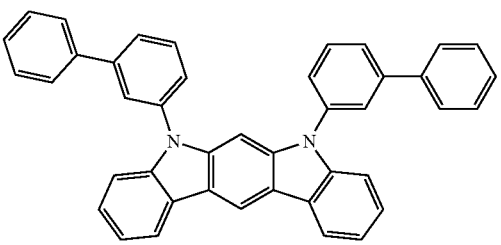
E-8
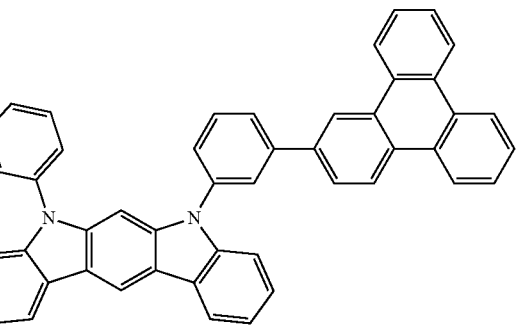
E-9
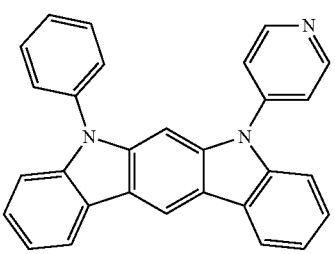

E-10
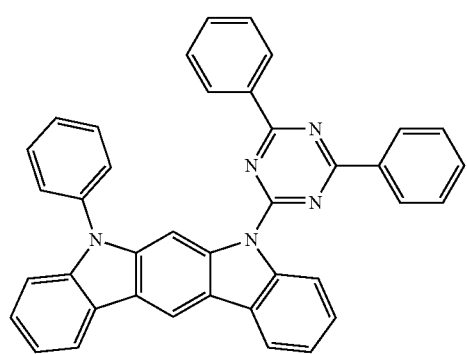
E-11
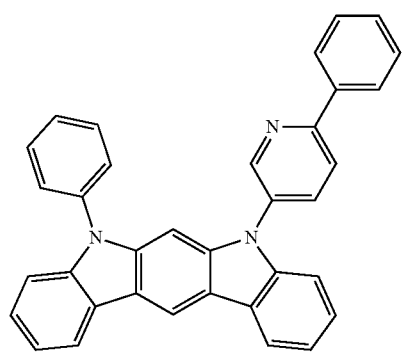
E-12
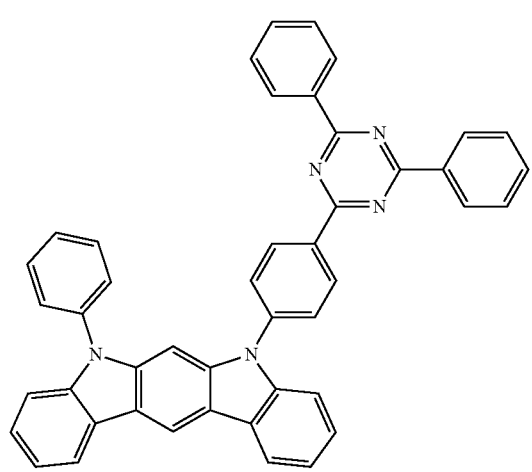
E-13
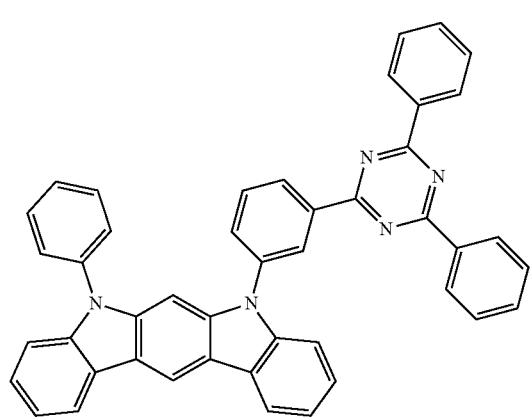
E-14
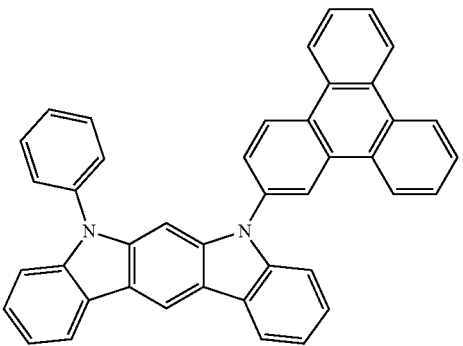
E-15
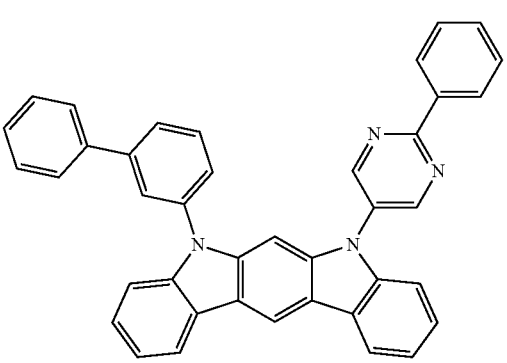
E-16
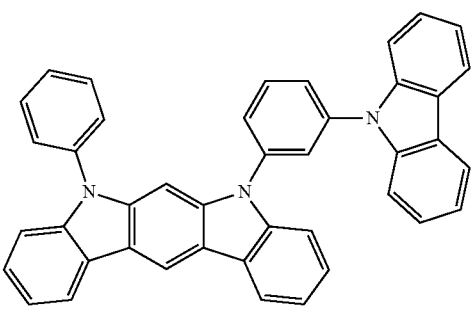
E-17
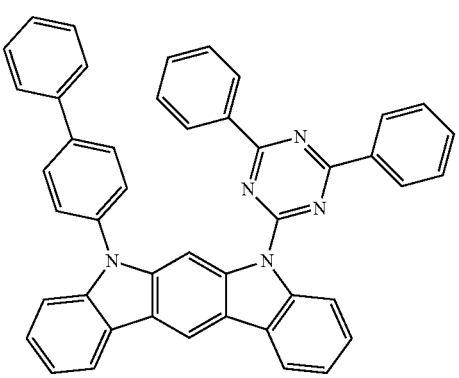

E-18
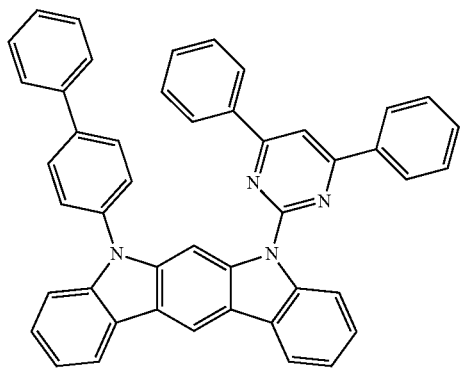
E-19
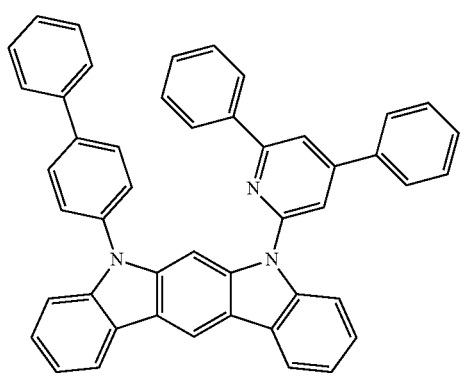
E-20
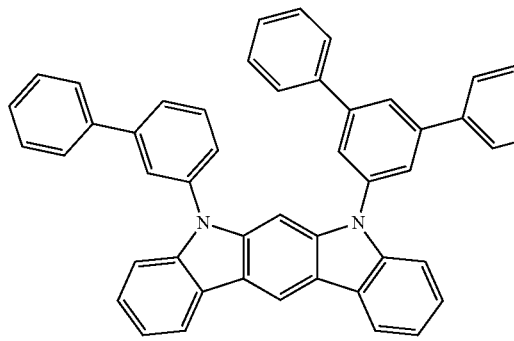
E-21
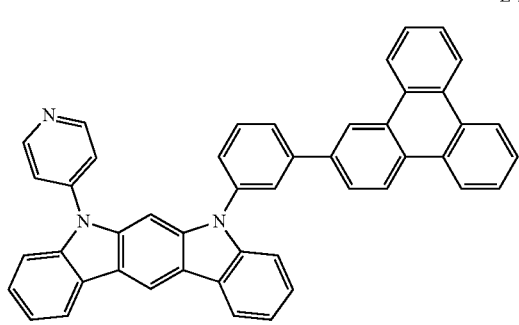
E-22
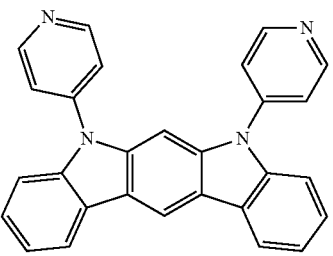
E-23
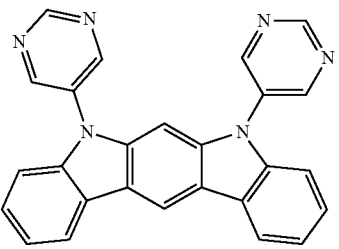
E-24
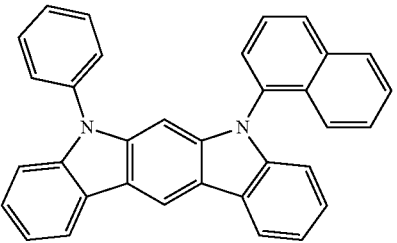
E-25
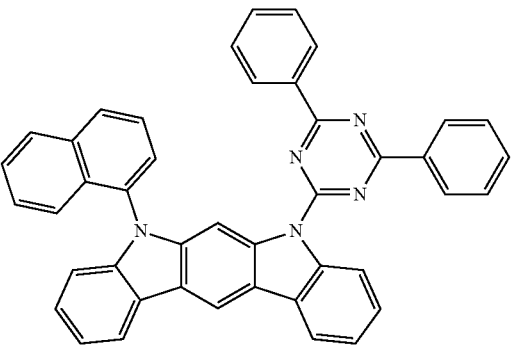
E-26
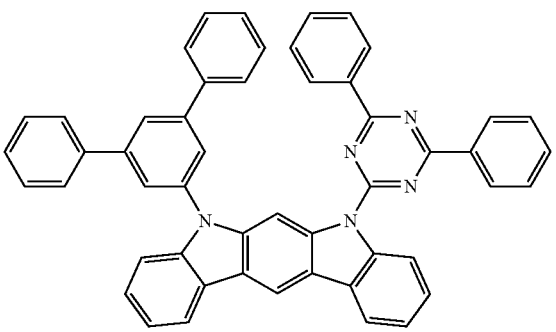

E-27
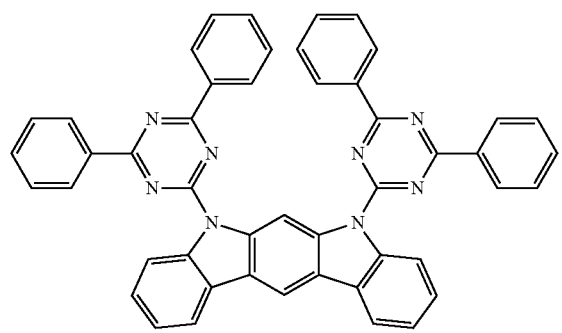
E-28
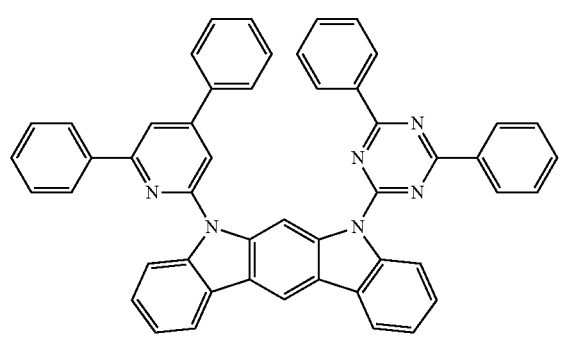
E-29
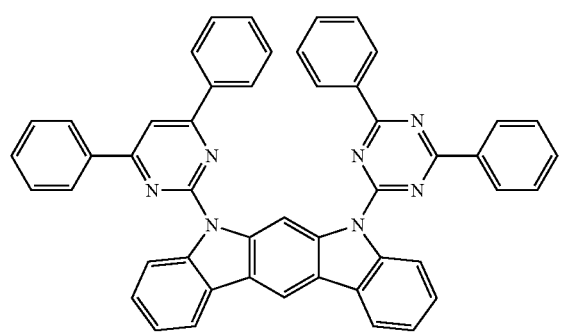
E-30
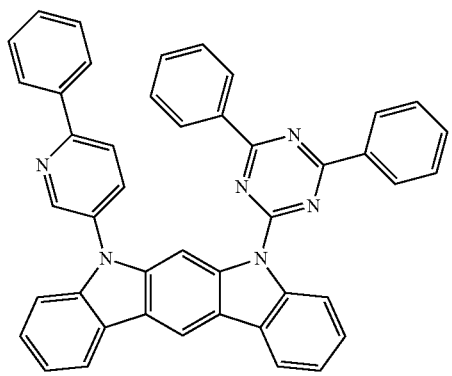
E-31
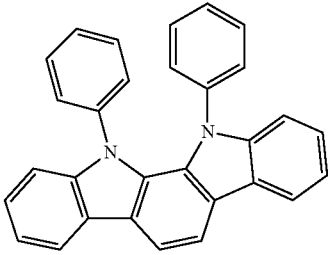
E-32
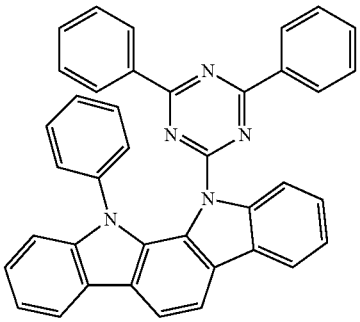
E-33
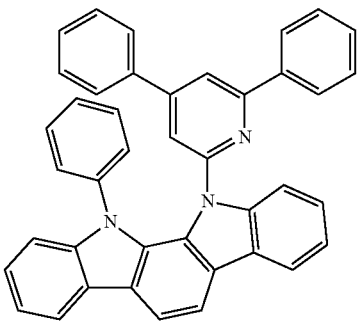
E-34
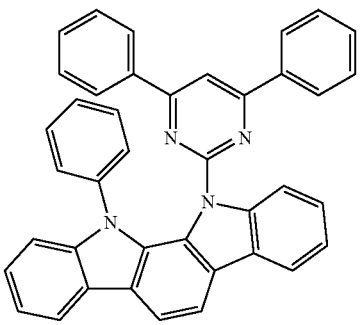
E-35
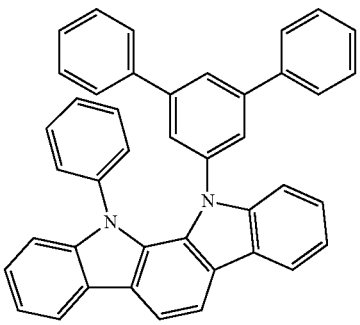

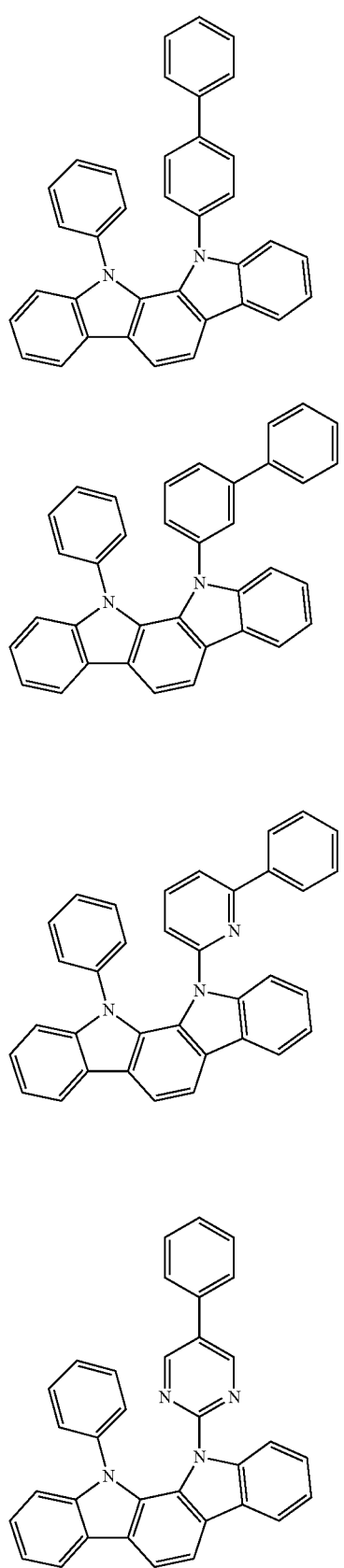
E-36
E-37
E-38
E-39
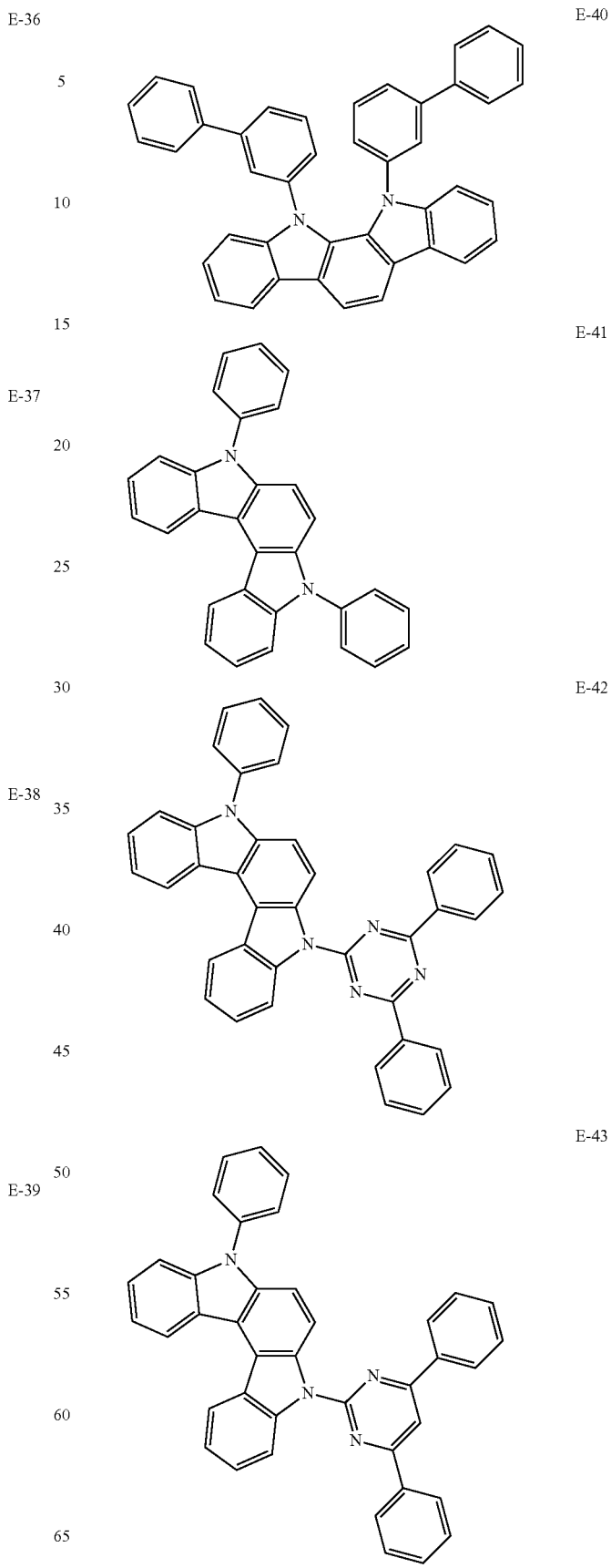
E-40
E-41
E-42
E-43

E-44
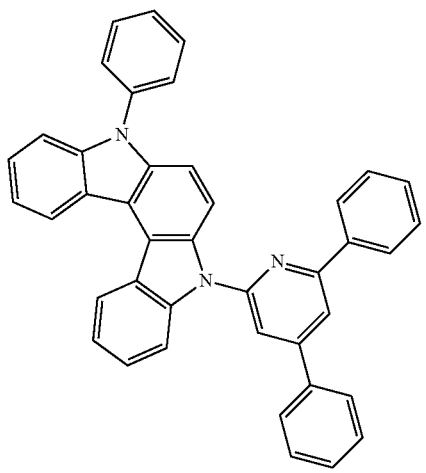
E-45
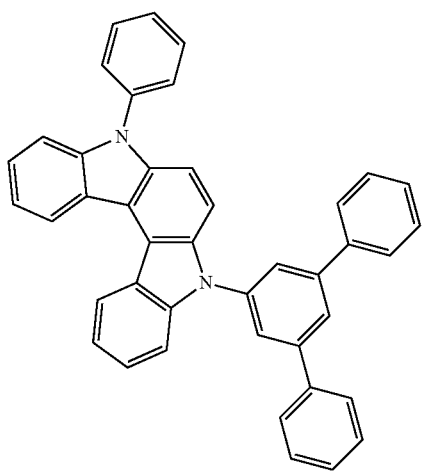
E-46
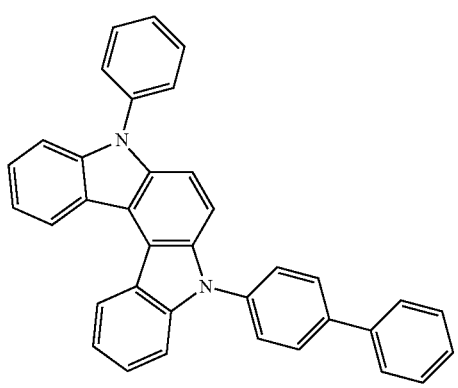
E-47
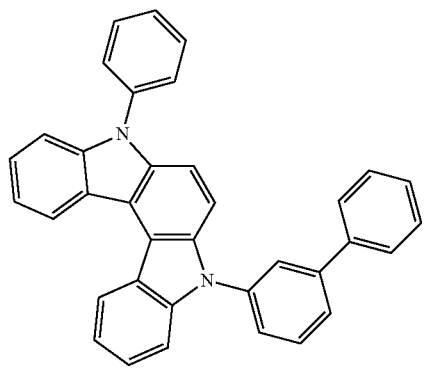
E-48
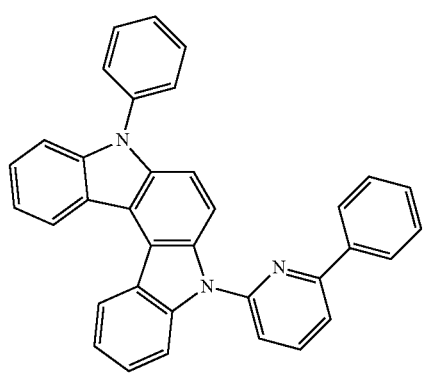
E-49
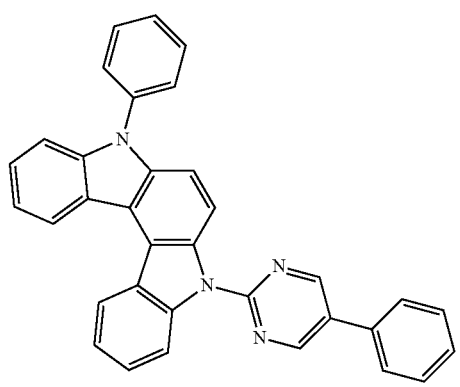

E-50
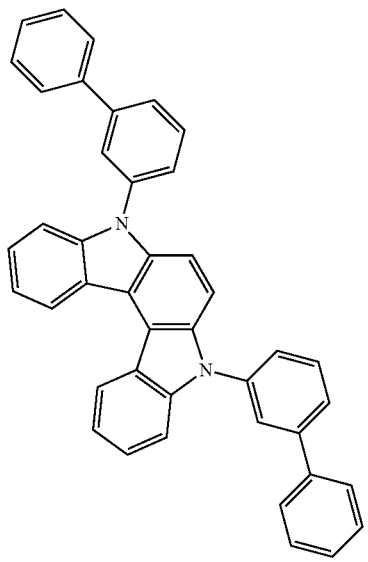
E-51
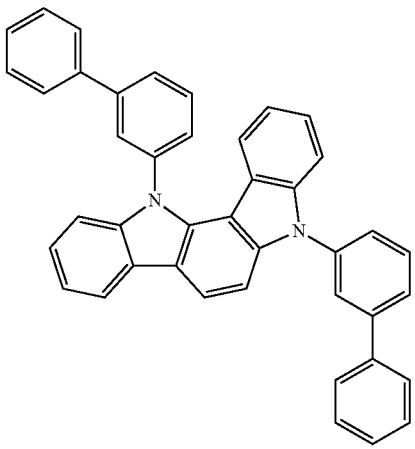
E-52
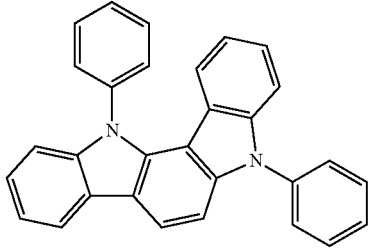
E-53
E-54
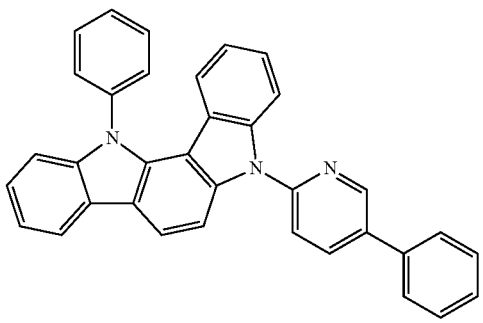
E-55
E-56
E-57
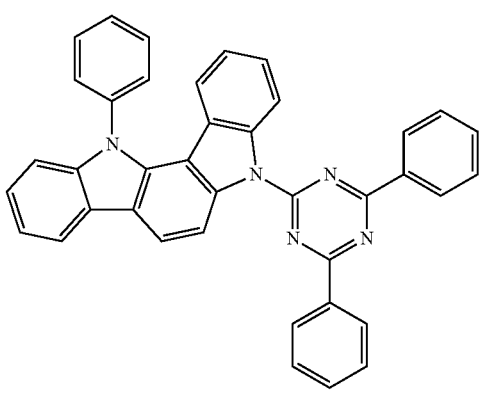

E-58
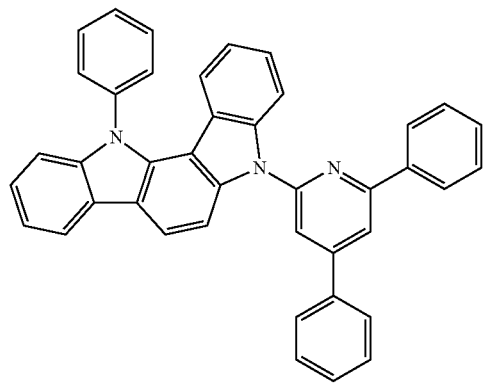
E-59
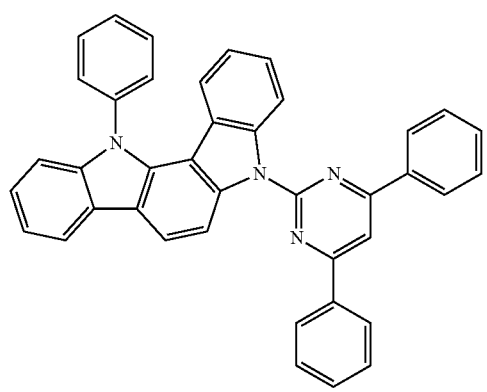
E-60
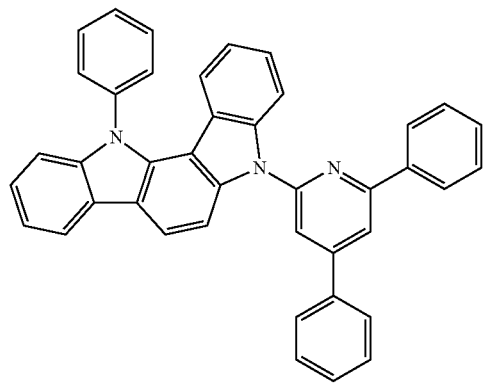
E-61
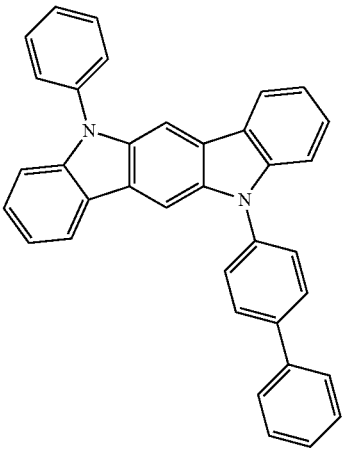
E-62
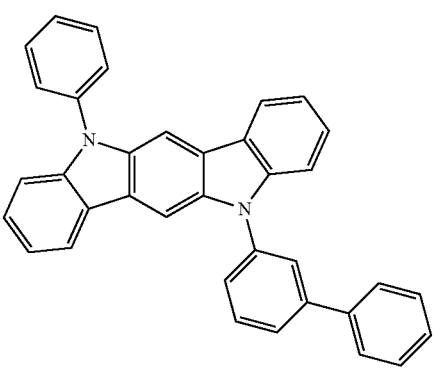
E-63
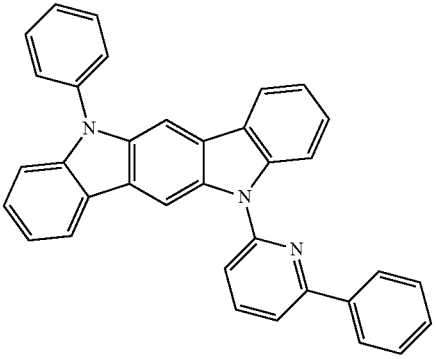
E-64
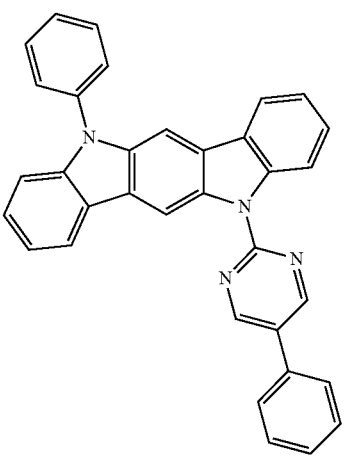

-continued

E-65

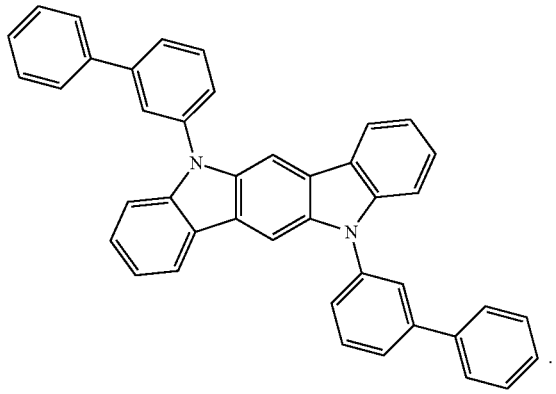

7. The composition for an organic optoelectronic diode of claim 2, wherein the first organic compound and the second organic compound are included in a weight ratio of 1:10 to 10:1.

8. The composition for an organic optoelectronic diode of claim 2, further comprising a phosphorescent dopant.

9. An organic optoelectronic diode, comprising:
an anode and a cathode facing each other, and
at least one organic layer between the anode and the cathode,
wherein the organic layer comprises the organic compound of claim 1.

10. The organic optoelectronic diode of claim 9, wherein:
the organic layer comprises an emission layer, and
the emission layer comprises the organic compound.

11. The organic optoelectronic diode of claim 10, wherein the organic compound is a host of the emission layer.

12. A display device comprising the organic optoelectronic diode of claim 9.

13. An organic optoelectronic diode, comprising
an anode and a cathode facing each other, and
at least one organic layer between the anode and the cathode,
wherein the organic layer comprises the composition for an organic optoelectronic diode of claim 2.

14. The organic optoelectronic diode of claim 13, wherein:
the organic layer comprises an emission layer, and
the emission layer includes the composition for an organic optoelectronic diode.

15. The organic optoelectronic diode of claim 13, wherein the composition for an organic optoelectronic diode is included as a host of the emission layer.

16. A display device comprising the organic optoelectronic diode of claim 13.

* * * * *